United States Patent

Satow et al.

[11] Patent Number: 5,716,904
[45] Date of Patent: Feb. 10, 1998

[54] 4,5-DISUBSTITUTED PYRIMIDINE DERIVATIVES AND HERBICIDES

[75] Inventors: Jun Satow; Yasuo Kondo; Yoshihiro Kudo; Takumi Mikashima, all of Funabashi; Tsutomu Nawamaki, Shiraoka-machi; Yoichi Ito, Shiraoka-machi; Kazuhisa Sudo, Shiraoka-machi; Kunimitsu Nakahira, Shiraoka-machi; Shigeomi Watanabe, Shiraoka-machi; Kimihiro Ishikawa, Shiraoka-machi, all of Japan

[73] Assignee: Nissan Chemical Industries, Ltd., Tokyo, Japan

[21] Appl. No.: 635,950

[22] PCT Filed: Nov. 1, 1994

[86] PCT No.: PCT/JP94/01847

§ 371 Date: May 1, 1996

§ 102(e) Date: May 1, 1996

[87] PCT Pub. No.: WO95/12582

PCT Pub. Date: May 11, 1995

[30] Foreign Application Priority Data

| Nov. 1, 1993 | [JP] | Japan | 5-273392 |
| Apr. 27, 1994 | [JP] | Japan | 6-089904 |
| Jun. 9, 1994 | [JP] | Japan | 6-127456 |
| Jun. 14, 1994 | [JP] | Japan | 6-131709 |
| Jun. 27, 1994 | [JP] | Japan | 6-144774 |

[51] Int. Cl.$^6$ .......... A01N 43/54; C07D 239/26
[52] U.S. Cl. .......... 504/239; 504/225; 544/122; 544/242; 544/333; 544/335
[58] Field of Search ............ 504/239, 225; 544/242, 335, 333

[56] References Cited

FOREIGN PATENT DOCUMENTS

| 0 057 357 | 8/1982 | European Pat. Off. . |
| 0 058 347 | 8/1982 | European Pat. Off. . |
| WO 95/04725 | 2/1995 | WIPO . |

OTHER PUBLICATIONS

Chambers et al. Tetrahedron Letters No. 26, pp. 2405–2406, 1973.

Primary Examiner—Yogendra N. Gupta
Attorney, Agent, or Firm—Oblon, Spivak, McClelland, Maier & Neustadt, P.C.

[57] ABSTRACT

A novel 4,5-disubstituted pyrimidine derivative of the formula (I):

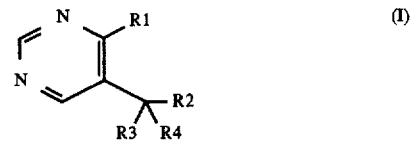

wherein R1 is $CF_2X$ (X is Cl or Br), $R_2$ is a $C_1$–$C_8$ alkyl group, a $C_3$–$C_8$ cycloalkyl group, etc., R3 is a halogen atom, SH, $NH_2$, etc., and R4 is a hydrogen atom, a halogen atom, a $C_1$–$C_6$ alkyl group, etc., is a herbicide having excellent activities.

11 Claims, No Drawings

4,5-DISUBSTITUTED PYRIMIDINE DERIVATIVES AND HERBICIDES

TECHNICAL FIELD

The present invention relates to novel 4,5-disubstituted pyrimidine derivatives and herbicides containing such derivatives as active ingredients.

BACKGROUND TECHNIQUE

The group of compounds of the present invention which contain a pyrimidine ring having hydrogen atoms at the 2- and 6- positions and having specific substituents introduced at the 4- and 5- positions, is a group of novel compounds and, heretofore, their herbicidal activities have not been known.

In order to protect important crop plants such as rice, soybean, wheat, corn, cotton and sugar beet from weeds and to increase their productivities, many herbicides have been put into practical use. These herbicides can roughly be classified into three categories, i.e. those for upland fields, for paddy fields, and for non-agricultural fields, according to the application site. Further, each category can be classified into, for example, a soil incorporation treatment type, a pre-emergence soil treatment type and a post-emergence treatment (foliage treatment) type, according to the manner of application.

With the recent global population increase, the productivities of important crop plants will undoubtedly affect the food economy of each country. With such changes, the conventional mode of agriculture will be inevitably changed toward the 21st century. Actually, it has been increasingly required than ever for persons engaged in agriculture to develop herbicides which can economically and effectively kill or control weeds detrimental to the growth of crop plants.

As such herbicides, chemicals which meet the following requirements are desired to be developed.

Preferred are those having high herbicidal effects at low doses (it is necessary to kill weeds at as low doses as possible from the viewpoint of environmental protection), those having adequate residual activities (since a problem that soil-persistent chemicals damage next crops has arisen recently, it is important to show an adequate residual activity after application), those which promptly kill weeds upon application (it is possible to sow or transplant next crops soon after chemical treatment), those which do not require frequent treatment (it is important for farmers to minimize the frequency of cumbersome weed control operations), those intended to control a wide range of weeds (chemicals capable of controlling a variety of weeds having different properties such as broad-leaves weeds, graminaceous weeds and perennial weeds, are desirable), those which can be applied by various methods (a stronger herbicidal effect can be obtained by combining an effect of soil treatment, an effect of foliage treatment and so on), and those which do not show any problematic phytotoxicity against crop plants (in a field where a crop plant coexists with weeds, those capable of selectively killing weeds are desired). However, no existing herbicides satisfy all of these requirements.

DISCLOSURE OF THE INVENTION

The present inventors have conducted extensive studies on the herbicidal action of the novel pyrimidine derivatives under these circumstances. As a result, they have found that 4,5-disubstituted pyrimidine derivatives of the following formula exhibit excellent herbicidal activities. The present invention has been accomplished on the basis of this discovery.

Namely, the present invention provides a novel 4,5-disubstituted pyrimidine derivative of the formula (I) (hereinafter referred to as the compound of the present invention):

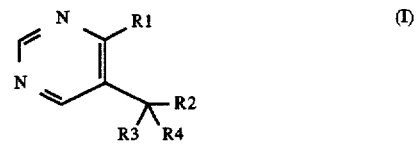

wherein R1 is a $C_1$ or $C_2$ haloalkyl group,

R2 is a $C_1$–$C_8$ alkyl group, a $C_3$–$C_8$ cycloalkyl group, a $C_3$–$C_8$ cycloalkyl($C_1$–$C_4$)alkyl group, a phenyl group which may be substituted [wherein the substituent is selected from the group consisting of a halogen atom, a $C_1$–$C_4$ alkyl group, a $C_1$–$C_4$ alkoxy group, a $C_1$–$C_4$ haloalkyl group, a $C_1$–$C_4$ haloalkoxy group, a $C_3$–$C_8$ alkenyl group, a $C_3$–$C_8$ alkynyl group, a $CO_2$($C_1$–$C_4$ alkyl) group, a $N(C_1$–$C_3$ alkyl$)_2$ group, a cyano group, a nitro group, a sulfo group, an amino group, a hydroxy group, a mercapto group, a $SCH_3$ group, a $SO_2CH_3$ group, a phenoxy group and a phenyl group], a thienyl group, a furyl group, a pyridyl group, a $C_1$–$C_6$ haloalkyl group, a $C_3$–$C_6$ halocycloalkyl group, a $C_3$–$C_8$ alkenyl group, a $C_3$–$C_8$ alkynyl group, a $C_1$–$C_2$ sulfonyl($C_1$–$C_4$)alkyl group or $C_1$–$C_4$ alkylthio($C_3$–$C_6$) cycloalkyl group, R3 is a halogen atom, SH, $NH_2$, —O—R11 [wherein R11 is a $C_1$–$C_8$ alkyl group, a $C_3$–$C_8$ alkenyl group, a $C_3$–$C_8$ alkynyl group, a $C_3$–$C_6$ cycloalkyl group, a $C_3$–$C_6$ cycloalkyl($C_1$ or $C_2$)alkyl group, a $C_1$–$C_6$ haloalkyl group, a $C_3$–$C_8$ haloalkenyl group, a $C_3$–$C_8$ haloalkynyl group, a $C_1$–$C_4$ alkoxy ($C_1$–$C_4$)alkyl group, a cyano ($C_1$–$C_4$)alkyl group, a $C_1$–$C_4$ alkylthio($C_1$–$C_4$)alkyl group, a $C_1$–$C_4$ alkoxycarbonyl($C_1$–$C_4$)alkyl group, a $C_1$–$C_4$ alkoxycarbonyl group, a carboxy($C_1$–$C_4$)alkyl group, a $C_1$–$C_4$ alkylcarbonyl group, a C(=O)NR21(R22) group (each of R21 and R22 is independently a hydrogen atom, a $C_1$–$C_4$ alkyl group, a $C_3$–$C_8$ alkenyl group or a $C_3$–$C_8$ alkynyl group), C(=S)NR21 (R22) group (R21 and R22 are as defined above), a hydroxy($C_1$–$C_4$)alkyl group, a $SO_2N(C_1$–$C_6$ alkyl$)_2$ group, $CO(C_1$–$C_6$ alkyl) group, a $CO_2(C_1$–$C_6$ alkyl) group, a $SO(C_1$–$C_6$ alkyl) group, a $SO_2(C_1$–$C_6$ alkyl) group, a phenethyl group, a phenacyl group, a 1- or 2-naphthyl group, a tetrahydropyranyl group, a tetrahydrothiopyranyl group, a 3-bromotetrahydropyranyl group, a 4-methoxytetrahydropyranyl group, a 4-methoxytetrahydrothiopyranyl group, a tetrahydrofuranyl group, a tetrahydrothiofuranyl group, a 1,4-dioxan-2-yl group, a 1-methoxycyclohexyl group, a benzyloxymethyl group, a 2,2,2-trichloroethoxymethyl group, a bis(2-chloroethoxy)methyl group, a 1-(2-chloroethoxy)ethyl group, a 2-methoxyethoxymethyl group, a 1-methyl-1-benzyloxyethyl group, a tertiary butyldimethylsilyl group, a trimethylsilyl group, a triethylsilyl group, a 2-thenyl group, a furfuryl group, a 2-thenoyl group, a phenyl group which may be substituted (wherein the substituent is selected from the group consisting of a halogen atom, a $C_1$–$C_4$ alkyl group, a $C_1$–$C_4$ alkoxy group, a $C_1$–$C_4$ haloalkyl group, a $C_1$–$C_4$ haloalkoxy group, a $C_3$–$C_8$ alkenyl group, a $C_3$–$C_8$ alkynyl group, a $CO_2(C_1$–$C_4$ alkyl) group, a $N(C_1$–$C_3$ alkyl)$_2$ group, a cyano group, a nitro group, a $SCH_3$ group, a $SO_2CH_3$ group, a phenoxy group and a phenyl group), a benzyl group which may be substituted (wherein the substituent is selected from the group consisting of a halogen atom, a $C_1$–$C_4$ alkyl group, a $C_1$–$C_4$ alkoxy group, a $C_1$–$C_4$ haloalkyl group, a $C_1$–$C_4$ haloalkoxy group, a $C_3$–$C_8$ alkenyl group, a $C_3$–$C_8$ alkynyl group, a $CO_2(C_1$–$C_4$ alkyl) group, a $N(C_1$–$C_3$ alkyl)$_2$ group, a cyano group, a nitro group, a $SCH_3$ group, a $SO_2CH_3$ group, a phenoxy group and a phenyl group), a —Q— phenyl group which may be substituted (wherein Q is a $C_2$–$C_6$ saturated or unsaturated carbon chain which may be branched, and the substituent of the phenyl group is selected from the group consisting of a halogen atom, a $C_1$–$C_4$ alkyl group, a $C_1$–$C_4$ alkoxy group, a $C_1$–$C_4$ haloalkyl group, a $C_1$–$C_4$ haloalkoxy group, a $C_3$–$C_8$ alkenyl group, a $C_3$–$C_8$ alkynyl group, a $CO_2(C_1$–$C_4$ alkyl) group, a $N(C_1$–$C_3$ alkyl)$_2$ group, a cyano group, a nitro group, a $SCH_3$ group, a $SO_2CH_3$ group, a phenoxy group and a phenyl group), a —Q—$CO_2R23$ group (wherein Q is a $C_2$–$C_6$ saturated or unsaturated carbon chain which may be branched, and R23 is a $C_1$–$C_4$ alkyl group), a benzoyl group which may be substituted (wherein the substituent is selected from the group consisting of a halogen atom, a $C_1$–$C_4$ alkyl group, a $C_1$–$C_4$ alkoxy group, a $C_1$–$C_4$ haloalkyl group, a $C_1$–$C_4$ haloalkoxy group, a $C_3$–$C_8$ alkenyl group, a $C_3$–$C_8$ alkynyl group, a $CO_2(C_1$–$C_4$ alkyl) group, a $N(C_1$–$C_3$ alkyl)$_2$ group, a cyano group, a nitro group, a $SCH_3$ group, a $SO_2CH_3$ group, a phenoxy group and a phenyl group), or a benzenesulfonyl group which may be substituted (wherein the substituent is selected from the group consisting of a halogen atom, a $C_1$–$C_4$ alkyl group, a $C_1$–$C_4$ alkoxy group, a $C_1$–$C_4$ haloalkyl group, a $C_1$–$C_4$ haloalkoxy group, a $C_3$–$C_8$ alkenyl group, a $C_3$–$C_8$ alkynyl group, a $CO_2(C_1$–$C_4$ alkyl) group, a $N(C_1$–$C_3$ alkyl)$_2$ group, a cyano group, a nitro group, a $SCH_3$ group, a $SO_2CH_3$ group, a phenoxy group and a phenyl group)], —S—R11 (wherein R11 is as defined above), —N(R11)R12 (wherein R11 is as defined above, and R12 is a hydrogen atom, a $C_1$–$C_8$ alkyl group, $C_3$–$C_8$ alkenyl group, a $C_3$–$C_8$ alkynyl group, a $C_3$–$C_6$ cycloalkyl group, a $C_3$–$C_6$ cycloalkyl($C_1$ or $C_2$)alkyl group, a phenyl group, a benzyl group, a $C_1$–$C_6$ alkoxy group, a formyl group, a $C_1$–$C_6$ acyl group, a —NHR24 group (wherein R24 is a $C_1$–$C_6$ alkyl group), a $C_1$–$C_6$ alkylsulfonyl group or a benzoyl group), where in —N(R11)R12, R11 and R12 may form a 3- to 8-membered saturated, unsaturated or partially saturated heterocyclic ring together with the N atom to which R11 and R12 are bonded, where the constituting elements of the ring is selected from the group consisting of a nitrogen atom, an oxygen atom, a sulfur atom and a carbon atom, and the heterocyclic ring may be substituted (wherein the substituent is selected from the group consisting of a halogen atom, a $C_1$–$C_8$ alkyl group, a $C_1$–$C_8$ alkoxy group, a $C_1$–$C_6$ haloalkyl group, a $C_1$–$C_6$ haloalkoxy group, a $C_1$–$C_8$ acyl group, a $C_3$–$C_8$ alkenyl group, a $C_3$–$C_8$ alkynyl group, a benzoyl group and a phenyl group), or —NH(R12) [R12 is as defined above], R4 is a hydrogen atom, a halogen atom, a $C_1$–$C_6$ alkyl group, a $C_1$–$C_6$ alkoxy group, a $C_3$–$C_6$ cycloalkyl group, a $C_3$–$C_8$ alkenyl group, a $C_3$–$C_8$ alkynyl group, a $C_1$–$C_6$ haloalkyl group, a $C_3$–$C_6$ halocycloalkyl group, a $C_3$–$C_6$ cycloalkoxy group, a $C_3$–$C_8$ alkenyloxy group, a $C_3$–$C_8$ alkynyloxy group, a $C_1$–$C_6$ haloalkoxy group, a $C_3$–$C_6$ halocycloalkoxy group, a $C_1$–$C_6$ alkylthio group, or a phenyl group which may be substituted [wherein the substituent is selected from the group consisting of a halogen atom, a $C_1$–$C_4$ alkyl group, a $C_1$–$C_4$ alkoxy group, a $C_1$–$C_3$ haloalkyl group, a $C_1$–$C_3$ haloalkoxy group, a $C_3$–$C_8$ alkenyl group, a $C_3$–$C_8$ alkynyl group, a $CO_2(C_1$–$C_2$ alkyl) group, a $N(C_1$–$C_3$ alkyl)$_2$ group, a phenoxy group and a phenyl group], R3 and R4 may form a 5- to 6-membered ring which may be substituted, where the constituting elements thereof are groups selected from the group consisting of an oxygen atom, $CH_2$, $CH_2CH_2$, $CH_2C(=CH_2)$ and $CH_2CBr_2$, together with the C atom to which R3 and R4 are bonded [wherein the substituent is selected from the group consisting of a halogen atom, a $CH_{20}H$ group, a $CH_2SH$ group, a $CH_2NH_2$ group, a $CH_2OSi(CH_3)_3$ group, a $CH_2O$-tetrahydropyranyl group, a $C_1$–$C_4$ alkoxy $C_1$–$C_2$ alkoxymethyl group, a $CH_2OCH_2$— cyclopropyl group, a phenyl $C_1$–$C_4$ alkoxymethyl group which may be substituted (wherein the substituent is selected from the group consisting of a halogen atom, a $C_1$–$C_4$ alkyl group, a $C_1$–$C_4$ alkoxy group, a $C_1$–$C_4$ haloalkyl group and a nitro group), a phenyl $C_1$–$C_4$ alkylthiomethyl group which may be substituted (wherein the substituent is selected from the group consisting of a halogen atom, a $C_1$–$C_4$ alkyl group, a $C_1$–$C_4$ alkoxy group, a $C_1$–$C_4$ haloalkyl group and a nitro group), a phenylthiomethyl group which may be substituted (wherein the substituent is selected from the group consisting of a halogen atom, a $C_1$–$C_4$ alkyl group, a $C_1$–$C_4$ alkoxy group, a $C_1$–$C_4$ haloalkyl group and a nitro group), a piperidyl group, a pyridylmethyl group, a pyridyl group, a morpholinomethyl group, a piperazinomethyl group, a pyrrolidinylmethyl group, a piperazinomethyl group, a pyrrolylmethyl group, a phenylaminomethyl group which may be substituted (wherein the substituent is selected from the group consisting of a halogen atom, a $C_1$–$C_4$ alkyl group, a $C_1$–$C_4$ alkoxy group, a $C_1$–$C_4$ haloalkyl group and a nitro group), a phenyl $C_1$–$C_4$ alkylaminomethyl group which may be substituted (wherein the substituent is selected from the group consisting of a halogen atom, a $C_1$–$C_4$ alkyl group, a $C_1$–$C_4$ alkoxy group, a $C_1$–$C_4$ haloalkyl group and a nitro group), a 4-phenylpiperazinomethyl group, a N-benzyl-N-methylaminomethyl group, a 4-(4-acylpiperazinyl)phenoxymethyl group, a 4-(4-isopropylpiperazinyl)phenoxymethyl group, a 4-[4-[4-[2,4-dihydro-2-(1-methylpropyl)-3H-1,2,4-triazol-3-one-4-yl]phenyl]piperazino]phenoxymethyl group, a $C_1$–$C_{16}$ alkyl group, a $C_1$–$C_{18}$ alkoxy group, a $C_1$–$C_8$ haloalkyl group, a $C_1$–$C_{16}$ haloalkoxy group, a $C_2$–$C_8$ alkenyl group, a $C_2$–$C_8$ alkynyl group, a $C_1$–$C_{18}$ alkoxymethyl group, a $C_2$–$C_{18}$ alkenyloxymethyl group, a $C_2$–$C_{18}$ alkynyloxymethyl group, a $C_2$–$C_{18}$ alkenylthiomethyl group, a $C_2$–$C_{18}$ alkenylaminomethyl group, a 3-substituted-1-pyrrolylmethyl group, a $C_1$–$C_4$ alkylthiomethyl group, a $C_1$–$C_6$ alkylaminomethyl group, a $C_1$–$C_{19}$ alkylcarbonyloxymethyl group, a $C_2$–$C_{19}$ alkenylcarbonyloxymethyl group, a phenyl $C_{1-3}$ alkyl group, a $(C_1$–$C_6$ alkyl)$_2$ aminomethyl group (wherein the alkyl groups as substituents of the amino group may form a 5- or 6-membered cyclocyclic ring), a phenoxymethyl group which may be substituted (the substituent of the phenyl group is selected from the group consisting of a halogen atom, a $C_1$–$C_4$ alkyl group, a $C_1$–$C_4$ alkoxy group, a $C_1$–$C_4$ haloalkyl group, a $C_1$–$C_4$ haloalkoxy group, a $C_3$–$C_8$ alkenyl group, a $C_3$–$C_8$ alkynyl group, a $CO_2(C_1$–$C_4$ alkyl) group, a $N(C_1$–$C_3$ alkyl)$_2$ group, a cyano group, a nitro group, a $SCH_3$ group, a $SO_2CH_3$ group, a phenoxy group and a phenyl group), and a phenyl group which may be substituted (wherein the substituent is selected from the group consisting of a halogen atom, a nitro group, a $C_1$–$C_4$ alkyl group, a $C_1$–$C_4$ alkoxy group, a $C_1$–$C_4$ haloalkyl group, a $C_1$–$C_4$ haloalkoxy group, a $N(C_1$–$C_3$ alkyl)$_2$ group, a phenoxy group and a phenyl group)], provided that when the carbon atom substituted by R3 and R4 is an optically active carbon atom, the lacemate and both of the two isolated optical isomers are included, and when two optically active sites are present in the molecule, the diastereomer mixture and all of the isolated two diastereomers and four optical isomers are included, and R3 and R4 may together form =NH, =NNH$_2$, =NOB, =NOR11 (wherein R11 is as defined above, and the geometrical isomers include the E/Z mixture and both of the isolated E and Z), =NO—Q—R11 (wherein Q and R11 are as defined above, and the geometrical isomers include the E/Z mixture and both of the isolated E and Z), =NO—Q—CO$_2$—($C_1$–$C_4$ alkyl group) (wherein Q is as defined above, and the geometrical isomers include the E/Z mixture and both of the isolated E and Z), or =NNR11 (R16) (wherein R11 is as defined above, R16 is a hydrogen atom, a $C_1$–$C_6$ alkyl group, a $C_3$–$C_8$ alkenyl group, a $C_3$–$C_8$ alkynyl group, a benzyl group or a phenyl group, and the geometrical isomers include the E/Z mixture and both of the isolated E and Z). The present invention also provides herbicides containing the compounds of the present invention.

Preferred compounds of the present invention are as follows:

(a) A compound wherein R1 is $CF_2X$ (X is a chlorine atom or a bromine atom).

(b) A compound wherein R2 is a phenyl group which may be substituted (wherein the substituent is selected from the group consisting of a halogen atom, a $C_1$–$C_4$ alkyl group, a $C_1$–$C_4$ alkoxy group, a trifluoromethoxy group and a trifluoromethyl group), a thienyl group, a furyl group or a pyridyl group; R3 is a halogen atom, a $C_1$–$C_8$ alkoxy group, a $C_3$–$C_6$ cycloalkyloxy group, a phenoxy group which may be substituted (wherein the substituent is selected from the group consisting of a halogen atom, a $C_1$–$C_4$ alkyl group, a $C_1$–$C_4$ alkoxy group and a trifluoromethyl group), a tetrahydropyranyloxy group, a phenyl $C_1$–$C_4$ alkoxy group which may be substituted (wherein the substituent is selected from the group consisting of a halogen atom, a $C_1$–$C_4$ alkyl group and a $C_1$–$C_4$ alkoxy group), a $C_3$–$C_6$ cycloalkyl $C_1$ or $C_2$ alkoxy group, a $C_3$–$C_6$ alkenyloxy group, a $C_3$–$C_6$ alkynyloxy group, a $C_1$–$C_4$ alkoxycarbonyl($C_1$–$C_4$)alkoxy group, a $C_1$–$C_4$ alkoxycarbonyloxy group, a $C_1$–$C_4$ alkoxy($C_1$–$C_4$)alkoxy group, a $C_1$–$C_4$ alkylthio($C_1$–$C_4$)alkoxy group, a cyano $C_1$–$C_4$ alkoxy group, a mono or di $C_1$–$C_4$ alkylaminocarbonyloxy group, a mono or di $C_1C_4$ alkylaminothiocarbonyloxy group, a $C_1$–$C_4$ alkylcarbonyloxy group, a $C_1$–$C_4$ alkylsulfonyloxy group, a di $C_1$–$C_4$ alkylaminosulfonyloxy group, a mercapto group, a $C_1$–$C_4$ alkylthio group, a phenylthio group, a benzylthio group, a $C_3$–$C_6$ alkenylthio group, a $C_3$–$C_6$ alkynylthio group, a $C_1$–$C_4$ alkoxycarbonyl($C_1$–$C_3$)alkylthio group, a $C_1$–$C_4$ alkoxycarbonylthio group, a $C_1$–$C_4$ alkoxy $C_1$–$C_4$ alkylthio group, a cyano $C_1$–$C_4$ alkylthio group, a mono or di $C_1$–$C_4$ alkylaminocarbonylthio group, a mono or di $C_1$–$C_4$ alkylaminothiocarbonylthio group, a $C_1$–$C_4$ alkylthiocarbonylthio group, an amino group, a mono or di $C_1$–$C_4$ alkylamino group, a methyl(methoxy)amino group, a methoxyamino group, a hydroxy $C_1$–$C_4$ alkylamino group, a mono or di $C_3$–$C_5$ alkenylamino group, a mono or di $C_3$–$C_5$ alkynylamino group, a carboxy $C_1$–$C_4$ alkylamino group, a $C_1$–$C_4$ alkoxycarbonyl $C_1$–$C_4$ alkylamino group, a $C_1$–$C_4$ alkoxycarbonyl $C_1$–$C_4$ alkyl(methyl)amino group, a $C_3$–$C_6$ cycloalkylamino group, a phenylamino group, a phenyl $C_1$–$C_4$ alkylamino group which may be substituted (wherein the substituent is selected from the group consisting of a halogen, methyl and methoxy), a benzyl(methyl)amino group, a benzyl(formyl)amino group, a phenyl(formyl)amino group, a $C_1$–$C_4$ alkylsulfonylamino group, a mono or di $C_1$–$C_4$ alkylaminosulfonylamino group, a cyano $C_1$–$C_4$alkylamino group, a $C_1$–$C_4$ alkylcarbonylamino group, a mono or di $C_1$–$C_4$ alkylaminocarbonylamino group, a mono or di $C_1$–$C_4$ alkylaminothiocarbonylamino group, a mono or di $C_1$–$C_4$ alkylhydrazino group, a di $C_1$–$C_4$ alkylamino group, an imidazolyl group, a triazol-1-yl group, a morpholino group, a dimethyl-substituted morpholino group, a piperazino group, a piperidino group, a pyrrolidinyl group or an aziridinyl group; and R4 is a hydrogen atom or a methyl group.

(c) A compound wherein R2 is a phenyl group which may be substituted (wherein the substituent is a halogen, a $C_1$–$C_4$ alkyl group, a $C_1$–$C_4$ alkoxy group or a trifluoromethyl group), a thienyl group, a furyl group or a pyridyl group; and R3 and R4 form together with the carbon atom to which R3 and R4 are bonded, a 1,3-dioxane ring which may be substituted (wherein the substituent is methylene or a halogen), or a 1,3-dioxolan ring which may be substituted (wherein the substituent is a $C_1$–$C_8$ alkyl group, a halo $C_1$–$C_4$ alkyl group, a methoxymethyl group or a $C_3$–$C_6$ alkenyl group).

(d) A compound wherein R2 is a $C_1$–$C_8$ alkyl group, a $C_3$–$C_6$ halocycloalkyl group, a $C_3$–$C_6$ cycloalkyl group or a $C_3$–$C_6$ cycloalkyl $C_1$ or $C_2$ alkyl group; and R3 and R4 together form a formula

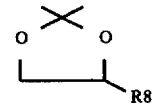

together with the carbon atom to which R3 and R4 are bonded, wherein R8 is a hydrogen atom, a $C_1$–$C_{20}$ alkyl group, a phenyl group which may be substituted by a nitro group, a phenyl $C_{1-3}$ alkyl group, a $C_3$–$C_6$ alkenyl group, a halo $C_1$–$C_8$ alkyl group, a $C_1$–$C_{18}$ alkoxymethyl group, a benzyloxymethyl group which may be substituted (the substituent is selected from the group consisting of a methoxy group, a methyl group and a halogen atom), a phenoxymethyl group which may be substituted (wherein the substituent is selected from the group consisting of a methoxy group, a $C_1$–$C_4$ alkyl group, a halogen atom and a nitro group), an allyloxymethyl group, a propinyloxymethyl group, a hydroxymethyl group, a trimethylsilyloxymethyl group, a tetrahydropyranyloxymethyl group, a methoxymethoxymethyl group, a cyclopropylmethoxymethyl group, a mono or di $C_1$–$C_{12}$ alkylaminomethyl group, an aminomethyl group, a phenylamino $C_1$–$C_4$ alkyl group which may be substituted by a nitro group, a phenyl $C_1$–$C_4$ alkylaminomethyl group which may be substituted by a halogen atom, a $C_3$–$C_6$ cycloalkylaminomethyl group, a pyrrolidinylmethyl group, a piperazinomethyl group, a morpholinomethyl group, a piperidinomethyl group, a $C_1$–$C_4$ alkylthiomethyl group, a mercaptomethyl group, a phenylthiomethyl group which may be substituted by a halogen atom, a phenyl $C_1$–$C_4$ alkylthiomethyl group which may be substituted by a halogen atom, a $C_1$–$C_{17}$ alkylcarbonyloxymethyl group, a $C_3$–$C_6$ alkenylcarbonyloxymethyl group, a benzoyloxymethyl group, a piperidyl group, a 4-phenylpiperazinomethyl group, a 4-(4-acylpiperazinyl)phenoxymethyl group, a 3-substituted-1-pyrrolylmethyl group, a 4-[4-[4-[2,4-dihydro-2-(1-methylpropyl)-3H-1,2,4-triazol-3-one-4-yl]phenyl]piperazino]phenoxymethyl group, a pyridyl group or a pyridylmethyl group.

(e) A compound wherein R2 is a $C_1$–$C_8$ alkyl group or a $C_3$–$C_6$ cycloalkyl group; and R3 and R4 together form a 1,3-dioxane ring which may be substituted (wherein the substituent is a methylene group or a halogen atom) together with the carbon atom to which R3 and R4 are bonded.

(f) A compound wherein R2 is a $C_1$–$C_8$ alkyl group, a $C_3$–$C_6$ cycloalkyl group or a $C_3$–$C_6$ cycloalkyl $C_1$ or $C_2$ alkyl group; R3 is an amino group, a mono or di $C_1$–$C_4$alkylamino group, a hydroxy $C_1$–$C_4$ alkylamino group, a cyano $C_1$–$C_4$ alkylamino group, a $C_1$–$C_4$ alkoxycarbonylmethyl(methyl)amino group, a $C_3$–$C_6$ alkenylamino group, a $C_3$–$C_6$ alkynylamino group, a phenylamino group which may be substituted by a halogen atom, a phenyl $C_1$–$C_4$ alkylamino group which may be substituted (wherein the substituent is selected from the group consisting of a halogen atom, a $C_1$–$C_4$ alkyl group, a trifluoromethyl group and a methoxy group), a phenyl $C_1$–$C_4$ alkyl(formyl)amino group which may be substituted by a halogen atom, a $C_1$–$C_4$ alkyl(formyl)amino group, a phenyl $C_{1-4}$ alkyl($C_1$–$C_4$ alkyl)amino group which may be substituted by a halogen atom, a diphenylmethylamino group, a thienylmethylamino group, a morpholino group, a dimethyl-substituted morpholino group, a thiomorpholino group, a piperidino group, a dimethyl-substituted piperidino group, an aziridyl group, a dimethylaziridyl group, a pyrrolyl group, a pyrrolidyl group, a $C_1$–$C_3$ alkyl-substituted piperidyl group, a methyl-substituted piperazyl group, a phenyl-substituted piperazyl group, a $C_6$ or $C_7$ alkyleneimino group, an imidazol-1-yl group, a pyrazol-1-yl group, a triazol-1-yl group, a phenyl-substituted piperidyl group, a benzyl-substituted piperidyl group, a dimethylamino-substituted piperidyl group, a trifluoromethylpiperidyl group, a perhydroquinolyl group, a tetrahydroquinolyl group, a tetrahydro-mono or dimethyl-substituted quinolyl group, a dihydro-dimethyl-substituted quinolyl group or a dihydro-dimethyl-chloroquinolyl group; and R4 is a hydrogen atom.

(g) A compound wherein R2 is a $C_1$–$C_6$ alkyl group, a $C_3$–$C_6$ cycloalkyl group or a $C_3$–$C_6$ cycloalkyl $C_1$ or $C_2$ alkyl group; R3 is an O-R6 group, wherein R6 is a $C_1$–$C_6$ alkyl group, a $C_3$–$C_6$ cycloalkyl group, a $C_3$–$C_5$ alkenyl group, a $C_3$–$C_5$ alkynyl group, a halo $C_1$–$C_4$ alkyl group, a halo $C_3$–$C_5$ alkenyl group, a phenyl group which may be substituted (wherein the substituent is selected from the group consisting of a halogen atom, a $C_1$–$C_4$ alkyl group and a methoxy group), a phenyl $C_1$–$C_4$ alkyl group which may be substituted (wherein the substituent is selected from the group consisting of a halogen atom, a $C_1$–$C_4$ alkyl group and a methoxy group), a $C_1$–$C_4$ alkylcarbonyl group, a phenylcarbonyl group which may be substituted (wherein the substituent is selected from the group consisting of a halogen atom, a $C_1$–$C_4$ alkyl group and a methoxy group), a benzylcarbonyl group, a $C_1$–$C_4$ alkylsulfonyl group, a phenylsulfonyl group which may be substituted (wherein the substituent is selected from the group consisting of a halogen atom, a $C_1$–$C_4$ alkyl group and a methoxy group), a $C_1$–$C_4$ alkoxy $C_{1-4}$ alkyl group which may be substituted by a halogen, a $C_1$–$C_4$ alkylthiomethyl group, a mono or di $C_1$–$C_4$ alkylaminocarbonyl group, a mono or di $C_1$–$C_4$ alkylaminothiocarbonyl group, a $C_1$–$C_4$ alkoxycarbonyl group, a $C_1$–$C_4$ alkoxycarbonyl $C_1$–$C_2$ alkyl group, a cyanomethyl group, a tetrahydropyranyl group, a 3-bromotetrahydropyranyl group, a methoxytetrahydropyranyl group, a tetrahydrothiopyranyl group which may be substituted by a methoxy group, a tetrahydrofuranyl group, a tetrahydrothiofuranyl group, a 1,4-dioxan-2-yl group, a methoxy-substituted cyclohexyl group, a $C_1$–$C_2$ alkoxy $C_1$–$C_2$ alkoxymethyl group, a benzyloxymethyl group or a $C_{1-4}$ trialkylsilyl group; and R4 is a hydrogen atom.

(h) A compound wherein R2 is a $C_{1-6}$ alkyl group, a phenyl group which may be substituted (wherein the substituent is selected from the group consisting of a halogen atom, a $C_1$–$C_4$ alkyl group, a $C_1$–$C_4$ alkoxy group and a trifluoromethyl group), a thienyl group, a furyl group or a pyridyl group; and R3 and R4 together form a formula =N—R5, wherein R5 is a $C_1$–$C_6$ alkoxy group, a $C_3$–$C_6$ cycloalkyloxy group, a $C_3$–$C_6$ alkenyloxy group, a $C_3$–$C_6$ alkynyloxy group, a $C_1$–$C_4$ alkoxycarbonyl $C_1$–$C_4$ alkoxy group, a carbonylmethoxy group, a benzyloxy group which may be substituted by a halogen atom, a hydroxy group, a mono or di $C_1$–$C_4$ alkylamino group, a phenylamino group which may be substituted (wherein the substituent is selected from the group consisting of a halogen atom, a $C_1$–$C_4$ alkyl group, a methoxy group and a trifluoromethyl group), a benzylamino group which may be substituted by a halogen atom or a benzyloxy group which may be substituted (wherein the substituent is selected from the group consisting of a $C_1$–$C_4$ alkyl group, a halogen atom and a methoxy group).

The compounds of the present invention exhibit high herbicidal activities as a herbicide for upland fields and non-agricultural fields, either in soil treatment or in foliage treatment at low doses against broad-leaved weeds such as Solanaceous weeds (Solanaceae) represented by black nightshade (*Solanum nigrum*) and jimsonweed (*Datura stramonium*), Malvaceous weeds (Malvaceae) represented by velvetleaf (*Abutilon theophrasti*) and prickly sida (*Sida spinosa*), Conolvulaceous weeds (Convolvulaceae) represented by morningglories (Ipomoea spps.) including common morningglory (*Ipomoea purpurea*) and bindweeds (Calystegia spps.), Amaranthaceous weeds (Amaranthaceae) represented by livid amaranth (*Amaranthus lividus*) and redroot pigweed (*Amaranthus retroflexus*), Composite weeds (Compositae) represented by common cocklebur (*Xanthium pensylvanicum*), common ragweed (*Ambrosia artemisiaefolia*), sunflower (*Helianthus annuus*), hairy galinsoga (*Galinsoga ciliata*), creeping thistle (*Cirsium arvense*), common groundsel (*Senecio vulgaris*) and annual fleabane (*Erigeron annus*), Cruciferous weeds (Cruciferae) represented by India field cress (*Rorippa indica*), kedlock (*Sinapis arvensis*) and shepherd's purse (*Capsella Bursapastoris*), Polygonaceous weeds (Polygonaceae) represented by posumbu knotweed (*Polyqonum Blumei*) and wild buckwheat (*Polygonum convolvulus*), Portulacaceous weeds (Portulacaceae) represented by common purslane (*Portulaca oleracea*), Chenopodiaceous weeds (Chenopodiaceae) represented by common lambsquater (*Chenopodium album*), figleaved goosefoot (*Chenopodium ficifolium*) and kochia (*Kochia scoparia*), Caryophyllaceous weeds (Caryophyllaceae) represented by common chickweed (*Stellaria media*), Scrophulariaceous weeds (Scrophulariaceae) represented by persian speedwell (*Veronica persica*), Commelinaceous weeds (Commelinaceae) represented by asiatic dayflower (*Commelina communis*), Labiate weeds (Labiatae) represented by dead-nettle (*Lamium amplexicaule*) and red dead-nettle (*Lamium purpureum*), Euphorbiaceous weeds (Euphorbiaceae) represented by prostrate spurge (*Euphorbia supina*) and spotted spurge (*Euphorbia maculata*), Rubiaceous weeds (Rubiaceae) represented by bed straw (*Galium spurium*) and indian madder (*Rubia akane*), Violaceous weeds (Violaceae) represented by violet (*Viola mandshurica*), and Leguminous weeds (Leguminosae) represented by hempsesbania (*Sesbania exaltata*) and sicklepod (*Cassia obtusifolia*); and various cropland weeds such as Graminaceous weeds represented by shattercane (*Sorgham bicolor*), fall panicum (*Panicum dichotomiflorum*), johnsongrass (*Sorghum halepense*), barnyardgrass (*Echinochloa crus-galli var. crus-qalli*), barnyardgrass (*Echinochloa crus-galli var. praticola*), barnyardgrass (crop) (*Echinochloa utilis*), large crabgrass (*Digitaria adscendens*), wild oat (*Avena fatua*), goosegrass (*Eleusine indica*), green foxtail (Setaria viridis) and water foxtail (*Alopecurus aegualis*), and Cyperaceous weeds represented by purple nutsedge (*Cyperus rotundus, Cyperus esculentus*).

Further, the compounds of the present invention exhibit high herbicidal activities as a herbicide for paddy fields either in submerged soil treatment or in foliage treatment at low doses against various paddy weeds such as Alismataceous weeds (Alismataceae) represented by narrow leaf waterplantain (*Alisma canaliculatum*), arrowhead (*Sagittaria trifolia*) and japanese ribbon wapato (*Sagittaria pygmaea*), Cyperaceous weeds (Cyperaceae) represented by smallflower umbrellaplant (*Cyperus difformis*), perennial flat sedge (*Cyperus serotinus*), bulrush (*Scirpus juncoides*) and water chestnut (*Eleocharis kuroguwai*), Scrophulariaceous weeds (Scrothulariaceae) represented by false pimpernel (*Lindemia pyxidaria*), Potenderiaceous weeds (Potenderiaceae) represented by ducksalad (*Monochoria vaginalis*), Potamogenaceous weeds (*Potamogetonaceae*) represented by roundleaf pondweed (*Potamogeton distinctus*), Lythraceous weeds (Lythraceae) represented by toothcup (*Rotala indica*), barnyardgrass (*Echinochloa oryzicola*), barnyardgrass (*Echinochloa crus-qalli var. formosensis*) and barnyardgrass (*Echinochloa crus-qalli var. crus-galli*).

Therefore, the compounds of the present invention can be used as an active ingredient of herbicides for upland fields, paddy fields, lawns, orchards, pastures and other non-agricultural fields. Now, various methods for producing them will be described in detail.

The compounds of the present invention can be synthesized by the methods represented by the following Schemes 1 to 6 (in Schemes 1 to 6, R1 to R4 are as defined above, each of Ra and Rb is a $C_1$–$C_3$ alkyl group, L is a leaving group, Met is a metal atom such as Mg or Zn, and Hal is a halogen atom).

The starting material, 2,4-dicarbonyl compound (II), can be easily synthesized in accordance with the methods disclosed in "The Chemistry of the Carbonyl Group", p. 273, written by D. P. N. Satchell and R. S. Satchell, edited by Saul Patai (published by Wiley-Interscience, 1966) and "Organic Reactions Vol. 1", p. 266, written by C. R. Hauser and B. E. Hudson, Jr. (published by John Wiley & Sons, Inc., 1942).

Synthesis route (1)

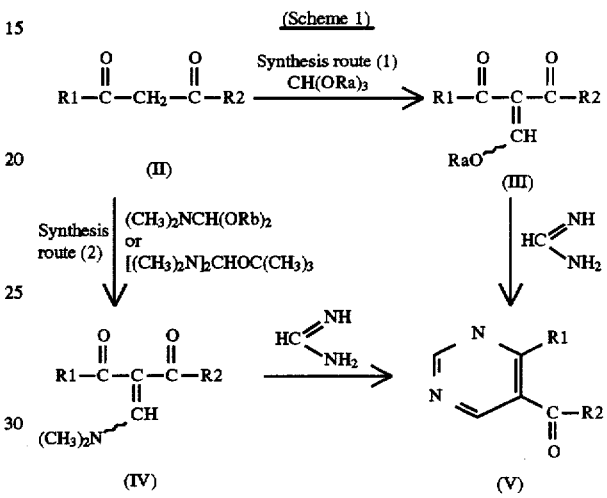

(1) Synthesis route (1) in Scheme 1 indicates a method of producing a pyrimidine derivative (V) which comprises reacting a 2,4-dicarbonyl compound (II) with an orthoformic ester derivative and, as a case requires, a catalytic amount of zinc chloride ($ZnCl_2$), and then reacting the resulting 3-alkoxy methylene-2,4-dicarbonyl derivative (III) with a formamidine.

(2) Synthesis route (2) in Scheme 1 indicates a method of producing a pyrimidine derivative (V) which comprises reacting a 2,4-dicarbonyl compound (II) with a N,N-dimethylformamide dialkylacetal or tert-butoxy-bis(dimethylamino)methane and then reacting the resulting 3-dimethylaminomethylene-2,4-dicarbonyl derivative (IV) with a formamidine.

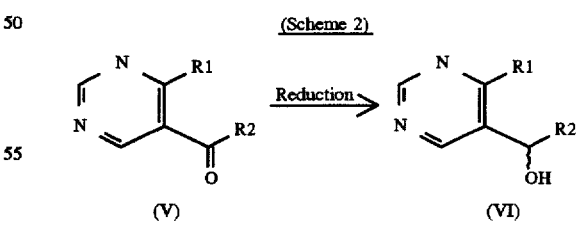

(3) Scheme 2 indicates a method wherein a pyrimidine derivative (V) is converted into a corresponding alcohol (VI) by a suitable reduction method (for example, reduction with a reagent such as $NaBH_4$, $BH_3$ or a $BH_3$ amine complex) or asymmetric reduction.

When the resulting alcohol (VI) is racemic, each of the optically active alcohols can be obtained through a suitable optical resolution, if necessary.

(Scheme 3)

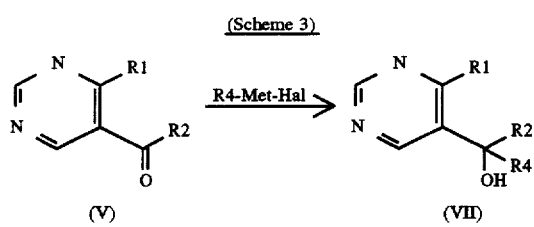

(4) Scheme 3 indicates a method of producing a compound (VII), which comprises reacting a pyrimidine derivative (V) with an organic metal reagent R4-Met-Hal (provided that the case that R4 is a hydrogen atom is excluded).

Scheme 4

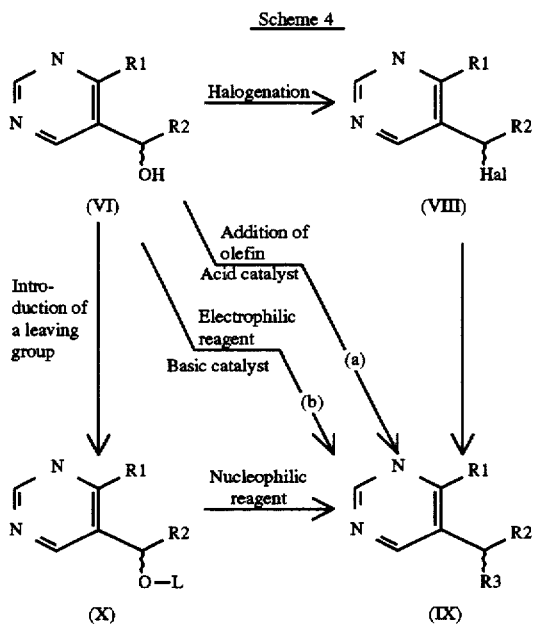

(5) The synthesis route (VI→VIII→IX) in Scheme 4 indicates a method which comprises reacting an alcohol (VI) with a suitable halogenating agent such as phosphorus oxychloride, phosphorus oxybromide, phosphorus pentachloride, thionyl chloride, thionyl bromide or concentrated hydrochloric acid to synthesize a corresponding halogenated compound (VIII), and a method which comprises subsequently reacting the compound (VIII) with a nucleophilic reagent (such as O, N or S) in the presence or absence of a base to produce the compound (IX) of the present invention.

The synthesis route ((a) VI→IX) indicates a method for producing a compound (IX) of the present invention by reacting the alcohol (VI) with an olefin in the presence of a suitable acid catalyst, for example, sulfuric acid, paratoluenesulfonic acid, trifluoroacetic acid or Lewis acid (such as TiCl$_4$, EtAlCl$_2$, BF$_3$ etherate or AlCl$_3$) (provided that, in this case, R3 is limited to a substituent bonding with an oxygen atom).

The synthesis route ((b) VI→IX) indicates a method for producing the compound (IX) of the present invention by reacting the alcohol (VI) with an electrophilic reagent in the presence of a basic catalyst such as sodium hydride, potassium tertiary butoxide, potassium hydride or potassium carbonate (provided that, in this case, R3 is limited to a substituent bonding with an oxygen atom).

The synthesis route (VI→X→IX) indicates a method for producing the compound (IX) of the present invention by reacting the alcohol (VI) with a suitable leaving group such as a methanesulfonyl group, a paratoluenesulfonyl group or a trifluoromethylsulfonyl group to synthesize a compound (X) and subsequently reacting the compound (X) with a nucleophilic reagent (such as O, N and S).

Scheme 5

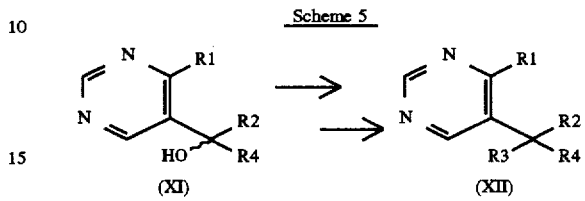

(6) The synthesis route (XI→→XII) in Scheme 5 provides a method for obtaining a compound (XII) of the present invention from an alcohol (XI) in the same manner as in Scheme 4.

Scheme 6

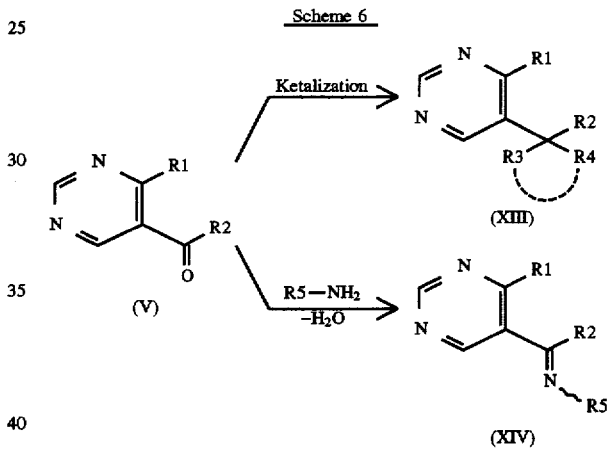

(7) By the synthesis route (V→XIII) in Scheme 6, a compound (XIII) of the present invention can be produced by a method of reacting the pyrimidine derivative (V) by a suitable acetalization reaction, for example, a) with an alcohol in the presence of an acid catalyst (such as paratoluenesulfonic acid), b) with an orthoester in the presence of an acid catalyst, or c) with an alcohol in the presence of trimethylsilyl chloride (Me$_3$SiCl).

In the synthesis route (V→XIV), a compound (XIV) of the present invention can be produced by dehydrating the pyrimidine derivative with R5-NH$_2$ (R5 means a substituent in claims which forms an imino group).

BEST MODE OF AN EMBODIMENT OF THE PRESENT INVENTION

Now, the syntheses of the compounds of the present invention and their intermediates will be described in detail with reference to Examples. However, it should be understood that the present invention is by no means restricted by such specific Examples.

EXAMPLE 1

Synthesis of 1-chloro-4-(4-chlorophenyl)-1,1-difluoro-2,4-butanedione

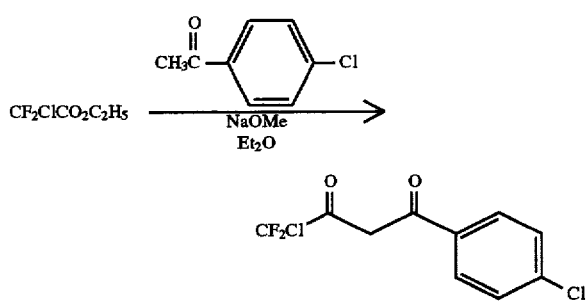

38 g of ethyl chlorodifluoroacetate was added to 22.7 g of sodium methoxide and 300 ml of dry ethyl ether under cooling with ice. 31 g of p-chloroacetophenone was gradually added thereto under cooling with ice. The mixture was stirred at room temperature for 12 hours. The solvent was distilled off under reduced pressure. 150 ml of 6N hydrochloric acid was added under cooling with ice, and extraction with ethyl acetate was carried out. The extract layer was washed with water, and the solvent was distilled off under reduced pressure. The resulting crude product was purified by silica gel column chromatography (developing solvent: chloroform), to obtain 49.5 g of the desired product as a pale yellow viscous liquid.

EXAMPLE 2

Synthesis of 1-chloro-4-(4-chlorophenyl)-1,1-difluoro-3-ethoxymethylene-2,4-butanedione

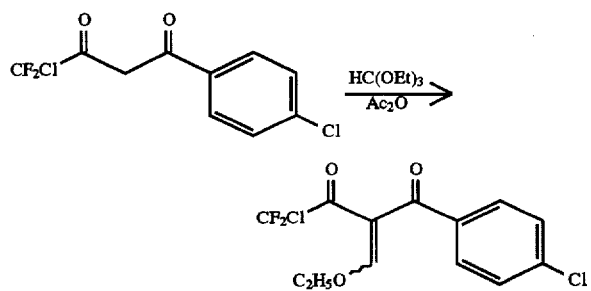

A mixture of 49.5 g of 1-choro-4-(4-chlorophenyl)-1,1-difluoro-2,4-butanedione, 41.3 g of ethyl orthoformate and 57 g of acetic anhydride was refluxed under heating for 4 days. The solvent was distilled off under reduced pressure to obtain 60.4 g of a crude product, which was used for the next reaction as it is.

EXAMPLE 3

Synthesis of 5-(4-chlorobenzoyl)-4-chlordifluoromethylpyrimidine (Compound No. 1-1)

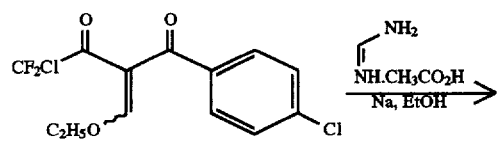

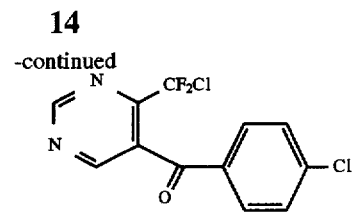

6 g of metal sodium and 500 ml of dry ethanol were mixed to prepare a sodium ethoxide solution. 23.3 g of formamidine acetate was added to the solution, and the mixture was stirred at room temperature for 15 minutes. 60.4 g of 1-chloro-4-(4-chlorophenyl)-1,1-difluoro-3-ethoxymethylene-2,4-butanedione (crude product) was gradually added under cooling with ice. The mixture was refluxed under heating for 2 hours. The solvent was distilled off under reduced pressure. 300 ml of ice water was added, and then extraction with ethyl acetate was carried out. The extract layer was washed with water, and the solvent was distilled off under reduced pressure.

The resulting crude product was purified by silica gel column chromatography (developing solvent: chloroform/hexane=1/1) to obtain 27 g of the desired product as a pale yellow liquid. Refractive index $n_D^{20.8} 1.5742$

EXAMPLE 4

Synthesis of 4-chlorodifluoromethyl-5-[1-(4-chlorophenyl)-1-hydroxymethyl]pyrimidine (Compound No. 1-2)

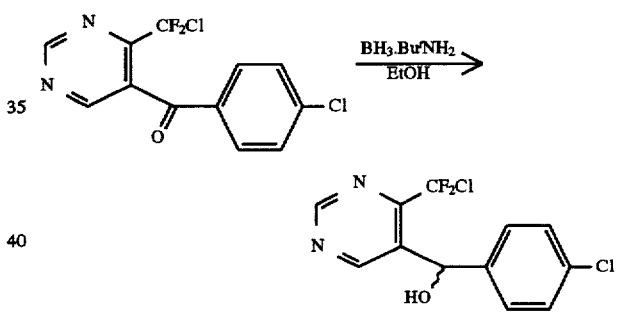

12 g of 5-(4-chlorobenzoyl)-4-chlorodifluoromethylpyrimidine and 6 g of a t-butylamine borane complex were added to 100 ml of ethanol, and the resulting mixture was stirred at 0° C. for 2 hours. Then, 20 ml of acetone was added thereto, and the mixture was stirred at 0° C. for 1 hour. The solvent was distilled off under reduced pressure, and the residue was purified by silica gel column chromatography (developing solvent: chloroform) to obtain 11.1 g of the desired product as a pale yellow viscous liquid. Refractive index $n_D^{20.3} 1.5563$

EXAMPLE 5

Synthesis of 4-chlorodifluoromethyl-5-[1-(4-chlorophenyl)-1-chloromethyl]pyrimidine (Compound No. 1-5)

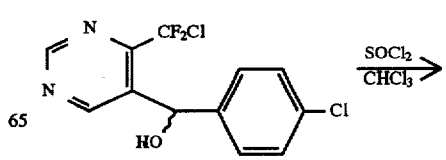

15

-continued

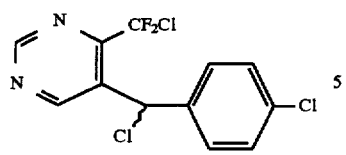

11.1 g of 4-chlorodifluoromethyl-5-[1-(4-chlorophenyl)-1-hydroxymethyl]pyrimidine was dissolved in 100 ml of chloroform. 30 ml of thionyl chloride was added thereto. The mixture was refluxed under heating for 1 hour. The solvent and an excess amount of thionyl chloride were distilled off under reduced pressure, and the residue was used for the next reaction as it is. Refractive index $n_D^{19.3}$ 1.5653

EXAMPLE 6

Synthesis of 4-chlorodifluoromethyl-5-[1-(4-chlorophenyl)-1-(1,1-dimethylethoxy)methyl]pyrimidine (Compound No. 1-9)

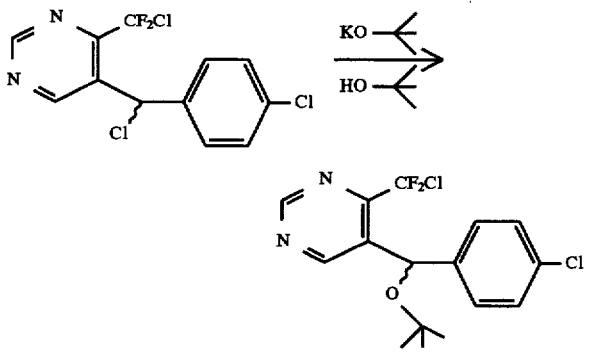

0.8 g of 4-chlorodifluoromethyl-5-[1-(4-chlorophenyl)-1-chloromethyl]pyrimidine was dissolved in 30 ml of t-butyl alcohol. 1 g of potassium t-butoxide was added thereto. The mixture was stirred at room temperature for 3 hours, and 100 ml of water was added thereto, followed by extraction with ethyl acetate. The solvent was distilled off under reduced pressure, and the residue was purified by silica gel column chromatography (developing solvent; chloroform:ethyl acetate =7:3) to obtain 0.4 g of the desired product. Refractive index $n_D^{20.1}$ 1.5291

EXAMPLE 7

Synthesis of 4-chlorodifluoromethyl-5-[1-(4-chlorophenyl)-1-(1,1-dimethylethoxy)methyl]pyrimidine (Compound No. 1-9)

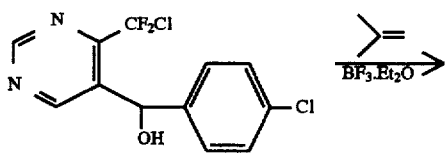

16

-continued

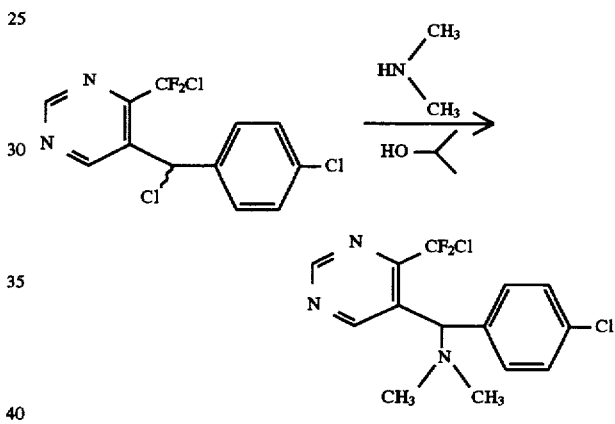

2.44 g of phenyl)-1-hydroxymethyl]pyrimidine was dissolved in 150 ml of chloroform, and 3.5 g of isobutylene was blown thereinto at 0° C. 1.2 ml of boron trifluoride etherate was added thereto. The mixture was sealed and left to stand for three days. The reaction solution was purified directly by silica gel column chromatography (developing solvent: chloroform) (φ35×400 mm) to obtain 1.61 g of the desired product.

EXAMPLE 8

Synthesis of 4-chlorodifluoromethyl-5-[1-(4-chlorophenyl)-1-(N,N-dimethylamino)methyl]pyrimidine (Compound No. 1-15)

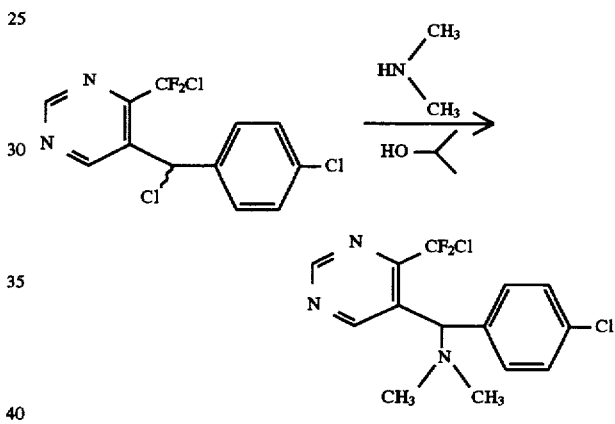

0.7 g of 4-chlorodifluoromethyl-5-[1-(4-chlorophenyl)-1-chloromethyl]pyrimidine was dissolved in 30 ml of isopropyl alcohol, and 3 ml of a 50% dimethylamine aqueous solution was added thereto. The mixture was stirred at room temperature for 1 hour and then at 50° C. for 2 hours. The solvent was distilled off under reduced pressure and 100 ml of water was added thereto, followed by extraction with ethyl acetate. The solvent was distilled off under reduced pressure, and the residue was purified by preparative thin-layer chromatography (developing solvent; chloroform:ethyl acetate=8:2) to obtain 0.2 g of the desired product. Melting point 60°–61° C.

EXAMPLE 9

Synthesis of 4-chlorodifluoromethyl-5-[1-(4-fluorophenyl)-1-(1-methylethoxy)methyl]pyrimidine (Compound No. 1-36)

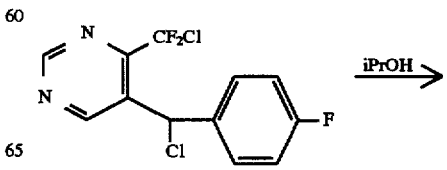

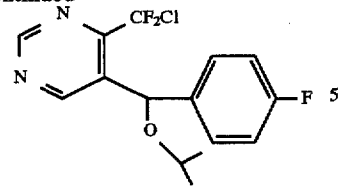

0.41 g of 4-chlorodifluoromethyl-5-[1-(4-fluorophenyl)-1-chloromethyl]pyrimidine was dissolved in 50 ml of isopropyl alcohol, and the mixture was refluxed under heating at 100° C. for 14.5 hours. The solvent was distilled off under reduced pressure and the residue was purified by preparative thin-layer chromatography (developing solvent; hexane-:ethyl acetate=5:1) to obtain 0.47 g of the desired product. Refractive index $n_D^{20.0} 1.5106$

EXAMPLE 10

Synthesis of 4-chlorodifluoro-5-[1-(4-chlorophenyl)-1-(N,N-dimethylcarbamoyloxy)methyl]pyrimidine (Compound No. 1-68)

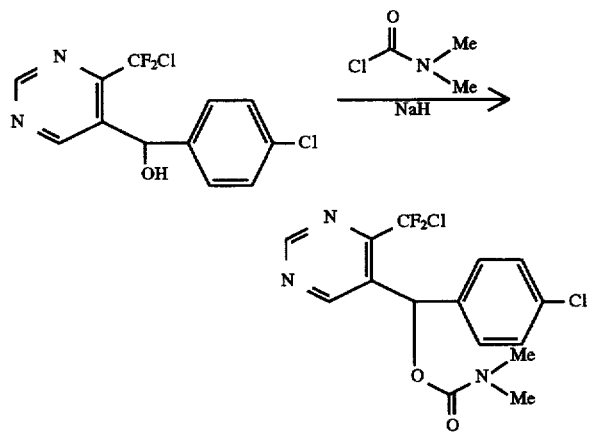

1.64 g of 4-chlorodifluoromethyl-5-[1-(4-chlorophenyl)-1-hydroxymethyl]pyrimidine was dissolved in 30 ml of dry ethyl ether. 0.75 ml of N,N-dimethylcarbamoyl chloride was added thereto, and 0.33 g of a 60% sodium hydride was added under cooling with water. The mixture was stirred at room temperature for 3 hours and then 50 ml of ice water was added thereto. The solution was extracted with 100 ml of ethyl ether, and after drying over anhydrous magnesium sulfate, the solvent was distilled off under reduced pressure. The residue was purified by silica gel column chromatography (developing solvent: chloroform/hexane=7:3) to obtain 1.32 g of the desired product. Refractive index $n_D^{19.7} 1.5358$

EXAMPLE 11

Synthesis 4-chlorodifluoromethyl-5-[1-(4-chlorophenyl)-1-(cyanomethoxy)methyl]pyrimidine (Compound No. 1-76)

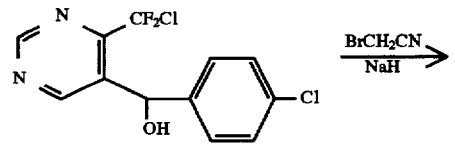

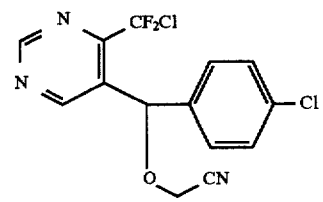

1.1 g of 4-chlorodifluoromethyl-5-[1-(4-chlorophenyl)-1-hydroxymethyl]pyrimidine was dissolved in a mixture solvent of DMF and ethyl ether (5 ml, 30 ml), and 0.43 g of a 60% sodium hydride was added thereto under cooling with water. The mixture was stirred for 10 minutes. 1.73 g of bromoacetonitrile was added thereto. The mixture was stirred at room temperature for 3 hours and then 50 ml of water was added. The mixture was extracted with 100 ml of ethyl ether and dried over anhydrous sodium sulfate, and then the solvent was distilled off under reduced pressure. The residue was purified by preparative thin-layer chromatography (developing solvent: chloroform/hexane=7:3) to obtain 0.4 g of the desired product. Refractive index $n_D^{20.9} 1.5535$

EXAMPLE 12

Synthesis of 4-chlorodifluoromethyl-5-[1-(4-chlorophenyl)-1-(ethylcarbamoyloxy)methyl]pyrimidine (Compound No. 1-77)

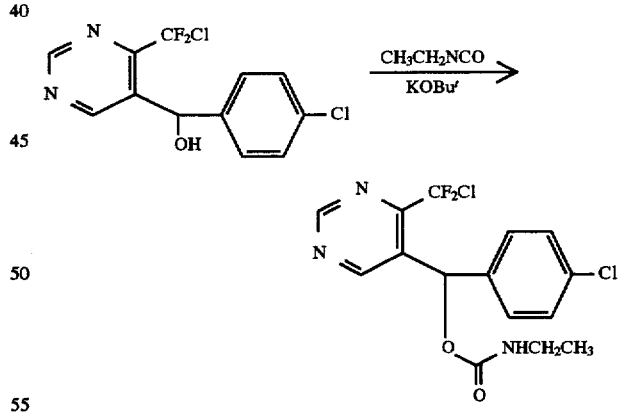

0.9 g of 4-chlorodifluoromethyl-5-[1-(4-chlorophenyl)-1-hydroxymethyl]pyrimidine and 0.5 g of ethyl isocyanate were dissolved in 30 ml of dry ethyl ether. 0.05 g of potassium t-butoxide was added thereto and the mixture was stirred at room temperature for 12 hours. The solvent was distilled off and the residue was purified by silica gel column chromatography (developing solvent: chloroform) to obtain 0.88 g of the desired product. Refractive index $n_D^{20.8} 1.5315$

EXAMPLE 13

Synthesis of 1-choro-1,1-difluoro-3-ethoxymethylene-2,4-pentanedione

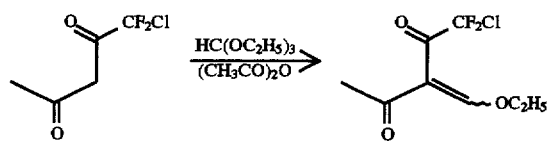

A mixed solution of 50 g of 1-chloro-1,1-difluoro-2,4-pentanedione, 60 g of ethyl orthoformate and 82 g of acetic anhydride was refluxed under stirring for 2 hours. Then, a Dean-Stark apparatus (water separator) was fixed, and the solution was further refluxed under heating for 4 hours to distill about 100 ml of solvent off. After leaving to cool, distillation was carried out under reduced pressure to obtain 32.2g of the desired product as a pale red liquid. Boiling point: 95°–118° C./1.6 mmHg.

EXAMPLE 14

Synthesis of 1-chloro-1,1-difluoro-3-ethoxyemthylene-2,4-heptanedione

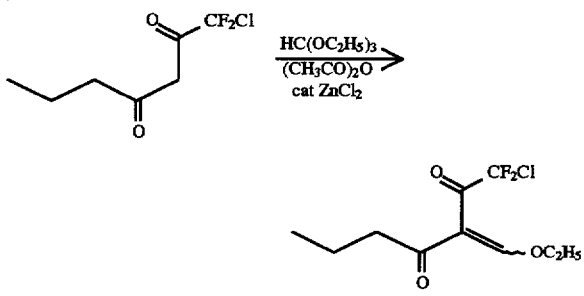

A catalytic amount of dried zinc chloride was added to a mixed solution of 5 g of 1-chloro-1,1-difluoro-2,4-heptanedione, 4.5 g of ethyl orthoformate and 5.4 g of acetic anhydride, and the mixture was stirred at 125° C. for 1.5 hours. Then, a Dean-Stark apparatus was fixed, and the mixture was further stirred at 125° C. for 4 hours to distill about 30 ml of the solvent off.

After leaving to cool, filtration was carried out under reduced pressure. Then, a reduced pressure distillation apparatus was fabricated. A low boiling fraction of at most 100° C./3 mmHg was removed to obtain 5.3 g of the desired product (yield: 83%). A part thereof was distilled and the following boiling point was confirmed. Boiling point 118° to 123° C./2 mmHg

EXAMPLE 15

Synthesis of 5-acetyl-4-chlorodifluoromethylpyrimidine

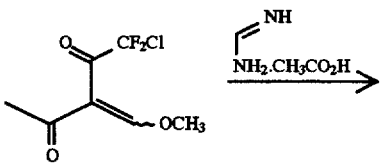

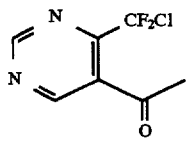

To 50 ml of dry ethanol, 0.9 g of metal sodium was added under cooling with ice to prepare sodium ethoxide. To this solution, 8.4 g of formamidine acetate which had been fully dried by means of a vacuum pump was added under stirring. Then, a solution of 8 g of 1-chloro-1,1-difluoro-3-ethoxymethylene-2,4-pentanedione dissolved in 20 ml of ethanol was dropwise added under cooling with ice. After the dropwise addition, the reaction solution was left to return to room temperature, and refluxed under heating for 1.5 hours. The reaction solution was left to cool and water was added, followed by extraction with ethyl ether. After drying over anhydrous sodium sulfate, the solvent was distilled off under reduced pressure. The residue was subjected to distillation under reduced pressure, and purified by column chromatography (developing solvent: $CHCl_3$) to obtain 2.5 g of the desired product. Boiling point 65°–70° C./1.3 mmHg. Refractive index $n_D^{20.7} 1.4787$

EXAMPLE 16

Synthesis of 4-chlorodifluoromethyl-5-(2,4-dipropyl-1,3-dioxolan-2-yl)pyrimidine (Compound No. 2-8)

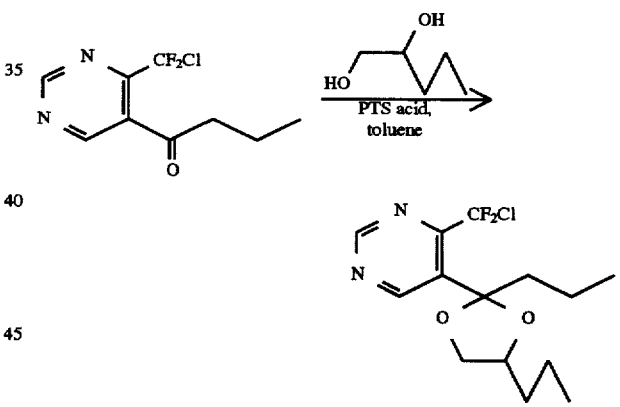

0.4 g of 5-butyryl-4-chlorodifluoromethylpyrimidine, 1 ml of 1,2-pentanediol and a catalytic amount of P-toluenesulfonic acid-monohydride were dissolved in 100 ml of toluene, and the mixture was refluxed under heating while dehydrating by means of a Dean-Stark apparatus. After completion of the reaction, water was added thereto and extraction was carried out with ethyl ether, followed by drying over anhydrous magnesium sulfate. The solvent was distilled off under reduced pressure and the crude product was purified by preparative thin-layer chromatography of alumina (developing solvent: chloroform) to obtain quantitatively the desired product. Refractive index $n_D^{20.4} 1.4701$

EXAMPLE 17

Synthesis of 4-chlorodifluoromethyl-5-(4-butyl-2-methyl-1,3-dioxolan-2-yl)pyrimidine (Compound No. 2-13)

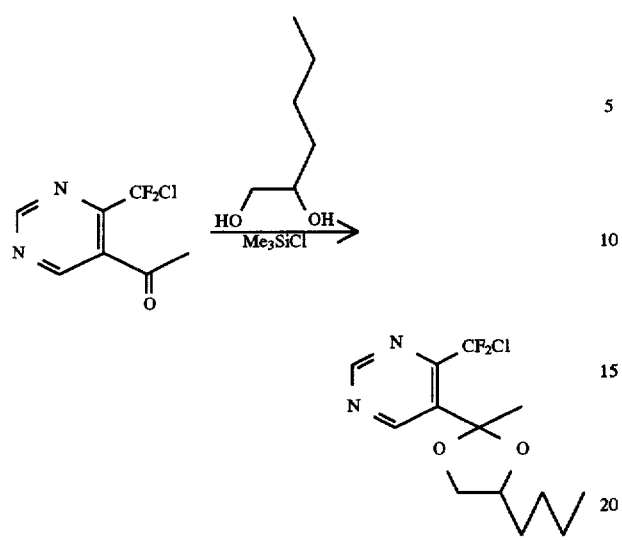

A mixed solution of 0.4 g of 5-acetyl-4-chlorodifluoromethylpyrimidine, 5 ml of 1,2-hexanediol and 0.84 g of trimethylsilyl chloride was stirred at room temperature for 16 hours.

After completion of the reaction, 100 ml of a 5% NaHCO$_3$ aqueous solution was added thereto and extraction was carried out with ethyl ether. The ethyl ether layer was washed with saturated aqueous salt solution and then dried over anhydrous sodium sulfate, and the solvent was distilled off under reduced pressure. The obtained oil was purified by thin-layer chromatography of alumina (developing solvent: hexane/ethyl acetate=10/1) to obtain 0.48 g of the desired product as a liquid. Refractive index $n_D^{20.1}$ 1.4761

EXAMPLE 18

Synthesis of 1-chloro-4-cyclohexyl-1,1-difluoro-2,4-butanedione

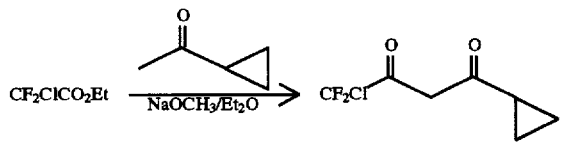

74.8 g of sodium methoxide was added to 1l of ethyl ether, and a solution of 200 g of ethyl chlorodifluoroacetate in 300 ml of ethyl ether was dropwise added thereto under stirring at 0° C. Then, a solution of 106 g of cyclopropyl methyl ketone in 300 ml of ethyl ether was gradually dropwise added to the reaction solution, and after completion of the dropwise addition, the mixture was stirred at room temperature for 8 hours. The solvent was distilled off under reduced pressure, 300 ml of 6N hydrochloric acid was added to the residue, and extraction with ethyl acetate was carried out. The extract layer was washed with water, and the solvent was distilled off under reduced pressure to obtain 235.9 g of the desired product as a pale yellow liquid. Refractive index $n_D^{20.6}$ 1.4788

EXAMPLE 19

Synthesis of 1-chloro-4-cyclohexyl-3-ethoxymethylene-1,1-difluoro-2,4-butanedione

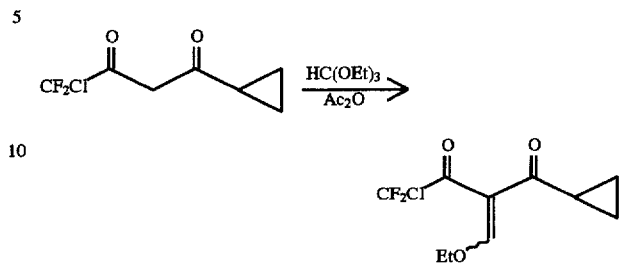

A mixture of 235.9 g of 1-chloro-4-cyclohexyl-1,1-difluoro-2,4-butanedione, 266.4 g of ethyl orthoformate and 367.2 g of acetic anhydride was refluxed under heating for 12 hours. The solvent was distilled off under reduced pressure to obtain 280.3 g of the desired product (crude product), which was then used for the next reaction as it is.

EXAMPLE 20

Synthesis of 4-chlorodifluoromethyl-5-cyclopropylcarbonylpyrimidine

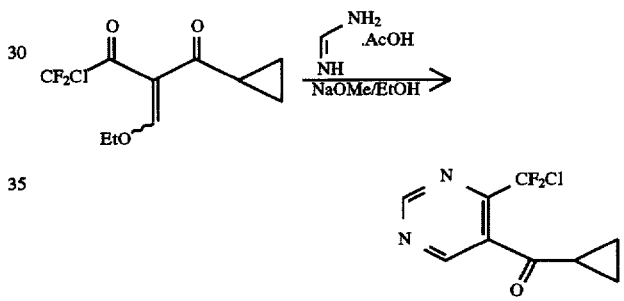

71.9 of sodium methoxide was added to 1l of ethanol, and then 121.2 g of formamidine acetate was added thereto. To the resulting mixture, 280 g of 1-chloro-4-cyclohexyl-3-ethoxymethylene-1,1-difluoro-2,4-butanedione was gradually added dropwise under cooling with ice. The mixture was refluxed under heating for 1 hour, and the solvent was distilled off under reduced pressure. 500 ml of water was added to the residue, and extraction with ethyl acetate was carried out. The solvent in the extract layer was distilled off under reduced pressure, and the residue was purified by silica gel column chromatography (developing solvent: chloroform/hexane=1/1) to obtain 101 g of the desired product. Refractive index $n_D^{20.5}$ 1.4998

EXAMPLE 21

Synthesis of 4-chlorodifluoromethyl-5-(1-hydroxy-1-cyclopropylmethyl)pyrimidine

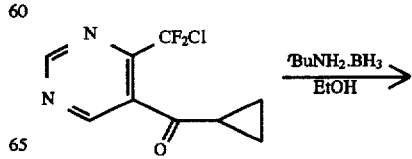

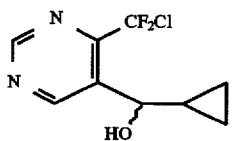

70 g of 4-chlorodifluoromethyl-5-cyclopropylcarbonylpyrimidine was added to 100 ml of ethanol, and 15 g of a t-butylamine borane complex was further added under cooling with ice, followed by stirring at room temperature for 2 hours. After addition of 30 ml of acetone, the mixture was stirred at room temperature for 1 hour, and the solvent was distilled off under reduced pressure. 100 ml of water was added to the residue, and extraction with ethyl acetate was carried out. The extract layer was washed with water, and the solvent was distilled off under reduced pressure. The residue was dried in vacuum to obtain 45 g of the desired product. Refractive index $n_D^{20.5}1.5020$

EXAMPLE 22

Synthesis of 4-chlorodifluoromethyl-5-(1-chloro-1-cyclopropylmethyl)pyrimidine

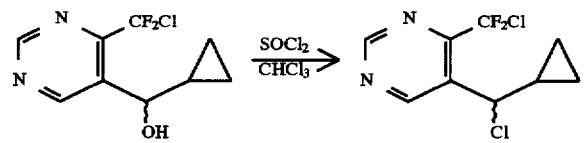

A mixture of 7 g of 4-chlorodifluoromethyl-5-(1-hydroxy-1-cyclopropylmethyl)pyrimidine, 10 ml of thionyl chloride and 50 ml of chloroform was refluxed under heating for 1 hour. Then, the solvent and excess amount of thionyl chloride were distilled off under reduced pressure. The resulting crude product was purified by silica gel column chromatography (developing solvent: chloroform/hexane= 1/1) to obtain 5 g of the desired product as a viscous liquid. Refractive index $n_D^{21.3}1.5076$

EXAMPLE 23

Synthesis of 4-chlorodifluoromethyl-5-(1-morpholino-1-cyclopropylmethyl)pyrimidine (Compound No. 3-2)

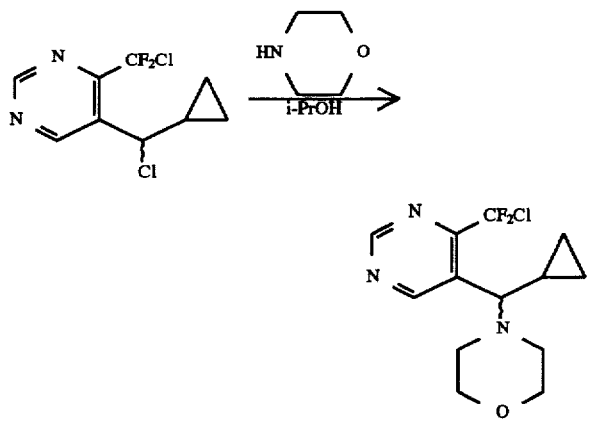

A mixture of 0.5 g of 4-chlorodifluoromethyl-5-(1-chloro-1-cyclopropylmethyl)pyrimidine, 1 g of morpholine and 20 ml of isopropyl alcohol was refluxed under heating for 1 hour and then the solvent was distilled off under reduced pressure. The resulting crude product was purified by preparative thin-layer chromatography (alumina, developing solvent: chloroform/hexane=7/3) to obtain 0.45 g of the desired product as a viscous liquid. Refractive index $n_D^{21.2}1.5132$

EXAMPLE 24

Synthesis of 4-chlorodifluoromethyl-5-(1-benzylamino-1-cyclopropylmethyl)pyrimidine (Compound No. 3-1)

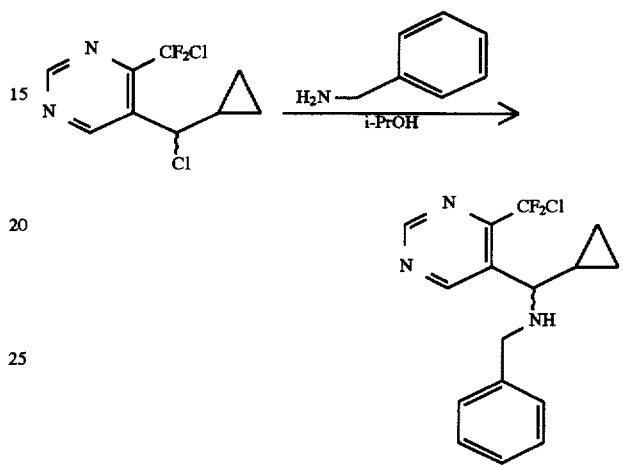

0.5 of 4-chlorodifluoromethyl-5-(1-chloro-1-cyclopropylmethyl)pyrimidine was dissolved in 20 ml of isopropyl alcohol. 2 ml of benzylamine was added thereto and the mixture was refluxed under heating for 1 hour. The solvent was distilled off under reduced pressure and the residue was purified by preparative thin-layer chromatography (alumina, developing solvent: chloroform/hexane=7/3) to obtain 0.57 g of the desired product. Refractive index $n_D^{21.3}1.5478$

EXAMPLE 25

Synthesis of 1-chloro-1,1-difluoro-5,5-dimethyl-2,4-hexanedione

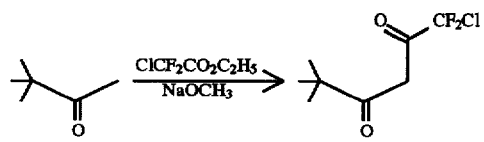

7.1 g of sodium methoxide was added to 100 ml of dry ethyl ether, and the mixture was stirred. A solution of 20 g of ethyl chlorodifluoroacetate and 25 ml of dry ethyl ether was dropwise added at room temperature. Further, a solution of 12.5 g of pinacolone diluted with 25 ml of dry ethyl ether was dropwise added, and the mixture was stirred overnight at room temperature. Then, to the reaction solution, a solution of 8.4 g of glacial acetic acid diluted with 100 ml of water and a solution of 23.6 g of copper (II) acetate dissolved in a proper amount of water were dropwise added successively. After the dropwise addition, the mixture was stirred for about 10 minutes. Then, the ethyl ether was distilled off under reduced pressure and a solid was filtered off. After drying under reduced pressure, 100 ml of 6N hydrochloric acid was added, and extraction with ethyl acetate was carried out. After drying over anhydrous sodium sulfate, the solvent was distilled off under reduced pressure. Then, the residue was subjected to distillation under reduced pressure to obtain 13 g of the desired product. b.p. 54°–57° C./5 mmHg

EXAMPLE 26

Synthesis of 1-chloro-1,1-difluoro-5,5-dimethyl-3-ethoxymethylene-2,4-hexanedione

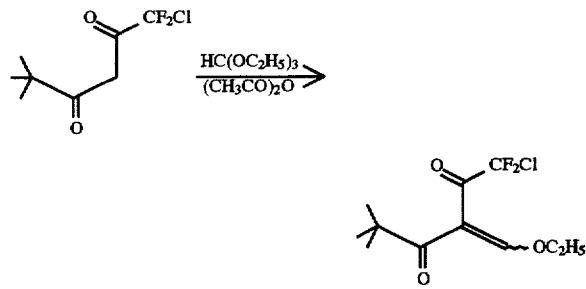

12.4 g of 1-chloro-1,1-difluoro-5,5-dimethyl-2,4-hexanedione and 12.4 g of ethyl orthoformate were added to 50 ml of acetic anhydride, and the mixture was refluxed under heating for 2 hours. After the solvent was distilled off under reduced pressure, the residue was subjected to distillation under reduced pressure to obtain 6.8 g of the desired product. b.p. 105°–107° C./2 mmHg

EXAMPLE 27

Synthesis of 4-chlorodifluoromethyl-5-pivaloylpyrimidine

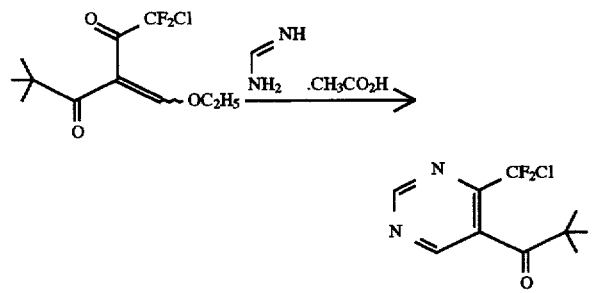

0.7 g of sodium methoxide and 1.25 g of formamidine acetate were added to 30 ml of dry methanol, and the mixture was stirred at room temperature for 30 minutes. A solution of 3 g of 1-chloro-1,1-difluoro-5,5-dimethyl-3-ethoxymethylene-2,4-hexanedione diluted with 5 ml of dry methanol was dropwise added. After completion of the dropwise addition, the mixture was refluxed under heating for 2 hours. The solvent was distilled off under reduced pressure, and water was added thereto, and then extraction with ethyl acetate was carried out. After drying over anhydrous sodium sulfate, the solvent was distilled off under reduced pressure. The residue was purified by thin-layer chromatography (developing solvent: hexane 80%, ethyl acetate 20%) to obtain 0.6 g of the desired product. Refractive index $n_D^{20.0}$ 1.4675

EXAMPLE 28

Synthesis of 4-chlorodifluoromethyl-5-(2,2-dimethyl-1-hydroxypropyl)pyrimidine

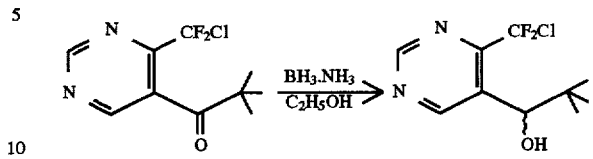

1.5 g of 4-chlorodifluoromethyl-5-pivaloylpyrimidine was dissolved in 50 ml of ethanol, and 1 g of a borane ammonia complex was added, followed by stirring at room temperature for 1 hour. The solvent was distilled off under reduced pressure, and water was added thereto, followed by extraction with chloroform. The extract layer was washed with water and then dried over anhydrous sodium sulfate. The solvent was distilled off under reduced pressure, and the residue was purified by thin-layer chromatography (developing solvent: chloroform/ethyl acetate=7/3) to obtain 1.1 g of the desired product as a viscous liquid. Refractive index $n_D^{19.8}$ 1.4623

EXAMPLE 29

Synthesis of 4-chlorodifluoromethyl-5-(1-acetyloxy-2,2-dimethylpropyl)pyrimidine (Compound No. 4-1)

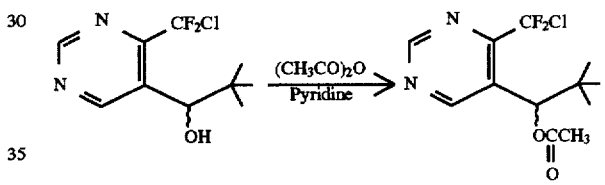

1.5 of 4-chlorodifluoromethyl-5-(2,2-dimethyl-1-hydroxypropyl)pyrimidine and 3 ml of acetic anhydride were dissolved in 30 ml of pyridine, followed by stirring at 50° C. for 90 minutes. The solvent was distilled off under reduced pressure, and the residue was purified by thin-layer chromatography (developing solvent: chloroform). 0.7 g of the desired product as a viscous liquid was obtained. Refractive index $n_D^{20.0}$ 1.4644

EXAMPLE 30

Synthesis of 4-chlorodifluoromethyl-5-(1-20 hydroxyethyl)pyrimidine

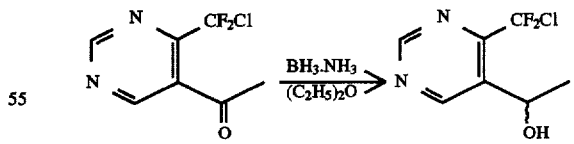

0.4 g of 5-acetyl-4-chlorodifluoromethylpyrimidine was dissolved in 10 ml of dry diethyl ether, and an excess amount of a borane ammonia complex was added under cooling with ice, and then the mixture was stirred overnight at room temperature. Water was added thereto and extraction with diethyl ether was carried out. After drying over anhydrous sodium sulfate, the solvent was distilled off under reduced pressure to obtain 0.32 g of the desired product as a viscous liquid. Refractive index $n_D^{19.9}$ 1.4899

EXAMPLE 31

Synthesis of 4-chlorodifluoromethyl-5-(1-methanesulfonyloxyethyl)pyrimidine (Compound No. 4-7)

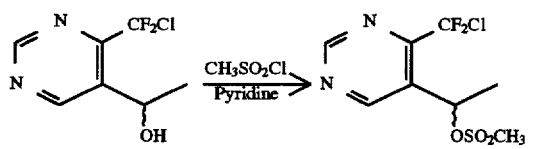

A mixed solution of 0.4 g of 4-chlorodifluoromethyl-5-(1-hydroxyethyl)pyrimidine, 0.27 g of methanesulfonyl chloride and 8 ml of pyridine was stirred at room temperature for 1 day.

After completion of the reaction, the pyridine was distilled off under reduced pressure and water was added, followed by extraction with chloroform. After drying over anhydrous sodium sulfate, the solvent was distilled off under reduced pressure. The resulting crude product was purified by preparative thin-layer chromatography (developing solvent: chloroform) to obtain 0.25 g of a solid as the desired product. m.p. 96°–100° C.

EXAMPLE 32

Synthesis of 5-(1-tert-butyldimethylsilyloxyethyl)-4-chlorodifluoromethylpyrimidine (Compound No. 4-9)

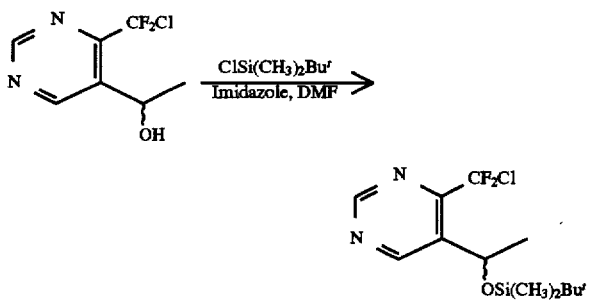

Into a mixed solution of 0.5 g of 4-chlorodifluoromethyl-5-(1-hydroxyethyl)pyrimidine, 0.78 g of imidazole and 50 ml of dimethylformamide, 0.83 g of t-butyldimethylsilyl chloride was dropwise added, followed by stirring at room temperature for 1 day. After completion of the reaction, water was added thereto and extraction with ethyl ether was carried out. After drying over anhydrous magnesium sulfate, the solvent was distilled off under reduced pressure. The resulting crude product was purified by preparative thin-layer chromatography (developing solvent: chloroform) to obtain the desired product quantitatively. Refractive index $n_D^{20.2}$ 1.4602

EXAMPLE 33

Synthesis of 4-chlorodifluoromethyl-5-(1-cyclopropyl-1-phenoxymethyl)pyrimidine (Compound No. 4-12)

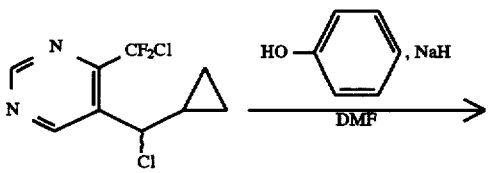

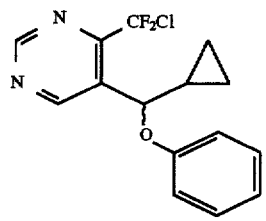

A mixture of 1 g of phenol, 0.2 g of sodium hydride and 20 ml of dimethylformamide was stirred at room temperature for 1 hour. 0.5 g of 4-chlorodifluoromethyl-5-(1-chloro-1-cyclopropylmethyl)pyrimidine was added thereto, and the mixture was stirred at room temperature for 3 hours. The mixture was poured into 200 ml of water and extraction with ethyl acetate was carried out. The extract layer was washed with water and the solvent was distilled off under reduced pressure. The resulting crude product was purified by preparative thin-layer chromatography (developing solvent: chloroform/hexane=1/1) to obtain 0.3 g of the desired product as a viscous liquid. Refractive index $n_D^{21.4}$ 1.5472

EXAMPLE 34

Synthesis of 4-chlorodifluoromethyl-5-[1-(tetrahydropyran-2-yl-oxy)ethyl]pyrimidine (Compound No. 4-14)

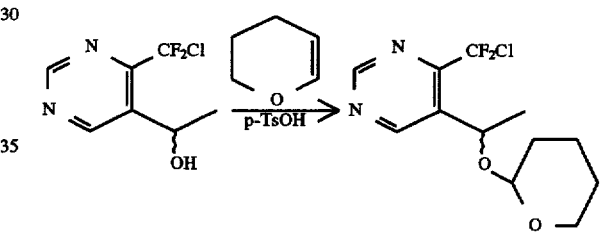

0.3 g of 4-chlorodifluoromethyl-5-(1-hydroxyethyl)pyrimidine and 0.26 g of 3,4-dihydro-2H-pyran were dissolved in 20 ml of dehydrated methylene chloride and a catalytic amount of p-toluenesulfonic acid was added thereto, followed by stirring at room temperature overnight.

After completion of the reaction, 100 ml of ethyl ether was added thereto, washing was carried out with a saturated sodium bicarbonate aqueous solution and saturated aqueous salt solution, and water, respectively, followed by drying over anhydrous sodium sulfate. The solvent was distilled off, and the purification was carried out by thin-layer chromatography of alumina to obtain 0.38 g of the desired product as oil. Refractive index $n_D^{20.6}$ 1.4812

EXAMPLE 35

Synthesis of 4-difluorochloromethyl-5-(1-methoxyiminoethyl)pyrimidine (Compound No. 5-1)

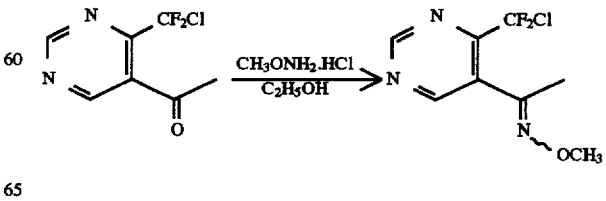

0.3 g of 5-acetyl-4-chlorodifluoromethylpyrimidine was dissolved in 10 ml of ethanol and 0.12 g of methoxyamine hydrochloride was added thereto, followed by reflux under heating. After completion of the reaction, the solvent was distilled off and 0.2 g of the desired product as a liquid was obtained by column chromatography (developing solvent: $CHCl_3$). Refractive index $n_D^{20.2}$ 1.4865

EXAMPLE 36

Synthesis of 4-chlorodifluoromethyl-5-[1-(4-trifluoromethylphenylhydrazono)ethyl]pyrimidine (Compound 5-4)

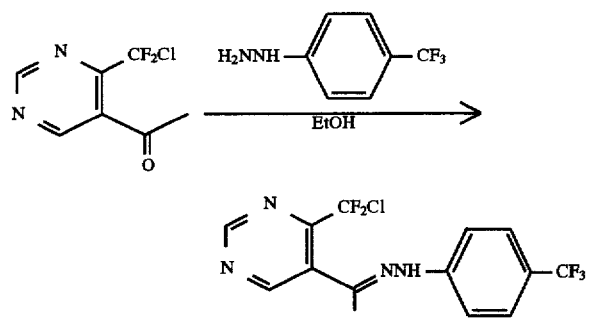

A mixture of 500 mg of 5-acetyl-4-chlorodifluoromethylpyrimidine, 420 mg of 4-trifluoromethylphenylhydrazine and 30 ml of dehydrated ethanol was stirred at room temperature for 1 day, and further reflux was carried out for 8 hours. The solvent was distilled off under reduced pressure. The resulting crude product was purified by preparative thin-layer chromatography (developing solvent: chloroform) to obtain 129 mg of the desired product as a pale brown liquid.

The structures, the physical properties and the spectral data of the compounds of the present invention synthesized in accordance with the above Examples, including the compounds synthesized in the above Examples, are shown in the following Tables.

TABLE 1-1

| Compound No. | X | R3 | R4 | R2 |
|---|---|---|---|---|
| 1-1 | Cl | =O | | 4-Cl—Ph |
| 1-2 | Cl | OH | H | 4-Cl—Ph |
| 1-3 | Cl | =O | | 2,4-Cl$_2$—Ph |
| 1-4 | Cl | OH | H | 2,4-Cl$_2$—Ph |
| 1-5 | Cl | Cl | H | 4-Cl—Ph |
| 1-6 | Cl | O—Ph | H | 4-Cl—Ph |
| 1-7 | Cl | 2,6-Dimethyl-morpholino | H | 4-Cl—Ph |
| 1-8 | Cl | Morpholino | H | 4-Cl—Ph |
| 1-9 | Cl | O—Bu$^{tert}$ | H | 4-Cl—Ph |
| 1-10 | Cl | Piperidino | H | 4-Cl—Ph |
| 1-11 | Cl | Pyrrolidino | H | 4-Cl—Ph |
| 1-12 | Cl | NHCH$_2$—Ph | H | 4-Cl—Ph |
| 1-13 | Cl | 1,2,4-Triazol-1-yl | H | 4-Cl—Ph |
| 1-14 | Cl | NHMe | H | 4-Cl—Ph |
| 1-15 | Cl | N(Me)$_2$ | H | 4-Cl—Ph |
| 1-16 | Cl | OMe | H | 4-Cl—Ph |
| 1-17 | Cl | =O | | Ph |
| 1-18 | Cl | OH | H | Ph |

TABLE 1-1-continued

| Compound No. | X | R3 | R4 | R2 |
|---|---|---|---|---|
| 1-19 | Cl | Cl | H | Ph |
| 1-20 | Cl | =O | | 4-F—Ph |
| 1-21 | Cl | N(Me)$_2$ | H | Ph |
| 1-22 | Cl | OH | H | 4-F—Ph |
| 1-23 | Cl | Cl | H | 4-F—Ph |
| 1-24 | Cl | N(Me)$_2$ | H | 4-F—Ph |
| 1-25 | Cl | NHMe | H | Ph |
| 1-26 | Cl | NHEt | H | Ph |
| 1-27 | Cl | NHMe | H | 4-F—Ph |
| 1-28 | Cl | N(Me)Et | H | 4-F—Ph |
| 1-29 | Cl | OMe | H | Ph |
| 1-30 | Cl | N(Me)Et | H | Ph |
| 1-31 | Cl | NHCH$_2$CH$_2$OH | H | 4-F—Ph |
| 1-32 | Cl | NHCH$_2$CH=CH$_2$ | H | 4-F—Ph |
| 1-33 | Cl | =O | | 2-F—Ph |
| 1-34 | Cl | NH—Bu$^{tert}$ | H | Ph |
| 1-35 | Cl | NH—Bu$^{tert}$ | H | 4-F—Ph |
| 1-36 | Cl | P—Pr$^{iso}$ | H | 4-F—Ph |
| 1-37 | Cl | OH | H | 2-F—Ph |
| 1-38 | Cl | Cl | H | 2-F—Ph |
| 1-39 | Cl | =O | | 3-F—Ph |
| 1-40 | Cl | NHOMe | H | Ph |
| 1-41 | Cl | NHC(Me)$_2$CO$_2$H | H | Ph |
| 1-42 | Cl | NH—Pr$^{cyclo}$ | H | 4-F—Ph |
| 1-43 | Cl | NHCH$_2$C≡CH | H | 4-F—Ph |
| 1-44 | Cl | N(Me)CH$_2$CO$_2$Et | H | Ph |
| 1-45 | Cl | O—Bu$^{tert}$ | H | 2-Cl—Ph |
| 1-46 | Cl | O—Bu$^{tert}$ | H | 3-Cl—Ph |
| 1-47 | Cl | O—Bu$^{tert}$ | H | 3,4-Cl$_2$—Ph |
| 1-48 | Cl | OH | H | 2-Cl—Ph |
| 1-49 | Cl | OH | H | 3-Cl—Ph |
| 1-50 | Cl | OH | H | 3,4-Cl$_2$—Ph |
| 1-51 | Cl | =O | | 2-Cl—Ph |
| 1-52 | Cl | =O | | 3-Cl—Ph |
| 1-53 | Cl | =O | | 3,4-Cl$_2$—Ph |
| 1-54 | Cl | O—Pn$^{neo}$ | H | 4-Cl—Ph |
| 1-55 | Cl | N(Me)$_2$ | H | 2-F—Ph |
| 1-56 | Cl | N(Me)$_2$ | H | 3-F—Ph |
| 1-57 | Cl | OH | H | 3-F—Ph |
| 1-58 | Cl | Cl | H | 3-F—Ph |
| 1-59 | Cl | OCH$_2$—Pr$^{cyclo}$ | H | 3-F—Ph |
| 1-60 | Cl | O—Bu$^{tert}$ | H | 2-F—Ph |
| 1-61 | Cl | O—Bu$^{tert}$ | H | 4-F—Ph |
| 1-62 | Cl | O—Bu$^{tert}$ | H | Ph |
| 1-63 | Cl | O—C(Me)$_2$OMe | H | 4-Cl—Ph |
| 1-64 | Cl | O—C(Me)$_2$OMe | H | 3-Cl—Ph |
| 1-65 | Cl | O—C(Me)$_2$OMe | H | 2-Cl—Ph |
| 1-66 | Cl | O—C(Me)$_2$Pr$^n$ | H | 4-Cl—Ph |
| 1-67 | Cl | NH—Bu$^{tert}$ | H | 4-Cl—Ph |
| 1-68 | Cl | OC(=O)N(Me)$_2$ | H | 4-Cl—Ph |
| 1-69 | Cl | OC(=O)N(Me)$_2$ | H | 3-Cl—Ph |
| 1-70 | Cl | OC(=O)N(Me)$_2$ | H | 2-Cl—Ph |
| 1-71 | Cl | O—Bu$^{tert}$ | H | 3-F—Ph |
| 1-72 | Cl | =O | | 2-Me—Ph |
| 1-73 | Cl | O—C(Me)$_2$Et | H | 4-Cl—Ph |
| 1-74 | Cl | OC(=O)Bu$^{tert}$ | H | 4-Cl—Ph |
| 1-75 | Cl | OCH$_2$C≡CH | H | 4-Cl—Ph |
| 1-76 | Cl | OCH$_2$C≡N | H | 4-Cl—Ph |
| 1-77 | Cl | OC(=O)NHEt | H | 4-Cl—Ph |
| 1-78 | Cl | OC(=S)NHPr$^{iso}$ | H | 4-Cl—Ph |
| 1-79 | Cl | OCO$_2$Et | H | 4-Cl—Ph |
| 1-80 | Cl | OCH$_2$CO$_2$Et | H | 4-Cl—Ph |
| 1-81 | Cl | OCH$_2$OMe | H | 4-Cl—Ph |
| 1-82 | Cl | OCH$_2$SMe | H | 4-Cl—Ph |
| 1-83 | Cl | OH | H | 2-Me—Ph |
| 1-84 | Cl | Cl | H | 2-Me—Ph |

TABLE 1-1-continued

| Compound No. | X | R3 | R4 | R2 |
|---|---|---|---|---|
| 1-85 | Cl | O—Bu$^{tert}$ | H | 2-Me—Ph |
| 1-86 | Cl | OC(=O)NMe$_2$ | H | 2-Me—Ph |
| 1-87 | Cl | OCH$_2$CH(Pr$^n$)O | | 3-F—Ph |
| 1-88 | Cl | OCH$_2$CH(Pr$^n$)O | | 2-F—Ph |
| 1-89 | Cl | OCH$_2$CH(Pr$^n$)O | | 2-Me—Ph |
| 1-90 | Cl | =O | | 2-CF$_3$—Ph |
| 1-91 | Cl | N(Me)$_2$ | H | 2-Me—Ph |
| 1-92 | Cl | OCH$_2$CH(Pr$^n$)O | | 4-Cl—Ph |
| 1-93 | Cl | O—Bu$^{tert}$ | | 2,4-Cl$_2$—Ph |
| 1-94 | Cl | O—Bu$^{tert}$ | | 2,5-Cl$_2$—Ph |
| 1-95 | Cl | OH | H | 2,5-Cl$_2$—Ph |
| 1-96 | Cl | =O | | 2,5-Cl$_2$—Ph |
| 1-97 | Cl | OH | H | 2-CF$_3$—Ph |
| 1-98 | Cl | =O | | 3-Thienyl |
| 1-99 | Cl | =O | | 2-Thienyl |
| 1-100 | Cl | OH | H | 2-Thienyl |
| 1-101 | Cl | OC(=O)NMe$_2$ | H | 2-Thienyl |
| 1-102 | Cl | Cl | H | 2-CF$_3$—Ph |
| 1-103 | Cl | NMe$_2$ | H | 2-CF$_3$—Ph |
| 1-104 | Cl | O—Bu$^{tert}$ | H | 2-CF$_3$—Ph |
| 1-105 | Cl | OC(=O)NHBu$^{tert}$ | H | 4-Cl—Ph |
| 1-106 | Cl | OC(=O)NEt$_2$ | H | 4-Cl—Ph |
| 1-107 | Cl | =O | | 2-Furyl |
| 1-108 | Cl | NH$_2$ | H | 4-F—Ph |
| 1-109 | Cl | OC(=O)NMe$_2$ | H | 3-Thienyl |
| 1-110 | Cl | OC(=O)NMe$_2$ | H | 2-Furyl |
| 1-111 | Cl | OH | H | 3-Thienyl |
| 1-112 | Cl | OH | H | 2-Furyl |
| 1-113 | Cl | NH—Bu$^{tert}$ | H | 3-F—Ph |
| 1-114 | Cl | =O | | 2-MeO—Ph |
| 1-115 | Cl | OH | H | 2-MeO—Ph |
| 1-116 | Cl | Cl | H | 2-MeO—Ph |
| 1-117 | Cl | NMe$_2$ | H | 2-MeO—Ph |

TABLE 1-2

| Compound No. | Spectral data | Physical properties |
|---|---|---|
| 1-1 | $^1$H-NMR δ (ppm) [solvent]:<br>7.51(d, J=9Hz, 2H, Benzene ring)<br>7.72(d, J=9Hz, 2H, Benzene ring)<br>8.88(s, 1H, Pyrimidine ring)<br>9.50(s, 1H, Pyrimidine ring)<br>[CDCl$_3$] | n$_D^{20.8}$ 1.5742 |
| 1-2 | $^1$H-NMR δ (ppm) [solvent]:<br>3.40(br s, 1H, OH)<br>6.34(s, 1H, φCH)<br>7.29(s, 4H, Benzene ring)<br>9.09(s, 1H, Pyrimidine ring)<br>9.14(s, 1H, Pyrimidine ring)<br>[CDCl$_3$] | n$_D^{20.3}$ 1.5563 |
| 1-3 | $^1$H-NMR δ (ppm) [solvent]:<br>7.19–7.69(m, 3H, Benzene ring)<br>8.78(s, 1H, Pyrimidine ring)<br>9.36(s, 1H, Pyrimidine ring)<br>[CDCl$_3$] | n$_D^{20.5}$ 1.5837 |
| 1-4 | $^1$H-NMR δ (ppm) [solvent]:<br>3.42(br d, J=5Hz, 1H, OH)<br>6.58(d, J=5Hz, 1H, φCH)<br>7.30–7.45(m, 3H, Benzene ring)<br>8.82(s, 1H, Pyrimidine ring)<br>9.20(s, 1H, Pyrimidine ring)<br>[CDCl$_3$] | mp 141–142° C. |
| 1-5 | $^1$H-NMR δ (ppm) [solvent]:<br>6.53(s, 1H, φCH)<br>7.28(s, 4H, Benzene ring)<br>9.06(s, 1H, Pyrimidine ring)<br>9.15(s, 1H, Pyrimidine ring)<br>[CDCl$_3$] | n$_D^{19.3}$ 1.5653 |
| 1-6 | $^1$H-NMR δ (ppm) [solvent]:<br>4.14(s, 1H, φCH)<br>6.88–7.30(m, 10H, Benzene ring + Pyrimidine ring)<br>8.23(s, 1H, Pyrimidine ring)<br>[CDCl$_3$] | n$_D^{19.3}$ 1.5773 |
| 1-7 | $^1$H-NMR δ (ppm) [solvent]:<br>1.24(d, J=6Hz, 6H, Morpholine CH$_3$)<br>2.39–2.78(m, 4H, Morpholine ring)<br>3.43–3.83(m, 2H, Morpholine ring)<br>6.57(s, 1H, φCH)<br>6.99(d, J=9Hz, 2H, Benzene ring)<br>7.22(d, J=9Hz, 2H, Benzene ring)<br>7.31(s, 1H, Pyrimidine ring)<br>8.12(s, 1H, Pyrimidine ring)<br>[CDCl$_3$] | mp 74–76° C. |
| 1-8 | $^1$H-NMR δ (ppm) [solvent]:<br>3.75(s, 8H, Morpholine ring)<br>6.94(d, J=9Hz, 2H, Benzene ring)<br>7.19(d, J=9Hz, 2H, Benzene ring)<br>7.27(s, 1H, Pyrimidine ring)<br>8.09(s, 1H, Pyrimidine ring)<br>[CDCl$_3$] | n$_D^{19.4}$ 1.5550 |
| 1-9 | $^1$H-NMR δ (ppm) [solvent]:<br>1.22(s, 9H, C(CH$_3$)$_3$)<br>6.08(s, 1H, φCH)<br>7.22(s, 4H, Benzene ring)<br>9.19(s, 1H, Pyrimidine ring)<br>9.34(s, 1H, Pyrimidine ring)<br>[CDCl$_3$] | n$_D^{20.1}$ 1.5291 |
| 1-10 | $^1$H-NMR δ (ppm) [solvent]:<br>1.49–1.74(m, 6H, Piperidine ring)<br>3.65–3.87(m, 4H, Piperidine ring)<br>6.94–7.31(m, 6H, Benzene ring + Pyrimidine ring + φCH)<br>8.11 (s, 1H, Pyrimidine ring)<br>[CDCl$_3$] | mp 54–56° C. |
| 1-11 | $^1$H-NMR δ (ppm) [solvent]:<br>1.83–2.10(m, 4H, Pyrrolidine ring)<br>3.41–3.70(m, 4H, Pyrrolidine ring)<br>6.90–7.32(m, 6H, Benzene ring + Pyrimidine ring + φCH)<br>8.12(s, 1H, Pyrimidine ring)<br>[CDCl$_3$] | mp 59–61° C. |
| 1-12 | $^1$H-NMR δ (ppm) [solvent]:<br>1.10–1.39(m, 2H, NHCH$_2$Ph)<br>1.75–1.88(m, 1H, NH)<br>5.37–5.50(m, 1H, φCH)<br>7.07–7.37(m, 9H, Benzene ring)<br>9.13(s, 1H, Pyrimidine ring)<br>9.33(s, 1H, Pyrimidine ring)<br>[CDCl$_3$] | n$_D^{20.0}$ 1.5876 |
| 1-13 | $^1$H-NMR δ (ppm) [solvent]:<br>4.69(s, 1H, φCH)<br>7.01(d, J=9Hz, 2H, Benzene ring)<br>7.26(d, J=9Hz, 2H, Benzene ring)<br>7.95(s, 1H, Pyrimidine ring or Triazole ring)<br>8.05(s, 1H, Pyrimidine ring or Triazole ring)<br>8.66(s, 1H, Pyrimidine ring or Triazole ring)<br>8.94(s, 1H, Pyrimidine ring or Triazole ring)<br>[CDCl$_3$] | mp 110–112° C. |
| 1-14 | $^1$H-NMR δ (ppm) [solvent]:<br>1.63(br s, 1H, NH)<br>2.41(s, 3H, NHCH$_3$)<br>5.28(br s, 1H, φCH)<br>7.31(br s, 4H, Benzene ring)<br>9.15(s, 1H, Pyrimidine ring)<br>9.25(s, 1H, Pyrimidine ring) | n$_D^{19.4}$ 1.5592 |

TABLE 1-2-continued

| Compound No. | Spectral data | Physical properties |
|---|---|---|
| 1-15 | [CDCl$_3$]<br>$^1$H-NMR δ (ppm) [solvent]:<br>2.18(s, 6H, N(CH$_3$)$_2$)<br>4.62–4.73(m, 1H, φCH)<br>7.33(br s, 4H, Benzene ring)<br>9.08(s, 1H, Pyrimidine ring)<br>9.48(s, 1H, Pyrimidine ring) | mp 60–61° C. |
| 1-16 | [CDCl$_3$]<br>$^1$H-NMR δ (ppm) [solvent]:<br>3.37(s, 3H, OCH$_3$)<br>5.64(s, 1H, φCH)<br>7.26(br s, 4H, Benzene ring)<br>9.05(s, 1H, Pyrimidine ring)<br>9.17(s, 1H, Pyrimidine ring) | $n_D^{19.2}$ 1.5462 |
| 1-17 | [CDCl$_3$]<br>$^1$H-NMR δ (ppm) [solvent]:<br>7.34–7.84(m, 5H, Benzene ring)<br>8.76(s, 1H, Pyrimidine ring)<br>8.87(s, 1H, Pyrimidine ring) | $n_D^{20.1}$ 1.5571 |
| 1-18 | [CDCl$_3$]<br>$^1$H-NMR δ (ppm) [solvent]:<br>4.79–5.04(m, 1H, OH)<br>6.23(br s, 1H, φCH)<br>7.17(br s, 5H, Benzene ring)<br>8.82(s, 1H, Pyrimidine ring)<br>8.97(s, 1H, Pyrimidine ring) | $n_D^{20.0}$ 1.5566 |
| 1-19 | [CDCl$_3$]<br>$^1$H-NMR δ (ppm) [solvent]:<br>6.59(s, 1H, CHCl)<br>7.34–7.38(m, 5H, Benzene ring)<br>8.76(s, 1H, Pyrimidine ring)<br>8.87(s, 1H, PYrimidine ring) | $n_D^{20.1}$ 1.5496 |
| 1-20 | [CDCl$_3$]<br>$^1$H-NMR δ (ppm) [solvent]:<br>6.95–8.00(m, 4H, Benzene ring)<br>8.82(s, 1H, Pyrimidine ring)<br>9.43(s, 1H, Pyrimidine ring) | mp 63–64° C. |
| 1-21 | [CDCl$_3$]<br>$^1$H-NMR δ (ppm) [solvent]:<br>2.15(s, 6H, N(CH$_3$)$_2$)<br>4.57–4.70(m, 1H, CHN(CH$_3$)$_2$)<br>7.07–7.45(m, 5H, Benzene ring)<br>9.05(s, 1H, Pyrimidine ring)<br>9.53(s, 1H, Pyrimidine ring) | mp 75–76° C. |
| 1-22 | [CDCl$_3$]<br>$^1$H-NMR δ (ppm) [solvent]:<br>3.68(d, J=6Hz, 1H, OH)<br>6.20–6.40(m, 1H, CHOH)<br>6.90–7.53(m, 4H, Benzene ring)<br>9.06(s, 2H, Pyrimidine ring) | $n_D^{20.5}$ 1.5394 |
| 1-23 | [CDCl$_3$]<br>$^1$H-NMR δ (ppm) [solvent]:<br>6.61(s, 1H, CHCl)<br>6.75–7.57(m, 4H, Benzene ring)<br>9.18(br s, 2H, Pyrimidine ring) | $n_D^{20.6}$ 1.5409 |
| 1-24 | [CDCl$_3$]<br>$^1$H-NMR δ (ppm) [solvent]:<br>2.18(s, 6H, N(CH$_3$)$_2$)<br>4.60–4.80(m, 1H, CHN(CH$_3$)$_2$)<br>6.70–7.05(m, 4H, Benzene ring)<br>9.05(s, 1H, Pyrimidine ring)<br>9.50(s, 1H, Pyrimidine ring) | mp 62–63° C. |
| 1-25 | [CDCl$_3$]<br>$^1$H-NMR δ (ppm) [solvent]:<br>1.70(br s, 1H, NH)<br>2.41(s, 3H, NHCH$_3$)<br>4.95–5.10(m, 1H, CHNHCH$_3$)<br>7.25–7.75(m, 5H, Benzene ring)<br>9.30(s, 1H, Pyrimidine ring)<br>9.50(s, 1H, Pyrimidine ring) | $n_D^{20.5}$ 1.5464 |
| 1-26 | [CDCl$_3$]<br>$^1$H-NMR δ (ppm) [solvent]:<br>1.10(t, J=7Hz, 3H, CH$_2$CH$_3$)<br>2.40–2.60(m, 2H, NHCH$_2$CH$_3$)<br>4.85–5.00(m, 1H, CHNH)<br>7.05–7.50(m, 5H, Benzene ring)<br>9.03(s, 1H, Pyrimidine ring)<br>9.30(s, 1H, Pyrimidine ring) | $n_D^{20.5}$ 1.5384 |
| 1-27 | [CDCl$_3$]<br>$^1$H-NMR δ (ppm) [solvent]:<br>1.70(s, 1H, NHCH$_3$)<br>2.40(s, 3H, NHCH$_3$)<br>5.20–5.40(m, 1H, CHNHCH$_3$)<br>6.70–7.60(m, 4H, Benzene ring)<br>9.10(s, 1H, Pyrimidine ring)<br>9.23(s, 1H, Pyrimidine ring) | $n_D^{20.5}$ 1.5342 |
| 1-28 | [CDCl$_3$]<br>$^1$H-NMR δ (ppm) [solvent]:<br>1.03(t, J=7Hz, 3H, CH$_2$CH$_3$)<br>2.12(s, 3H, CH$_3$)<br>2.39(q, J=7Hz, 2H, CH$_2$CH$_3$)<br>4.85–5.10(m, 1H, CH)<br>6.70–7.55(m, 4H, Benzene ring)<br>9.09(s, 1H, Pyrimidine ring)<br>9.52(s, 1H, Pyrimidine ring) | $n_D^{20.6}$ 1.5214 |
| 1-29 | [CDCl$_3$]<br>$^1$H-NMR δ (ppm) [solvent]:<br>3.35(s, 3H, OCH$_3$)<br>5.65–5.80(m, 1H, CH)<br>7.12–7.42(m, 5H, Benzene ring)<br>9.00(s, 1H, Pyrimidine ring)<br>9.08(s, 1H, Pyrimidine ring) | $n_D^{20.0}$ 1.5343 |
| 1-30 | [CDCl$_3$]<br>$^1$H-NMR δ (ppm) [solvent]:<br>1.02(t, J=7Hz, 3H, CH$_2$CH$_3$)<br>2.12(s, 3H, CH$_3$)<br>2.38(q, J=7Hz, 2H, CH$_2$CH$_3$)<br>4.80–5.00(m, 1H, CH)<br>7.00–7.55(m, 5H, Benzene ring)<br>9.08(s, 1H, Pyrimidine ring)<br>9.57(s, 1H, Pyrimidine ring) | $n_D^{20.0}$ 1.5347 |
| 1-31 | [CDCl$_3$]<br>$^1$H-NMR δ (ppm) [solvent]:<br>2.17(s, 2H, NH, OH)<br>2.52–2.90(m, 2H, CH$_2$CH$_2$)<br>3.57–3.82(m, 2H, CH$_2$CH$_2$)<br>5.32–5.50(m, 1H, CH)<br>6.75–7.55(m, 4H, Benzene ring)<br>9.05(s, 1H, Pyrimidine ring)<br>9.20(s, 1H, Pyrimidine ring) | $n_D^{20.0}$ 1.5402 |
| 1-32 | [CDCl$_3$]<br>$^1$H-NMR δ (ppm) [solvent]:<br>1.50–1.80(m, 1H, NH)<br>3.05–3.30(m, 2H, CH$_2$CH=CH$_2$)<br>4.85–6.20(m, 4H, CH, CH$_2$CH=CH$_2$)<br>6.70–7.60(m, 4H, Benzene ring)<br>9.08(s, 1H, Pyrimidine ring)<br>9.28(s, 1H, Pyrimidine ring) | $n_D^{20.0}$ 1.5366 |
| 1-33 | [CDCl$_3$]<br>$^1$H-NMR δ (ppm) [solvent]:<br>6.85–8.10(m, 4H, Benzene ring)<br>8.77(s, 1H, Pyrimidine ring)<br>9.34(s, 1H, Pyrimidine ring) | $n_D^{20.8}$ 1.5468 |
| 1-34 | [CDCl$_3$]<br>$^1$H-NMR δ (ppm) [solvent]:<br>1.10(s, 9H, C(CH$_3$)$_3$)<br>1.35–1.55(m, 1H, NHC(CH$_3$)$_3$)<br>5.50–5.65(m, 1H, CH)<br>7.00–7.30(m, 5H, Benzene ring)<br>9.15(s, 1H, Pyrimidine ring)<br>9.88(s, 1H, Pyrimidine ring) | $n_D^{20.1}$ 1.5311 |
| 1-35 | [CDCl$_3$]<br>$^1$H-NMR δ (ppm) [solvent]:<br>1.08(s, 9H, C(CH$_3$)$_3$)<br>1.40–1.50(m, 1H, NH)<br>5.48–5.58(m, 1H, CH)<br>6.80–7.30(m, 4H, Benzene ring)<br>9.10(s, 1H, Pyrimidine ring)<br>9.78(s, 1H, Pyrimidine ring) | $n_D^{20.0}$ 1.5162 |
| 1-36 | [CDCl$_3$]<br>$^1$H-NMR δ (ppm) [solvent]:<br>1.16(d, J=7Hz, 3H, OCH(CH$_3$)$_2$) | $n_D^{20.0}$ 1.5106 |

TABLE 1-2-continued

| Compound No. | Spectral data | Physical properties |
|---|---|---|
| | 1.26(d, J=7Hz, 3H, OCH(CH$_3$)$_2$)<br>3.30–4.00(m, 1H, OCH(CH$_3$)$_2$)<br>5.85–6.10(m, 1H, CH)<br>6.70–7.50(m, 4H, Benzene ring)<br>9.20(s, 1H, Pyrimidine ring)<br>9.30(s, 1H, Pyrimidine ring)<br>[CDCl$_3$] | |
| 1-37 | $^1$H-NMR δ (ppm) [solvent]:<br>3.38–4.08(m, 1H, OH)<br>6.55(s, 1H, CH)<br>6.68–7.58(m, 4H, Benzene ring)<br>9.06(s, 2H, Pyrimidine ring)<br>[CDCl$_3$] | n$_D^{19.7}$ 1.5434 |
| 1-38 | $^1$H-NMR δ (ppm) [solvent]:<br>6.81(s, 1H, CH)<br>6.90–7.65(m, 4H, Benzene ring)<br>9.15(s, 1H, Pyrimidine ring)<br>9.18(s, 1H, Pyrimidine ring)<br>[CDCl$_3$] | n$_D^{19.7}$ 1.5436 |
| 1-39 | $^1$H-NMR δ (ppm) [solvent]:<br>7.10–7.82(m, 4H, Benzene ring)<br>8.75(s, 1H, Pyrimidine ring)<br>9.46(s, 1H, Pyrimidine ring)<br>[CDCl$_3$] | mp 40–42° C. |
| 1-40 | $^1$H-NMR δ (ppm) [solvent]:<br>3.42(s, 3H, OCH$_3$)<br>5.65–5.80(m, 1H, CH)<br>7.07–7.37(m, 5H, Benzene ring)<br>9.10(s, 1H, Pyrimidine ring)<br>9.37(s, 1H, Pyrimidine ring)<br>[CDCl$_3$] | n$_D^{19.7}$ 1.5452 |
| 1-41 | $^1$H-NMR δ (ppm) [solvent]:<br>1.19(s, 3H, C(CH$_3$)$_2$COOH)<br>1.41(s, 3H, C(CH$_3$)$_2$COOH)<br>5.50–5.65(m, 1H, CH)<br>6.20–6.40(m, 2H, NH, COOH)<br>7.18–7.38(m, 5H, Benzene ring)<br>9.24(s, 1H, Pyrimidine ring)<br>9.85–10.00(m, 1H, Pyrimidine ring)<br>[CDCl$_3$] | mp 114–116° C. |
| 1-42 | $^1$H-NMR δ (ppm) [solvent]:<br>0.10–0.60(m, 4H, cyclo-propyl CH$_2$)<br>0.70–1.00(m, 1H, cyclo-propyl CH)<br>2.15–2.30(m, 1H, NH)<br>5.40–5.65(m, 1H, CH)<br>6.70–7.55(m, 4H, Benzene ring)<br>9.07(s, 1H, Pyrimidine ring)<br>9.16(s, 1H, Pyrimidine ring)<br>[CDCl$_3$] | n$_D^{19.6}$ 1.5377 |
| 1-43 | $^1$H-NMR δ (ppm) [solvent]:<br>1.90–2.20(m, 1H, NH)<br>2.30–2.50(m, 1H, CH$_2$C≡CH)<br>5.35(d, J=2Hz, 2H, CH$_2$C≡CH)<br>5.60–5.85(m, 1H, CH)<br>6.80–7.65(m, 4H, Benzene ring)<br>9.12(s, 1H, Pyrimidine ring)<br>9.41(s, 1H, Pyrimidine ring)<br>[CDCl$_3$] | n$_D^{19.6}$ 1.5417 |
| 1-44 | $^1$H-NMR δ (ppm) [solvent]:<br>2.27(t, J=7Hz, 3H, CH$_2$CH$_3$)<br>2.37(s, 3H, NCH$_3$)<br>3.24(s, 2H, CH$_2$CO$_2$CH$_2$CH$_3$)<br>4.10(q, J=7Hz, 2H, CH$_2$CH$_3$)<br>5.45–5.65(m, 1H, CH)<br>7.00–7.60(m, 5H, Benzene ring)<br>9.08(s, 1H, Pyrimidine ring)<br>9.62(s, 1H, Pyrimidine ring)<br>[CDCl$_3$] | n$_D^{19.7}$ 1.5237 |
| 1-45 | $^1$H-NMR δ (ppm) [solvent]:<br>1.25(s, 9H, OC(CH$_3$)$_3$)<br>6.51(s, 1H, CH)<br>7.07–7.41(m, 4H, Benzene ring)<br>9.14(s, 1H, Pyrimidine ring)<br>9.39(s, 1H, Pyrimidine ring)<br>[CDCl$_3$] | n$_D^{19.9}$ 1.5300 |
| 1-46 | $^1$H-NMR δ (ppm) [solvent]: | n$_D^{22.4}$ 1.5252 |
| | 1.22(s, 9H, OC(CH$_3$)$_3$)<br>6.04(s, 1H, CH)<br>7.06–7.34(m, 4H, Benzene ring)<br>9.16(s, 1H, Pyrimidine ring)<br>9.33(s, 1H, Pyrimidine ring)<br>[CDCl$_3$] | |
| 1-47 | $^1$H-NMR δ (ppm) [solvent]:<br>1.22(s, 9H, OC(CH$_3$)$_3$)<br>6.02(s, 1H, CH)<br>6.94–7.40(m, 3H, Benzene ring)<br>9.16(s, 1H, Pyrimidine ring)<br>9.31(s, 1H, Pyrimidine ring)<br>[CDCl$_3$] | n$_D^{22.8}$ 1.5293 |
| 1-48 | $^1$H-NMR δ (ppm) [solvent]:<br>4.20–4.41(br m, 1H, OH)<br>6.53–6.67(br m, 1H, CH)<br>7.12–7.56(m, 4H, Benzene ring)<br>8.85(s, 1H, Pyrimidine ring)<br>9.12(s, 1H, Pyrimidine ring)<br>[CDCl$_3$] | n$_D^{20.5}$ 1.5378 |
| 1-49 | $^1$H-NMR δ (ppm) [solvent]:<br>4.22–4.43(br m, 1H, OH)<br>6.21–6.35(br m, 1H, CH)<br>7.06–7.35(m, 4H, Benzene ring)<br>8.99(s, 1H, Pyrimidine ring)<br>9.02(s, 1H, Pyrimidine ring)<br>[CDCl$_3$] | n$_D^{19.8}$ 1.5402 |
| 1-50 | $^1$H-NMR δ (ppm) [solvent]:<br>3.10–3.50(br m, 1H, OH)<br>6.23–6.32(br m, 1H, CH)<br>6.97–7.48(m, 3H, Benzene ring)<br>8.98(s, 1H, Pyrimidine ring)<br>9.10(s, 1H, Pyrimidine ring)<br>[CDCl$_3$] | mp 66–68° C. |
| 1-51 | $^1$H-NMR δ (ppm) [solvent]:<br>7.17–7.76(m, 4H, Benzene ring)<br>8.77(s, 1H, Pyrimidine ring)<br>9.35(s, 1H, Pyrimidine ring)<br>[CDCl$_3$] | n$_D^{19.8}$ 1.5612 |
| 1-52 | $^1$H-NMR δ (ppm) [solvent]:<br>7.34–7.76(m, 4H, Benzene ring)<br>8.79(s, 1H, Pyrimidine ring)<br>9.39(s, 1H, Pyrimidine ring)<br>[CDCl$_3$] | n$_D^{19.8}$ 1.5756 |
| 1-53 | $^1$H-NMR δ (ppm) [solvent]:<br>7.37–7.91(m, 3H, Benzene ring)<br>8.73(s, 1H, Pyrimidine ring)<br>9.36(s, 1H, Pyrimidine ring)<br>[CDCl$_3$] | mp 51–53° C. |
| 1-54 | $^1$H-NMR δ (ppm) [solvent]:<br>0.92(s, 9H, C(CH$_3$)$_3$)<br>3.11(q, J=11Hz, 8Hz, 2H, CH$_2$)<br>5.79(d, J=1.5Hz, 1H, CH)<br>7.19–7.27(m, 4H, Benzene ring)<br>9.07(s, 1H, Pyrimidine ring)<br>9.15(s, 1H, Pyrimidine ring)<br>[CDCl$_3$] | n$_D^{19.8}$ 1.5159 |
| 1-55 | $^1$H-NMR δ (ppm) [solvent]:<br>2.20(s, 6H, N(CH$_3$)$_2$)<br>5.05–5.35(m, 1H, CH)<br>6.75–7.35(m, 4H, Benzene ring)<br>9.05–9.15(m, 1H, Pyrimidine ring)<br>9.57(s, 1H, Pyrimidine ring)<br>[CDCl$_3$] | n$_D^{19.7}$ 1.5338 |
| 1-56 | $^1$H-NMR δ (ppm) [solvent]:<br>2.19(s, 6H, N(CH$_3$)$_2$)<br>4.10–4.30(m, 1H, CH)<br>6.60–7.40(m, 4H, Benzene ring)<br>9.08(s, 1H, Pyrimidine ring)<br>9.47(s, 1H, Pyrimidine ring)<br>[CDCl$_3$] | n$_D^{19.7}$ 1.5358 |
| 1-57 | $^1$H-NMR δ (ppm) [solvent]:<br>3.40–3.80(m, 1H, OH)<br>6.28–6.38(m, 1H, CH)<br>6.74–7.60(m, 4H, Benzene ring)<br>9.01(s, 1H, Pyrimidine ring) | n$_D^{19.7}$ 1.5438 |

TABLE 1-2-continued

| Compound No. | Spectral data | Physical properties |
|---|---|---|
| | 9.09(s, 1H, Pyrimidine ring)<br>[CDCl₃] | |
| 1-58 | ¹H-NMR δ (ppm) [solvent]:<br>6.01(s, 1H, CH)<br>6.70–7.50(m, 4H, Benzene ring)<br>9.00(s, 1H, Pyrimidine ring)<br>9.11(s, 1H, Pyrimidine ring)<br>[CDCl₃] | $n_D^{19.8}$ 1.5496 |
| 1-59 | ¹H-NMR δ (ppm) [solvent]:<br>0.11–0.87(m, 4H, cyclo-propyl CH₂)<br>0.90–1.50(m, 1H, cyclo-propyl CH)<br>3.28–3.60(m, 2H, OCH₂)<br>5.87–6.07(m, 1H, CH)<br>6.73–7.57(m, 4H, Benzene ring)<br>9.07(s, 1H, Pyrimidine ring)<br>9.16(s, 1H, Pyrimidine ring)<br>[CDCl₃] | $n_D^{19.9}$ 1.5240 |
| 1-60 | ¹H-NMR δ (ppm) [solvent]:<br>1.23(s, 9H, OC(CH₃)₃)<br>6.33–6.50(m, 1H, CH)<br>6.71–7.30(m, 4H, Benzene ring)<br>9.17(s, 1H, Pyrimidine ring)<br>9.52(s, 1H, Pyrimidine ring)<br>[CDCl₃] | $n_D^{20.0}$ 1.5140 |
| 1-61 | ¹H-NMR δ (ppm) [solvent]:<br>1.23(s, 9H, OC(CH₃)₃)<br>6.00–6.15(m, 1H, CH)<br>6.70–7.40(m, 4H, Benzene ring)<br>9.01(s, 1H, Pyrimidine ring)<br>9.35(s, 1H, Pyrimidine ring)<br>[CDCl₃] | $n_D^{20.3}$ 1.5048 |
| 1-62 | ¹H-NMR δ (ppm) [solvent]:<br>1.23(s, 9H, OC(CH₃)₃)<br>6.00–6.15(m, 1H, CH)<br>7.00–7.35(m, 5H, Benzene ring)<br>9.12(s, 1H, Pyrimidine ring)<br>9.37(s, 1H, Pyrimidine ring)<br>[CDCl₃] | $n_D^{20.2}$ 1.5154 |
| 1-63 | ¹H-NMR δ (ppm) [solvent]:<br>1.28(s, 3H, CH₃)<br>1.37(s, 3H, CH₃)<br>2.94(s, 3H, OCH₃)<br>6.22(s, 1H, CH)<br>7.11–7.27(m, 4H, Benzene ring)<br>9.12(s, 1H, Pyrimidine ring)<br>9.33(s, 1H, Pyrimidine ring)<br>[CDCl₃] | $n_D^{21.7}$ 1.5285 |
| 1-64 | ¹H-NMR δ (ppm) [solvent]:<br>1.30(s, 3H, CH₃)<br>1.38(s, 3H, CH₃)<br>2.94(s, 3H, OCH₃)<br>6.24(s, 1H, CH)<br>7.12–7.40(m, 4H, Benzene ring)<br>9.13(s, 1H, Pyrimidine ring)<br>9.34(s, 1H, Pyrimidine ring)<br>[CDCl₃] | $n_D^{20.1}$ 1.5371 |
| 1-65 | ¹H-NMR δ (ppm) [solvent]:<br>1.32(s, 3H, CH₃)<br>1.39(s, 3H, CH₃)<br>2.97(s, 3H, OCH₃)<br>6.69(s, 1H, CH)<br>7.04–7.39(m, 4H, Benzene ring)<br>9.14(s, 1H, Pyrimidine ring)<br>9.35(s, 1H, Pyrimidine ring)<br>[CDCl₃] | $n_D^{19.8}$ 1.5317 |
| 1-66 | ¹H-NMR δ (ppm) [solvent]:<br>0.82–1.03(m, 3H, CH₂CH₂CH₃)<br>1.15(s, 3H, CH₃)<br>1.22(s, 3H, CH₃)<br>1.34–1.93(m, 4H, CH₂CH₂CH₃)<br>6.06(s, 1H, CH)<br>7.18–7.27(m, 4H, Benzene ring)<br>9.17(s, 1H, Pyrimidine ring)<br>9.37(s, 1H, Pyrimidine ring)<br>[CDCl₃] | $n_D^{19.7}$ 1.5282 |
| 1-67 | ¹H-NMR δ (ppm) [solvent]: | $n_D^{19.7}$ 1.5344 |
| | 1.05(s, 9H, NHC(CH₃)₃)<br>1.93–2.64(br m, 1H, NH)<br>5.47–5.60(br m, 1H, CH)<br>7.07–7.35(m, 4H, Benzene ring)<br>9.11(s, 1H, Pyrimidine ring)<br>9.78(s, 1H, Pyrimidine ring)<br>[CDCl₃] | |
| 1-68 | ¹H-NMR δ (ppm) [solvent]:<br>2.93(s, 6H, N(CH₃)₂)<br>7.01–7.35(m, 5H, CH + Benzene ring)<br>8.99(s, 1H, Pyrimidine ring)<br>9.15(s, 1H, Pyrimidine ring)<br>[CDCl₃] | $n_D^{19.7}$ 1.5358 |
| 1-69 | ¹H-NMR δ (ppm) [solvent]:<br>2.93(s, 6H, N(CH₃)₂)<br>7.04–7.26(m, 5H, CH + Benzene ring)<br>8.97(s, 1H, Pyrimidine ring)<br>9.16(s, 1H, Pyrimidine ring)<br>[CDCl₃] | $n_D^{19.7}$ 1.5443 |
| 1-70 | ¹H-NMR δ (ppm) [solvent]:<br>2.92(s, 6H, N(CH₃)₂)<br>7.00–7.42(m, 5H, CH + Benzene ring)<br>8.71(s, 1H, Pyrimidine ring)<br>9.16(s, 1H, Pyrimidine ring)<br>[CDCl₃] | $n_D^{19.7}$ 1.5375 |
| 1-71 | ¹H-NMR δ (ppm) [solvent]:<br>1.22(s, 9H, OC(CH₃)₃)<br>5.95–6.11(m, 1H, CH)<br>6.60–7.40(m, 4H, Benzene ring)<br>9.05(s, 1H, Pyrimidine ring)<br>9.23(s, 1H, Pyrimidine ring)<br>[CDCl₃] | $n_D^{20.3}$ 1.5136 |
| 1-72 | ¹H-NMR δ (ppm) [solvent]:<br>2.67(s, 3H, CH₃)<br>7.15–7.45(m, 4H, Benzene ring)<br>8.88(s, 1H, Pyrimidine ring)<br>9.46(s, 1H, Pyrimidine ring)<br>[CDCl₃] | $n_D^{20.4}$ 1.5588 |
| 1-73 | ¹H-NMR δ (ppm) [solvent]:<br>0.90–1.08(m, 3H, CH₂CH₃)<br>1.22(s, 3H, CH₃)<br>1.28(s, 3H, CH₃)<br>1.52–1.92(m, 2H, CH₂CH₃)<br>6.22(s, 1H, CH)<br>7.34–7.47(m, 4H, Benzene ring)<br>9.34(s, 1H, Pyrimidine ring)<br>9.56(s, 1H, Pyrimidine ring)<br>[CDCl₃] | $n_D^{21.1}$ 1.5284 |
| 1-74 | ¹H-NMR δ (ppm) [solvent]:<br>1.23(s, 9H, C(CH₃)₃)<br>7.05–7.42(m, 5H, CH + Benzene ring)<br>9.07(s, 1H, Pyrimidine ring)<br>9.25(s, 1H, Pyrimidine ring)<br>[CDCl₃] | $n_D^{20.1}$ 1.5215 |
| 1-75 | ¹H-NMR δ (ppm) [solvent]:<br>2.39–2.53(m, 1H, C≡CH)<br>4.12(d, J=2.5Hz, 2H, OCH₂)<br>6.10(s, 1H, CH)<br>7.16–7.30(m, 4H, Benzene ring)<br>9.09(s, 1H, Pyrimidine ring)<br>9.13(s, 1H, Pyrimidine ring)<br>[CDCl₃] | $n_D^{21.1}$ 1.5526 |
| 1-76 | ¹H-NMR δ (ppm) [solvent]:<br>4.23(s, 2H, OCH₂CN)<br>6.12(s, 1H, CH)<br>7.18–7.34(m, 4H, Benzene ring)<br>9.07(s, 1H, Pyrimidine ring)<br>9.19(s, 1H, Pyrimidine ring)<br>[CDCl₃] | $n_D^{20.9}$ 1.5535 |
| 1-77 | ¹H-NMR δ (ppm) [solvent]:<br>1.11(t, J=7Hz, 3H, NHCH₂CH₃)<br>2.97–3.41(mm, 2H, NHCH₂CH₃)<br>4.97–5.86(br m, 1H, NHCH₂CH₃)<br>7.11–7.27(m, 5H, CH + Benzene ring)<br>8.98(s, 1H, Pyrimidine ring)<br>9.16(s, 1H, Pyrimidine ring) | $n_D^{20.8}$ 1.5315 |

TABLE 1-2-continued

| Compound No. | Spectral data | Physical properties |
|---|---|---|
| 1-78 | [CDCl$_3$]<br>$^1$H-NMR δ (ppm) [solvent]:<br>1.22(d, J=6Hz, 6H, CH(CH$_3$)$_2$)<br>3.87–4.40(m, 1H, CH(CH$_3$)$_2$)<br>6.57–6.76(br m, 1H, NH)<br>7.14–7.31(m, 4H, Benzene ring)<br>7.90(s, 1H, CH)<br>9.02(s, 1H, Pyrimidine ring)<br>9.19(s, 1H, Pyrimidine ring) | $n_D^{20.8}$ 1.5588 |
| 1-79 | [CDCl$_3$]<br>$^1$H-NMR δ (ppm) [solvent]:<br>1.28(t, J=7Hz, 3H, CH$_2$CH$_3$)<br>4.38(q, J=7Hz, 2H, CH$_2$CH$_3$)<br>7.11(s, 1H, CH)<br>7.19–7.30(m, 4H, Benzene ring)<br>9.05(s, 1H, Pyrimidine ring)<br>9.19(s, 1H, Pyrimidine ring) | $n_D^{21.0}$ 1.5318 |
| 1-80 | [CDCl$_3$]<br>$^1$H-NMR δ (ppm) [solvent]:<br>1.25(t, J=7Hz, 3H, CH$_2$CH$_3$)<br>4.05(s, 2H, OCH$_2$CO$_2$Et)<br>4.18(q, J=7Hz, 2H, CH$_2$CH$_3$)<br>6.05(s, 1H, CH)<br>7.23–7.29(m, 4H, Benzene ring)<br>9.16(s, 2H, Pyrimidine ring) | $n_D^{21.0}$ 1.5335 |
| 1-81 | [CDCl$_3$]<br>$^1$H-NMR δ (ppm) [solvent]:<br>3.27(s, 3H, OCH$_2$OCH$_3$)<br>4.59(s, 2H, OCH$_2$OCH$_3$)<br>6.10(s, 1H, CH)<br>7.14–7.22(m, 4H, Benzene ring)<br>9.11(s, 2H, Pyrimidine ring) | $n_D^{21.0}$ 1.5282 |
| 1-82 | [CDCl$_3$]<br>$^1$H-NMR δ (ppm) [solvent]:<br>2.11(s, 3H, OCH$_2$SCH$_3$)<br>4.61(s, 3H, OCH$_2$SCH$_3$)<br>6.33(s, 1H, CH)<br>7.32–7.41(m, 4H, Benzene ring)<br>9.29(s, 2H, Pyrimidine ring) | $n_D^{20.8}$ 1.5655 |
| 1-83 | [CDCl$_3$]<br>$^1$H-NMR δ (ppm) [solvent]:<br>2.21(s, 3H, CH$_3$)<br>3.60–3.75(m, 1H, OH)<br>6.10–6.35(m, 1H, CH)<br>6.50–7.20(m, 4H, Benzene ring)<br>8.30(s, 1H, Pyrimidine ring)<br>8.92(s, 1H, Pyrimidine ring) | $n_D^{20.5}$ 1.5616 |
| 1-84 | [CDCl$_3$]<br>$^1$H-NMR δ (ppm) [solvent]:<br>2.41(s, 3H, CH$_3$)<br>6.65–6.80(m, 1H, CH)<br>6.95–7.40(m, 4H, Benzene ring)<br>9.17(s, 1H, Pyrimidine ring)<br>9.26(s, 1H, Pyrimidine ring) | $n_D^{20.6}$ 1.5431 |
| 1-85 | [CDCl$_3$]<br>$^1$H-NMR δ (ppm) [solvent]:<br>1.21(s, 9H, C(CH$_3$)$_3$)<br>2.41(s, 3H, CH$_3$)<br>6.20–6.35(m, 1H, CH)<br>6.90–7.40(m, 4H, Benzene ring)<br>9.11(s, 1H, Pyrimidine ring)<br>9.43(s, 1H, Pyrimidine ring) | $n_D^{21.1}$ 1.5322 |
| 1-86 | [CDCl$_3$]<br>$^1$H-NMR δ (ppm) [solvent]:<br>2.33(s, 3H, CH$_3$)<br>3.10(s, 6H, N(CH$_3$)$_2$)<br>6.70–7.45(m, 5H, Benzene ring, CH)<br>8.82(s, 1H, Pyrimidine ring)<br>9.25(s, 1H, Pyrimidine ring) | $n_D^{21.1}$ 1.5354 |
| 1-87 | [CDCl$_3$]<br>$^1$H-NMR δ (ppm) [solvent]:<br>0.70–1.25(m, 3H, CH$_2$CH$_2$CH$_3$)<br>1.25–2.15(m, 4H, CH$_2$CH$_2$CH$_3$)<br>3.30–4.60(m, 3H, OCH$_2$CHO)<br>6.80–7.70(m, 4H, Benzene ring)<br>9.20–9.70(s, 2H, Pyrimidine ring) | $n_D^{20.9}$ 1.5072 |
| 1-88 | [CDCl$_3$]<br>$^1$H-NMR δ (ppm) [solvent]:<br>0.70–1.18(m, 3H, CH$_2$CH$_2$CH$_3$)<br>1.18–2.00(m, 4H, CH$_2$CH$_2$CH$_3$)<br>3.35–4.45(m, 3H, OCH$_2$CHO)<br>6.55–7.80(m, 4H, Benzene ring)<br>9.19(s, 1H, Pyrimidine ring)<br>9.32–9.60(s, 1H, Pyrimidine ring) | $n_D^{19.6}$ 1.5117 |
| 1-89 | [CDCl$_3$]<br>$^1$H-NMR δ (ppm) [solvent]:<br>0.68–1.13(m, 3H, CH$_2$CH$_2$CH$_3$)<br>1.13–1.83(m, 4H, CH$_2$CH$_2$CH$_3$)<br>2.13(s, 3H, CH$_3$)<br>3.33–4.33(m, 3H, OCH$_2$CHO)<br>6.83–7.53(m, 4H, Benzene ring)<br>9.03(s, 1H, Pyrimidine ring)<br>9.16(s, 1H, Pyrimidine ring) | $n_D^{19.8}$ 1.5203 |
| 1-90 | [CDCl$_3$]<br>$^1$H-NMR δ (ppm) [solvent]:<br>7.20–8.00(m, 4H, Benzene ring)<br>8.90(s, 1H, Pyrimidine ring)<br>9.48(s, 1H, Pyrimidine ring) | $n_D^{20.0}$ 1.5174 |
| 1-91 | [CDCl$_3$]<br>$^1$H-NMR δ (ppm) [solvent]:<br>2.18(s, 6H, N(CH$_3$)$_2$)<br>2.41(s, 3H, CH$_3$)<br>5.10–5.15(m, 1H, CH)<br>6.90–7.30(m, 4H, Benzene ring)<br>9.06(s, 1H, Pyrimidine ring)<br>9.54(s, 1H, Pyrimidine ring) | $n_D^{20.0}$ 1.5447 |
| 1-92 | [CDCl$_3$]<br>$^1$H-NMR δ (ppm) [solvent]:<br>0.70–1.15(m, 3H, CH$_2$CH$_2$CH$_3$)<br>1.15–1.80(m, 4H, CH$_2$CH$_2$CH$_3$)<br>3.50–4.41(m, 3H, OCH$_2$CHO)<br>7.18(s, 4H, Benzene ring)<br>9.12–9.40(m, 2H, Pyrimidine ring) | $n_D^{20.1}$ 1.5330 |
| 1-93 | [CDCl$_3$]<br>$^1$H-NMR δ (ppm) [solvent]:<br>1.22(s, 9H, C(CH$_3$)$_3$)<br>6.44(s, 1H, CHOC(CH$_3$)$_3$)<br>7.06–7.14(m, 2H, Benzene ring)<br>7.27–7.35(m, 1H, Benzene ring)<br>9.12(s, 1H, Pyrimidine ring)<br>9.34(s, 1H, Pyrimidine ring) | $n_D^{19.3}$ 1.5421 |
| 1-94 | [CDCl$_3$]<br>$^1$H-NMR δ (ppm) [solvent]:<br>1.23(s, 9H, C(CH$_3$))<br>6.42(s, 1H, CHOC(CH$_3$))<br>7.12–7.2(m, 3H, Benzene ring)<br>9.14(s, 1H, Pyrimidine ring)<br>9.31(s, 1H, Pyrimidine ring) | mp 73–75° C. |
| 1-95 | [CDCl$_3$]<br>$^1$H-NMR δ (ppm) [solvent]:<br>3.66–3.87(br m, 1H, OH)<br>6.48–6.54(m, 1H, CHOH)<br>7.12–7.45(m, 3H, Benzene ring)<br>8.73(s, 1H, Pyrimidine ring)<br>9.13(s, 1H, Pyrimidine ring) | mp 39–41° C. |
| 1-96 | [CDCl$_3$]<br>$^1$H-NMR δ (ppm) [solvent]:<br>7.29–7.74(m, 3H, Benzene ring)<br>8.89(s, 1H, Pyrimidine ring)<br>9.48(s, 1H, Pyrimidine ring) | $n_D^{19.4}$ 1.5722 |
| 1-97 | [CDCl$_3$]<br>$^1$H-NMR δ (ppm) [solvent]:<br>3.40–3.80(m, 1H, OH)<br>6.50–6.80(m, 1H, CH)<br>7.10–7.80(m, 4H, Benzene ring)<br>8.86(s, 1H, Pyrimidine ring)<br>9.08(s, 1H, Pyrimidine ring) | $n_D^{19.6}$ 1.5139 |
| 1-98 | [CDCl$_3$]<br>$^1$H-NMR δ (ppm) [solvent]:<br>7.24–7.48(m, 2H, Thiophene ring)<br>7.61–7.70(m, 1H, Thiophene ring)<br>8.78(s, 1H, Pyrimidine ring) | $n_D^{19.7}$ 1.5854 |

TABLE 1-2-continued

| Compound No. | Spectral data | Physical properties |
|---|---|---|
| | 9.26(s, 1H, Pyrimidine ring) [CDCl₃] | |
| 1-99 | ¹H-NMR δ (ppm) [solvent]: 6.95~7.29(m, 2H, Thiophene ring) 7.66~7.80(m, 1H, Thiophene ring) 8.81(s, 1H, Pyrimidine ring) 9.30(s, 1H, Pyrimidine ring) [CDCl₃] | $n_D^{19.8}$ 1.5920 |
| 1-100 | ¹H-NMR δ (ppm) [solvent]: 4.20~4.31(br m, 1H, OH) 6.52~6.61(m, 1H, CHOH) 6.82~7.03(m, 2H, Thiophene ring) 7.26~7.36(m, 1H, Thiophene ring) 9.15(s, 1H, Pyrimidine ring) 9.32(s, 1H, Pyrimidine ring) [CDCl₃] | $n_D^{19.7}$ 1.5702 |
| 1-101 | ¹H-NMR δ (ppm) [solvent]: 2.94(s, 6H, N(CH₃)₂) 6.74~6.96(m, 2H, Thiophene ring) 7.17~7.29(m, 1H, Thiophene ring) 7.37(s, 1H, CHOCON) 9.14(s, 1H, Pyrimidine ring) 9.18(s, 1H, Pyrimidine ring) [CDCl₃] | $n_D^{19.7}$ 1.5422 |
| 1-102 | ¹H-NMR δ (ppm) [solvent]: 6.90~7.10(m, 1H, CH) 7.15~7.90(m, 4H, Benzene ring) 8.97(s, 1H, Pyrimidine ring) 9.16(s, 1H, Pyrimidine ring) [CDCl₃] | $n_D^{19.9}$ 1.5164 |
| 1-103 | ¹H-NMR δ (ppm) [solvent]: 2.22(s, 6H, N(CH₃)₂) 5.45~5.60(m, 1H, CH) 7.10~7.80(m, 4H, Benzene ring) 9.06(s, 1H, Pyrimidine ring) 9.16(s, 1H, Pyrimidine ring) [CDCl₃] | $n_D^{19.9}$ 1.5089 |
| 1-104 | ¹H-NMR δ (ppm) [solvent]: 2.26(s, 9H, O(CH₃)₃) 6.65~6.80(m, 1H, CH) 7.15~8.05(m, 4H, Benzene ring) 8.85(s, 1H, Pyrimidine ring) 9.12(s, 1H, Pyrimidine ring) [CDCl₃] | $n_D^{19.8}$ 1.4937 |
| 1-105 | ¹H-NMR δ (ppm) [solvent]: 1.30(s, 9H, C(CH₃)₃) 4.81~4.89(br s, 1H, NH) 7.03~7.38(m, 4H, Benzene ring) 7.18(s, 1H, CHOCO) 9.00(s, 1H, Pyrimidine ring) 9.20(s, 1H, Pyrimidine ring) [CDCl₃] | $n_D^{20.2}$ 1.5197 |
| 1-106 | ¹H-NMR δ (ppm) [solvent]: 1.12(t, J=7Hz, 6H, N(CH₂CH₃)₂) 3.10~3.64(m, 4H, N(CH₂CH₃)₂) 7.13~7.28(m, 5H, CHOCO + Benzene ring) 9.01(s, 1H, Pyrimidine ring) 9.17(s, 1H, Pyrimidine ring) [CDCl₃] | $n_D^{20.0}$ 1.5323 |
| 1-107 | ¹H-NMR δ (ppm) [solvent]: 6.57(q, J=4Hz, 2Hz, 1H, Furan ring) 7.15(d, J=4Hz, 1H, Furan ring) 7.61(d, J=2Hz, 1H, Furan ring) 8.84(s, 1H, Pyrimidine ring) 9.34(s, 1H, Pyrimidine ring) [CDCl₃] | $n_D^{20.0}$ 1.5589 |
| 1-108 | ¹H-NMR δ (ppm) [solvent]: 1.80~2.80(m, 2H, NH₂) 5.60~5.90(m, 1H, CH) 6.50~7.60(m, 4H, Benzene ring) 9.01(s, 1H, Pyrimidine ring) [CDCl₃] | $n_D^{20.1}$ 1.5528 |
| 1-109 | ¹H-NMR δ (ppm) [solvent]: 2.93(s, 6H, N(CH₃)₂) 6.87~7.29(m, 4H, CHOCO +Thiophene ring) 9.03(s, 1H, Pyrimidine ring) 9.13(s, 1H, Pyrimidine ring) [CDCl₃] | $n_D^{20.9}$ 1.5279 |
| 1-110 | ¹H-NMR δ (ppm) [solvent]: 2.93(s, 6H, N(CH₃)₂) 6.19~6.32(m, 2H, Furan ring) 7.20(s, 1H, CHOCO) 7.29~7.37(m, 1H, Furan ring) 9.16~9.26(m, 2H, Pyrimidine ring) [CDCl₃] | $n_D^{20.2}$ 1.5116 |
| 1-111 | ¹H-NMR δ (ppm) [solvent]: 3.88~4.02(br m, 1H, OH) 6.32~6.41(m, 1H, CHOH) 6.78~7.01(m, 1H, Thiophene ring) 7.02~7.30(m, 2H, Thiophene ring) 9.05(s, 1H, Pyrimidine ring) 9.11(s, 1H, Pyrimidine ring) [CDCl₃] | $n_D^{20.2}$ 1.5351 |
| 1-112 | ¹H-NMR δ (ppm) [solvent]: 2.94~3.07(br m, 1H, OH) 6.07~6.15(m, 1H, CHOH) 6.19~6.32(m, 2H, Furan ring) 7.27~7.35(m, 1H, Furan ring) 9.14(s, 1H, Pyrimidine ring) 9.30(s, 1H, Pyrimidine ring) [CDCl₃] | $n_D^{20.2}$ 1.5224 |
| 1-113 | ¹H-NMR δ (ppm) [solvent]: 1.08(s, 9H, NHC(CH₃)₃) 1.40~1.60(m, 1H, NH) 5.45~5.60(m, 1H, CH) 6.50~7.45(m, 4H, Benzene ring) 9.13(s, 1H, Pyrimidine ring) 9.78(s, 1H, Pyrimidine ring) [CDCl₃] | $n_D^{20.1}$ 1.5236 |
| 1-114 | ¹H-NMR δ (ppm) [solvent]: 3.54(s, 3H, OCH₃) 6.80~8.10(m, 4H, Benzene ring) 8.79(s, 1H, Pyrimidine ring) 9.39(s, 1H, Pyrimidine ring) [CDCl₃] | $n_D^{20.4}$ 1.5597 |
| 1-115 | ¹H-NMR δ (ppm) [solvent]: 3.30~3.60(m, 1H, OH) 3.69(s, 3H, OCH₃) 6.30~6.50(m, 1H, CH) 6.60~7.40(m, 4H, Benzene ring) 8.85(s, 1H, Pyrimidine ring) 9.00(s, 1H, Pyrimidine ring) [CDCl₃] | $n_D^{21.7}$ 1.5403 |
| 1-116 | ¹H-NMR δ (ppm) [solvent]: 3.74(s, 3H, OH) 6.60~7.80(m, 5H, Benzene ring, CH) 9.06(s, 1H, Pyrimidine ring) 9.23(s, 1H, Pyrimidine ring) [CDCl₃] | $n_D^{22.0}$ 1.5518 |
| 1-117 | ¹H-NMR δ (ppm) [solvent]: 2.18(s, 6H, N(CH₃)₂) 3.75(s, 3H, OCH₃) 5.25~5.40(m, 1H, CH) 6.60~7.40(m, Benzene ring) 9.03(s, 1H, Pyrimidine ring) 9.41(s, 1H, Pyrimidine ring) [CDCl₃] | mp 47–49° C. |

TABLE 2-1

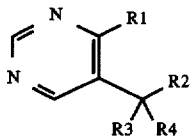

| Compound No. | R1 | R2 | R3 R4 |
|---|---|---|---|
| 2-1 | CF₂Cl | Me | —OCH₂CH₂O— |
| 2-2 | CF₂Cl | Buᵗᵉʳᵗ | —OCH₂CH₂O— |
| 2-3 | CF₂Cl | Me | —OCH(Et)CH₂O— |
| 2-4 | CF₂Cl | Me | —OCH₂CH₂CH₂O— |
| 2-5 | CF₂Cl | Me | —OCH(Prⁿ)CH₂O— |
| 2-6 | CF₂Cl | Et | —OCH₂CH₂O— |
| 2-7 | CF₂Cl | Prⁿ | —OCH₂CH₂O— |
| 2-8 | CF₂Cl | Prⁿ | —OCH(Prⁿ)CH₂O— |
| 2-9 | CF₂Cl | Prⁿ | —OCH(Et)CH₂O— |
| 2-10 | CF₂Cl | Me | —OCH(Buᵗᵉʳᵗ)CH₂O— |
| 2-11 | CF₂Br | Me | —OCH(Prⁿ)CH₂O— |
| 2-12 | CF₂Cl | Me | —OCH(CH₂CH₂CH=CH₂)CH₂O— |
| 2-13 | CF₂Cl | Me | —OCH(Buⁿ)CH₂O— |
| 2-14 | CF₂Cl | Me | —OCH(CH₂OCH₃)CH₂O— |
| 2-15 | CF₂Cl | Prᶜʸᶜˡᵒ | —OCH₂CH₂O— |
| 2-16 | CF₂CF₃ | Me | —OCH₂CH₂O— |
| 2-17 | CF₂CF₂Cl | Me | —OCH(Prⁿ)CH₂O— |
| 2-18 | CHFCl | Prⁿ | —OCH(Prⁿ)CH₂O— |
| 2-19 | CHF₂ | Prⁿ | —OCH(Prⁿ)CH₂O— |
| 2-20 | CF₂Cl | Prᶜʸᶜˡᵒ | —OCH(Prⁿ)CH₂O— |
| 2-21 | CF₂Cl | Prⁱˢᵒ | —OCH(Prⁿ)CH₂O— |
| 2-22 | CF₂Cl | Prⁿ | —OCH(CH₂Br)CH₂O— |
| 2-23 | CF₂Cl | Buⁱˢᵒ | —OCH(Prⁿ)CH₂O— |
| 2-24 | CF₂Cl | Prⁿ | —OCH(Buⁿ)CH₂O— |
| 2-25 | CF₂Cl | Prⁿ | —OCH(CH₂CH₂CH=CH₂)CH₂O— |
| 2-26 | CF₂Cl | Prⁿ | —OCH(Hexⁿ)CH₂O— |

TABLE 2-2

| Compound No. | Spectral data | Physical properties |
|---|---|---|
| 2-1 | ¹H-NMR δ (ppm) [solvent]: 1.79(s, 3H, C$\underline{H}_3$), 3.60–4.20(m, 4H, OC$\underline{H}_2$C$\underline{H}_2$O), 9.13(s, 1H, Pyrimidine ring), 9.23(s, 1H, Pyrimidine ring), [CDCl₃] | $n_D^{20.3}$ 1.4895 |
| 2-2 | ¹H-NMR δ (ppm) [solvent]: 0.93–1.01(m, 9H, C(C$\underline{H}_3$)₃), 3.81–3.93(m, 4H, OC$\underline{H}_2$C$\underline{H}_2$O), 9.08(s, 1H, Pyrimidine ring), 9.12(s, 1H, Pyrimidine ring), [CDCl₃] | $n_D^{19.9}$ 1.4775 |
| 2-3 | ¹H-NMR δ (ppm) [solvent]: 0.98(t, J=7Hz, 3H, CH₂C$\underline{H}_3$), 1.79(s, 3H, C$\underline{H}_3$), 1.29–2.19(m, 2H, C$\underline{H}_2$CH₃), 3.38–4.38(m, 3H, OC$\underline{H}_2$CH(Et)O), 9.08(s, 1H, Pyrimidine ring), 9.16(s, 1H, Pyrimidine ring), [CDCl₃] | $n_D^{20.0}$ 1.4769 |
| 2-4 | ¹H-NMR δ (ppm) [solvent]: 1.72(s, 3H, C$\underline{H}_3$), 1.1–2.5(m, 2H, CH₂C$\underline{H}_2$CH₂), 3.3–4.3(m, 4H, OC$\underline{H}_2$), 9.05(s, 1H, Pyrimidine ring), 9.23(s, 1H, Pyrimidine ring), [CDCl₃] | $n_D^{20.3}$ 1.4923 |
| 2-5 | ¹H-NMR δ (ppm) [solvent]: 0.6–1.15(m, 3H, CH₂CH₂C$\underline{H}_3$), 1.15–1.9(m, 4H, C$\underline{H}_2$C$\underline{H}_2$CH₃), 1.76(s, 3H, C$\underline{H}_3$), 3.3–4.5(m, 3H, C$\underline{H}_2$C$\underline{H}$(Prⁿ)O), 9.02(s, 1H, Pyrimidine ring), 9.12(s, 1H, Pyrimidine ring), [CDCl₃] | $n_D^{20.3}$ 1.4689 |
| 2-6 | ¹H-NMR δ (ppm) [solvent]: 0.95(t, J=7Hz, 3H, CH₂C$\underline{H}_3$), 2.02(q, J=7Hz, 2H, C$\underline{H}_2$CH₃), 3.05–4.32(m, 4H, OC$\underline{H}_2$), 9.0(s, 1H, Pyrimidine ring), 9.13(s, 1H, Pyrimidine ring), [CDCl₃] | $n_D^{21.6}$ 1.4884 |
| 2-7 | ¹H-NMR δ (ppm) [solvent]: 0.9(t, J=6Hz, 3H, CH₂CH₂C$\underline{H}_3$), 1.12–2.18(m, 4H, C$\underline{H}_2$C$\underline{H}_2$CH₃), 3.62–4.15(m, 4H, OC$\underline{H}_2$), 9.04(s, 1H, Pyrimidine ring), 9.17(s, 1H, Pyrimidine ring), [CDCl₃] | $n_D^{21.7}$ 1.4852 |
| 2-8 | ¹H-NMR δ (ppm) [solvent]: 0.68(m, 14H, C$\underline{H}_2$C$\underline{H}_2$C$\underline{H}_3$), 3.28–4.33(m, 3H, OC$\underline{H}_2$C$\underline{H}$O), 9.06(s, 1H, Pyrimidine ring), 9.20(s, 1H, Pyrimidine ring), [CDCl₃] | $n_D^{20.4}$ 1.4701 |
| 2-9 | ¹H-NMR δ (ppm) [solvent]: 0.68–1.18(m, 6H, C$\underline{H}_3$), 1.18–2.20(m, 6H, C$\underline{H}_2$), 3.13–4.38(m, 3H, OC$\underline{H}_2$C$\underline{H}$O), 9.06(s, 1H, Pyrimidine ring), 9.19(s, 1H, Pyrimidine ring), [CDCl₃] | $n_D^{20.5}$ 1.4769 |
| 2-10 | ¹H-NMR δ (ppm) [solvent]: 0.94(s, 9H, C(C$\underline{H}_3$)₃), 1.74(s, 3H, C$\underline{H}_3$), 3.27–4.20(m, 3H, OC$\underline{H}_2$C$\underline{H}$O), 9.0(s, 1H, Pyrimidine ring), 9.11(s, 1H, Pyrimidine ring), [CDCl₃] | $n_D^{19.3}$ 1.4782 |
| 2-11 | ¹H-NMR δ (ppm) [solvent]: 0.67–1.14(m, 3H, CH₂CH₂C$\underline{H}_3$), 1.14–1.92(m, 4H, C$\underline{H}_2$C$\underline{H}_2$CH₃), 1.75(t, J=1Hz, 3H, C$\underline{H}_3$), 3.42–4.42(m, 3H, OC$\underline{H}_2$C$\underline{H}$O), 9.08(s, 1H, Pyrimidine ring), 9.20(s, 1H, Pyrimidine ring), [CDCl₃] | $n_D^{20.2}$ 1.4894 |
| 2-12 | ¹H-NMR δ (ppm) [solvent]: 1.4–2.5(m, 4H, C$\underline{H}_2$C$\underline{H}_2$), 1.79(s, 3H, C$\underline{H}_3$), 3.34–4.42(m, 3H, OC$\underline{H}_2$C$\underline{H}$O), 4.85(dd, J$_{AX}$=2Hz, J$_{AB}$=1Hz, 1H, CH$_x$=C(H$_B$)H$_A$ (provided that H$_X$ and H$_B$ are in a cis configuration) 5.09(dd, J$_{AX}$=6Hz, J$_{AB}$=1Hz, 1H, CH$_x$=C(H$_B$)$\underline{H}_A$ (provided that H$_X$ and H$_B$ are in a cis configuration) 5.35–6.06(m, 1H, C$\underline{H}_x$=C(H$_B$)H$_A$ (provided that H$_X$ and H$_B$ are in a cis configuration) 9.1(s, 1H, Pyrimidine ring), 9.21(s, 1H, Pyrimidine ring), [CDCl₃] | $n_D^{20.0}$ 1.4877 |
| 2-13 | ¹H-NMR δ (ppm) [solvent]: 0.58–1.10(m, 3H, CH₂CH₂CH₂C$\underline{H}_3$), 1.10–1.99(m, 6H, C$\underline{H}_2$C$\underline{H}_2$C$\underline{H}_2$CH₃), 1.77(s, 3H, C$\underline{H}_3$), 3.12–4.33(m, 3H, OC$\underline{H}_2$C$\underline{H}$O), 9.07(s, 1H, Pyrimidine ring), 9.17(s, 1H, Pyrimidine ring), [CDCl₃] | $n_D^{20.1}$ 1.4761 |
| 2-14 | ¹H-NMR δ (ppm) [solvent]: 1.79(s, 3H, C$\underline{H}_3$), 3.13–4.68(m, 8H, OC$\underline{H}_2$C$\underline{H}$C$\underline{H}_2$OC$\underline{H}_3$), 9.08(s, 1H, Pyrimidine ring), 9.14(s, 1H, Pyrimidine ring), [CDCl₃] | $n_D^{20.0}$ 1.4806 |

TABLE 2-2-continued

| Compound No. | Spectral data | Physical properties |
|---|---|---|
| 2-15 | $^1$H-NMR δ (ppm) [solvent]: 1.62~2.52(m, 4H, Cyclopropane ring (methylene)) 3.41~4.34(m, 5H, OC$\underline{H}_2$C$\underline{H}_2$O, Cyclopropane ring(methylene)) 9.02(s, 1H, Pyrimidine ring), 9.15(s, 1H, Pyrimidine ring), [CDCl$_3$] | $n_D^{19.8}$ 1.5008 |
| 2-16 | $^1$H-NMR δ (ppm) [solvent]: 1.78(br s, 3H, C$\underline{H}_3$) 3.48~4.18(m, 4H, OC$\underline{H}_2$C$\underline{H}_2$O) 9.08(s, 1H, Pyrimidine ring) 9.13(s, 1H, Pyrimidine ring) [CDCl$_3$] | $n_D^{19.6}$ 1.4417 |
| 2-17 | $^1$H-NMR δ (ppm) [solvent]: 0.60~1.15(m, 3H, CH$_2$CH$_2$C$\underline{H}_3$) 1.15~1.91(m, 4H, C$\underline{H}_2$C$\underline{H}_2$CH$_3$) 1.76(s, 3H, C$\underline{H}_3$) 3.10~4.36(m, 3H, OC$\underline{H}_2$CHO) 9.05~9.25(m, 2H, Pyrimidine ring) [CDCl$_3$] | $n_D^{19.8}$ 1.4574 |
| 2-18 | $^1$H-NMR δ (ppm) [solvent]: 0.67~1.15(m, 6H, CH$_2$CH$_2$C$\underline{H}_3$, CH$_2$CH$_2$C$\underline{H}_3$) 1.15~2.08(m, 8H, C$\underline{H}_2$C$\underline{H}_2$CH$_3$, C$\underline{H}_2$C$\underline{H}_2$CH$_3$) 3.17~4.36(m, 3H, OC$\underline{H}_2$CHO) 7.63(d, J=48.5Hz, 1H, C$\underline{H}$FCl) 8.81(s, 1H, Pyrimidine ring) 9.18(s, 1H, Pyrimidine ring) [CDCl$_3$] | $n_D^{19.7}$ 1.4823 |
| 2-19 | $^1$H-NMR δ (ppm) [solvent]: 0.69~1.18(m, 6H, CH$_2$CH$_2$C$\underline{H}_3$, CH$_2$CH$_2$C$\underline{H}_3$) 1.18~2.08(m, 8H, C$\underline{H}_2$C$\underline{H}_2$CH$_3$, C$\underline{H}_2$C$\underline{H}_2$CH$_3$) 3.20~4.36(m, 3H, OC$\underline{H}_2$CHO) 7.23, 7.26(each data is t; J=54Hz, Including 1H, C$\underline{H}$F$_2$ 8.94(s, 1H, Pyrimidine ring) 9.26(s, 1H, Pyrimidine ring) [CDCl$_3$] | $n_D^{20.1}$ 1.4664 |
| 2-20 | $^1$H-NMR δ (ppm) [solvent]: 0.70~1.15(m, 3H, CH$_2$CH$_2$C$\underline{H}_3$) 1.15~1.80(m, 4H, C$\underline{H}_2$C$\underline{H}_2$CH$_3$) 1.80~2.35(m, 4H, cyclo-propyl C$\underline{H}_2$) 3.40~4.00(m, 4H, cyclo-propyl C$\underline{H}$, OC$\underline{H}_2$CHO) 9.00(s, 1H, Pyrimidine ring) 9.15(s, 1H, Pyrimidine ring) [CDCl$_3$] | $n_D^{21.1}$ 1.4863 |
| 2-21 | $^1$H-NMR δ (ppm) [solvent]: 0.60~1.10(m, 3H, CH$_2$CH$_2$C$\underline{H}_3$) 1.42(br s, 6H, iso-propyl C$\underline{H}_3$) 1.70~2.10(m, 4H, C$\underline{H}_2$C$\underline{H}_2$) 3.10~3.70(m, 4H, cyclo-propyl C$\underline{H}$, OC$\underline{H}_2$CHO) 8.72(s, 1H, Pyrimidine ring) 9.30(s, 1H, Pyrimidine ring) [CDCl$_3$] | $n_D^{20.6}$ 1.4814 |
| 2-22 | $^1$H-NMR δ (ppm) [solvent]: 0.72~1.24(m, 3H, CH$_2$CH$_2$C$\underline{H}_3$) 1.24~2.25(m, 4H, C$\underline{H}_2$C$\underline{H}_2$CH$_3$) 3.30~4.58(m, 5H, OC$\underline{H}_2$CHO, C$\underline{H}_2$Br) 9.16, 9.20(2s, 1H, Pyrimidine ring) 9.32(s, 1H, Pyrimidine ring) [CDCl$_3$] | $n_D^{20.0}$ 1.5011 |
| 2-23 | $^1$H-NMR δ (ppm) [solvent]: 0.66~1.16(m, 9H, C$\underline{H}_3$, C$\underline{H}_3$, C$\underline{H}_3$) 1.16~1.71(m, 4H, C$\underline{H}_2$C$\underline{H}_2$CH$_3$) 1.71~2.10(m, 3H, C$\underline{H}_2$C$\underline{H}$(CH$_3$)$_2$) 3.26~4.35(m, 3H, OC$\underline{H}_2$CHO) 9.01(s, 1H, Pyrimidine ring) 9.12(s, 1H, Pyrimidine ring) [CDCl$_3$] | $n_D^{20.2}$ 1.4737 |
| 2-24 | $^1$H-NMR δ (ppm) [solvent]: 0.62~1.09(m, 6H, C$\underline{H}_3$, C$\underline{H}_3$) 1.09~2.14(m, 10H, C$\underline{H}_2$C$\underline{H}_2$CH$_3$, CH$_2$CH$_2$CH$_3$) 3.24~4.31(m, 3H, OC$\underline{H}_2$CHO) 8.98(s, 1H, Pyrimidine ring) 9.12(s, 1H, Pyrimidine ring) [CDCl$_3$] | $n_D^{20.1}$ 1.4715 |
| 2-25 | $^1$H-NMR δ (ppm) [solvent]: 0.68~1.08(m, 3H, C$\underline{H}_3$) 1.08~2.48(m, 8H, C$\underline{H}_2$C$\underline{H}_2$CH$_3$, CH$_2$CH$_2$CH=CH$_2$) 3.28~4.28(m, 3H, OC$\underline{H}_2$CHO) 4.68~4.90(m, 1H, CH=C$\underline{H}_2$) 4.90~5.18(m, 1H, CH=C$\underline{H}_2$) 5.28~6.08(m, 1H, C$\underline{H}$=CH$_2$) 8.98(s, 1H, Pyrimidine ring) 9.11(s, 1H, Pyrimidine ring) [CDCl$_3$] | $n_D^{20.0}$ 1.4805 |
| 2-26 | $^1$H-NMR δ (ppm) [solvent]: 0.60~1.08(m, 6H, C$\underline{H}_3$, C$\underline{H}_3$) 1.08~2.14(m, 14H, C$\underline{H}_2$C$\underline{H}_2$CH$_3$, CH$_2$CH$_2$CH$_2$CH$_2$CH$_2$CH$_3$) 3.35~4.35(m, 3H, OC$\underline{H}_2$CHO) 8.95(s, 1H, Pyrimidine ring) 9.10(s, 1H, Pyrimidine ring) [CDCl$_3$] | $n_D^{20.0}$ 1.4737 |

TABLE 3-1

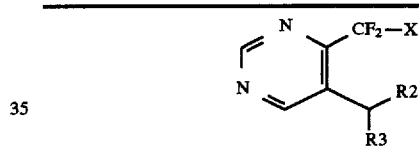

| Compound No. | X | R3 | R2 |
|---|---|---|---|
| 3-1 | Cl | NHCH$_2$Ph | Pr$^{cyclo}$ |
| 3-2 | Cl | morphorino | Pr$^{cyclo}$ |
| 3-3 | Cl | 4-phenylpiperazinyl | Pr$^{cyclo}$ |
| 3-4 | Cl | heptamethyleneimino | Pr$^{cyclo}$ |
| 3-5 | Cl | 2,6-dimethylmorphorino | Pr$^{cyclo}$ |
| 3-6 | Cl | NH(2-Cl-benzyl) | Pr$^{cyclo}$ |
| 3-7 | Cl | NH(3-Cl-benzyl) | Pr$^{cyclo}$ |
| 3-8 | Cl | NH(4-Cl-benzyl) | Pr$^{cyclo}$ |
| 3-9 | Cl | NH(4-Me-benzyl) | Pr$^{cyclo}$ |
| 3-10 | Cl | NH(2-Cl-phenetyl) | Pr$^{cyclo}$ |
| 3-11 | Cl | NH(2,4-Cl$_2$-benzyl) | Pr$^{cyclo}$ |
| 3-12 | Cl | 3,3-Me$_2$-piperidino | Pr$^{cyclo}$ |
| 3-13 | Cl | NH(CH(Ph)$_2$) | Pr$^{cyclo}$ |
| 3-14 | Cl | N(Me)CH$_2$Ph | Pr$^{cyclo}$ |
| 3-15 | Cl | NHCH$_2$Ph | Pr$^n$ |
| 3-16 | Cl | NH$_2$ | Pr$^{cyclo}$ |
| 3-17 | Cl | NHEt | Pr$^{cyclo}$ |
| 3-18 | Cl | NHMe.HCl | Pr$^{cyclo}$ |
| 3-19 | Cl | NHMe | Pr$^{cyclo}$ |
| 3-20 | Cl | NMe | Pr$^{cyclo}$ |
| 3-21 | Cl | NHCH$_2$Ph | Pr$^{iso}$ |

TABLE 3-2

| Compound No. | Spectral data | Physical properties |
|---|---|---|
| 3-1 | $^1$H-NMR δ (ppm) [solvent]: 0.23~0.72(m, 4H, cyclo-propyl C$\underline{H}_2$) 0.94~1.32(m, 1H, cyclo-propyl C$\underline{H}$) 1.70~1.90(m, 1H, N$\underline{H}$) | $n_D^{21.3}$ 1.5478 |

TABLE 3-2-continued

| Compound No. | Spectral data | Physical properties |
|---|---|---|
| | 3.55~3.70(m, 3H, NHC<u>H</u>₂Ph + φC<u>H</u>)<br>7.15(s, 5H, Benzene ring)<br>9.03(s, 1H, Pyrimidine ring)<br>9.28(s, 1H, Pyrimidine ring)<br>[CDCl₃] | |
| 3-2 | ¹H-NMR δ (ppm) [solvent]:<br>0.17~0.50(m, 4H, cyclo-Propyl C<u>H</u>₂)<br>0.72~1.12(m, 1H, cyclo-Propyl C<u>H</u>)<br>2.09~2.83(m, 4H, Morpholine ring)<br>2.93~3.12(m, 1H, φC<u>H</u>)<br>3.53~3.74(m, 4H, Morpholine ring)<br>9.08(s, 1H, Pyrimidine ring)<br>9.19(s, 1H, Pyrimidine ring)<br>[CDCl₃] | $n_D^{21.2}$ 1.5132 |
| 3-3 | ¹H-NMR δ (ppm) [solvent]:<br>0.15~1.15(m, 5H, cyclo-Propyl)<br>2.50~3.35(m, 9H, NC<u>H</u>₂C<u>H</u>₂N and NC<u>H</u>)<br>6.51~7.35(m, 5H, Benzene ring)<br>9.05(s, 1H, Pyrimidine ring)<br>9.18(s, 1H, Pyrimidine ring)<br>[CDCl₃] | mp 75-79° C. |
| 3-4 | ¹H-NMR δ (ppm) [solvent]:<br>0.10~1.20(m, 5H, cyclo-Propyl)<br>1.48(br s, 10H, C<u>H</u>₂)<br>2.15~3.55(m, 5H, NC<u>H</u>₂ and NC<u>H</u>)<br>9.10(s, 1H, Pyrimidine ring)<br>9.27(s, 1H, Pyrimidine ring)<br>[CDCl₃] | $n_D^{20.0}$ 1.5168 |
| 3-5 | ¹H-NMR δ (ppm) [solvent]:<br>0.12~0.63(m, 4H, cyclo-Propyl C<u>H</u>₂)<br>0.63~1.40(m, 1H, cyclo-Propyl C<u>H</u>)<br>1.00(d, J=6Hz, 3H, C<u>H</u>₃)<br>1.18(d, J=6Hz, 3H, C<u>H</u>₃)<br>1.53~2.49(m, 3H)<br>2.63~4.01(m, 4H)<br>9.11(s, 1H, Pyrimidine ring)<br>9.19(s, 1H, Pyrimidine ring)<br>[CDCl₃] | $n_D^{19.8}$ 1.5008 |
| 3-6 | ¹H-NMR δ (ppm) [solvent]:<br>0.21~0.82(m, 4H, cyclo-Propyl C<u>H</u>₂)<br>0.82~1.50(m, 1H, cyclo-Propyl C<u>H</u>)<br>2.4~3.0(m, 1H, N—<u>H</u>)<br>3.17~3.84(m, 3H, NC<u>H</u> and NC<u>H</u>₂)<br>7.17(br d, J=2 Hz, 4H, Benzene ring)<br>9.12(s, 1H, Pyrimidine ring)<br>9.38(s, 1H, Pyrimidine ring)<br>[CDCl₃] | $n_D^{20.2}$ 1.5503 |
| 3-7 | ¹H-NMR δ (ppm) [solvent]:<br>0.22~0.8(m, 4H, cyclo-Propyl C<u>H</u>₂)<br>0.8~1.42(m, 1H, cyclo-Propyl C<u>H</u>)<br>1.82 (br s, 1H, N<u>H</u>)<br>3.58(d, J=5Hz, 2H, NC<u>H</u>₂)<br>3.33~3.75(m, 1H, NC<u>H</u>)<br>6.92~7.34(m, 4H, Benzene ring)<br>9.08(s, 1H, Pyrimidine ring)<br>9.3(s, 1H, Pyrimidine ring)<br>[CDCl₃] | $n_D^{20.3}$ 1.5337 |
| 3-8 | ¹H-NMR δ (ppm) [solvent]:<br>0.25~0.85(m, 4H, cyclo-Propyl C<u>H</u>₂)<br>0.85~1.49(m, 1H, cyclo-Propyl C<u>H</u>)<br>1.88(br s, 1H, N<u>H</u>)<br>3.45~3.85(m, 1H, NC<u>H</u>)<br>3.63(br d, J=6Hz, 2H, NC<u>H</u>₂)<br>7.19(s, 4H, Benzene ring)<br>9.16(s, 1H, Pyrimidine ring)<br>9.38(s, 1H, Pyrimidine ring)<br>[CDCl₃] | $n_D^{20.3}$ 1.5419 |
| 3-9 | ¹H-NMR δ (ppm) [solvent]:<br>0.22~0.75(m, 4H, cyclo-Propyl C<u>H</u>₂)<br>0.75~1.42(m, 1H, cyclo-Propyl C<u>H</u>)<br>1.8(br s, 1H, N<u>H</u>)<br>2.28(s, 3H, C<u>H</u>₃)<br>3.34~3.85(m, 1H, NC<u>H</u>)<br>3.56(d, J=4Hz, 2H, NC<u>H</u>₂)<br>7.04(s, 4H, Benzene ring) | $n_D^{20.3}$ 1.5245 |

TABLE 3-2-continued

| Compound No. | Spectral data | Physical properties |
|---|---|---|
| | 9.10(s, 1H, Pyrimidine ring)<br>9.35(s, 1H, Pyrimidine ring)<br>[CDCl₃] | |
| 3-10 | ¹H-NMR δ (ppm) [solvent]:<br>0.2~0.77(m, 4H, cyclo-Propyl C<u>H</u>₂)<br>0.77~1.3(m, 1H, cyclo-Propyl C<u>H</u>)<br>1.58(br s, 1H, N<u>H</u>)<br>2.5~3.25(m, 4H, NC<u>H</u>₂C<u>H</u>₂)<br>3.5~3.82(m, 1H, NC<u>H</u>)<br>7.0~7.5(m, 4H, Benzene ring)<br>9.19(s, 1H, Pyrimidine ring)<br>9.27(s, 1H, Pyrimidine ring)<br>[CDCl₃] | $n_D^{20.3}$ 1.5302 |
| 3-11 | ¹H-NMR δ (ppm) [solvent]:<br>0.18~0.79(m, 4H, cyclo-Propyl C<u>H</u>₂)<br>0.79~1.53(m, 1H, cyclo-Propyl C<u>H</u>)<br>1.88(br s, 1H, N<u>H</u>)<br>3.29~3.83(m, 3H, NC<u>H</u>₂ and NC<u>H</u>)<br>7.05~7.38(m, 3H, Benzene ring)<br>9.09(s, 1H, Pyrimidine ring)<br>9.30(s, 1H, Pyrimidine ring)<br>[CDCl₃] | $n_D^{20.2}$ 1.5499 |
| 3-12 | ¹H-NMR δ (ppm) [solvent]:<br>0.13~0.63(m, 4H, cyclo-Propyl C<u>H</u>₂)<br>0.88(s, 6H, C<u>H</u>₃)<br>0.63~3.75(m, 10<u>H</u>)<br>9.20(s, 1H, Pyrimidine ring)<br>9.34(s, 1H, Pyrimidine ring)<br>[CDCl₃] | $n_D^{20.1}$ 1.4914 |
| 3-13 | ¹H-NMR δ (ppm) [solvent]:<br>0.12~0.82(m, 4H, cyclo-Propyl C<u>H</u>₂)<br>0.82~1.47(m, 1H, cyclo-Propyl C<u>H</u>)<br>1.79~2.52(br s, 1H, N<u>H</u>)<br>3.52~3.81(m, 1H, NC<u>H</u>)<br>4.73(s, 1H, NC<u>H</u>)<br>7.18(s, 5H, Benzene ring)<br>7.29(s, 5H, Benzene ring)<br>9.16(s, 1H, Pyrimidine ring)<br>9.45(s, 1H, Pyrimidine ring)<br>[CDCl₃] | $n_D^{20.0}$ 1.5538 |
| 3-14 | ¹H-NMR δ (ppm) [solvent]:<br>0.10~1.45(m, 4H, cyclo-Propyl C<u>H</u>₂)<br>2.20(s, 3H, C<u>H</u>₃)<br>3.10~3.70(m, 3H, C<u>H</u>, C<u>H</u>₂)<br>7.18(s, 5H, Benzene ring)<br>9.08(s, 1H, Pyrimidine ring)<br>9.33(s, 1H, Pyrimidine ring)<br>[CDCl₃] | $n_D^{20.3}$ 1.5245 |
| 3-15 | ¹H-NMR δ (ppm) [solvent]:<br>0.67~1.17(m, 3H, C<u>H</u>₃)<br>1.17~2.07(m, 5H, C<u>H</u>C<u>H</u>₂C<u>H</u>₂)<br>3.57(br s, 2H, C<u>H</u>₂)<br>4.14~4.56(br s, 1H, N<u>H</u>)<br>7.17(s, 5H, Benzene ring)<br>9.06(s, 1H, Pyrimidine ring)<br>9.23(s, 1H, Pyrimidine ring)<br>[CDCl₃] | $n_D^{20.4}$ 1.5274 |
| 3-16 | ¹H-NMR δ (ppm) [solvent]:<br>0.23~0.78(m, 4H, cyclo-Propyl C<u>H</u>₂)<br>1.03~1.37(m, 1H, cyclo-Propyl C<u>H</u>)<br>1.69(s, 2H, N<u>H</u>₂)<br>3.81(m, 1H, φC<u>H</u>)<br>9.13(s, 1H, Pyrimidine ring)<br>9.26(s, 1H, Pyrimidine ring)<br>[CDCl₃] | $n_D^{21.4}$ 1.5095 |
| 3-17 | ¹H-NMR δ (ppm) [solvent]:<br>0.34~0.74(m, 4H, cyclo-Propyl C<u>H</u>₂)<br>0.87~1.36(m, 1H, cyclo-Propyl C<u>H</u>)<br>1.04(t, J=7Hz, 3H, NHCH₂C<u>H</u>₃)<br>1.60(br s, 1H, N<u>H</u>)<br>2.17~2.82(m, 2H, NHC<u>H</u>₂CH₃)<br>3.42~3.62(m, 1H, φC<u>H</u>)<br>9.07(s, 1H, Pyrimidine ring)<br>9.24(s, 1H, Pyrimidine ring)<br>[CDCl₃] | $n_D^{21.4}$ 1.4947 |
| 3-18 | ¹H-NMR δ (ppm) [solvent]: | mp 197-199° C. |

TABLE 3-2-continued

| Compound No. | Spectral data | Physical properties |
|---|---|---|
| | 0.37~1.26(m, 4H, cyclo-Propyl C$\underline{H}_2$) | |
| | 1.47~2.12(m, 1H, cyclo-Propyl C$\underline{H}$) | |
| | 2.50~2.86(m, 3H, C$\underline{H}_3$) | |
| | 9.29(s, 1H, Pyrimidine ring) | |
| | 9.90(s, 1H, Pyrimidine ring) | |
| | 10.27~10.67(m, 2H, N$\underline{H}_2$CH$_3$) | |
| | [DMSO-d6 + CDCl$_3$] | |
| 3-19 | $^1$H-NMR δ (ppm) [solvent]: | $n_D^{21.5}$ 1.5002 |
| | 0.20~0.74(m, 4H, cyclo-Propyl C$\underline{H}_2$) | |
| | 0.86~1.29(m, 1H, cyclo-Propyl C$\underline{H}$) | |
| | 1.64(br s, 1H, N$\underline{H}$) | |
| | 2.29(s, 3H, NHC$\underline{H}_3$) | |
| | 3.29~3.55(m, 1H, φC$\underline{H}$) | |
| | 9.07(s, 1H, Pyrimidine ring) | |
| | 9.18(s, 1H, Pyrimidine ring) | |
| | [CDCl$_3$] | |
| 3-20 | 0.18~0.62(m, 4H, cyclo-Propyl C$\underline{H}_2$) | $n_D^{21.2}$ 1.4975 |
| | 0.95~1.33(m, 1H, cyclo-Propyl C$\underline{H}$) | |
| | 2.31(s, 6H, N(C$\underline{H}_3$)$_2$) | |
| | 2.91(d, J=8Hz, 1H, φC$\underline{H}$) | |
| | 9.15(s, 1H, Pyrimidine ring) | |
| | 9.23(s, 1H, Pyrimidine ring) | |
| | [CDCl$_3$] | |
| 3-21 | $^1$H-NMR δ (ppm) [solvent]: | $n_D^{19.7}$ 1.5285 |
| | 0.90(d, J=6Hz, 3H, C$\underline{H}_3$) | |
| | 1.00(d, J=6Hz, 3H, C$\underline{H}_3$) | |
| | 1.70(br s, 1H, N$\underline{H}$) | |
| | 1.95(qq, J=6Hz, 1H, C$\underline{H}$) | |
| | 3.52(s, 2H, C$\underline{H}_2$) | |
| | 3.99~4.20(m, 1H, C$\underline{H}$) | |
| | 6.72(s, 5H, Benzene ring) | |
| | 9.09(s, 1H, Pyrimidine ring) | |
| | 9.21(s, 1H, Pyrimidine ring) | |
| | [CDCl$_3$] | |

TABLE 4-1

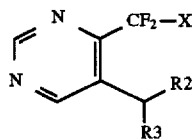

| Compound No. | X | R3 | R2 |
|---|---|---|---|
| 4-1 | Cl | OCOMe | Bu$^{tert}$ |
| 4-2 | Cl | OCOMe | Pr$^{cyclo}$ |
| 4-3 | Cl | OCH$_2$OMe | Me |
| 4-4 | Cl | OCOMe | Me |
| 4-5 | Cl | OCOEt | Me |
| 4-6 | Cl | OCOPh | Me |
| 4-7 | Cl | OSO$_2$Me | Me |
| 4-8 | Cl | OSO$_2$-(4-F-Phenyl) | Me |
| 4-9 | Cl | OSi(Me)$_2$Bu$^{tert}$ | Me |
| 4-10 | Cl | OMe | Pr$^{cyclo}$ |
| 4-11 | Cl | OCH$_2$CH=CH$_2$ | Pr$^{cyclo}$ |
| 4-12 | Cl | OPh | Pr$^{cyclo}$ |
| 4-13 | Cl | OBu$^{tert}$ | Pr$^{cyclo}$ |
| 4-14 | Cl | OTHP | Me |
| 4-15 | Cl | OPh | Pr$^n$ |
| 4-16 | Cl | OTHP | Pr$^{cyclo}$ |

TABLE 4-2

| Compound No. | Spectral data | Physical properties |
|---|---|---|
| 4-1 | $^1$H-NMR δ (ppm) [solvent]: | $n_D^{20.0}$ 1.4644 |
| | 0.88~1.18(m, 9H, C(C$\underline{H}_3$)$_3$). | |

TABLE 4-2-continued

| Compound No. | Spectral data | Physical properties |
|---|---|---|
| | 2.08(s, 3H, OCOC$\underline{H}_3$). | |
| | 6.09(s, 1H, C$\underline{H}$OAc). | |
| | 8.95(s, 1H, Pyrimidine ring). | |
| | 9.18(s, 1H, Pyrimidine ring). | |
| | [CDCl$_3$] | |
| 4-2 | $^1$H-NMR δ (ppm) [solvent]: | $n_D^{20.1}$ 1.4841 |
| | 0.51~0.72(m, 4H, cyclo-propyl C$\underline{H}_2$) | |
| | 1.06~1.38(m, 1H, cyclo-propyl C$\underline{H}$) | |
| | 2.08(s, 3H, COC$\underline{H}_3$) | |
| | 5.83(d, J=7Hz, 1H, φC$\underline{H}$) | |
| | 9.09(s, 1H, Pyrimidine ring) | |
| | 9.20(s, 1H, Pyrimidine ring) | |
| | [CDCl$_3$] | |
| 4-3 | $^1$H-NMR δ (ppm) [solvent]: | $n_D^{21.3}$ 1.4654 |
| | 1.53(d, J=6Hz, 3H, CHC$\underline{H}_3$) | |
| | 3.28(s, 3H, OC$\underline{H}_3$) | |
| | 4.47(d, J=7Hz, 1H, C$\underline{H}_2$) | |
| | 4.65(d, J=7Hz, 1H, C$\underline{H}_2$) | |
| | 5.01~5.51(m, 1H, C$\underline{H}$) | |
| | 9.10(s, 2H, Pyrimidine ring) | |
| | [CDCl$_3$] | |
| 4-4 | $^1$H-NMR δ (ppm) [solvent]: | $n_D^{21.6}$ 1.4720 |
| | 1.59(d, J=6Hz, 3H, C$\underline{H}_3$) | |
| | 2.09(s, 3H, C$\underline{H}_3$CO) | |
| | 6.01~6.44(m, 1H, C$\underline{H}$) | |
| | 8.97(s, 1H, Pyrimidine ring) | |
| | 9.12(s, 1H, Pyrimidine ring) | |
| | [CDCl$_3$] | |
| 4-5 | $^1$H-NMR δ (ppm) [solvent]: | $n_D^{20.4}$ 1.4646 |
| | 1.14(t, J=7Hz, 3H, CH$_2$C$\underline{H}_3$) | |
| | 1.60(d, J=6Hz, 3H, CHC$\underline{H}_3$) | |
| | 2.38(q, J=7Hz, 2H, C$\underline{H}_2$CH$_3$) | |
| | 6.26(q, J=6Hz, 1H, C$\underline{H}$CH$_3$) | |
| | 9.00(s, 1H, Pyrimidine ring) | |
| | 9.15(s, 1H, Pyrimidine ring) | |
| | [CDCl$_3$] | |
| 4-6 | $^1$H-NMR δ (ppm) [solvent]: | $n_D^{20.5}$ 1.5309 |
| | 1.74(t, J=7Hz, 3H, CHC$\underline{H}_3$) | |
| | 6.46(q, J=7Hz, 1H, C$\underline{H}$CH$_3$) | |
| | 7.08~8.12(m, 5H, Benzene ring) | |
| | 9.07(s, 1H, Pyrimidine ring) | |
| | 9.12(s, 1H, Pyrimidine ring) | |
| | [CDCl$_3$] | |
| 4-7 | $^1$H-NMR δ (ppm) [solvent]: | mp 96–100° C. |
| | 1.74(d, J=6Hz, 3H, CHC$\underline{H}_3$) | |
| | 3.24(s, 3H, SO$_2$C$\underline{H}_3$) | |
| | 6.12(q, J=6Hz, 1H, C$\underline{H}$CH$_3$) | |
| | 9.04(s, 1H, Pyrimidine ring) | |
| | 9.16(s, 1H, Pyrimidine ring) | |
| | [CDCl$_3$] | |
| 4-8 | $^1$H-NMR δ (ppm) [solvent]: | viscous oil |
| | 1.69(d, J=7Hz, 3H, CHC$\underline{H}_3$) | |
| | 6.01(q, J=7Hz, 1H, C$\underline{H}$CH$_3$) | |
| | 6.89~8.05(m, 4H, Benzene ring) | |
| | 8.99(s, 1H, Pyrimidine ring) | |
| | 9.15(s, 1H, Pyrimidine ring) | |
| | [CDCl$_3$] | |
| 4-9 | $^1$H-NMR δ (ppm) [solvent]: | $n_D^{20.2}$ 1.4602 |
| | −0.03(s, 3H, Si—C$\underline{H}_3$) | |
| | 0.11(s, 3H, Si—C$\underline{H}_3$) | |
| | 0.89(s, 9H, C(C$\underline{H}_3$)$_3$) | |
| | 1.47(d, J=6Hz, 3H, CHC$\underline{H}_3$) | |
| | 5.06~5.59(m, 1H, C$\underline{H}$CH$_3$) | |
| | 9.09(s, 1H, Pyrimidine ring) | |
| | 9.17(s, 1H, Pyrimidine ring) | |
| | [CDCl$_3$] | |
| 4-10 | $^1$H-NMR δ (ppm) [solvent]: | $n_D^{21.3}$ 1.4885 |
| | 0.33~0.70(m, 4H, cyclo-propyl C$\underline{H}_2$) | |
| | 1.04~1.41(m, 1H, cyclo-propyl C$\underline{H}$) | |
| | 3.32(s, 3H, OC$\underline{H}_3$) | |
| | 4.47(d, J=6Hz, 1H, φC$\underline{H}$) | |
| | 9.16(s, 1H, Pyrimidine ring) | |
| | 9.24(s, 1H, Pyrimidine ring) | |
| | [CDCl$_3$] | |
| 4-11 | $^1$H-NMR δ (ppm) [solvent]: | $n_D^{21.5}$ 1.4912 |
| | 0.45~0.69(m, 4H, cyclo-propyl C$\underline{H}_2$) | |

TABLE 4-2-continued

| Compound No. | Spectral data | Physical properties |
|---|---|---|
| | 0.89~1.36(m, 1H, cyclo-propyl C$\underline{H}$) 2.86(d, J=6Hz, 2H, OC$\underline{H_2}$CH=CH$_2$) 4.47~4.66(m, 1H, φC$\underline{H}$) 4.92~5.06(m, 1H, OCH$_2$C$\underline{H}$=CH$_2$) 5.16~5.34(m, 2H, OCH$_2$CH=C$\underline{H_2}$) 9.12(s, 1H, Pyrimidine ring) 9.13(s, 1H, Pyrimidine ring) [CDCl$_3$] | |
| 4-12 | $^1$H-NMR δ (ppm) [solvent]: 0.51~0.74(m, 4H, cyclo-propyl C$\underline{H_2}$) 1.15~1.44(m, 1H, cyclo-propyl C$\underline{H}$) 5.42~5.64(m, 1H, φC$\underline{H}$) 6.67~7.27(m, 6H, Benzene ring + Pyrimidine ring) 9.14(s, 1H, Pyrimidine ring) [CDCl$_3$] | $n_D^{21.4}$ 1.5472 |
| 4-13 | $^1$H-NMR δ (ppm) [solvent]: 0.31~0.53(m, 4H, cyclo-propyl C$\underline{H_2}$) 0.87~1.24(m, 1H, cyclo-propyl C$\underline{H}$) 1.09(s, 9H, C(C$\underline{H_3}$)$_3$) 4.95~5.10(m,m 1H, φC$\underline{H}$) 9.17(s, 1H, Pyrimidine ring) 9.20(s, 1H, Pyrimidine ring) [CDCl$_3$] | $n_D^{21.5}$ 1.4770 |
| 4-14 | $^1$H-NMR δ (ppm) [solvent]: 1.17~1.97(m, 9H, CHC$\underline{H_3}$, C$\underline{H_2}$) 3.17~4.18(m, 3H, OC$\underline{H}$O, OC$\underline{H_2}$) 5.07~5.67(m, 1H, C$\underline{H}$CH$_3$) 9.07~9.27(m, 2H, Pyrimidine ring) [CDCl$_3$] | $n_D^{20.6}$ 1.4812 |
| 4-15 | $^1$H-NMR δ (ppm) [solvent]: 0.96(t, J=7Hz, 3H, C$\underline{H_3}$) 1.27~2.14(m, 4H,, C$\underline{H_2}$C$\underline{H_2}$) 5.37~5.77(m, 1H,, C$\underline{H}$) 6.63~7.35(m, 5H, Benzene ring) 9.05(s, 1H, Pyrimidine ring) 9.10(s, 1H, Pyrimidine ring) [CDCl$_3$] | $n_D^{20.5}$ 1.5237 |
| 4-16 | $^1$H-NMR δ (ppm) [solvent]: 0.41~0.70(m, 4H, cyclo-propyl C$\underline{H_2}$) 0.94~1.29(m, 1H, cyclo-propyl C$\underline{H}$) 1.29~1.94(m, 6H, C$\underline{H_2}$ × 3) 3.22~3.87(m, 2H, OC$\underline{H_2}$) 4.78~5.04(m, 2H, φC$\underline{H}$+ OC$\underline{H}$O) 9.12 (br s, 2H, Pyrimidine ring) [CDCl$_3$] | $n_D^{21.2}$ 1.4874 |

TABLE 5-1

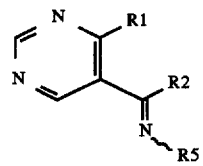

| Compound No | R1 | R2 | R5 |
|---|---|---|---|
| 5-1 | CF$_2$Cl | Me | OMe |
| 5-2 | CF$_3$ | Me | OCH$_2$CO$_2$Et |
| 5-3 | CF$_2$Cl | Me | OCH$_2$CO$_2$Et |
| 5-4 | CF$_2$Cl | Me | NH-(4-CF$_3$-phenyl) |
| 5-5 | CF$_2$Cl | Et | OCH$_2$CO$_2$Et |
| 5-6 | CF$_2$Cl | Pr$^n$ | OCH$_2$CO$_2$Et |
| 5-7 | CF$_2$CF$_2$Cl | Me | OCH$_2$CO$_2$Et |
| 5-8 | CF$_2$Cl | 2-F-Phenyl | N(Me)$_2$ |

TABLE 5-2

| Compound No. | Spectral data | Physical properties |
|---|---|---|
| 5-1 | $^1$H-NMR δ (ppm) [solvent]: 2.10~2.40(m, 3H, C(C$\underline{H_3}$)=NO), 3.26, 3.97 (each data is s; including both peaks, 3H, OC$\underline{H_3}$ 3.26, 3.97 (each data is s; including both peaks, 1H, Pyrimidine ring 6-position), 9.25(s, 1H, Pyrimidine ring 2-position), [CDCl$_3$] | $n_D^{20.3}$ 1.4865 |
| 5-2 | $^1$H-NMR δ (ppm) [solvent]: 1.30(t, J=8Hz, 3H, CH$_2$C$\underline{H_3}$). 2.26, 2.33(each data is.s; including both peaks, 3H, C(C$\underline{H_3}$)=NO). 4.27(q, J=8Hz, 2H, C$\underline{H_2}$CH$_3$), 4.57, 4.78(each data is s; including both peaks, 2H, OC$\underline{H_2}$CO$_2$), 8.94(s, 1H, Pyrimidine ring). 9.42(s, 1H, Pyrimidine ring). [CDCl$_3$] | $n_D^{20.1}$ 1.4640 |
| 5-3 | $^1$H-NMR δ (ppm) [solvent]: 1.30(t, J=7Hz, 3H, CH$_2$C$\underline{H_3}$). 2.24, 2.28(each data is t; J=1 Hz, including both peaks, 3H. C(C$\underline{H_3}$)=NO). 4.23(q, J=7Hz, 2H, C$\underline{H_2}$CH$_3$). 4.53, 4.70(each data is s; including both peaks, 2H, OC$\underline{H_2}$CO$_2$). 8.80, 8.82(each data is s; including both peaks, 1H, Pyrimidine ring 6-position), 9.30(s, 1H, Pyrimidine ring 2-position), [CDCl$_3$] | $n_D^{20.0}$ 1.4851 |
| 5-4 | $^1$H-NMR δ (ppm) [solvent]: 2.32, 2.65(each data is s; including both peaks, 3H, C$\underline{H_3}$ 7.21(d, J=9Hz, 2H, Benzene ring) 7.57(d, J=9Hz, 2H, Benzene ring) 7.91(s, 1H, N$\underline{H}$) 8.94, 9.02(each data is s; including both peaks, 1H, Pyrimidine ring) 9.38, 9.46(each data is s; including bothe peaks, 1H, Pyrimidine ring) [CDCl$_3$] | oil |
| 5-5 | $^1$H-NMR δ (ppm) [solvent]: 1.06(t, J=8Hz, 3H, C$\underline{H_3}$) 1.28(t, J=7Hz, 3H, C$\underline{H_3}$) 2.80(q, J=8Hz, 2H, C$\underline{H_2}$) 4.22(q, J=7Hz, 2H, C$\underline{H_2}$) 4.68(s, 2H, OC$\underline{H_2}$) 8.73(s, 1H, Pyrimidine ring) 9.29(s, 1H, Pyrimidine ring) [CDCl$_3$] | $n_D^{20.7}$ 1.4808 |
| 5-6 | $^1$H-NMR δ (ppm) [solvent]: 0.95(t, J=7Hz, 3H, CH$_2$CH$_2$C$\underline{H_3}$) 1.27(t, J=7Hz, 3H, CH$_2$C$\underline{H_3}$) 0.75~1.95(m, 2H, CH$_2$C$\underline{H_2}$CH$_3$) 2.33~2.97(m, 2H, C$\underline{H_2}$CH$_2$CH$_3$) 4.20(q, J=7Hz, 2H, C$\underline{H_2}$CH$_3$) 4.66(s, 2H, OC$\underline{H_2}$) 8.69(s, 1H, Pyrimidine ring) 9.25(s, 1H, Pyrimidine ring) [CDCl$_3$] | $n_D^{20.5}$ 1.4780 |
| 5-7 | $^1$H-NMR δ (ppm) [solvent]: 1.29(t, J=7Hz, 3H, CH$_2$C$\underline{H_3}$) 2.01~2.46(m, 3H, =C—C$\underline{H_3}$) 4.23(q, J=7Hz, 2H, C$\underline{H_2}$CH$_3$) 4.70(s, 2H, OC$\underline{H_2}$) 8.76(s, 1H, Pyrimidine ring) 9.30(s, 1H, Pyrimidine ring) [CDCl$_3$] | $n_D^{19.8}$ 1.4574 |

TABLE 5-2-continued

| Compound No. | Spectral data | Physical properties |
|---|---|---|
| 5-8 | $^1$H-NMR δ (ppm) [solvent]:<br>2.59(s, 6H, N(C$\underline{H}_3$)$_2$)<br>6.7–7.6(m, 4H, Benzene ring)<br>8.72(s, 1H, Pyrimidine ring)<br>9.23(s, 1H, Pyrimidine ring)<br>[CDCl$_3$] | $n_D^{19.8}$ 1.5732 |

Tables 1-3, 1-4, 2-3, 2-4, 3-3, 4-3 and 5-3 show the compounds of the present invention which can be synthesized in accordance with the above-mentioned Schemes for synthesis and Examples, including the compounds synthesized in the above Examples. However, it should be understood that the present invention is by no means restricted by such specific Examples.

TABLE 1-3

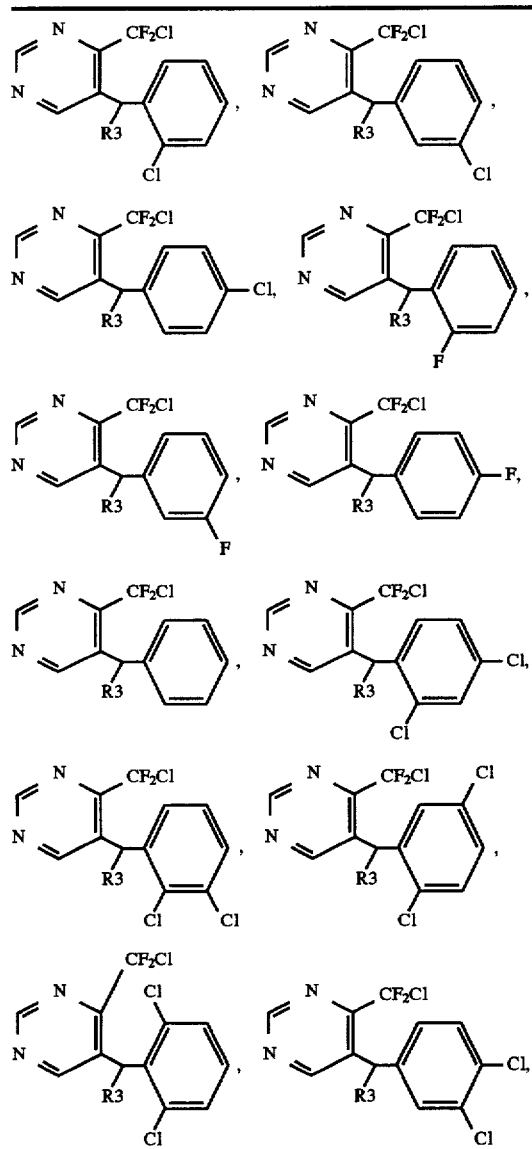

TABLE 1-3-continued

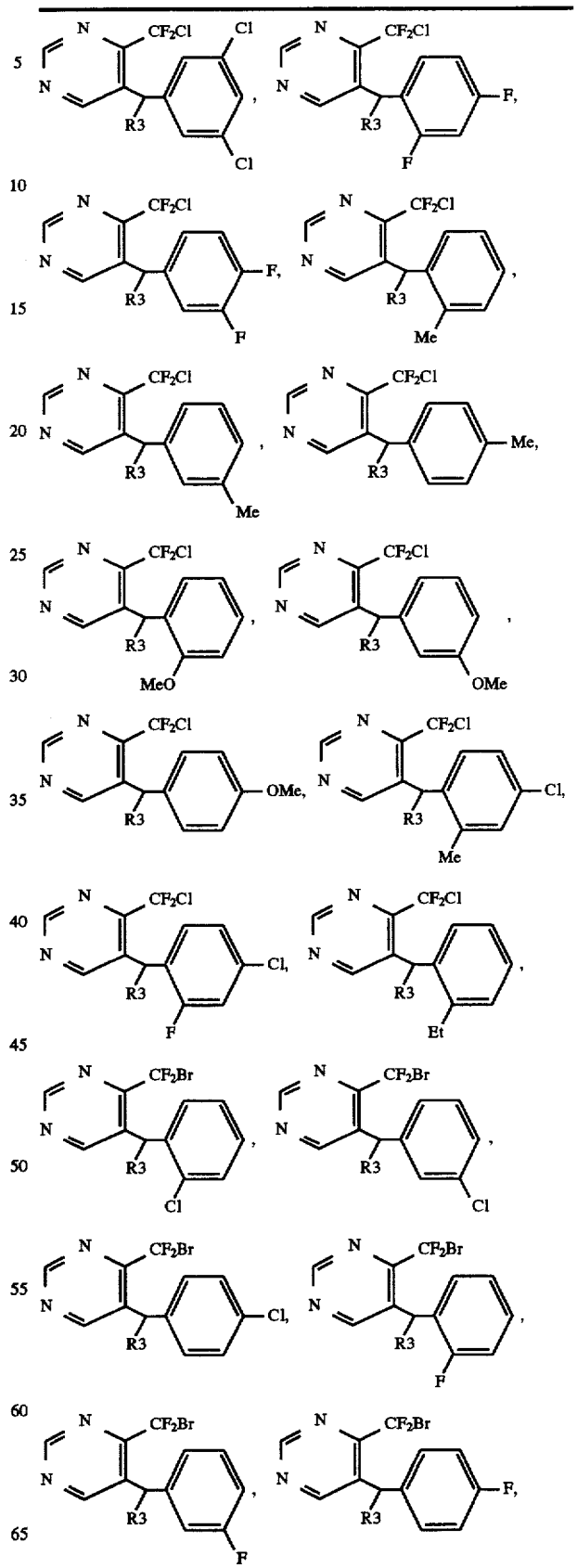

TABLE 1-3-continued
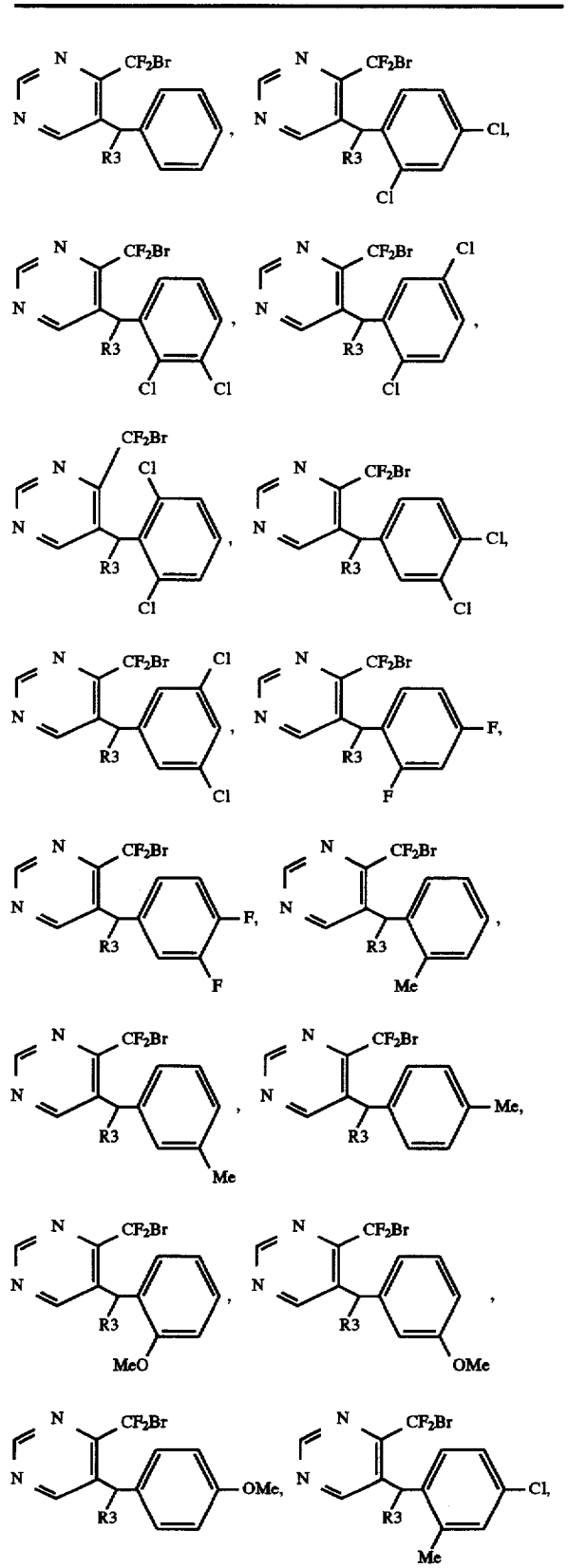
TABLE 1-3-continued
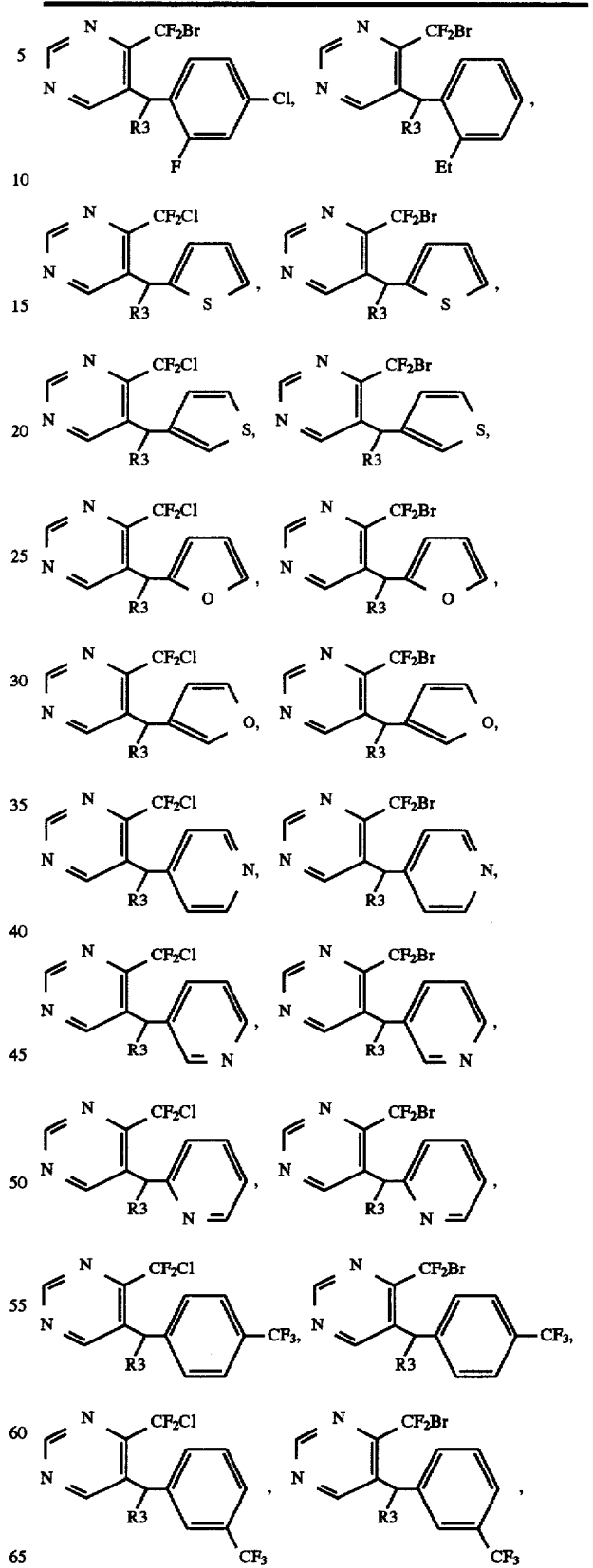

TABLE 1-3-continued

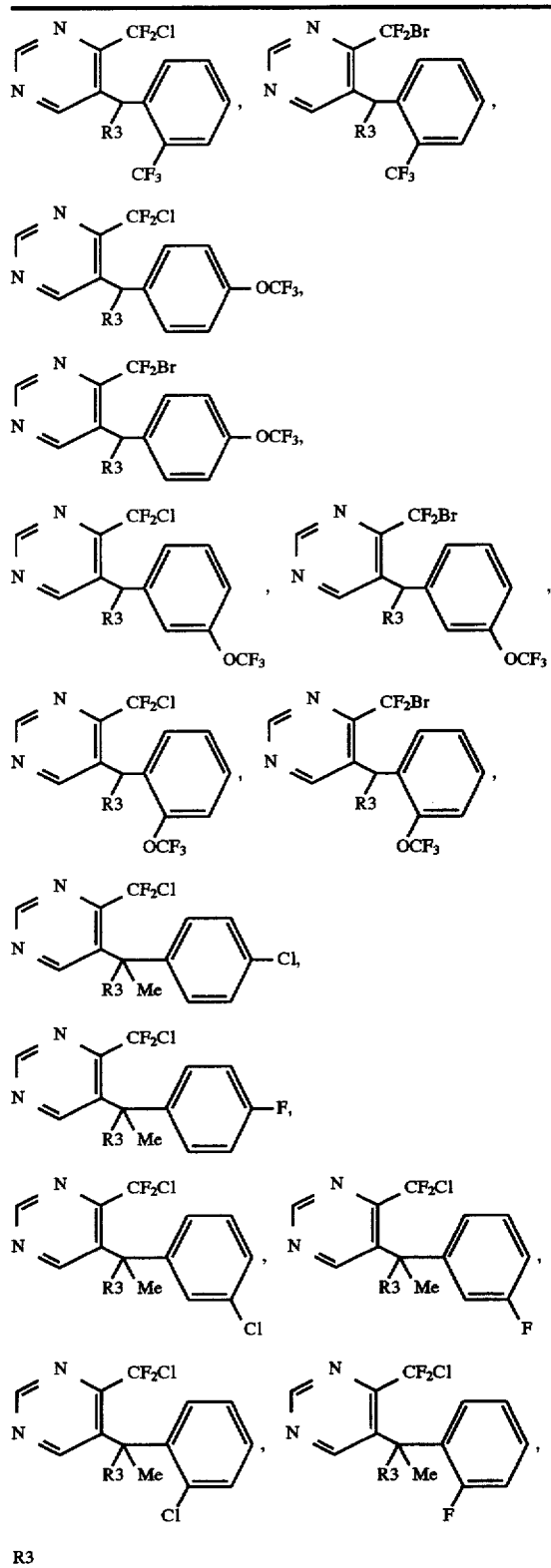

R3
Cl, Br, I,
OMe, OEt, OPr$^n$, OPr$^{iso}$, OBu$^n$, OBu$^{cyclo}$,
OPr$^{cyclo}$, OBu$^{iso}$, OBu$^{sec}$, OBu$^{tert}$, OPn$^n$,
OPn$^{cyclo}$, OPn$^{tert}$, OPn$^{iso}$, OPn$^{neo}$, OHex$^n$, OHep$^n$, TABLE 1-3-continued OOct$^n$, OHex$^{cyclo}$, OPh, O-(4-Cl—Ph),
O-(3-Cl—Ph), O-(2-Cl—Ph), O-(4-F—Ph),
O-(3-F—Ph), O-(2-F—Ph), O-(4-Br—Ph),
O-(3-Br—Ph), O-(2-Br—Ph), O-(4-Me—Ph),
O-(3-Me—Ph), O-(2-Me—Ph), O-(4-MeO—Ph),
O-(3-MeO—Ph), O-(2-MeO—Ph),
O-(4-CF$_3$—Ph), O-(3-CF$_3$—Ph),
O-(2-CF$_3$—Ph), O—THP
OCH$_2$Ph, OCH$_2$CH$_2$Ph, OCH(Me)CH$_2$Ph,
OCH$_2$CH(Me)Ph, OCH(Me)Ph,
OCH$_2$-(4-Cl—Ph), OCH$_2$-(3-Cl—Ph),
OCH$_2$-(2-Cl—Ph), OCH$_2$-(4-F—Ph),
OCH$_2$-(3-F—Ph), OCH$_2$-(2-F—Ph),
OCH$_2$-(4-Me—Ph), OCH$_2$-(3-Me—Ph),
OCH$_2$-(2-Me—Ph), OCH$_2$-(4-MeO—Ph),
OCH$_2$-(3-MeO—Ph), OCH$_2$-(2-MeO—Ph),
OCH$_2$(2,4-Cl$_2$—Ph), OCH$_2$-(3,4-Cl$_2$—Ph)
OCH$_2$-(3,5-Cl$_2$—Ph), OCH$_2$-(2,6-Cl$_2$—Ph)
OCH$_2$-(2,3-Cl$_2$—Ph), OCH$_2$Pr$^{cyclo}$,
OCH$_2$CH=CH$_2$, OCH$_2$C≡CH, OCH(Me)C≡CH,
OCH(Me)CH=CH$_2$, OC(Me)$_2$C≡CH, OC(Me)$_2$CH=CH$_2$,
OCH$_2$CO$_2$Me, OCH$_2$CO$_2$Et,
OCH(Me)CO$_2$Me, OCH(Me)CO$_2$Et,
OCO$_2$Me, OCO$_2$Et,
OCH$_2$OMe, OCH$_2$OEt, OCH$_2$SMe,
OCH$_2$SEt, OC(Me)$_2$OMe, OC(Me)$_2$Pr,
OC(Me)$_2$C≡N, OCH$_2$C≡N, OCH(Me)C≡N, OC(=O)N(Me)$_2$, OC(=O)NHMe, OC(=O)NHEt,
OC(=O)NHPr$^n$, OC(=O)NHPr$^{iso}$,
OC(=O)N(Et)$_2$, OC(=O)NHBu$^{tert}$,
OC(=O)N(Pr$^n$)$_2$, OC(=O)N(Pr$^{iso}$)$_2$,
OC(=S)NHMe, OC(=S)NHEt, OC(=S)NHPr$^n$,
OC(=S)NHPr$^{iso}$, OC(=S)NHBu$^{tert}$,
OC(=S)N(Me)$_2$, OC(=O)Bu$^{tert}$, OC(=O)Bu$^{sec}$,
OC(=O)Bu$^{sec}$, OC(=)Bu$^n$, OC(=O)Pr$^{iso}$,
OC(=O)Pr$^n$, OC(=O)Et, OC(=O)Me,
OC(=S)N(Et)$_2$
OSO$_2$Me, OSO$_2$Et, OSO$_2$N(Me)$_2$, OSO$_2$N(Et)$_2$,
SH, SMe, SEt, SPr$^n$, SPr$^{iso}$, SBu$^{tert}$,
SBu$^n$, SBu$^{tert}$, SBu$^{iso}$, SPh, SCH$_2$Ph
SCH$_2$CH=CH$_2$, SCH$_2$C≡CH, SCH(Me)C≡CH, SCH(Me)CH=CH$_2$, SC(Me)$_2$C≡CH, SC(Me)$_2$CH=CH$_2$, SCH$_2$CO$_2$Me, SCH$_2$CO$_2$Et,
SCH(Me)CO$_2$Me, SCH(Me)CO$_2$Et, SCO$_2$Me,
SCO$_2$Et, SCH$_2$OMe, SCH$_2$OEt, SCH$_2$SMe,
SCH$_2$SEt, SC(Me)$_2$OMe, SC(Me)$_2$Pr,
SC(Me)$_2$C≡N, SCH$_2$C≡N, SCH(Me)C≡N, SC(=O)N(Me)$_2$, SC(=O)N(Et)$_2$,
SC(=O)NHMe, SC(=O)NHPr$^n$,
SC(=O)NHPr$^{iso}$, SC(=O)NHBu$^{tert}$,
SC(=O)NHEt, SC(=S)N(Me)$_2$,
SC(=S)N(Et)$_2$, SC(=O)Bu$^{tert}$, SC(=O)Pr$^{iso}$,
SC(=S)Bu$^{tert}$, SC(=S)Pr$^{iso}$
NH$_2$, NHMe, NHEt, NHPr$^{iso}$, NHPr$^n$, NHBu$^{tert}$,
NHBu$^{sec}$, NHBu$^{iso}$, NHBu$^n$, NMe$_2$, NEt$_2$,
N(ME)Et, N(OMe)Me, NHOMe, NHCH$_2$CH$_2$OH,
NHCH$_2$CH=CH$_2$, NHCH$_2$C≡CH, NHC(Me)$_2$C≡CH, NHC(Me)$_2$CH=CH$_2$, NHCH(Me)C≡CH, NHCH(Me)CH=CH$_2$, NHC(Me)$_2$CO$_2$H,
N(Me)CH$_2$CO$_2$Et, NHPn$^n$, NHPn$^{cyclo}$,
NHPr$^{cyclo}$, NHBu$^{cyclo}$, NHPn$^{tert}$, NHPn$^{iso}$,
NHPn$^{neo}$, NHHex$^n$, MHHep$^n$, NHHex$^{cyclo}$,
NHOCt$^n$, NHPh, NHCH$_2$Ph, NHCH$_2$CH$_2$Ph,
NHC(Me)$_2$Ph, N(Pr$^{iso}$)$_2$, N(Pr$^n$)$_2$
NHC(Me)$_2$CO$_2$Me, NHC(Me)$_2$CO$_2$Et,
N(Me)CH$_2$CO$_2$Et, N(Me)CH$_2$CO$_2$Me
N(CH$_2$C≡CH)$_2$, N(CH$_2$CH=CH$_2$)$_2$, NHCH$_2$-(4-Cl—Ph), NHCH$_2$-(3-Cl—Ph),
NHCH$_2$-(2-Cl—Ph), NHCH$_2$-(4-F—Ph),
NHCH$_2$-(3-F—Ph), NHCH$_2$-(2-F—Ph),

TABLE 1-3-continued

NHCH$_2$-(4-Me—Ph), NHCH$_2$-(3-Me—Ph),
NHCH$_2$-(2-Me—Ph), NHCH$_2$-(4-MeO—Ph),
NHCH$_2$-(3-MeO—Ph), NHCH$_2$-(2-MeO—Ph),
N(Me)CH$_2$Ph, N(CHO)CH$_2$Ph, N(CHO)Ph,
NHSO$_2$Me, NHSO$_2$Et, NHSO$_2$N(Me)$_2$
NHSO$_2$N(Et)$_2$, NHC(Me)$_2$C≡N,

NHC(=O)Me, NHC(=O)Et, NHC(=O)Pr$^n$,
NHC(=O)Pr$^{iso}$, NHC(=O)Bu$^{tert}$,
NHC(=O)N(Me)$_2$, NHC(=O)N(Et)$_2$,
NHC(=O)NHMe, NHC(=O)NHEt,
NHC(=O)NHPr$^{iso}$, NHC(=O)NHPr$^n$,
NHC(=O)NHBu$^{tert}$, NHC(=S)NHMe,
NHC(=S)NHEt, NHC(=S)NHPr$^n$,
NHC(=S)NHPr$^{iso}$, NHC(=S)NHBu$^{tert}$,
NHC(=S)N(Me)$_2$, NHC(=S)N(Et)$_2$,
NHN(Me)$_2$, NHNHBu$^{tert}$, NHCH$_2$C≡N, NHCH(Me)C≡N, N(Me)Bu$^{tert}$, N(Et)Bu$^{tert}$, N(Me)Pr$^{iso}$, N(Et)Pr$^{iso}$,
1-imidazolyl, 1,2,4-triazol-1-yl, morpholino,
2,6-dimethylmorpholino, piperazino, piperidino, pyrrolidinyl, aziridinyl

TABLE 1-4

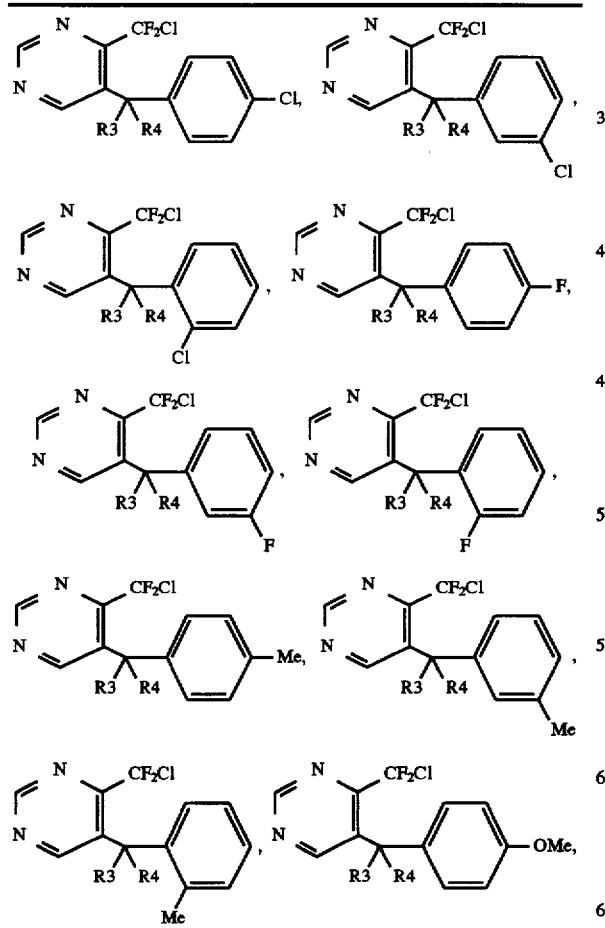

TABLE 1-4-continued

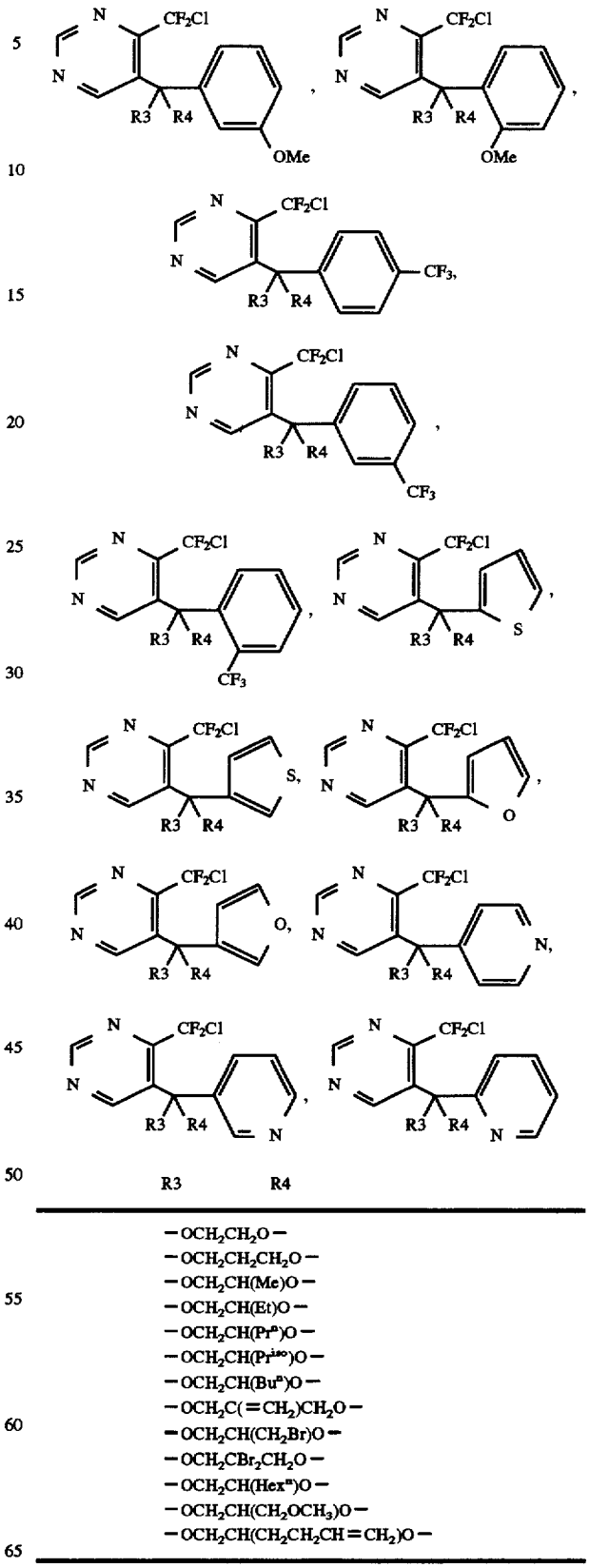

—OCH$_2$CH$_2$O—
—OCH$_2$CH$_2$CH$_2$O—
—OCH$_2$CH(Me)O—
—OCH$_2$CH(Et)O—
—OCH$_2$CH(Pr$^n$)O—
—OCH$_2$CH(Pr$^{iso}$)O—
—OCH$_2$CH(Bu$^n$)O—
—OCH$_2$C(=CH$_2$)CH$_2$O—
—OCH$_2$CH(CH$_2$Br)O—
—OCH$_2$CBr$_2$CH$_2$O—
—OCH$_2$CH(Hex$^n$)O—
—OCH$_2$CH(CH$_2$OCH$_3$)O—
—OCH$_2$CH(CH$_2$CH$_2$CH=CH$_2$)O—

TABLE 2-3
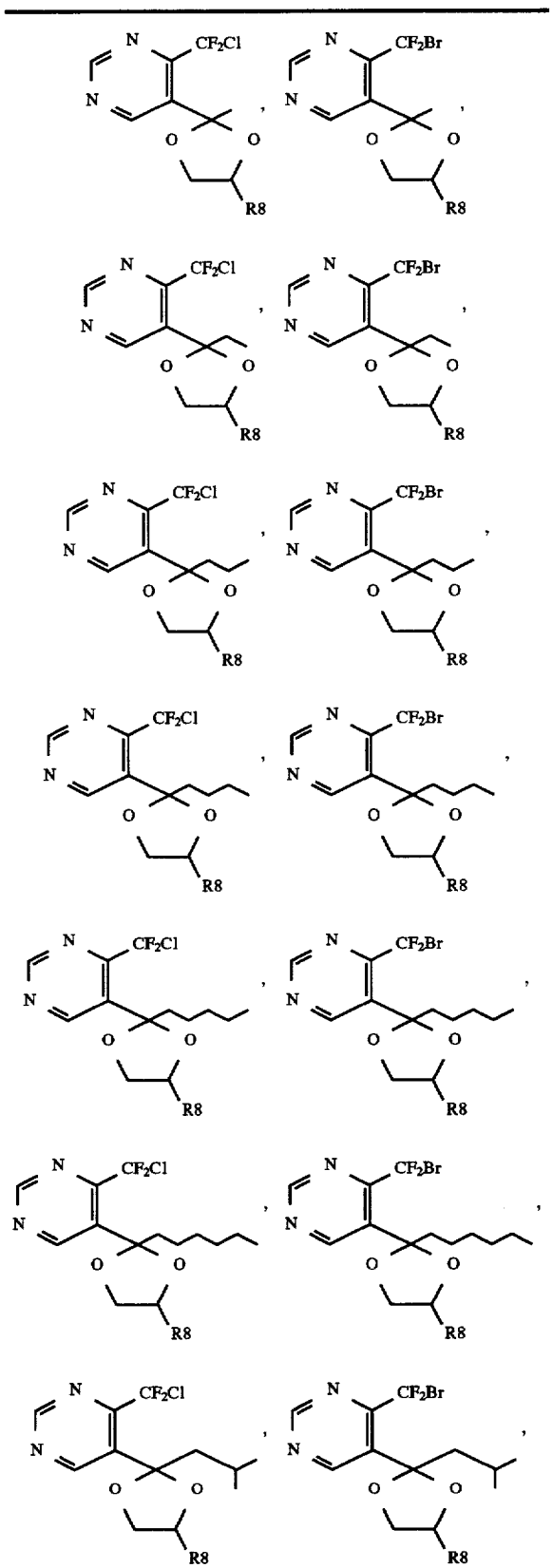
TABLE 2-3-continued
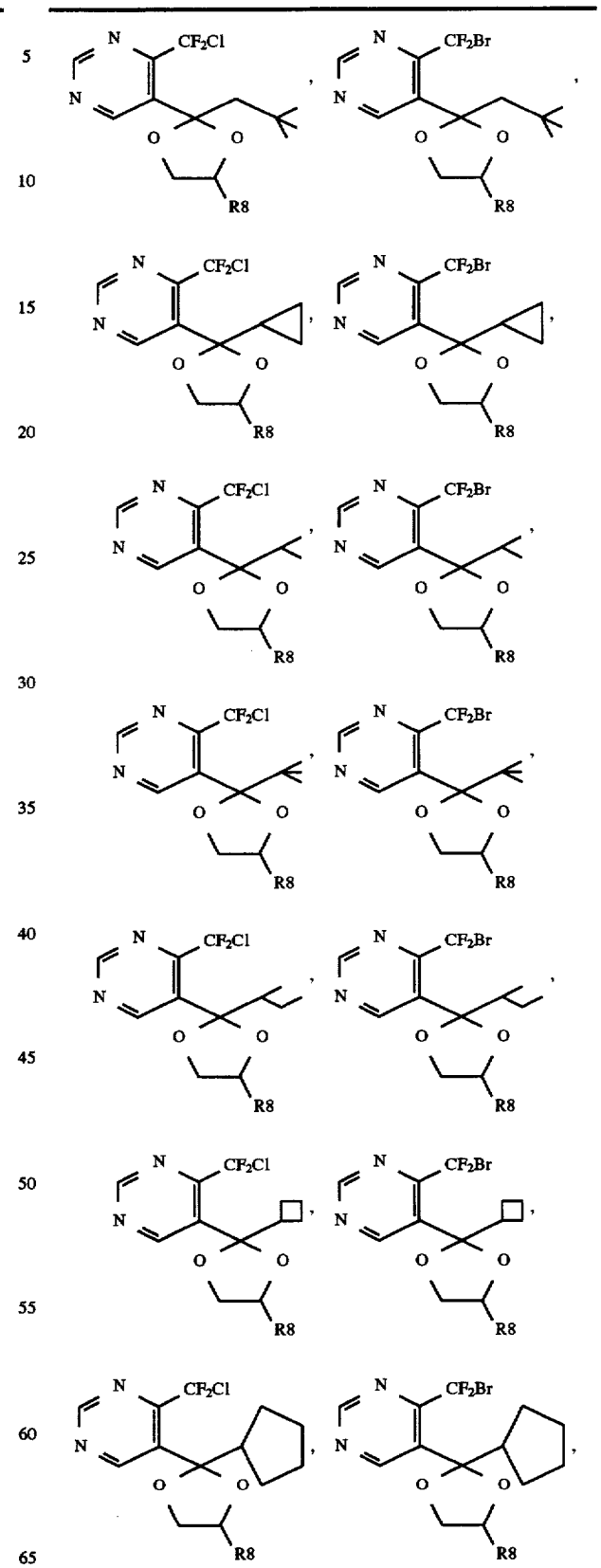

TABLE 2-3-continued

[Structures: Four pyrimidine-based compounds with CF₂Cl or CF₂Br groups, dioxane rings, and cyclohexyl or cyclopropyl substituents, all with R8 groups]

R8

H
Me
Et
Pr$^n$
Pr$^{iso}$
Bu$^n$
Bu$^{sec}$
Bu$^{iso}$
Bu$^{tert}$
Pn$^n$
Pn$^{neo}$
Hex$^n$
n-C$_{10}$H$_{21}$
n-C$_{14}$H$_{29}$
n-C$_{12}$H$_{25}$
n-C$_6$H$_{13}$
n-C$_8$H$_{17}$
n-C$_{16}$H$_{33}$
Ph
2-NO$_2$—Ph
CH$_2$CH$_2$CH=CH$_2$
CH$_2$CH$_2$CH$_2$CH$_2$CH=CH$_2$
CH$_2$F
CH$_2$Cl
CH$_2$Br
n-C$_6$F$_{13}$—CH$_2$CH$_2$
n-C$_8$F$_{17}$
CH$_2$OPh
CH$_2$O—(2-Me—Ph)
CH$_2$O—(n-C$_{18}$H$_{37}$)
CH$_2$OC$_2$H$_5$
CH$_2$OCH$_2$Ph
CH$_2$O—(2-MeO—Ph)
CH$_2$O—(3-MeO—Ph)
CH$_2$OCH$_2$—(2-MeO—Ph)
CH$_2$OCH$_2$—(2-Me—Ph)
CH$_2$O—(2-Et—Ph)
CH$_2$O—(2-F—Ph)
CH$_2$O—(4-F—Ph)
CH$_2$O—(2-Cl-6-Me—Ph)
CH$_2$O—(n-C$_{16}$H$_{33}$)
CH$_2$O—(4-MeO—Ph)
CH$_2$O—(n-C$_{10}$H$_{21}$)
CH$_2$O—(n-C$_{12}$H$_{25}$)
CH$_2$O—(4-NO$_2$—Ph)
CH$_2$O—(n-C$_{12}$H$_{25}$)
CH$_2$O—Bu$^{tert}$
CH$_2$O—(2,4,6-tri-Me—Ph)
CH$_2$O—Bu$^n$
CH$_2$O—Pr$^n$
CH$_2$O—(n-C$_{14}$H$_{29}$)
CH$_2$OCH$_3$
CH$_2$O—Pr$^{iso}$
CH$_2$OCH$_2$CH=CH$_2$
CH$_2$OCH$_2$C≡CH CH$_2$OH
CH$_2$O—(2-Cl—Ph)
CH$_2$O—(3-Cl—Ph)
CH$_2$O—(4-Cl—Ph)
CH$_2$OCH$_2$—(4-MeO—Ph)
CH$_2$OCH$_2$—(4-Me—Ph)
CH$_2$OCH$_2$—(2-Cl—Ph)
CH$_2$OCH$_2$—(3-Cl—Ph)
CH$_2$OCH$_2$—(4-Cl—Ph)
CH$_2$OCH(Me)Ph
CH$_2$OSiMe$_3$
CH$_2$O-THP
CH$_2$OCH$_2$OMe
CH$_2$OCH$_2$—Pr$^{cyclo}$
CH$_2$—(1-pyrrolidinyl)
CH$_2$NH—Bu$^{tert}$
CH$_2$NMe$_2$
CH$_2$N(Me)CH$_2$Ph
CH$_2$NEt$_2$
CH$_2$—(4-morpholino)
CH$_2$—(1-piperizino)
CH$_2$N(Pr$^{iso}$)$_2$
CH$_2$N(Pr$^n$)$_2$
CH$_2$—(1-piperazino)
CH$_2$NH—Me
CH$_2$NH—(2-NO$_2$-phenyl)
CH$_2$NHCH$_2$Ph
CH$_2$NH—Bu$^n$
CH$_2$NH—He$^{cyclo}$
CH$_2$N(Bu$^n$)$_2$
CH$_2$NH(n-C$_{12}$H$_{25}$)
CH$_2$NH—Et
CH$_2$NH—Ph
CH$_2$NH—Pr$^{iso}$
CH$_2$NH$_2$
CH$_2$NHCH$_2$—(2-Cl—Ph)
CH$_2$NHCH$_2$—(3-Cl—Ph)
CH$_2$NHCH$_2$—(4-Cl—Ph)
CH$_2$NHCH(Me)Ph
CH$_2$NHC(Me)$_2$Ph
CH$_2$SMe
CH$_2$SEt
CH$_2$SPh
CH$_2$SBu$^n$
CH$_2$SPr$^{iso}$
CH$_2$SPr$^n$
CH$_2$SH
CH$_2$CH$_2$Ph
CH$_2$S—(4-Cl—Ph)
CH$_2$OCOCH$_3$
CH$_2$OCOPr$^n$
CH$_2$OCO—(n-C$_{17}$H$_{35}$)
CH$_2$OCO—(n-C$_{11}$H$_{23}$)
CH$_2$OCO—(n-C$_{15}$H$_{31}$)
CH$_2$OCO—(n-C$_{13}$H$_{27}$)
CH$_2$OCO—(n-C$_{19}$H$_{39}$)
CH$_2$OCO—(n-C$_9$H$_{19}$)
CH$_2$OCO—(n-C$_7$H$_{15}$)
CH$_2$OCO—(n-C$_{12}$H$_{25}$)
CH$_2$OCOC(=CH$_2$)CH$_3$
CH$_2$OCOCH=CH$_2$
CH$_2$OCOEt
CH$_2$OCO(n-C$_{14}$H$_{29}$)
CH$_2$OCOPr$^{iso}$
CH$_2$OCOBu$^{tert}$
CH$_2$OCOPh
2-piperidyl
2-pyridyl
2-pyridylmethyl TABLE 2-3-continued

[Structures shown:]

CH₃O—⟨phenyl⟩—N(piperazine)N—COCH₃

CH₂N(piperazine)N—⟨phenyl⟩

CH₃O—⟨phenyl⟩—N(piperazine)N—⟨phenyl⟩—N(triazolinone with sec-butyl)

CH₂N—⟨pyrrole⟩—CH=CH—⟨phenyl⟩—Cl

CH₂O—CH₂—C(CH₃)=CH—CH₂—CH₂—C(CH₃)=CH—CH₃

CH₂O—CH₂—C(CH₃)=CH—CH₂—CH₂—C(CH₃)=CH—CH₂—CH₂—C(CH₃)=CH—CH₃

CH₃S—CH₂—C(CH₃)=CH—CH₂—CH₂—C(CH₃)=CH—CH₂—CH₂—C(CH₃)=CH—CH₃

CH₃S—CH₂—C(CH₃)=CH—CH₂—CH₂—C(CH₃)=CH—CH₃

CH₂NH—CH₂—C(CH₃)=CH—CH₂—CH₂—C(CH₃)=CH—CH₃

CH₂NH—CH₂—C(CH₃)=CH—CH₂—CH₂—C(CH₃)=CH—CH₂—CH₂—C(CH₃)=CH—CH₃

TABLE 2-4

[Pyrimidine structure with CF₂Cl substituent, R9, and 1,3-dioxane ring]

[Pyrimidine structure with CF₂Br substituent, R9, and 1,3-dioxane ring]

TABLE 2-4-continued

[Pyrimidine structure with CF₂Cl substituent, R9, and 1,3-dioxane ring with methylene]

[Pyrimidine structure with CF₂Br substituent, R9, and 1,3-dioxane ring with methylene]

[Pyrimidine structure with CF₂Cl substituent, R9, and 1,3-dioxane ring with two Br substituents]

[Pyrimidine structure with CF₂Br substituent, R9, and 1,3-dioxane ring with two Br substituents]

R9

Me, Et, Pr$^n$, Pr$^{iso}$, Bu$^n$, Bu$^{sec}$, Bu$^{neo}$, Bu$^{tert}$
Pn$^n$, Pn$^{neo}$, Hex$^n$, Hep$^n$, Oct$^n$, Pr$^{cyclo}$, Bu$^{cyclo}$

TABLE 3-3

[Pyrimidine structure with CF₂Cl substituent, CH(R7)—isopropyl]

[Pyrimidine structure with CF₂Br substituent, CH(R7)—isopropyl]

[Pyrimidine structure with CF₂Cl substituent, CH(R7)—cyclopropyl]

TABLE 3-3-continued

TABLE 3-3-continued

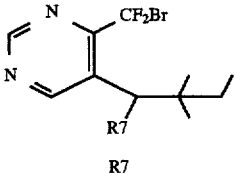

R7

NHCH₂Ph
N(Me)CH₂Ph
N(Et)CH₂Ph
NHCH₂—2-Cl-Phenyl
NHCH₂—3-Cl-Phenyl
NHCH₂—4-Cl-Phenyl
NHCH₂—2-F-Phenyl
NHCH₂—3-F-Phenyl
NHCH₂—4-F-Phenyl
NHCH₂—2,4-Cl₂-Phenyl
NHCH₂—2,3-Cl₂-Phenyl
NHCH₂—2,5-Cl₂-Phenyl
NHCH₂—2,6-Cl₂-Phenyl
NHCH₂—3,4-Cl₂-Phenyl
NHCH₂—3,5-Cl₂-Phenyl
NHCH₂CH₂Ph
NHCH₂CH₂—2-Cl-Phenyl
NHCH₂CH₂—3-Cl-Phenyl
NHCH₂CH₂—4-Cl-Phenyl
NHCH₂CH₂—2-F-Phenyl
NHCH₂CH₂—3-F-Phenyl
NHCH₂CH₂—4-F-Phenyl
NHCH₂CH₂—2-Cl-Phenyl
NHCH₂CH₂CH₂Ph
NHCH₂CH₂CH₂CH₂Ph
NHCH(Me)Ph
NHC(Me)₂Ph
NHC(Me)₂C≡CH

NHCH₂C≡CH

NHCH₂CH=CH₂
NHCH(Me)C≡CH morphorino
2,6-dimethylmorphorino
thiomorphorino
piperidino
2,6-dimethylpiperidino
3,5-dimethylpiperidino
3,3-dimethylpiperidino
aziridyl
2,2-dimethylaziridyl
pyrrolyl
pyrrolydyl
4-methylpiperidyl
2-ethylpiperidyl
4-methylpiperadyl
4-phenylpiperadyl
heptamethyleneimino
hexamethyleneimino
imidazole-1-yl
pyrazole-1-yl
1,2,4-triazole-1-yl
4-phenylpiperidyl
4-benzylpiperidyl
4-dimethylaminopiperidyl
perhydroquinolyl
1,2,3,4-tetrahydroquinoline-1-yl
1,2,3,4-tetrahydro-2-methylquinoline-1-yl
1,2,3,4-tetrahydro-2,2-dimethylquinoline-1-yl
4-trifluoromethylpiperidyl
1,2-dihydro-2,2-dimethylquinoline-1-yl
1,2-dihydro-2,2-dimethyl-6-chloroquinoline-1-yl
N(Me)CH₂—2-Cl-Phenyl
N(Me)CH₂—3-Cl-Phenyl
N(Me)CH₂—4-Cl-Phenyl
N(Me)CH₂CH₂Ph
N(Me)CH(Me)Ph
N(Me)C(Me)₂Ph TABLE 3-3-continued N(Me)CH₂CH₂CH₂Ph
NHCH(Ph)₂
NHCH₂-(2-thienyl)
NH₂, NHMe, NHMe.HCl, NHEt,
NMe₂, NHPrⁿ, NHPrⁱˢᵒ,
N(Me)Et, N(Et)₂, NHBuᵗᵉʳᵗ,
NHPrⁱˢᵒ, N(Me)CH₂CO₂Et,
NHCH₂CH₂OH,
NHPrᶜʸᶜˡᵒ, NHPnᶜʸᶜˡᵒ,
NHHexᶜʸᶜˡᵒ,
N(CHO)CH₂Ph, N(CHO)Buᵗᵉʳᵗ,
N(CHO)Me,
N(CHO)Et
N(CHO)CH₂—2-Cl-Phenyl
N(CHO)CH₂—3-Cl-Phenyl
N(CHO)CH₂—4-Cl-Phenyl
NH—4-Cl-Phenyl
NHPh
NHCH₂—4-Me-Phenyl
NHCH₂—4-Br-Phenyl
NHCH₂—4-CF₃-Phenyl
NHCH₂—4-MeO-Phenyl
NHCH₂—2-F—4-Cl-Phenyl
NHCH₂—3-F—4-Cl-Phenyl
NHCH₂C≡N NHC(Me)₂C≡N

TABLE 4-3

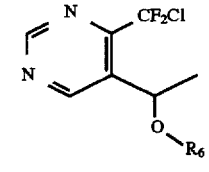

TABLE 4-3-continued

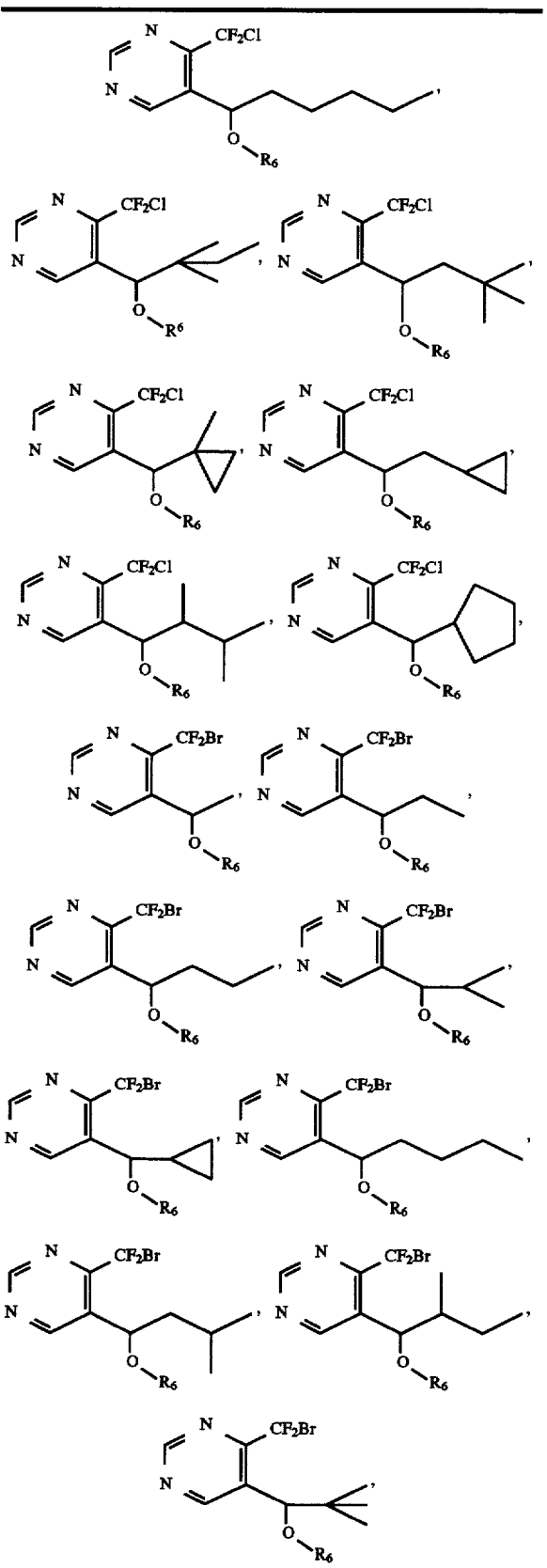
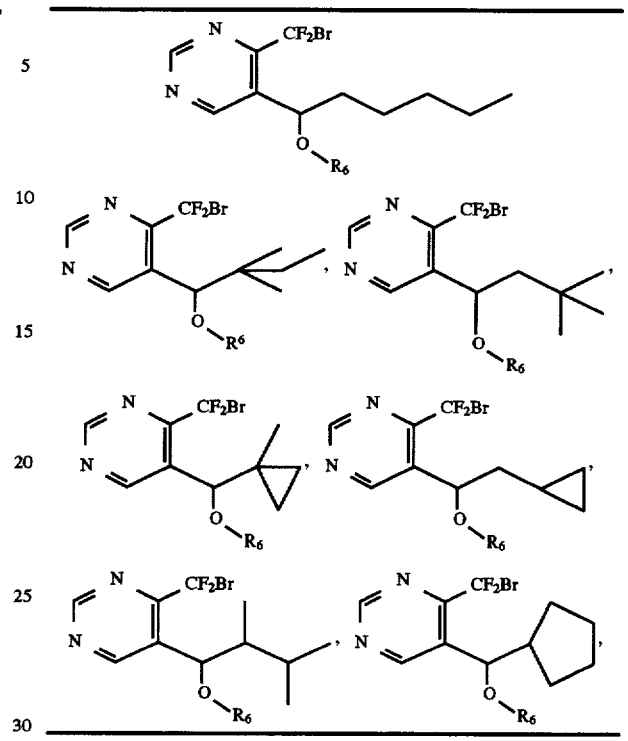

R6

Me, Et, Pr$^n$, Pr$^{iso}$, Bu$^n$, Bu$^{iso}$, Bu$^{sec}$, Bu$^{tert}$,
Pn$^n$, Pn$^{neo}$, Pn$^{iso}$, Hex$^n$, Pr$^{cyclo}$, Pn$^{cyclo}$,
Hex$^{cyclo}$, CH$_2$CH═CH$_2$, CH(Me)CH═CH$_2$,
C(Me)$_2$CH═CH$_2$, CH$_2$C≡CH, CH(Me)C≡CH, C(Me)$_2$C≡CH, CH$_2$CF$_3$, CH(Me)CF$_3$, CH$_2$C(Cl)═CH$_2$, Ph, 2-Cl-Phenyl,
3-Cl-Phenyl, 4-Cl-Phenyl, 2-F-Phenyl,
3-F-Phenyl, 4-F-Phenyl, 2-Me-Phenyl,
3-Me-Phenyl, 4-Me-Phenyl, 2-MeO-Phenyl,
3-MeO-Phenyl, 4-MeO-Phenyl,
2,3-Cl$_2$-Phenyl, 2,4-Cl$_2$-Phenyl,
2,5-Cl$_2$-Phenyl, 2,6-Cl$_2$-Phenyl,
3,4-Cl$_2$-Phenyl, 3,5-Cl$_2$-Phenyl, CH$_2$Ph,
CH$_2$CH$_2$Ph, COCH$_2$Ph, 2-Cl-Benzyl,
3-Cl-Benzyl, 4-Cl-Benzyl, 2-F-Benzyl,
3-F-Benzyl, 4-F-Benzyl, 2-Me-Benzyl,
3-Me-Benzyl, 4-Me-Benzyl, 2-MeO-Benzyl,
3-MeO-Benzyl, 4-MeO-Benzyl, COMe, COEt,
COPr$^n$, COPr$^{iso}$, COPr$^{cyclo}$, COBu$^n$, COBu$^{sec}$,
COBu$^{iso}$, COBu$^{tert}$, COPh, CO-(2-Cl-Phenyl),
CO-(3-Cl-Phenyl), CO(4-Cl-Phenyl),
CO-(2-F-Phenyl), CO-(3-F-Phenyl),
CO-(4-F-Phenyl), CO-(2-Me-Phenyl),
CO-(3-Me-Phenyl), CO-(4-Me-Phenyl),
CO-(2-MeO-Phenyl), CO-(3-MeO-Phenyl),
CO(4-MeO-Phenyl), SO$_2$Me, SO$_2$Et, SO$_2$Pr$^n$,
SO$_2$Pr$^{iso}$, SO$_2$Ph, SO$_2$-(2-Cl-Phenyl),
SO$_2$-(3-Cl-Phenyl), SO$_2$-(4-Cl-Phenyl),
SO$_2$-(2-F-Phenyl), SO$_2$-(3-F-Phenyl),
SO$_2$-(4-F-Phenyl), SO$_2$-(2-Me-Phenyl),
SO$_2$-(3-Me-Phenyl), SO$_2$-(4-Me-Phenyl),
SO$_2$-(2-MeO-Phenyl),
SO$_2$-(3-MeO-Phenyl),
SO$_2$-(4-MeO-Phenyl), CH$_2$OMe, CH$_2$SMe,
CH$_2$OBu$^{tert}$, CH$_2$SBu$^{tert}$,
Tetrahydropyrane-2-yl,
Tetradydrothiopyrane-2-yl
Tetrahydrofuranyl,
Tetrahydrothiofuranyl,
1,4-dioxane-2-yl,

TABLE 4-3-continued

3-Bromotetrahydropyrane-2-yl,
1-Methoxycyclohexyl, Benzyloxymethyl,
4-Methoxytetrahydropyranyl,
1-Ethoxyethyl,
4-Methoxytetrahydrothiopyranyl,
2,2,2-Trichloroethoxymethyl,
1-Methyl-1-methoxyethyl,
Bis(3-Chloroethoxy)methyl,
1-(2-Chloroethoxy)ethyl,
2-Methoxyethoxymethyl,
1-Methyl-1-benzyloxyethyl,
tert-Butyldimethylsilyl,
Trimethylsilyl, Triethylsilyl
C(Me)$_2$OMe, C(Me)$_2$Pr$^n$, C(Me)$_2$Et,
C(=O)N(Me)$_2$, C(=O)NHEt, C(=S)NHPr$^{iso}$,
CO$_2$Et, CH$_2$CO$_2$Et, C(=O)NHBu$^{tert}$,
C(=O)NEt$_2$, CH$_2$CN

TABLE 5-3

(Structures of compounds with CF$_2$Cl and pyrazine/pyrimidine rings, with various substituents including methyl, ethyl, propyl, isopropyl, cyclopropyl, tert-butyl, phenyl, 4-chlorophenyl, 3-chlorophenyl, 2-chlorophenyl)

TABLE 5-3-continued (Continued structures with 4-fluorophenyl, 3-fluorophenyl, 2-fluorophenyl, 4-methylphenyl, 3-methylphenyl, 2-methylphenyl, 4-methoxyphenyl, 3-methoxyphenyl substituents)

TABLE 5-3-continued

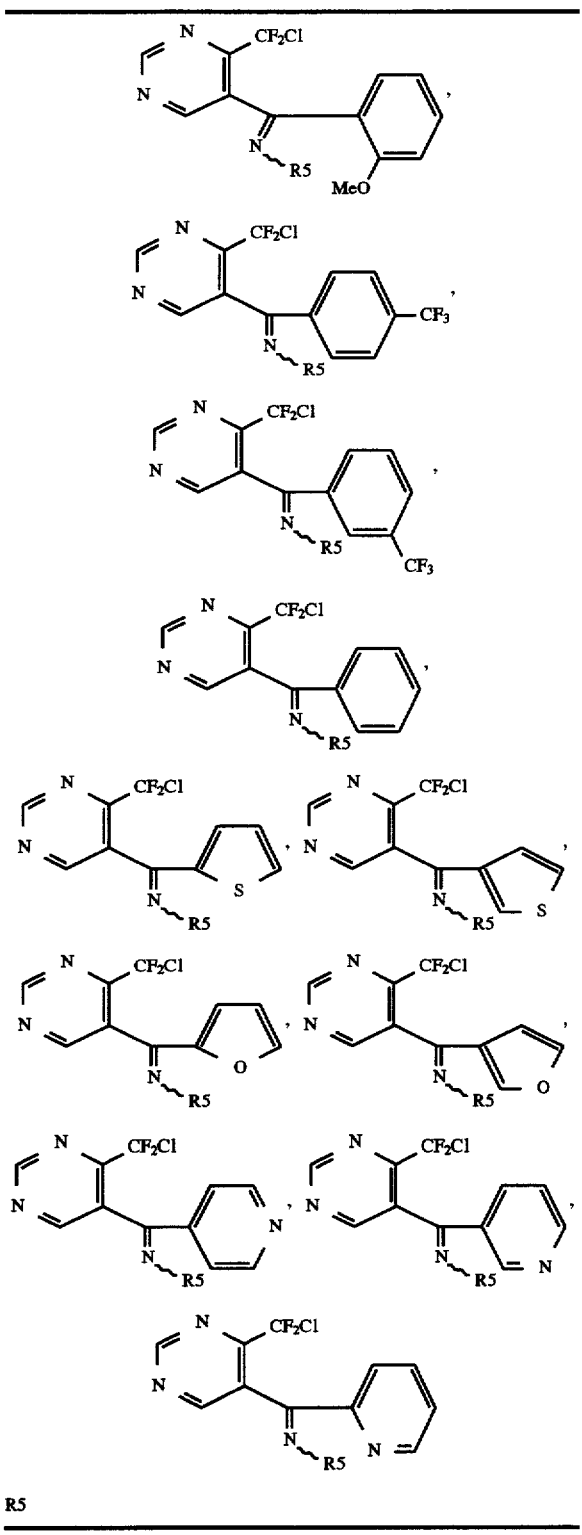

R5

OMe, OEt, OPr$^n$, OPr$^{iso}$, OBu$^n$, OBu$^{iso}$,
OBu$^{sec}$, OBu$^{tert}$, OPr$^{cyclo}$, OBu$^{cyclo}$, OCH$_2$Ph,
OPh, OCH$_2$CO$_2$Me, OCH$_2$CO$_2$Et, OCH$_2$CO$_2$H,
OCH(Me)CO$_2$Me, OCH(Me)CO$_2$Et,
OCH$_2$-(4-Cl—Ph), OCH$_2$-(3-Cl—Ph),
OCH$_2$-(2-Cl—Ph), OH, OCH$_2$C≡CH,

TABLE 5-3-continued

OCH$_2$CH=CH$_2$,
NHMe, N(Me)$_2$, NHEt, NHPr$^n$, NHPr$^{iso}$,
NHBu$^{tert}$, NHPh, NHCH$_2$Ph,
NHCH$_2$-(4-Cl—Ph), NHCH$_2$-(3-Cl—Ph),
NHCH$_2$-(2-Cl—Ph), NH-(4-Cl—Ph),
NH-(3-Cl—Ph), NH-(2-Cl—Ph)
NH-(4-CF$_3$—Ph), NH-(3-CF$_3$—Ph),
NH(2-CF$_3$—Ph), NH-(4-Me—Ph),
NH-(3-Me—Ph), NH-(2-Me—Ph),
NH-(4-MeO—Ph), NH-(3-MeO—Ph),
NH-(2-MeO—Ph), NH-(4-F—Ph),
NH-(3-F—Ph), NH-(2-F—Ph),
OCH$_2$-(4-Me—Ph), OCH$_2$-(3-Me—Ph),
OCH$_2$-(2-Me—Ph), OCH$_2$-(4-F—Ph),
OCH$_2$-(3-F—Ph), OCH$_2$-(2-F—Ph),
OCH$_2$-(4-MeO—Ph), OCH$_2$-(3-MeO—Ph),
OCH$_2$-(2-MeO—Ph)

When the compound of the present invention is used as a herbicide, it is usually mixed with a suitable carrier, for instance, a solid carrier such as clay, talc, bentonite, diatomaceous earth or white carbon, or a liquid carrier such as water, an alcohol (such as isopropanol, butanol, benzyl alcohol or furfuryl alcohol), an aromatic hydrocarbon (such as toluene or xylene), an ether (such as anisole), a ketone (such as cyclohexanone or isophorone), an ester (such as butyl acetate), an acid amide (such as N-methylpyrrolidone) or a hologenated hydrocabron (such as chlorobenzene). If desired, a surfactant, an emulsifier, a dispersing agent, a penetrating agent, a spreader, a thickner, an antifreezing agent, an anticaking agent, or a stabilizer may be added to prepare an optional formulation such as a liquid formulation, an emulsifiable concentrate, a wettable powder, a dry flowable, a flowable, a dust or a granule.

Further, the compound of the present invention may be combined with other herbicides, various insecticides, miticides, nematicides, fungicides, plant growth regulators, synergists, fertilizers, antidotes, or soil conditioning materials at the time of the preparation of the formulations or at the time of the application, as the case requires.

Particularly, combined use of the compound of the present invention with another agricultural chemical can be expected to result in lower cost attributable to reduction in the dose, a broader spectrum and a higher herbicidal effect attributable to synergistic action of the combined chemicals. In such a case, the compound of the present invention can be combined with plural known agricultural chemicals simultaneously. The agricultural chemicals which may be used in combination with the compound of the present invention, may, for example, be compounds disclosed in Farm Chemicals Bandbook (1994).

The dose of the compound of the present invention varies depending upon the application site, the season for application, the manner of application, the type of crop plants and the like. However, it is usually within a range of from 0.00001 to 10 kg, preferably from 0.0001 to 5 kg per hectar (ha) as the amount of the active ingredient.

Now, examples of formulations of the compounds of the present invention will be given. However, it should be understood that the present invention is by no means restricted to such specific examples. In the following Formulation Examples, "parts" means parts by weight.

| Wettable powder | |
|---|---|
| Compound of the present invention | 0.1–80 parts |
| Solid carrier | 10–90 parts |
| Surfactant | 1–10 parts |
| Others | 1–5 parts |

As the others, for example, an anticaking agent may be mentioned.

| Emulsifiable Concentrate | |
|---|---|
| Compound of the present invention | 0.1–30 parts |
| Liquid carrier | 30–95 parts |
| Surfactant | 5–15 parts |
| Flowable | |
| Compound of the present invention | 0.1–70 parts |
| Liquid carrier | 15–65 parts |
| Surfactant | 5–12 parts |
| Others | 5–30 parts |

As the others, for example, an antifreezing agent and a thickner may be mentioned.

| Granular wettable powder (dry flowable) | |
|---|---|
| Compound of the present invention | 0.1–90 parts |
| Solid carrier | 10–70 parts |
| Surfactant | 1–20 parts |
| Granule | |
| Compound of the present invention | 0.0001–10 parts |
| Solid carrier | 90–99.9999 parts |
| Others | 0.1–10 parts |
| Formulation Example 1 Wettable powder | |
| Compound No. 1-9 of the present invention | 50 parts |
| Zeeklite PFP (tradename for a kaolin-type clay, manufactured by Zeeklite Industries, Co., Ltd.) | 43 parts |
| Sorpol 5050 (tradename for an anionic surfactant, manufactured by Toho Chemical Industry Co., Ltd.) | 2 parts |
| Lunox 1000C (tradename for an anionic surfactant, manufactured by Toho Chemical Industry Co., Ltd.) | 3 parts |
| Carplex #80 (anticaking agent) (tradename for a white carbon, manufactured by Shionogi Pharmaceutical Co., Ltd.) | 2 parts |

The above ingredients are homogeneously pulverized and mixed to form a wettable powder.

| Formulation Example 2 Wettable powder | |
|---|---|
| Compound No. 1-15 of the present invention | 50 parts |
| Zeeklite PFP (tradename for a kaolin-type clay, manufactured by Zeeklite Industries, Co., Ltd.) | 43 parts |
| Sorpol 5050 (tradename for an anionic surfactant, manufactured by Toho Chemical Industry Co., Ltd.) | 2 parts |
| Lunox 1000C (tradename for an anionic surfactant, manufactured by Toho Chemical Industry Co., Ltd.) | 3 parts |
| Carplex #80 (anticaking agent) (tradename for a white carbon, manufactured by Shionogi Pharmaceutical Co., Ltd.) | 2 parts |

The above ingredients are homogeneously pulverized and mixed to form a wettable powder.

| Formulation Example 3 Emulsifiable concentrate | |
|---|---|
| Compound No. 1-35 of the present invention | 3 parts |
| Xylene | 76 parts |
| Isophorone | 15 parts |
| Sorpol 3005X (tradename for a mixture of a nonionic surfactant and an anionic surfactant, manufactured by Toho Chemical Industry Co., Ltd.) | 6 parts |

The above ingredients are homogeneously mixed to form an emulsifiable concentrate.

| Formulation Example 4 Emulsifiable conentrate | |
|---|---|
| Compound No. 1-68 of the present invention | 3 parts |
| Xylene | 76 parts |
| Isophorone | 15 parts |
| Sorpol 3005X (tradename for a mixture of a nonionic surfactant and an anionic surfactant, manufactured by Toho Chemical Industry Co., Ltd.) | 6 parts |

The above ingredients are homogeneously mixed to form an emulsifiable concentrate.

| Formulation Example 5 Flowable | |
|---|---|
| Compound No. 2-8 of the present invention | 35 parts |
| Agrizole S-711 (tradename for a nonionic surfactant, manufactured by Kao Corporation) | 8 parts |
| Lunox 1000C (tradename for an anionic surfactant, manufactured by Toho Chemical Industry Co., Ltd.) | 0.5 part |
| 1% Rodopol water (tradename for a thickner, manufactured by Rhone-Poulenc) | 20 parts |
| Ethylene glycol (antifreezing agent) | 8 parts |
| Water | 28.5 parts |

The above ingredients are homogeneously mixed to obtain a flowable.

| Formulation Example 6 Flowable | |
|---|---|
| Compound No. 3-2 of the present invention | 35 parts |
| Agrizole S-711 (tradename for a nonionic surfactant, manufactured by Kao Corporation) | 8 parts |
| Lunox 1000C (tradename for an anionic surfactant, manufactured by Toho Chemical Industry Co., Ltd.) | 0.5 part |
| 1% Rodopol water (tradename for a thickner, manufactured by Rhone-Poulenc) | 20 parts |
| Ethylene glycol (antifreezing agent) | 8 parts |
| Water | 28.5 parts |

The above ingredients are homogeneously mixed to obtain a flowable.

| Formulation Example 7 Granular wettable powder (dry flowable) | |
|---|---|
| Compound No. 3-8 of the present invention | 75 parts |
| Isoban No. 1 (tradename for an anionic surfactant, manufactured by Kuraray Isoprene Chemical Co., Ltd.) | 10 parts |

-continued

| Formulation Example 7 Granular wettable powder (dry flowable) | |
|---|---|
| Vanilex N (tradename for an anionic surfactant, manufactured by Sanyo-Kokusaku Pulp Co., Ltd.) | 5 parts |
| Carplex #80 (tradename for a white carbon, manufactured by Shionogi Pharmaceutical Co., Ltd.) | 10 parts |

The above ingredients were homogeneously pulverized and mixed to form a dry flowable.

| Formulation Example 8 Granular wettable powder (dry flowable) | |
|---|---|
| Compound No. 4-1 of the present invention | 75 parts |
| Isoban No. 1 (tradename for an anionic surfactant, manufactured by Kuraray Isoprene Chemical Co., Ltd.) | 10 parts |
| Vanilex N (tradename for an anionic surfactant, manufactured by Sanyo-Kokusaku Pulp Co., Ltd.) | 5 parts |
| Carplex #80 (tradename for a white carbon, manufactured by Shionogi Pharmaceutical Co., Ltd.) | 10 parts |

The above ingredients were homogeneously pulverized and mixed to form a dry flowable.

| Formulation Example 9 Granule | |
|---|---|
| Compound No. 4-15 of the present invention | 0.1 part |
| Bentonite | 50.0 parts |
| Talc | 44.9 parts |
| Toxanone GR-31A (tradename for an anionic surfactant, manufactured by Sanyo Chemical Industries LTD.) | 5 parts |

The above ingredients are homogeneously mixed and pulverized. A small amount of water was added, and the mixture was stirred, mixed and kneaded, and then granulated by an extrusion-type granulating machine, followed by drying to obtain a granule.

| Formulation Example 10 Granule | |
|---|---|
| Compound No. 4-16 of the present invention | 0.1 part |
| Bentonite | 50.0 parts |
| Talc | 44.9 parts |
| Toxane GR-31A (tradename for an anionic surfactant, manufactured by Sanyo Chemical Industries LTD.) | 5 parts |

The above ingredients are homogeneously mixed and pulverized. A small amount of water was added, and the mixture was stirred, mixed and kneaded, and then granulated by an extrusion-type granulating machine, followed by drying to obtain a granule.

The above wettable powders, emulsifiable concentrates, flowables and granular wettable powders are diluted with water from 50 to 1,000 times before application, and are applied at a dose of from 0.00001 to 10 kg per hectar (ha) as the amount of the active ingredient.

Now, the usefulness of the compounds of the present invention as herbicides will be described in detail with reference to the following Test Examples.

Test Example 1

Test on the herbicidal effects in pre-emergence treatment on weeds under submerged conditions Wagner pots of 1/5000 are were filled with alluvial soil, and water was admixed to form a submerged state with a water depth of 4 cm. Seeds of barnyardgrass, bulrush, ducksalad and toothcup, and tubers of japanese ribbon wapato and perennial flat sedge were planted in the pots, respectively. Then, rice seedlings of 2 leaf stage were transplanted in the pots. The pots were placed in a greenhouse at a temperature of from 25° to 30° C., to culture the plants. A day after the planting, compounds of the present invention formulated in accordance with Formulation Examples were applied to the water surfaces at predetermined doses. Three weeks after the application, the herbicidal effects against various weeds and the influences on rice were determined on the basis of the 5-rank grading such that 0 means no effect, and 5 means complete death. The results are shown in Tables 1-5, 2-5, 3-4, 4-4 and 5-4.

Each No. indicated in these tables corresponds to the compound No. in Examples. The symbols have the following meanings.

A: barnyardgrass, B: bulrush, C: ducksalad, D: toothcup, E: japanese ribbon wapato, F: perennial flat sedge, a: rice Test Example 2

Test on the herbicidal effects in post-emergence treatment on weeds under submerged conditions Wagner pots of 1/5000 are were filled with alluvial soil, and water was admixed to form a submerged state with a water depth of 4 cm. In each of the above pots, seeds of barnyardgrass, bulrush, ducksalad and toothcup were sown. The pots were placed in a greenhouse at a temperature of from 25° to 30° C. to culture the plants. 14 days after the seeding, the compound of the present invention formulated in accordance with Formulation Examples were applied to the water surfaces at predetermined doses. Three weeks after the application, the herbicidal effect against various weeds were determined on the basis of the 5-rank grading such that 0 indicates no effect, and 5 indicates complete death. The results are shown in Tables 1-6, 2-6, 3-5, 4-5 and 5-5.

Each No. indicated in these tables corresponds to the compound No. in Examples. The symbols have the following meanings.

A: barnyardgrass, B: bulrush, C: ducksalad, D: toothcup

Test Example 3

Test on the herbicidal effects in soil treatment

Plastic boxes having a length of 33 cm, a width of 33 cm and a depth of 8 cm were filled with diluvial soil, and seeds of barnyardgrass, green foxtail, wild oat, blackgrass, velvetleaf, common cocklebur, redroot pigweed, morningglory, persian speedwell, common chickweed, rice, corn, wheat, soybean, cotton and sugar beet were sown and covered with soil in a thickness of about 1.5 cm, and then the compounds of the present invention formulated in accordance with Formulation Examples were applied onto the surfaces of the soil uniformly at predetermined doses. Four weeks after the application, the herbicidal effects against each weed and the influences on each crop plant were determined on the basis of the 5-rank grading such that 0 indicates no effect, and 5 indicates complete death. The results are shown in Tables 1-7, 2-7, 3-6, 4-6 and 5-6.

Each No. indicated in these tables corresponds to the compound No. in Examples. The symbols have the following meanings.

G: barnyardgrass, H: green foxtail, I: wild oat, J: blackgrass, K: velvetleaf, L: common cocklebur, M: redroot pigweed, N: morningglory, O: persian speedwell, P: common chickweed, a: rice, b: corn, c: wheat, d: soybean, e: cotton, f: sugar beet

Test Example 4

Test on the herbicidal effects in foliage treatment

A plastic boxes having a length of 33 cm, a width of 33 cm and a depth of 8 cm were filled with a sterilized diluvial soil, and seeds of barnyardgrass, green foxtail, wild oat, blackgrass, velvetleaf, common cocklebur, redroot pigweed, morningglory, persian speedwell, common chickweed, rice, corn, wheat, soybean, cotton and sugar beet were sown, and covered with soil in a thickness of about 1.5 cm. And the boxes were placed in a greenhouse at a temperature of from 25° to 30° C. for 14 days to culture the plants, and the compounds of the present invention formulated in accordance with Formulation Examples were applied to the foliages uniformly at predetermined doses. Four weeks after the application, the herbicidal effects against each weed and the influences on each crop plant were determined on the basis of the 5-rank grading such that 0 indicates no effect, and 5 indicates complete death. The results are shown in Tables 1-8, 2-8, 3-7, 4-7 and 5-7.

Each No. indicated in these tables corresponds to the compound No. in Examples. The symbols have the following meanings.

G: barnyardgrass, H: green foxtail, I: wild oat, J: blackgrass, K: velvetleaf, L: common cocklebur, M: redroot pigweed, N: morningglory, O: persian speedwell, P: common chickweed, a: rice, b: corn, c: wheat, d: soybean, e: cotton, f: sugar beet

TABLE 1-5

| No. | Dose (g/a) | A | B | C | D | E | F | a |
|---|---|---|---|---|---|---|---|---|
| 1-1 | 10 | 5 | 5 | 5 | 5 | 0 | 3 | 0 |
| 1-2 | 10 | 5 | 5 | 5 | 5 | 2 | 3 | 0 |
| 1-3 | 10 | 5 | 5 | 5 | 5 | 0 | 2 | 0 |
| 1-4 | 10 | 5 | 5 | 5 | 5 | 0 | 2 | 0 |
| 1-5 | 10 | 5 | 5 | 5 | 5 | 0 | 3 | 0 |
| 1-6 | 10 | 2 | 0 | 2 | 0 | 2 | 0 | 0 |
| 1-7 | 10 | 5 | 5 | 5 | 5 | 0 | 0 | 0 |
| 1-8 | 10 | 0 | 0 | 0 | 2 | 0 | 0 | 0 |
| 1-9 | 10 | 5 | 5 | 5 | 5 | 0 | 0 | 0 |
| 1-10 | 2.5 | 2 | 0 | — | — | 0 | 0 | 0 |
| 1-12 | 2.5 | 5 | 0 | 5 | 5 | 0 | 0 | 0 |
| 1-14 | 10 | 5 | 5 | 5 | 5 | 2 | 5 | 0 |
| 1-15 | 10 | 5 | 5 | 5 | 5 | 2 | 3 | 0 |
| 1-16 | 10 | 5 | 5 | 5 | 5 | 2 | 3 | 0 |
| 1-17 | 10 | 5 | 5 | 5 | 5 | 0 | 3 | 0 |
| 1-18 | 10 | 5 | 5 | 5 | 5 | 5 | 3 | 1 |
| 1-19 | 10 | 5 | 5 | 5 | 5 | 2 | 3 | 0 |
| 1-20 | 10 | 5 | 5 | 5 | 5 | 4 | 3 | 1 |
| 1-21 | 10 | 5 | 5 | 5 | 5 | 0 | 5 | 0 |
| 1-22 | 10 | 5 | 5 | 5 | 5 | 3 | 5 | 0 |
| 1-23 | 10 | 5 | 5 | 5 | 5 | 4 | 5 | 0 |
| 1-24 | 10 | 5 | 5 | 5 | 5 | 5 | 0 | 0 |
| 1-25 | 10 | 5 | 5 | 5 | 5 | 0 | 5 | 0 |
| 1-26 | 10 | 5 | 5 | 5 | 5 | 0 | 5 | 0 |
| 1-27 | 10 | 5 | 5 | 5 | 5 | 4 | 4 | 1 |
| 1-28 | 10 | 5 | 5 | 5 | 5 | 5 | 0 | 0 |
| 1-29 | 10 | 5 | 5 | 5 | 5 | 5 | 3 | 0 |
| 1-30 | 10 | 5 | 5 | 5 | 5 | 5 | 5 | 0 |
| 1-31 | 10 | 5 | 5 | 5 | 5 | 5 | 3 | 1 |
| 1-32 | 10 | 5 | 5 | 5 | 5 | 5 | 3 | 0 |
| 1-33 | 10 | 5 | 5 | 5 | 5 | 5 | 5 | 0 |
| 1-34 | 2.52 | 5 | 3 | 5 | 5 | 0 | 0 | 0 |
| 1-35 | 10 | 5 | 5 | 5 | 5 | 5 | 5 | 0 |
| 1-36 | 10 | 5 | 5 | 5 | 5 | 5 | 5 | 0 |
| 1-37 | 10 | 5 | 5 | 5 | 5 | — | 5 | 1 |
| 1-38 | 10 | 5 | 5 | 5 | 5 | 5 | 4 | 1 |

TABLE 1-5-continued

| No. | Dose (g/a) | A | B | C | D | E | F | a |
|---|---|---|---|---|---|---|---|---|
| 1-39 | 10 | 5 | 5 | 5 | 5 | 0 | 4 | 1 |
| 1-40 | 10 | 5 | 5 | 5 | 5 | 5 | 5 | 1 |
| 1-41 | 10 | 3 | 2 | 3 | 5 | 5 | 0 | 0 |
| 1-42 | 10 | 5 | 5 | 5 | 5 | 5 | 2 | 0 |
| 1-43 | 10 | 5 | 5 | 5 | 5 | 5 | 3 | 0 |
| 1-44 | 10 | 5 | 5 | 5 | 5 | 5 | 3 | 0 |
| 1-45 | 10 | 5 | 5 | 5 | 5 | — | — | 0 |
| 1-46 | 10 | 5 | — | 5 | — | 4 | — | 1 |
| 1-47 | 10 | 5 | 5 | 5 | — | — | — | 0 |
| 1-48 | 10 | 5 | 5 | 5 | 5 | 5 | 2 | 0 |
| 1-49 | 10 | 5 | 5 | 5 | 5 | 0 | 5 | 0 |
| 1-50 | 10 | 5 | 5 | 5 | 5 | 0 | 0 | 3 |
| 1-51 | 10 | 5 | 5 | 5 | 5 | 0 | 3 | 0 |
| 1-52 | 10 | 5 | 5 | 5 | 5 | 0 | 3 | 0 |
| 1-53 | 10 | 5 | 5 | 5 | 5 | 0 | 0 | 1 |
| 1-54 | 10 | 5 | 5 | 5 | 5 | — | — | 0 |
| 1-55 | 6 | 5 | 5 | 5 | 5 | — | — | 0 |
| 1-56 | 2.52 | 5 | 5 | 5 | 5 | — | — | 1 |
| 1-57 | 10 | 5 | 5 | 5 | 5 | 0 | 0 | 0 |
| 1-58 | 10 | 5 | 5 | 5 | 5 | 0 | 0 | 0 |
| 1-59 | 10 | 5 | 5 | 5 | 5 | — | — | 0 |
| 1-60 | 10 | 5 | 5 | 5 | 5 | 0 | 0 | 0 |
| 1-61 | 10 | 5 | 5 | 5 | 5 | 0 | 0 | 0 |
| 1-62 | 10 | 5 | 5 | 5 | 5 | 0 | 2 | 0 |
| 1-63 | 10 | 5 | 5 | 5 | 5 | 0 | 0 | 0 |
| 1-64 | 10 | 5 | 5 | 5 | 5 | 0 | 3 | 0 |
| 1-65 | 10 | 5 | 5 | 5 | 5 | 0 | 3 | 1 |
| 1-66 | 10 | 5 | 5 | 5 | 5 | 0 | 0 | 0 |
| 1-67 | 10 | 5 | 5 | 5 | 5 | 0 | 0 | 0 |
| 1-68 | 10 | 5 | 5 | 5 | 5 | 0 | 3 | 0 |
| 1-69 | 10 | 5 | 5 | 5 | 5 | 0 | 0 | 0 |
| 1-70 | 10 | 5 | 5 | 5 | 5 | 3 | 0 | 0 |
| 1-71 | 10 | 5 | 5 | 5 | 5 | 0 | 0 | 0 |
| 1-72 | 10 | 5 | 5 | 5 | 5 | 0 | 0 | 0 |
| 1-73 | 10 | 5 | 5 | 5 | 5 | 0 | 0 | 0 |
| 1-74 | 10 | 5 | 5 | 5 | 5 | 0 | 0 | 0 |
| 1-75 | 10 | 5 | 5 | 5 | 5 | 0 | 0 | 0 |
| 1-76 | 10 | 5 | 5 | 5 | 5 | 0 | 1 | 0 |
| 1-77 | 10 | 5 | 5 | 5 | 5 | 0 | — | 0 |
| 1-78 | 10 | 5 | 5 | 5 | 5 | 2 | 1 | 0 |
| 1-79 | 10 | 5 | 5 | 5 | 5 | 0 | 0 | 0 |
| 1-80 | 10 | 5 | 4 | 4 | 5 | 4 | 3 | 2 |
| 1-81 | 10 | 5 | 5 | 5 | 5 | 2 | 0 | 0 |
| 1-82 | 10 | 5 | 5 | 5 | 5 | 0 | 0 | 0 |
| 1-83 | 10 | 5 | 5 | 5 | 5 | 3 | — | 0 |
| 1-84 | 10 | 5 | 5 | 5 | 5 | 0 | 0 | 0 |
| 1-85 | 10 | 5 | 5 | 5 | 5 | 0 | 0 | 0 |
| 1-86 | 10 | 5 | 5 | 5 | 5 | 2 | — | 3 |
| 1-87 | 10 | 3 | 3 | 4 | 5 | 0 | 0 | 0 |
| 1-88 | 10 | 5 | 5 | 5 | 5 | 0 | 0 | 0 |
| 1-89 | 10 | 5 | 5 | 5 | 5 | 0 | — | 0 |
| 1-90 | 10 | 5 | 5 | 5 | 5 | 0 | 0 | 0 |
| 1-91 | 10 | 5 | 5 | 5 | 5 | 0 | 0 | 0 |
| 1-92 | 10 | 5 | 5 | 5 | 5 | 0 | 3 | 0 |
| 1-93 | 10 | 5 | 5 | 5 | 5 | 2 | 0 | 0 |
| 1-94 | 10 | 5 | 5 | 5 | 5 | 0 | 0 | 0 |
| 1-95 | 10 | 5 | 5 | 5 | 5 | 0 | 5 | 0 |
| 1-96 | 10 | 5 | 5 | 5 | 5 | 0 | 0 | 0 |
| 1-97 | 10 | 5 | 5 | 5 | 5 | 4 | 5 | 3 |
| 1-98 | 10 | 2 | 3 | 3 | 5 | 0 | 0 | 0 |
| 1-99 | 10 | 2 | 3 | 3 | 5 | 0 | 0 | 0 |
| 1-100 | 10 | 3 | 5 | 5 | 5 | 0 | 2 | 0 |
| 1-101 | 10 | 5 | 5 | 5 | 5 | 0 | 2 | 0 |
| 1-102 | 10 | 3 | 2 | 5 | 5 | 0 | 0 | 0 |
| 1-103 | 4.4 | 3 | 3 | 5 | 5 | 0 | 0 | 0 |
| 1-104 | 10 | 5 | 5 | 5 | 5 | 0 | 0 | 0 |
| 1-105 | 10 | 5 | 5 | 5 | 5 | 0 | 0 | 0 |
| 1-106 | 10 | 5 | 5 | 5 | 5 | 0 | 0 | 0 |
| 1-107 | 10 | 3 | 0 | 0 | 5 | 0 | 0 | 0 |
| 1-108 | 10 | 5 | 5 | 5 | 5 | 0 | 0 | 0 |
| 1-109 | 10 | 5 | 5 | 5 | 5 | 0 | 0 | 0 |
| 1-110 | 10 | 4 | 3 | 5 | 5 | 0 | 0 | 0 |
| 1-111 | 10 | 4 | 5 | 5 | 5 | 0 | 3 | 0 |
| 1-112 | 10 | 0 | 0 | 3 | 5 | 0 | 0 | 0 |
| 1-113 | 10 | 5 | 5 | 5 | 5 | 0 | 0 | 0 |
| 1-114 | 10 | 2 | 4 | 4 | 5 | 0 | 0 | 0 |

TABLE 1-6

| No. | Dose (g/a) | A | B | C | D |
|---|---|---|---|---|---|
| 1-1 | 10 | 5 | 3 | 5 | 4 |
| 1-2 | 10 | 5 | 2 | 5 | 4 |
| 1-3 | 10 | 3 | 0 | 5 | 4 |
| 1-4 | 10 | 5 | 0 | 4 | 4 |
| 1-5 | 10 | 5 | 0 | 5 | 4 |
| 1-7 | 10 | 0 | 0 | 4 | 4 |
| 1-9 | 10 | 5 | 5 | 5 | 5 |
| 1-12 | 2.5 | 0 | 0 | 0 | 5 |
| 1-14 | 10 | 5 | 3 | 5 | 5 |
| 1-15 | 10 | 5 | 4 | 5 | 5 |
| 1-16 | 10 | 5 | 2 | 4 | 5 |
| 1-17 | 10 | 5 | 5 | 5 | 5 |
| 1-18 | 10 | 5 | 4 | 5 | 5 |
| 1-19 | 10 | 5 | 5 | 5 | 5 |
| 1-20 | 10 | 5 | 5 | 5 | 5 |
| 1-21 | 10 | 5 | 5 | 5 | 5 |
| 1-22 | 10 | 5 | 5 | 5 | 5 |
| 1-23 | 10 | 5 | 5 | 5 | 5 |
| 1-24 | 10 | 5 | 5 | 5 | 5 |
| 1-25 | 10 | 5 | 5 | 5 | 5 |
| 1-26 | 10 | 5 | 5 | 5 | 5 |
| 1-27 | 10 | 5 | 5 | 5 | 5 |
| 1-28 | 10 | 5 | 4 | 5 | 5 |
| 1-29 | 10 | 5 | 4 | 5 | 5 |
| 1-30 | 10 | 5 | 4 | 5 | 5 |
| 1-31 | 10 | 3 | 3 | 5 | 5 |
| 1-32 | 10 | 5 | 4 | 5 | 5 |
| 1-33 | 10 | 5 | 4 | 5 | 5 |
| 1-34 | 2.52 | 5 | 5 | 5 | 5 |
| 1-35 | 10 | 5 | 5 | 5 | 5 |
| 1-36 | 10 | 5 | 5 | 5 | 5 |
| 1-37 | 10 | 4 | 5 | 5 | 5 |
| 1-38 | 10 | 3 | 4 | 5 | 5 |
| 1-39 | 10 | 5 | 4 | 5 | 5 |
| 1-40 | 10 | 5 | 3 | 5 | 5 |
| 1-41 | 10 | 2 | 0 | 0 | 5 |
| 1-42 | 10 | 5 | 3 | 5 | 5 |
| 1-43 | 10 | 5 | 4 | 5 | 5 |
| 1-44 | 10 | 5 | 3 | 5 | 5 |
| 1-45 | 10 | 5 | 3 | 5 | 5 |
| 1-46 | 10 | 5 | 3 | 5 | 5 |
| 1-47 | 10 | 5 | 3 | 5 | 5 |
| 1-48 | 10 | 5 | 3 | 5 | 5 |
| 1-49 | 10 | 5 | 4 | 5 | 5 |
| 1-50 | 10 | 5 | 3 | 5 | 5 |
| 1-51 | 10 | 5 | 2 | 5 | 5 |
| 1-52 | 10 | 5 | 3 | 5 | 5 |
| 1-53 | 10 | 4 | 5 | 5 | 5 |
| 1-54 | 10 | 5 | 3 | 5 | 5 |
| 1-55 | 10 | 5 | 3 | 5 | 5 |
| 1-56 | 2.52 | 5 | 3 | 5 | 5 |
| 1-57 | 10 | 5 | 5 | 5 | 5 |
| 1-58 | 10 | 3 | 5 | 5 | 5 |
| 1-59 | 10 | 5 | 3 | 5 | 5 |
| 1-60 | 10 | 5 | 5 | 5 | 5 |
| 1-61 | 10 | 5 | 3 | 5 | 5 |
| 1-62 | 10 | 5 | 3 | 5 | 5 |
| 1-63 | 10 | 5 | 3 | 5 | 5 |
| 1-64 | 10 | 5 | 3 | 5 | 5 |
| 1-65 | 10 | 5 | 3 | 5 | 5 |
| 1-66 | 10 | 5 | 4 | 5 | 5 |
| 1-67 | 10 | 5 | 4 | 5 | 5 |
| 1-68 | 10 | 5 | 3 | 5 | 5 |
| 1-69 | 10 | 5 | 3 | 5 | 5 |
| 1-70 | 10 | 5 | 3 | 5 | 5 |
| 1-71 | 10 | 5 | 3 | 5 | 5 |
| 1-72 | 10 | 4 | 3 | 5 | 5 |
| 1-73 | 10 | 5 | 4 | 5 | 5 |
| 1-74 | 10 | 5 | 5 | 5 | 5 |
| 1-75 | 10 | 5 | 3 | 5 | 5 |
| 1-76 | 10 | 5 | 3 | 5 | 5 |
| 1-77 | 10 | 5 | 3 | 5 | 5 |
| 1-78 | 10 | 5 | 3 | 5 | 5 |
| 1-79 | 10 | 5 | 4 | 5 | 5 |
| 1-80 | 10 | 3 | 3 | 5 | 5 |
| 1-81 | 10 | 5 | 4 | 5 | 5 |
| 1-82 | 10 | 5 | 3 | 5 | 5 |
| 1-83 | 10 | 5 | 5 | 5 | 5 |
| 1-84 | 10 | 5 | 5 | 5 | 5 |
| 1-85 | 10 | 5 | 5 | 5 | 5 |
| 1-86 | 10 | 5 | 4 | 5 | 5 |
| 1-87 | 10 | 0 | 3 | 3 | 3 |
| 1-88 | 10 | 5 | 3 | 5 | 5 |
| 1-89 | 10 | 4 | 4 | 5 | 5 |
| 1-90 | 10 | 3 | 3 | 5 | 5 |
| 1-91 | 10 | 4 | 5 | 5 | 5 |
| 1-92 | 10 | 5 | 3 | 5 | 5 |
| 1-93 | 10 | 5 | 3 | 5 | 5 |
| 1-94 | 10 | 5 | 3 | 5 | 5 |
| 1-95 | 10 | 5 | 5 | 5 | 5 |
| 1-96 | 10 | 0 | 2 | 5 | 5 |
| 1-97 | 10 | 5 | 3 | 5 | 5 |
| 1-98 | 10 | 0 | 2 | 3 | 4 |
| 1-99 | 10 | 0 | 2 | 4 | 5 |
| 1-100 | 10 | 2 | 4 | 5 | 5 |
| 1-101 | 10 | 5 | 5 | 5 | 5 |
| 1-102 | 10 | 2 | 3 | 5 | 5 |
| 1-103 | 4.4 | 0 | 0 | 5 | 5 |
| 1-104 | 10 | 5 | 4 | 5 | 5 |
| 1-105 | 10 | 5 | 3 | 5 | 5 |
| 1-106 | 10 | 5 | 3 | 5 | 5 |
| 1-107 | 10 | 0 | 0 | 0 | 4 |
| 1-108 | 10 | 2 | 2 | 5 | 5 |
| 1-109 | 10 | 5 | 3 | 5 | 5 |
| 1-110 | 10 | 4 | 3 | 5 | 5 |
| 1-111 | 10 | 3 | 3 | 5 | 5 |
| 1-112 | 10 | 0 | 0 | 0 | 5 |
| 1-113 | 10 | 5 | 4 | 5 | 5 |
| 1-114 | 10 | 1 | 5 | 5 | 5 |

TABLE 1-7

| No. | Dose (g/a) | G | H | I | J | K | L | M | N | O | P | a | b | c | d | e | f |
|---|---|---|---|---|---|---|---|---|---|---|---|---|---|---|---|---|---|
| 1-1 | 25 | 5 | 4 | 0 | 2 | 0 | 0 | 5 | 0 | 5 | 5 | 0 | 0 | 0 | 0 | 0 | 2 |
| 1-2 | 25 | 5 | 5 | 0 | 0 | 4 | 4 | 5 | 5 | 5 | 5 | 1 | 0 | 0 | 0 | 0 | 4 |
| 1-3 | 25 | 0 | 0 | 0 | 0 | 0 | 0 | 5 | 0 | 5 | 5 | 0 | 0 | 0 | 0 | 0 | 0 |

TABLE 1-7-continued

| No. | Dose (g/a) | G | H | I | J | K | L | M | N | O | P | a | b | c | d | e | f |
|---|---|---|---|---|---|---|---|---|---|---|---|---|---|---|---|---|---|
| 1-4 | 25 | 0 | 0 | 0 | 0 | 0 | 0 | 5 | 0 | 5 | 5 | 0 | 0 | 0 | 0 | 0 | 1 |
| 1-5 | 25 | 5 | 5 | 0 | 2 | 4 | 0 | 5 | 2 | 5 | 5 | 0 | 0 | 0 | 0 | 0 | 2 |
| 1-7 | 25 | 5 | 0 | 0 | 0 | 0 | 0 | 5 | 0 | 2 | 5 | 0 | 0 | 0 | 0 | 0 | 0 |
| 1-9 | 25 | 5 | 5 | 0 | 3 | 4 | 0 | 5 | 0 | 5 | 5 | 0 | 0 | 0 | 0 | 0 | 4 |
| 1-10 | 6.3 | 0 | 0 | 0 | 0 | 0 | 2 | 0 | 0 | 0 | 0 | 0 | 0 | 0 | 1 | 0 | 0 |
| 1-14 | 25 | 5 | 5 | 3 | 5 | 5 | 4 | 5 | 5 | 5 | 5 | 5 | 1 | 3 | 1 | 3 | 4 |
| 1-15 | 25 | 5 | 5 | 4 | 5 | 5 | 5 | 5 | 5 | 5 | 5 | 5 | 1 | 5 | 2 | 4 | 5 |
| 1-16 | 25 | 5 | 5 | 0 | 5 | 5 | 0 | 5 | 5 | 5 | 5 | 1 | 0 | 5 | 0 | 2 | 5 |
| 1-17 | 25 | 0 | 0 | 0 | 0 | 0 | 0 | 5 | 2 | 5 | 5 | 0 | 0 | 0 | 0 | 1 | 3 |
| 1-18 | 25 | 5 | 5 | 3 | 5 | 5 | 5 | 5 | 4 | 5 | 5 | 3 | 3 | 3 | 3 | 3 | 5 |
| 1-19 | 25 | 5 | 5 | 0 | 3 | 4 | 3 | 5 | 3 | 5 | 5 | 1 | 1 | 0 | 0 | 1 | 4 |
| 1-20 | 25 | 5 | 4 | 3 | 5 | 0 | 3 | 5 | 3 | 5 | 5 | 1 | 0 | 2 | 0 | 0 | 5 |
| 1-21 | 25 | 5 | 5 | 5 | 5 | 5 | 5 | 5 | 5 | 5 | 5 | 5 | 2 | 5 | 4 | 5 | 5 |
| 1-22 | 25 | 5 | 5 | 3 | 5 | 5 | 5 | 5 | 5 | 5 | 5 | 5 | 3 | 3 | 3 | 4 | 4 |
| 1-23 | 25 | 5 | 5 | 3 | 5 | 5 | 0 | 5 | 4 | 5 | 5 | 3 | 0 | 3 | 1 | 3 | 4 |
| 1-24 | 25 | 5 | 5 | 5 | 5 | 5 | 5 | 5 | 5 | 5 | 5 | 5 | 2 | 5 | 3 | 5 | 5 |
| 1-25 | 25 | 5 | 5 | 2 | 4 | 5 | 4 | 5 | 0 | 5 | 5 | 3 | 0 | 1 | 0 | 0 | 5 |
| 1-26 | 25 | 5 | 5 | 5 | 5 | 5 | 3 | 5 | 0 | 5 | 5 | 5 | 0 | 1 | 0 | 0 | 5 |
| 1-27 | 25 | 5 | 5 | 5 | — | 5 | 4 | 5 | 5 | 5 | 5 | 5 | 1 | — | 1 | 1 | 5 |
| 1-28 | 25 | 5 | 5 | 5 | — | 5 | 4 | 5 | 5 | 5 | 5 | 5 | 2 | — | 0 | 2 | 5 |
| 1-29 | 25 | 5 | 5 | 3 | — | 3 | 3 | 5 | 3 | 5 | 5 | — | 0 | 2 | 0 | 0 | 5 |
| 1-30 | 25 | 5 | 5 | 4 | 5 | 5 | 3 | 5 | 4 | 5 | 5 | — | 1 | 5 | 0 | 1 | 5 |
| 1-31 | 25 | 5 | 4 | 2 | 3 | 4 | 3 | 5 | 0 | 5 | 5 | — | 0 | 1 | 0 | 1 | 4 |
| 1-32 | 25 | 5 | 5 | 3 | 4 | 5 | 5 | 5 | 4 | 5 | 5 | — | 0 | 4 | 0 | 0 | 5 |
| 1-33 | 25 | 5 | 0 | 2 | 3 | 5 | 3 | 5 | 2 | 5 | 5 | — | 2 | 2 | 0 | 4 | 4 |
| 1-34 | 6.3 | 5 | 5 | 3 | — | 5 | 4 | 5 | 0 | 5 | 5 | — | 0 | 5 | 0 | 0 | 4 |
| 1-35 | 25 | 5 | 5 | 5 | — | 5 | 5 | 5 | 5 | 5 | 5 | — | 5 | 5 | 3 | 4 | 5 |
| 1-36 | 25 | 5 | 5 | 5 | — | 5 | 5 | 5 | 5 | 5 | 5 | — | 1 | 5 | 0 | 0 | 5 |
| 1-37 | 25 | 5 | 4 | 2 | — | 5 | 5 | 5 | 5 | 5 | 5 | — | 3 | 4 | 1 | 4 | 4 |
| 1-38 | 25 | 3 | 0 | 0 | — | 5 | 3 | 4 | 2 | 5 | 5 | — | 0 | 0 | 0 | 0 | 3 |
| 1-39 | 25 | 4 | 3 | 0 | — | 4 | 4 | 5 | 3 | 5 | 5 | — | 1 | 5 | 0 | 1 | 4 |
| 1-40 | 25 | 5 | 5 | 2 | — | 3 | 4 | 5 | 2 | 5 | 5 | — | 0 | 3 | 0 | 0 | 5 |
| 1-41 | 25 | 3 | 5 | 0 | — | 0 | 4 | 5 | 0 | 5 | 5 | — | 0 | 0 | 0 | 0 | 0 |
| 1-42 | 25 | 5 | 5 | 4 | 0 | 3 | 5 | 5 | 0 | 5 | 5 | — | 0 | 2 | 0 | 0 | 3 |
| 1-43 | 25 | 5 | 5 | 5 | — | 5 | 4 | 5 | 5 | 5 | 5 | — | 0 | 4 | 0 | 2 | 5 |
| 1-44 | 25 | 5 | 5 | 4 | — | 5 | 5 | 5 | 5 | 5 | 5 | — | 0 | 2 | 0 | 0 | 3 |
| 1-45 | 25 | 5 | 5 | 5 | 5 | 5 | 5 | 5 | 5 | 5 | 5 | — | 0 | 5 | 0 | 2 | 5 |
| 1-46 | 25 | 5 | 5 | 5 | 5 | 5 | 4 | 5 | 5 | 5 | 5 | — | 0 | 5 | 0 | 1 | 4 |
| 1-47 | 25 | 5 | 5 | 5 | 5 | 5 | 3 | 5 | 2 | 5 | 5 | — | 0 | 3 | 0 | 0 | 4 |
| 1-48 | 25 | 5 | 5 | 3 | 4 | 5 | 4 | 5 | 5 | 5 | 5 | — | 1 | 1 | 0 | 2 | 4 |
| 1-49 | 25 | 5 | 5 | 0 | — | 5 | 4 | 5 | 5 | 5 | 5 | — | 2 | 1 | 0 | 3 | 5 |
| 1-50 | 25 | 5 | 5 | 2 | 0 | 4 | 3 | 5 | 2 | 5 | 5 | — | 0 | 0 | 0 | 0 | 4 |
| 1-51 | 25 | 0 | 0 | 3 | — | 2 | 0 | 5 | 0 | 5 | 5 | — | 0 | 0 | 3 | 0 | 4 |
| 1-52 | 25 | 3 | 2 | 0 | — | 5 | 4 | 5 | 0 | 5 | 5 | — | 3 | 0 | 1 | 2 | 4 |
| 1-53 | 25 | 4 | 3 | 2 | — | 5 | 2 | 5 | 0 | 5 | 5 | — | 0 | 0 | 0 | 0 | 3 |
| 1-54 | 25 | 5 | 5 | 5 | 5 | 3 | 2 | 5 | 0 | 5 | 5 | — | 0 | 5 | 0 | 0 | 4 |
| 1-55 | 15 | 5 | 5 | 5 | 5 | 5 | 4 | 5 | 5 | 5 | 5 | — | 0 | 5 | 0 | 2 | 5 |
| 1-56 | 6.3 | 5 | 5 | 0 | 5 | 5 | 0 | 5 | 3 | 5 | 5 | — | 0 | 3 | 0 | 2 | 4 |
| 1-57 | 25 | 5 | 5 | 4 | 0 | 5 | 5 | 5 | 5 | 5 | 5 | 5 | 2 | 2 | 2 | 3 | 3 |
| 1-58 | 25 | 3 | 0 | 3 | — | 0 | 0 | 5 | 0 | 5 | 5 | 5 | 0 | 0 | 0 | 0 | 3 |
| 1-59 | 25 | 5 | 5 | 5 | 5 | 5 | 4 | 5 | 5 | 5 | 5 | — | 0 | 5 | 0 | 3 | 5 |
| 1-60 | 25 | 5 | 5 | 4 | — | 5 | 4 | 5 | 5 | 5 | 5 | — | 3 | — | 0 | 2 | 4 |
| 1-61 | 25 | 5 | 5 | 5 | — | 5 | 5 | 5 | 5 | 5 | 5 | — | 2 | 5 | 0 | 4 | 5 |
| 1-62 | 25 | 5 | 5 | 5 | — | 5 | 3 | 5 | 5 | 5 | 5 | — | 2 | 5 | 0 | 4 | 5 |
| 1-63 | 25 | 5 | 5 | 3 | — | 5 | 5 | 5 | 5 | 5 | 5 | — | 2 | 5 | 3 | 5 | 5 |
| 1-64 | 25 | 5 | 5 | 0 | — | 5 | 5 | 5 | 5 | 5 | 5 | — | 4 | 3 | 3 | 4 | 4 |
| 1-65 | 25 | 5 | 5 | 3 | — | 5 | 5 | 5 | 5 | 5 | 5 | — | 2 | — | 1 | 5 | 5 |
| 1-66 | 25 | 5 | 5 | 3 | — | 5 | 1 | 5 | 2 | 5 | 5 | — | 0 | 5 | 0 | 0 | 5 |
| 1-67 | 25 | 5 | 5 | 5 | — | 5 | 2 | 5 | 5 | 5 | 5 | — | 0 | 5 | 0 | 3 | 4 |
| 1-68 | 25 | 5 | 5 | 4 | — | 5 | 5 | 5 | 5 | 5 | 5 | — | 5 | 4 | 0 | 5 | 4 |
| 1-69 | 25 | 5 | 5 | 3 | — | 5 | 5 | 5 | 5 | 5 | 5 | — | 1 | 5 | 0 | 3 | 4 |
| 1-70 | 25 | 5 | 5 | 4 | — | 5 | 5 | 5 | 5 | 5 | 5 | — | 2 | 5 | 1 | 4 | 5 |
| 1-71 | 25 | 5 | 5 | 5 | — | 4 | 4 | 5 | 5 | 5 | 5 | — | 1 | 5 | 0 | 2 | 4 |
| 1-72 | 25 | 5 | 4 | 0 | — | 4 | 3 | 5 | 0 | 5 | 5 | — | 0 | 3 | 0 | 1 | 4 |
| 1-73 | 25 | 5 | 5 | 4 | 0 | 5 | 0 | 0 | 1 | 4 | 5 | — | 0 | 5 | 0 | 0 | 4 |
| 1-74 | 25 | 5 | 5 | 3 | 2 | 4 | 3 | 5 | 0 | 5 | 5 | — | 0 | 4 | 0 | 0 | 4 |
| 1-75 | 25 | 5 | 5 | 3 | 3 | 5 | 3 | 5 | 3 | 5 | 5 | — | 0 | 2 | 0 | 0 | 4 |
| 1-76 | 25 | 5 | 5 | 3 | — | 4 | 3 | 5 | 2 | 5 | 5 | — | 0 | 2 | 0 | 0 | 5 |
| 1-77 | 25 | 5 | 5 | 3 | — | 5 | 2 | 5 | 3 | 4 | 5 | — | 1 | 2 | 0 | 1 | 4 |
| 1-78 | 25 | 5 | 5 | 0 | — | 2 | 3 | 5 | 3 | 4 | 5 | — | 0 | 4 | 0 | 0 | 4 |
| 1-79 | 25 | 5 | 5 | 2 | — | 5 | 5 | 5 | 3 | 5 | 5 | — | 0 | 4 | 0 | 3 | 4 |
| 1-80 | 25 | 3 | 4 | 3 | — | 3 | 3 | 5 | 3 | 5 | 5 | — | 0 | 3 | 0 | 0 | 4 |
| 1-81 | 25 | 5 | 5 | 4 | — | 5 | 3 | 5 | 4 | 5 | 5 | — | 0 | 5 | 0 | 1 | 5 |
| 1-82 | 25 | 5 | 5 | 0 | 0 | 5 | 5 | 5 | 2 | 5 | 5 | — | 0 | 0 | 0 | 0 | 4 |
| 1-83 | 25 | 5 | 5 | 5 | — | 5 | 5 | 5 | 5 | 5 | 5 | 5 | 3 | 3 | 0 | 2 | 4 |
| 1-84 | 25 | 5 | 5 | 3 | — | 5 | 5 | 5 | 3 | 5 | 5 | 5 | 0 | 1 | 0 | 3 | 3 |

TABLE 1-7-continued

| No. | Dose (g/a) | G | H | I | J | K | L | M | N | O | P | a | b | c | d | e | f |
|---|---|---|---|---|---|---|---|---|---|---|---|---|---|---|---|---|---|
| 1-85 | 25 | 5 | 5 | 3 | 0 | 5 | 3 | 4 | 0 | 5 | 5 | — | 0 | 4 | 0 | 0 | 4 |
| 1-86 | 25 | 5 | 5 | 3 | — | 5 | 5 | 5 | 5 | 5 | 5 | — | 2 | 5 | 0 | 3 | 4 |
| 1-87 | 25 | 0 | 0 | 0 | — | 3 | 0 | 5 | 0 | 5 | | 0 | 0 | 0 | 0 | 0 | 0 |
| 1-88 | 25 | 5 | 5 | 0 | — | 5 | 2 | 5 | 2 | 5 | 5 | 0 | 0 | 1 | 0 | 0 | 5 |
| 1-89 | 25 | 5 | 5 | 0 | — | 5 | 1 | 5 | 4 | 5 | 5 | 0 | 0 | 0 | 0 | 0 | 4 |
| 1-90 | 25 | 4 | 5 | 2 | — | 4 | 1 | 5 | 0 | 5 | 5 | 1 | 0 | 1 | 0 | — | 3 |
| 1-91 | 25 | 3 | 0 | 3 | — | 0 | 4 | 5 | 4 | 5 | 5 | 0 | 0 | 1 | 0 | 0 | 3 |
| 1-92 | 25 | 5 | 5 | 5 | — | 4 | 0 | 5 | 2 | 5 | 5 | 2 | 0 | 0 | 0 | 1 | 4 |
| 1-93 | 25 | 5 | 5 | 5 | — | 5 | 3 | 5 | 0 | 5 | 5 | | 0 | 4 | 0 | 0 | 4 |
| 1-94 | 25 | 5 | 5 | 5 | — | 5 | 0 | 5 | — | 5 | 5 | — | 0 | 4 | 0 | 0 | 4 |
| 1-95 | 25 | 5 | 5 | 4 | — | 5 | 5 | 5 | 5 | 5 | 5 | 5 | 1 | 2 | 1 | 3 | 4 |
| 1-96 | 25 | 0 | 3 | 0 | 0 | 5 | 0 | 5 | 0 | 4 | 5 | — | 0 | 0 | 0 | 0 | 2 |
| 1-97 | 25 | 5 | 5 | 5 | — | 5 | 5 | 5 | 5 | 5 | 5 | 5 | 2 | 4 | 0 | 5 | 4 |
| 1-98 | 25 | 0 | 0 | 0 | — | 0 | 0 | 3 | 3 | 5 | 5 | 0 | 0 | 0 | 0 | 0 | 0 |
| 1-99 | 25 | 0 | 0 | 0 | 0 | 0 | 0 | 3 | 0 | 2 | 5 | 0 | 0 | 0 | 0 | 0 | 1 |
| 1-100 | 25 | 5 | 5 | 5 | — | 3 | 4 | 5 | 5 | 5 | 5 | 5 | 0 | 0 | 0 | 2 | 3 |
| 1-101 | 25 | 5 | 5 | 5 | — | 5 | 3 | 5 | 5 | 5 | 5 | 5 | 0 | 2 | 0 | 1 | 3 |
| 1-102 | 25 | 5 | 3 | 0 | 0 | 3 | 0 | 5 | 0 | 5 | 5 | 5 | 0 | 0 | 0 | 0 | 2 |
| 1-103 | 11 | 3 | 4 | 3 | — | 0 | 0 | 5 | 2 | 5 | 5 | 5 | 0 | 0 | 0 | 0 | 3 |
| 1-104 | 25 | 5 | 5 | 3 | — | 0 | 0 | 4 | 0 | 5 | 5 | 5 | 0 | 3 | 0 | 0 | 2 |
| 1-105 | 25 | 5 | 5 | 0 | 0 | 4 | 4 | 5 | 0 | 2 | 2 | — | 0 | 0 | 0 | 0 | 0 |
| 1-106 | 25 | 5 | 5 | 0 | 0 | 5 | 5 | 5 | 0 | 3 | 5 | — | 0 | 0 | 0 | 0 | 2 |
| 1-107 | 25 | 0 | 0 | 0 | 0 | 0 | 0 | 4 | 0 | 5 | 5 | 0 | 0 | 0 | 0 | 0 | 1 |
| 1-108 | 25 | 0 | 4 | — | 0 | 0 | 0 | 5 | 0 | 3 | 5 | — | 0 | 0 | 0 | 0 | 0 |
| 1-109 | 25 | 5 | 5 | 3 | — | 4 | 1 | 5 | 0 | 5 | 5 | 0 | 0 | 1 | 0 | 1 | 3 |
| 1-110 | 25 | 3 | 3 | 3 | 1 | 3 | 0 | 5 | — | 5 | 5 | 1 | 0 | 0 | 0 | 0 | 4 |
| 1-111 | 25 | 5 | 1 | 0 | 3 | 3 | 2 | 5 | 0 | 5 | 5 | 0 | 0 | 0 | 0 | 2 | 4 |
| 1-112 | 25 | 0 | 0 | 2 | 3 | 2 | 0 | 5 | — | 3 | 5 | 0 | 0 | 0 | 0 | 0 | 2 |
| 1-113 | 25 | 5 | 5 | 3 | 4 | 5 | 4 | 5 | 5 | 5 | 5 | 5 | 0 | 4 | 0 | 3 | 4 |
| 1-114 | 25 | 5 | 5 | 3 | 5 | 5 | 1 | 5 | 5 | 5 | 5 | 1 | 0 | 2 | 0 | 3 | 4 |

TABLE 1-8

| No. | Dose (g/a) | G | H | I | J | K | L | M | N | O | P | a | b | c | d | e | f |
|---|---|---|---|---|---|---|---|---|---|---|---|---|---|---|---|---|---|
| 1-2 | 25 | 5 | 3 | 0 | 4 | 3 | 2 | 4 | 3 | 5 | 5 | 4 | 1 | 2 | 2 | 1 | 3 |
| 1-4 | 25 | 0 | 0 | 0 | 0 | 0 | 0 | 0 | 0 | 4 | 4 | 0 | 0 | 0 | 0 | 0 | 2 |
| 1-5 | 25 | 0 | 0 | 0 | 2 | 0 | 0 | 0 | 0 | 2 | 0 | 0 | 0 | 0 | 0 | 0 | 0 |
| 1-9 | 25 | 1 | 2 | 0 | 0 | 3 | 2 | 3 | 3 | 5 | 2 | 1 | 0 | 0 | 0 | 0 | 1 |
| 1-12 | 6.3 | 0 | 0 | 0 | 0 | 0 | 0 | 2 | 0 | 3 | 3 | 0 | 0 | 0 | 0 | 0 | 1 |
| 1-14 | 25 | 3 | 3 | 2 | 4 | 3 | 2 | 4 | 2 | 5 | 5 | 1 | 0 | 2 | 0 | 0 | 2 |
| 1-15 | 25 | 4 | 4 | 4 | 4 | 5 | 3 | 5 | 5 | 5 | 5 | 2 | 3 | 2 | 2 | 4 | 3 |
| 1-16 | 25 | 3 | 3 | 0 | 3 | 4 | 2 | 3 | 0 | 5 | 5 | 1 | 0 | 2 | 0 | 0 | 3 |
| 1-18 | 25 | 3 | 3 | 3 | 4 | 3 | 2 | 2 | 1 | 5 | 5 | 2 | 2 | 1 | 1 | 0 | 2 |
| 1-19 | 25 | 0 | 0 | 0 | 3 | 0 | 0 | 0 | 0 | 4 | 4 | 0 | 1 | 1 | 0 | 0 | 2 |
| 1-20 | 25 | 1 | 1 | 3 | 4 | 0 | 2 | 0 | 0 | 5 | 5 | 0 | 0 | 0 | 0 | 0 | 2 |
| 1-21 | 25 | 4 | 4 | 3 | 3 | 4 | 4 | 4 | 2 | 5 | 5 | 4 | 2 | 2 | 1 | 1 | 2 |
| 1-22 | 25 | 5 | 4 | 2 | 5 | 4 | 4 | 4 | 2 | 5 | 5 | 3 | 3 | 1 | 2 | 1 | 2 |
| 1-23 | 25 | 3 | 3 | 2 | 3 | 4 | 2 | 2 | 0 | 4 | 5 | 2 | 2 | 2 | 1 | 0 | — |
| 1-24 | 25 | 4 | 4 | 4 | 5 | 4 | 4 | 3 | 1 | 5 | 5 | 3 | 2 | 2 | 1 | 1 | 3 |
| 1-25 | 25 | 0 | 0 | 0 | 0 | 0 | 1 | 2 | 0 | 4 | 4 | 0 | 0 | 0 | 0 | 0 | 1 |
| 1-26 | 25 | 0 | 0 | 1 | 2 | 0 | 1 | 1 | 1 | 4 | 5 | 0 | 0 | 0 | 0 | 0 | 1 |
| 1-27 | 25 | 3 | 3 | 0 | 5 | 1 | 3 | 2 | 0 | 5 | 5 | 2 | 1 | 1 | 2 | 1 | 2 |
| 1-28 | 25 | 3 | 4 | 2 | 4 | 4 | 4 | 3 | 1 | 5 | 5 | 2 | 1 | 2 | 0 | 0 | 2 |
| 1-29 | 25 | 0 | 0 | 0 | 3 | 0 | 2 | 0 | 0 | 0 | 4 | 0 | 0 | 0 | 0 | 0 | 1 |
| 1-30 | 25 | 4 | 0 | 3 | 4 | 3 | 2 | 1 | 0 | 5 | 4 | 2 | 0 | 2 | 0 | 0 | 2 |
| 1-31 | 25 | 0 | 0 | 3 | 3 | 2 | 0 | 2 | 0 | 4 | 5 | 0 | 0 | 1 | 0 | 0 | 2 |
| 1-32 | 25 | 2 | 2 | 0 | 5 | 0 | 4 | 2 | 2 | 5 | 5 | 2 | 1 | 1 | 0 | 0 | 2 |
| 1-33 | 25 | 3 | 0 | 2 | 3 | 2 | 1 | 0 | 0 | 3 | 5 | 2 | 1 | 0 | 0 | 1 | 2 |
| 1-34 | 6.3 | 5 | 0 | 2 | 3 | 0 | 5 | 0 | 0 | 3 | 4 | 1 | 0 | 1 | 0 | 0 | 2 |
| 1-35 | 25 | 5 | 2 | 4 | 5 | 5 | 4 | 5 | 3 | 5 | 5 | 2 | 4 | 2 | 1 | 2 | 3 |
| 1-36 | 25 | 5 | 0 | 3 | 4 | 2 | 0 | 2 | 5 | 5 | 5 | 3 | 2 | 2 | 0 | 0 | 3 |
| 1-37 | 25 | 0 | 0 | 2 | 5 | 2 | 0 | 1 | 0 | 5 | 5 | 1 | 1 | 2 | 0 | 0 | 3 |
| 1-38 | 25 | 0 | 0 | 0 | 2 | 0 | 0 | 0 | 0 | 0 | 5 | 0 | 0 | 0 | 0 | 0 | 0 |
| 1-39 | 25 | 0 | 0 | 0 | 5 | 0 | 0 | 0 | 0 | 3 | 5 | 0 | 0 | 0 | 0 | 0 | 1 |
| 1-40 | 25 | 0 | 0 | 0 | 4 | 0 | 1 | 2 | 0 | 2 | 5 | 2 | 0 | 0 | 0 | 1 | 2 |
| 1-41 | 25 | 0 | 0 | 0 | 4 | 2 | 1 | 0 | 0 | 3 | 5 | 1 | 0 | 0 | 0 | 0 | 1 |
| 1-42 | 25 | 0 | 0 | 0 | 5 | 0 | 4 | 3 | 0 | 5 | 5 | 1 | 0 | 0 | 0 | 0 | 1 |
| 1-43 | 25 | 0 | 3 | 0 | 4 | 0 | 2 | 0 | 0 | 5 | 5 | 2 | 0 | 1 | 1 | 1 | 2 |
| 1-44 | 25 | 2 | 2 | 2 | 5 | 2 | 3 | 3 | 0 | 5 | 5 | 2 | 1 | 2 | 0 | 1 | 3 |
| 1-45 | 25 | 0 | 0 | 0 | 3 | 0 | 1 | 1 | 0 | 5 | 4 | 0 | 0 | 2 | 0 | 0 | 1 |
| 1-46 | 25 | 0 | 0 | 0 | 3 | 0 | 1 | 0 | 0 | 3 | 4 | 0 | 0 | 0 | 0 | 0 | 1 |

TABLE 1-8-continued

| No. | Dose (g/a) | G | H | I | J | K | L | M | N | O | P | a | b | c | d | e | f |
|---|---|---|---|---|---|---|---|---|---|---|---|---|---|---|---|---|---|
| 1-47 | 25 | 0 | 0 | 0 | 3 | 1 | 1 | 2 | 0 | 5 | 5 | 0 | 0 | 0 | 0 | 0 | 2 |
| 1-48 | 25 | 2 | 1 | 0 | 0 | 2 | 1 | 1 | 0 | 4 | 4 | 1 | 0 | 0 | 0 | 0 | 1 |
| 1-49 | 25 | 4 | 3 | 0 | 3 | 3 | 2 | 2 | 2 | 4 | 5 | 1 | 2 | 1 | 0 | 0 | 2 |
| 1-50 | 25 | 4 | 4 | 0 | — | 4 | 1 | 4 | 2 | 4 | 5 | 2 | 2 | 0 | 0 | 1 | 1 |
| 1-51 | 25 | 0 | 0 | 0 | 0 | 0 | 0 | 0 | 0 | 0 | 2 | 0 | 0 | 0 | 0 | 0 | 0 |
| 1-52 | 25 | 0 | 0 | 0 | — | 0 | 0 | 0 | 0 | 3 | 3 | 0 | 0 | 0 | 0 | 0 | 0 |
| 1-53 | 25 | 0 | 0 | 0 | 4 | 0 | 2 | 0 | 0 | 4 | 5 | 0 | 0 | 0 | 0 | 0 | 2 |
| 1-54 | 25 | 0 | 0 | 0 | 3 | 3 | 0 | 2 | 0 | 5 | 4 | 0 | 0 | 0 | 0 | 0 | 2 |
| 1-55 | 15 | 2 | 3 | 2 | 4 | 4 | 2 | 2 | 0 | 5 | 5 | 2 | 0 | 0 | 0 | 0 | 2 |
| 1-56 | 6.3 | 0 | 0 | 0 | 3 | 0 | 0 | 0 | 0 | 5 | 5 | 0 | 0 | 0 | 0 | 0 | 0 |
| 1-57 | 25 | 5 | — | 2 | — | 0 | 3 | 3 | 0 | 4 | 5 | 2 | 0 | 0 | 1 | 2 | 1 |
| 1-58 | 25 | 0 | 0 | 0 | — | 0 | 0 | 0 | 0 | 3 | 2 | 0 | 0 | 0 | 0 | 0 | 1 |
| 1-59 | 25 | 0 | 0 | 4 | 4 | 0 | 1 | 0 | 0 | 5 | 5 | 1 | 0 | 2 | 0 | 0 | 2 |
| 1-60 | 25 | 0 | 0 | 0 | — | 0 | 0 | 1 | 0 | 4 | 4 | 0 | 1 | 1 | 0 | 0 | 2 |
| 1-61 | 25 | 0 | 0 | 5 | — | 0 | 2 | 2 | 0 | 5 | 5 | 1 | 1 | 2 | 0 | 0 | 2 |
| 1-62 | 25 | 2 | 2 | 2 | — | 2 | 1 | 2 | 0 | 5 | 4 | 2 | 0 | 2 | 0 | 0 | 2 |
| 1-63 | 25 | 3 | 3 | 2 | — | 2 | 2 | 2 | 1 | 5 | 5 | 3 | 3 | 1 | 0 | 1 | 3 |
| 1-64 | 25 | 3 | 3 | 5 | 0 | 3 | 2 | 1 | 0 | 5 | 5 | 1 | 2 | 2 | 0 | 1 | 3 |
| 1-65 | 25 | 3 | 3 | 3 | — | 4 | 3 | 3 | 1 | 5 | 5 | 3 | 3 | 3 | 1 | 1 | 4 |
| 1-66 | 25 | 0 | 0 | 2 | — | 3 | 1 | 3 | 0 | 5 | 5 | 0 | 0 | 2 | 0 | 0 | 2 |
| 1-67 | 25 | 0 | 0 | 4 | — | 2 | 0 | 2 | 0 | 5 | 5 | 2 | 0 | 2 | 0 | 0 | 2 |
| 1-68 | 25 | 3 | 3 | 1 | — | 4 | 3 | 3 | 2 | 5 | 5 | 3 | 3 | 2 | 2 | 0 | 2 |
| 1-69 | 25 | 3 | 4 | 3 | — | 4 | 4 | 1 | 1 | 5 | 5 | 2 | 2 | 2 | 1 | 0 | 3 |
| 1-70 | 25 | 4 | 3 | 5 | — | 4 | 4 | 4 | — | 5 | 5 | 3 | 3 | 3 | 1 | 1 | 4 |
| 1-71 | 25 | 0 | 0 | 3 | — | 3 | 1 | 2 | 1 | 4 | 5 | 1 | 0 | 3 | 0 | 0 | 1 |
| 1-72 | 25 | 0 | 0 | 1 | — | 0 | 0 | 0 | 0 | 4 | 5 | 0 | 0 | 2 | 0 | 0 | 2 |
| 1-73 | 25 | 0 | 0 | 2 | — | 0 | 0 | 0 | 0 | 5 | 5 | 0 | 0 | 2 | 2 | 0 | 1 |
| 1-74 | 25 | 0 | 0 | 0 | — | 1 | 1 | 1 | 0 | 5 | 5 | 0 | 1 | 1 | 0 | 0 | 3 |
| 1-75 | 25 | 0 | 0 | 0 | 2 | 0 | 2 | 1 | 0 | 2 | 5 | 0 | 0 | 0 | 0 | 0 | 1 |
| 1-76 | 25 | 3 | 4 | 0 | — | 0 | 4 | 1 | 2 | 5 | 5 | 3 | 2 | 1 | 0 | 0 | 1 |
| 1-77 | 25 | 3 | 3 | 2 | — | 0 | 2 | 2 | 1 | 5 | 5 | 2 | 3 | 1 | 1 | 1 | 2 |
| 1-78 | 25 | 0 | 1 | 0 | — | 2 | 3 | 1 | 1 | 4 | 5 | 0 | 0 | 0 | — | 0 | 2 |
| 1-79 | 25 | 0 | 3 | 2 | — | 3 | 2 | 2 | 0 | 4 | 5 | 1 | 1 | 0 | 0 | 1 | 2 |
| 1-80 | 25 | 2 | 2 | 3 | — | 2 | 2 | 1 | 1 | 5 | 5 | 1 | 0 | 3 | 0 | 0 | 2 |
| 1-81 | 25 | 0 | 0 | 0 | — | 0 | 2 | 1 | 0 | 5 | 5 | 1 | 2 | 4 | 0 | 0 | 3 |
| 1-82 | 25 | 3 | 3 | 0 | — | 0 | 2 | 2 | 0 | 4 | 5 | 2 | 2 | 0 | 0 | 0 | 1 |
| 1-83 | 25 | 4 | 4 | 3 | — | 3 | 4 | 3 | 0 | 5 | 5 | 1 | 1 | 2 | 1 | 2 | 1 |
| 1-84 | 25 | 3 | — | 2 | — | 3 | 3 | 2 | 0 | 4 | 4 | 2 | 1 | 1 | 1 | 1 | 1 |
| 1-85 | 25 | 0 | 0 | 4 | 4 | 0 | 0 | 0 | 0 | 5 | 5 | 0 | 0 | 0 | 0 | 0 | 1 |
| 1-86 | 25 | 3 | 3 | 2 | — | 2 | 2 | 2 | 0 | 5 | 5 | 1 | 3 | 2 | 1 | 0 | 2 |
| 1-88 | 25 | 0 | 0 | 0 | — | 0 | 1 | 1 | 0 | 0 | — | 0 | 0 | 0 | 0 | 0 | 0 |
| 1-89 | 25 | 0 | — | 0 | — | 2 | 2 | 2 | 0 | 4 | 1 | 0 | 0 | 0 | 0 | 0 | 0 |
| 1-90 | 25 | 0 | 0 | 0 | — | 4 | 0 | 0 | 0 | 0 | 2 | 0 | 0 | 0 | 0 | 0 | 0 |
| 1-91 | 25 | 0 | 0 | 2 | — | 0 | 0 | 0 | 0 | 3 | 3 | 0 | 0 | 1 | 0 | 0 | 1 |
| 1-92 | 25 | 0 | 3 | 0 | — | 5 | 3 | 5 | 4 | 5 | 5 | 0 | 0 | 0 | 0 | 1 | 2 |
| 1-93 | 25 | 0 | 5 | 0 | — | 5 | 4 | 4 | 5 | 5 | 5 | 0 | 0 | 1 | 0 | 2 | 2 |
| 1-94 | 25 | 0 | 0 | 2 | — | 4 | 4 | 3 | 4 | 5 | 5 | 0 | 0 | 2 | 0 | 1 | 3 |
| 1-95 | 25 | 4 | 4 | 5 | — | 3 | 3 | 3 | 3 | 5 | 5 | 3 | 2 | 2 | 1 | 1 | 3 |
| 1-96 | 25 | 0 | 0 | 0 | 0 | 0 | 0 | 4 | 0 | 0 | 2 | 0 | 0 | 0 | 0 | 0 | 0 |
| 1-97 | 25 | 5 | 5 | 2 | 5 | 5 | 5 | 4 | 3 | 5 | 5 | 3 | 3 | 0 | 1 | 2 | 3 |
| 1-98 | 25 | 0 | 0 | 0 | — | 0 | 0 | 0 | 0 | 3 | 3 | 0 | 0 | 0 | 0 | 0 | 0 |
| 1-99 | 25 | 0 | 0 | 0 | — | 0 | 0 | 2 | 0 | 3 | 3 | 0 | 0 | 0 | 0 | 0 | 0 |
| 1-100 | 25 | 0 | 0 | 0 | — | 0 | 2 | 4 | 0 | 5 | 4 | 0 | 0 | 0 | 0 | 1 | 1 |
| 1-101 | 25 | 0 | 0 | 0 | — | 0 | 0 | 2 | 0 | 5 | 5 | 1 | 0 | 0 | 0 | 0 | 0 |
| 1-102 | 25 | 0 | 0 | 0 | — | 0 | 0 | 2 | 0 | 5 | 5 | 1 | 0 | 0 | 0 | 0 | 0 |
| 1-103 | 11 | 0 | 0 | 0 | — | 0 | 0 | 0 | 0 | 4 | — | 0 | 0 | 0 | 0 | 0 | 0 |
| 1-104 | 25 | 0 | 0 | 0 | — | 0 | 0 | 0 | 0 | 2 | 2 | 0 | 0 | 0 | 0 | 0 | 1 |
| 1-105 | 25 | 3 | 5 | 0 | 2 | 5 | 5 | 5 | 0 | 5 | 3 | 1 | 1 | 0 | 2 | 0 | 0 |
| 1-106 | 25 | 0 | 4 | 0 | 0 | 5 | 3 | 3 | 2 | 0 | 3 | 0 | 0 | 0 | 1 | 0 | 1 |
| 1-107 | 25 | 0 | 0 | 0 | 0 | 0 | 0 | 0 | 0 | 3 | 3 | 0 | 0 | 0 | 0 | 0 | 0 |
| 1-108 | 25 | 0 | 0 | 0 | 0 | 0 | 0 | 2 | 0 | 4 | 5 | 0 | 0 | 0 | 0 | 0 | 0 |
| 1-109 | 25 | 5 | 4 | 3 | 3 | 5 | 5 | 2 | 3 | 2 | 4 | 2 | 3 | 2 | 0 | 1 | 1 |
| 1-110 | 25 | 3 | 3 | 2 | 3 | 2 | 4 | 1 | 0 | 3 | 4 | 1 | 0 | 1 | 0 | 2 | 1 |
| 1-111 | 25 | 2 | 2 | 0 | 4 | 4 | 0 | 3 | 0 | 5 | 4 | 1 | 0 | 0 | 0 | 1 | 1 |
| 1-112 | 25 | 0 | 0 | 1 | 4 | 0 | 0 | 0 | 0 | 4 | 2 | 0 | 0 | 0 | 0 | 0 | 0 |
| 1-113 | 25 | 2 | 3 | 0 | 5 | 4 | 4 | 3 | 1 | 3 | 4 | 2 | 0 | 2 | 0 | 0 | 2 |
| 1-114 | 25 | 5 | 4 | 3 | 4 | 4 | 5 | 5 | 1 | 4 | 4 | 2 | 0 | 0 | 0 | 3 | 2 |

TABLE 2-5

| No. | Dose (g/a) | A | B | C | D | E | F | a |
|---|---|---|---|---|---|---|---|---|
| 2-1 | 20 | 5 | 4 | 5 | 4 | 0 | 5 | 2 |
| 2-2 | 10 | 5 | 5 | 5 | 5 | 5 | 5 | 5 |
| 2-3 | 20 | 5 | 5 | 5 | 5 | 5 | 5 | 2 |
| 2-4 | 20 | 5 | 5 | 5 | 5 | 5 | 5 | 3 |
| 2-5 | 10 | 5 | 5 | 5 | 5 | 2 | 5 | 2 |
| 2-6 | 10 | 5 | 5 | 5 | 5 | 5 | 5 | 3 |
| 2-7 | 10 | 5 | 5 | 5 | 5 | 5 | 0 | 3 |
| 2-8 | 10 | 5 | 5 | 5 | 5 | 5 | 4 | 1 |
| 2-9 | 10 | 5 | 5 | 5 | 5 | 3 | 5 | 2 |
| 2-10 | 10 | 5 | 5 | 5 | 5 | 2 | 4 | 1 |
| 2-11 | 10 | 5 | 5 | 5 | 5 | 3 | 3 | 0 |
| 2-12 | 2.5 | 5 | 5 | 5 | 5 | 0 | 0 | 0 |
| 2-13 | 2.5 | 5 | 5 | 5 | 5 | 0 | 0 | 0 |
| 2-14 | 10 | 5 | 5 | 5 | 5 | 5 | 3 | 4 |
| 2-15 | 10 | 5 | 5 | 5 | 5 | 4 | 5 | 1 |
| 2-18 | 10 | 5 | 5 | 5 | 5 | 2 | 2 | 0 |
| 2-19 | 10 | 5 | 5 | 5 | 5 | 0 | 0 | 0 |
| 2-20 | 10 | 5 | 5 | 5 | 5 | 3 | 0 | 0 |
| 2-21 | 10 | 5 | 5 | 5 | 5 | 0 | 0 | 0 |
| 2-22 | 10 | 5 | 5 | 5 | 5 | 3 | 3 | 0 |
| 2-23 | 10 | 5 | 4 | 5 | 5 | 0 | 0 | 0 |
| 2-24 | 10 | 5 | 5 | 5 | 5 | 0 | 0 | 0 |
| 2-25 | 10 | 5 | 5 | 5 | 5 | 0 | 2 | 0 |
| 2-26 | 10 | 5 | 5 | 5 | 5 | 0 | 0 | 0 |

TABLE 2-6

| No. | Dose (g/a) | A | B | C | D |
|---|---|---|---|---|---|
| 2-1 | 20 | 5 | 3 | 3 | 3 |
| 2-2 | 10 | 5 | 5 | 5 | 5 |
| 2-3 | 20 | 5 | 2 | 5 | 5 |
| 2-4 | 20 | 5 | 4 | — | 5 |
| 2-5 | 10 | 5 | 0 | 4 | 4 |
| 2-6 | 10 | 5 | 5 | 5 | 4 |
| 2-7 | 10 | 5 | 5 | 5 | 4 |
| 2-8 | 10 | 5 | 3 | 5 | 5 |
| 2-9 | 10 | 5 | 5 | 5 | 5 |
| 2-10 | 10 | 5 | 2 | 5 | 3 |
| 2-11 | 10 | 5 | 0 | 5 | 4 |
| 2-12 | 2.5 | 5 | 3 | 4 | 5 |
| 2-13 | 2.5 | 5 | 4 | 5 | 5 |
| 2-14 | 10 | 5 | 0 | 3 | 5 |
| 2-15 | 10 | 5 | 5 | 5 | 5 |
| 2-18 | 10 | 5 | 3 | 5 | 5 |
| 2-19 | 10 | 3 | 3 | 3 | 5 |
| 2-20 | 10 | 5 | 4 | 5 | 5 |
| 2-21 | 10 | 4 | 3 | 5 | 5 |
| 2-22 | 10 | 5 | 3 | 5 | 5 |
| 2-23 | 10 | 5 | 3 | 5 | 5 |
| 2-24 | 10 | 5 | 3 | 5 | 5 |
| 2-25 | 10 | 5 | 3 | 5 | 5 |
| 2-26 | 10 | 5 | 3 | 5 | 5 |

TABLE 2-7

| No. | Dose (g/a) | G | H | I | J | K | L | M | N | O | P | a | b | c | d | e | f |
|---|---|---|---|---|---|---|---|---|---|---|---|---|---|---|---|---|---|
| 2-1 | 50 | 5 | 5 | 2 | 3 | 5 | 4 | 5 | 4 | 5 | 5 | 5 | 5 | 2 | 5 | 5 | 5 |
| 2-2 | 25 | 5 | 5 | 2 | 2 | 5 | 5 | 5 | 5 | 5 | 5 | 5 | 4 | 1 | 4 | 4 | 2 |
| 2-3 | 50 | 5 | 5 | 5 | 5 | 5 | 4 | 5 | 5 | 5 | 5 | 5 | 3 | 3 | 3 | 3 | 4 |
| 2-4 | 50 | 5 | 5 | 5 | 5 | 5 | 5 | 5 | 4 | 5 | 5 | 5 | 3 | 3 | 3 | 4 | 4 |
| 2-5 | 25 | 5 | 5 | 2 | 4 | 5 | 4 | 5 | 5 | 5 | 5 | 4 | 1 | 2 | 3 | 4 | 4 |
| 2-6 | 25 | 5 | 5 | — | 4 | 5 | 4 | 5 | 5 | 5 | 5 | 4 | 1 | 2 | 3 | 4 | 4 |
| 2-7 | 25 | 5 | 5 | — | 3 | 5 | 3 | 5 | 5 | 5 | 5 | 5 | 0 | 2 | 0 | 3 | 4 |
| 2-8 | 25 | 5 | 5 | 3 | 4 | 5 | 4 | 5 | 5 | 5 | 5 | 5 | 0 | 3 | 1 | 3 | 4 |
| 2-9 | 25 | 5 | 5 | 0 | 4 | 5 | 4 | 5 | 5 | 5 | 5 | 5 | 0 | 3 | 0 | 2 | 4 |
| 2-10 | 25 | 5 | 5 | — | 5 | 0 | 5 | 0 | 5 | 5 | 0 | 2 | 0 | — | 0 | 0 | 4 |
| 2-11 | 25 | 5 | 5 | 0 | 4 | 5 | 0 | 5 | 3 | 5 | 5 | 3 | 0 | 3 | 0 | 0 | 5 |
| 2-12 | 6.3 | 5 | 5 | 3 | 3 | 5 | 2 | 5 | 2 | 5 | 5 | 2 | 0 | 1 | 0 | 1 | 1 |
| 2-13 | 6.3 | 5 | 5 | 3 | 3 | 5 | 0 | 5 | 2 | 5 | 5 | 2 | 0 | 2 | 0 | 0 | 1 |
| 2-14 | 25 | 5 | 4 | 0 | 4 | 4 | 2 | 5 | 2 | 5 | 5 | 1 | 1 | 1 | 0 | 1 | 4 |
| 2-15 | 25 | 5 | 5 | 2 | 5 | 5 | 5 | 5 | 5 | 5 | 5 | 5 | 2 | 4 | 1 | 3 | 4 |
| 2-17 | 25 | 0 | 0 | 3 | 0 | 0 | 0 | 3 | 0 | 0 | 0 | 0 | 0 | 0 | 0 | 0 | 1 |
| 2-18 | 25 | 5 | 5 | 5 | — | 5 | 2 | 5 | 0 | 5 | 5 | — | 0 | 5 | 0 | 0 | 5 |
| 2-19 | 25 | 2 | 2 | 3 | 0 | 2 | 0 | 5 | 0 | 0 | 5 | — | 0 | 1 | 0 | 0 | 4 |
| 2-20 | 25 | 5 | 5 | 0 | — | 5 | 3 | 5 | 2 | 5 | 5 | 0 | 0 | 0 | 0 | 0 | 5 |
| 2-21 | 25 | 2 | 5 | 0 | — | 4 | 2 | 5 | 2 | 5 | 4 | 1 | 0 | 1 | 0 | 0 | 4 |
| 2-22 | 25 | 5 | 5 | 0 | — | 5 | 2 | 5 | 2 | 5 | 5 | 1 | 0 | 3 | 0 | 0 | 5 |
| 2-23 | 25 | 5 | 5 | 3 | — | 4 | 0 | 5 | 0 | 5 | 5 | 1 | 0 | 2 | 0 | 0 | 4 |
| 2-24 | 25 | 5 | 5 | 5 | — | 3 | 2 | 5 | 3 | 5 | 5 | 0 | 0 | 5 | 0 | 2 | 4 |
| 2-25 | 25 | 5 | 5 | 5 | — | 5 | 2 | 5 | 5 | 5 | 5 | 5 | 0 | 5 | 0 | 5 | 4 |
| 2-26 | 25 | 5 | 5 | 3 | — | 5 | 4 | 5 | 0 | 5 | 5 | 2 | 0 | 1 | 0 | 0 | 4 |

TABLE 2-8

| No. | Dose (g/a) | G | H | I | J | K | L | M | N | O | P | a | b | c | d | e | f |
|---|---|---|---|---|---|---|---|---|---|---|---|---|---|---|---|---|---|
| 2-1 | 50 | 2 | 3 | 2 | 5 | 2 | 1 | 1 | 0 | 2 | 4 | 1 | 2 | 1 | 1 | 0 | 2 |
| 2-2 | 25 | 4 | 5 | 0 | 5 | 3 | 5 | 3 | 3 | 4 | 4 | 0 | 2 | 1 | 4 | 1 | 0 |
| 2-3 | 50 | 5 | 3 | 3 | 4 | 4 | 4 | 4 | 4 | 4 | 5 | 1 | 2 | 1 | 2 | 1 | 1 |
| 2-4 | 50 | 5 | 5 | 2 | 4 | 4 | 5 | 4 | 5 | 4 | 4 | 1 | 1 | 2 | 2 | 0 | 2 |
| 2-5 | 25 | 4 | 3 | 4 | 0 | 4 | 5 | 4 | 3 | 3 | 4 | 2 | 0 | 0 | 2 | 0 | 1 |
| 2-6 | 25 | 4 | 5 | 3 | 4 | 4 | 3 | 4 | 4 | 3 | 3 | 3 | 1 | 0 | 1 | 2 | 2 |
| 2-7 | 25 | 5 | 5 | 3 | 5 | 4 | 0 | 4 | 3 | 4 | 4 | 2 | 0 | 2 | 0 | 0 | 3 |
| 2-8 | 25 | 4 | 4 | 0 | 2 | 3 | 2 | 4 | 2 | 3 | 2 | 1 | 0 | 0 | — | 0 | 2 |
| 2-9 | 25 | 4 | 3 | 0 | 3 | 3 | 2 | 3 | 0 | 3 | 4 | 2 | 0 | 1 | 1 | 0 | 1 |
| 2-10 | 25 | 0 | 0 | 0 | 2 | 3 | 0 | 2 | — | 5 | 3 | 0 | 0 | 0 | 0 | 0 | 2 |
| 2-11 | 25 | 4 | 0 | 0 | 4 | 3 | 2 | 2 | 0 | 4 | 4 | 1 | 0 | 1 | 0 | 0 | 1 |
| 2-12 | 6.3 | 0 | 0 | 0 | 0 | 0 | 2 | 2 | 0 | 4 | 3 | 2 | 0 | 1 | 0 | 0 | 1 |
| 2-13 | 6.3 | 0 | 0 | 0 | 0 | 2 | 2 | 3 | 3 | 3 | 3 | 1 | 0 | 1 | 0 | 0 | 2 |
| 2-14 | 25 | 4 | 4 | 3 | 3 | 3 | 3 | 3 | 2 | 5 | 5 | 2 | 0 | 2 | 2 | 2 | 2 |
| 2-15 | 25 | 4 | 3 | 2 | 4 | 4 | 5 | 2 | 2 | 5 | 5 | 2 | 2 | 1 | 2 | 1 | 2 |
| 2-18 | 25 | 0 | 0 | 0 | — | 0 | 2 | 0 | 0 | 3 | 4 | 0 | 1 | 0 | 0 | 0 | 0 |
| 2-19 | 25 | 0 | 0 | 0 | 0 | 0 | 0 | 0 | 0 | 3 | 1 | 0 | 0 | 0 | 0 | 0 | 1 |
| 2-20 | 25 | 0 | 0 | 0 | — | 0 | 3 | 1 | 0 | 5 | 3 | 2 | 0 | 3 | 0 | 0 | 0 |
| 2-21 | 25 | 4 | — | 0 | — | 0 | 2 | 2 | 0 | 4 | 3 | 2 | 0 | 0 | 0 | 0 | 0 |
| 2-22 | 25 | 0 | — | 0 | — | 3 | 2 | 2 | 0 | 5 | 5 | 0 | 0 | 0 | 0 | 0 | 1 |
| 2-23 | 25 | 0 | — | 0 | — | 0 | 1 | 1 | 0 | 5 | 5 | 0 | 0 | 0 | 0 | 0 | 0 |
| 2-24 | 25 | 0 | 2 | 0 | 5 | 3 | 2 | 2 | 2 | 4 | 4 | 2 | 0 | 1 | 1 | 1 | 0 |
| 2-25 | 25 | 0 | 3 | 0 | 4 | 2 | 4 | 3 | 2 | 5 | 5 | 3 | 0 | 1 | 0 | 0 | 1 |
| 2-26 | 25 | 0 | 0 | 0 | — | 3 | 4 | 4 | 3 | 5 | 5 | 2 | 0 | 2 | 1 | 2 | 2 |

TABLE 3-4

| No. | Dose (g/a) | A | B | C | D | E | F | a |
|---|---|---|---|---|---|---|---|---|
| 3-1 | 10 | 5 | 5 | 5 | 5 | 0 | 0 | 1 |
| 3-2 | 10 | 5 | 5 | 5 | 5 | 5 | 5 | 2 |
| 3-3 | 10 | 5 | 5 | 5 | 5 | 0 | 0 | 0 |
| 3-4 | 10 | 4 | 3 | 5 | 5 | 2 | 0 | 0 |
| 3-5 | 10 | 5 | 5 | 5 | 5 | 3 | 3 | 0 |
| 3-6 | 10 | 5 | 5 | 5 | 5 | 0 | 0 | 0 |
| 3-7 | 10 | 5 | 5 | 5 | 5 | 0 | 0 | 0 |
| 3-8 | 10 | 5 | 5 | 5 | 5 | 0 | 0 | 0 |
| 3-9 | 10 | 5 | 5 | 5 | 5 | 4 | 2 | 0 |
| 3-10 | 10 | 5 | 5 | 5 | 5 | 0 | 0 | 0 |
| 3-11 | 10 | 5 | 5 | 5 | 5 | 0 | 0 | 0 |
| 3-12 | 10 | 5 | 5 | 5 | 5 | 2 | 3 | 0 |
| 3-13 | 10 | 5 | 5 | 5 | 5 | 0 | 0 | 0 |
| 3-14 | 10 | 5 | 5 | 5 | 5 | 0 | 0 | 0 |
| 3-15 | 10 | 5 | 5 | 5 | 5 | 2 | 5 | 0 |
| 3-16 | 20 | 4 | 1 | 5 | 5 | 1 | 5 | 2 |
| 3-17 | 20 | 4 | 5 | 5 | 5 | 1 | 2 | 1 |
| 3-18 | 10 | 5 | 2 | 4 | 4 | 0 | 0 | 0 |
| 3-19 | 10 | 4 | 0 | 0 | 3 | 0 | 0 | 0 |
| 3-20 | 10 | 5 | 5 | 5 | 5 | 0 | 1 | 0 |
| 3-21 | 10 | 5 | 5 | 5 | 5 | 4 | 4 | 0 |

TABLE 3-5

| No. | Dose (g/a) | A | B | C | D |
|---|---|---|---|---|---|
| 3-1 | 10 | 5 | 3 | 5 | 5 |
| 3-2 | 10 | 5 | 5 | 5 | 5 |
| 3-3 | 10 | 5 | 2 | 4 | 5 |
| 3-4 | 10 | 2 | 0 | 3 | 4 |
| 3-5 | 10 | 5 | 3 | 5 | 4 |
| 3-6 | 10 | 5 | 2 | 5 | 5 |
| 3-7 | 10 | 5 | 2 | 5 | 4 |
| 3-8 | 10 | 5 | 3 | 5 | 4 |
| 3-9 | 10 | 4 | 0 | 4 | 4 |
| 3-10 | 10 | 5 | 0 | 4 | 4 |
| 3-11 | 10 | 5 | 3 | 5 | 5 |
| 3-12 | 10 | 5 | 3 | 5 | 5 |
| 3-13 | 10 | 4 | 2 | 5 | 5 |
| 3-14 | 10 | 5 | 5 | 5 | 5 |
| 3-15 | 10 | 5 | 3 | 5 | 5 |
| 3-16 | 20 | 2 | 1 | 4 | 5 |
| 3-17 | 20 | 2 | — | — | 4 |
| 3-18 | 10 | 2 | 0 | 3 | 2 |
| 3-19 | 10 | 0 | 2 | 2 | 4 |
| 3-20 | 10 | 4 | 3 | 5 | 4 |
| 3-21 | 10 | 5 | 4 | 5 | 5 |

TABLE 3-6

| No. | Dose (g/a) | G | H | I | J | K | L | M | N | O | P | a | b | c | d | e | f |
|---|---|---|---|---|---|---|---|---|---|---|---|---|---|---|---|---|---|
| 3-1 | 25 | 5 | 5 | 0 | 0 | 4 | 0 | 5 | 3 | 5 | 5 | 0 | 0 | 0 | 0 | 1 | 3 |
| 3-2 | 25 | 5 | 5 | 2 | 2 | 5 | 4 | 5 | 3 | 5 | 5 | 3 | 2 | 2 | 0 | 2 | 4 |
| 3-3 | 25 | 5 | 5 | 0 | 3 | 2 | 3 | 5 | 0 | 5 | 5 | 1 | 0 | 0 | 1 | 0 | 2 |
| 3-4 | 25 | 5 | 5 | 3 | 3 | 5 | 1 | 5 | 3 | 5 | 5 | 2 | 0 | 3 | 0 | 2 | 5 |
| 3-5 | 25 | 5 | 5 | 5 | 5 | 5 | 5 | 5 | 5 | 5 | 5 | 5 | 2 | 4 | 1 | 4 | 4 |
| 3-6 | 25 | 5 | 5 | 0 | 2 | 5 | 0 | 5 | 0 | 5 | 5 | 0 | 0 | 2 | 0 | 0 | 4 |
| 3-7 | 25 | 5 | 5 | 0 | 1 | 5 | 0 | 5 | 0 | 5 | 5 | 0 | 0 | 0 | 0 | 0 | 3 |
| 3-8 | 25 | 5 | 5 | 0 | 0 | 4 | 0 | 5 | 0 | 5 | 5 | 0 | 0 | 0 | 0 | 0 | 4 |
| 3-9 | 25 | 5 | 5 | 0 | 0 | 5 | 0 | 5 | 2 | 5 | 5 | 1 | 0 | 1 | 0 | 0 | 3 |
| 3-10 | 25 | 5 | 5 | 2 | 2 | 3 | 0 | 5 | 0 | 5 | 5 | 0 | 0 | 1 | 0 | 0 | 2 |
| 3-11 | 25 | 5 | 5 | 0 | 0 | 4 | 0 | 5 | 0 | 5 | 5 | 0 | 0 | 0 | 0 | 0 | 3 |
| 3-12 | 25 | 5 | 5 | 5 | 5 | 5 | 5 | 5 | 5 | 5 | 5 | 5 | 2 | 4 | 2 | 4 | 4 |
| 3-13 | 25 | 5 | 5 | 0 | 3 | 4 | 0 | 5 | 1 | 5 | 5 | 1 | 0 | 0 | 0 | 0 | 4 |
| 3-14 | 25 | 5 | 5 | 4 | 4 | 5 | 0 | 5 | 4 | 5 | 5 | 2 | 0 | 0 | 0 | 0 | 4 |
| 3-15 | 25 | 5 | 5 | 4 | 3 | 5 | 3 | 5 | 4 | 5 | 5 | 3 | 0 | 1 | 0 | 0 | 4 |
| 3-16 | 25 | 3 | 4 | — | 0 | 3 | 0 | 5 | 0 | 4 | 4 | 1 | 1 | 0 | 1 | 0 | 0 |
| 3-17 | 25 | 4 | 5 | — | 0 | 5 | 2 | 5 | 0 | 5 | 5 | 1 | 1 | 0 | 3 | 0 | 2 |
| 3-18 | 25 | 0 | 0 | 0 | 0 | 2 | 0 | 4 | 0 | 5 | 0 | 0 | 0 | 0 | 0 | 0 | 0 |
| 3-19 | 25 | 3 | 0 | 0 | 0 | 2 | 0 | 4 | 0 | 5 | 3 | 0 | 0 | 0 | 0 | 0 | 0 |
| 3-20 | 25 | 5 | 3 | 0 | 0 | 4 | 0 | 5 | 0 | 5 | 5 | 0 | 1 | 0 | 0 | 0 | 0 |
| 3-21 | 25 | 5 | 5 | 3 | — | 5 | 2 | 5 | 0 | 5 | 5 | — | 1 | 5 | 0 | 1 | 5 |

TABLE 3-7

| No. | Dose (g/a) | G | H | I | J | K | L | M | N | O | P | a | b | c | d | e | f |
|---|---|---|---|---|---|---|---|---|---|---|---|---|---|---|---|---|---|
| 3-1 | 25 | 4 | 3 | 0 | 3 | 3 | 0 | 4 | 2 | 5 | 5 | 1 | 0 | 0 | 2 | 1 | 2 |
| 3-2 | 25 | 5 | 5 | 0 | 1 | 4 | 5 | 5 | 3 | 5 | 4 | 3 | 3 | 1 | 2 | 2 | 2 |
| 3-3 | 25 | 4 | 2 | 0 | 0 | 2 | 3 | 3 | 2 | 5 | 4 | 2 | 0 | 0 | 1 | 1 | 1 |
| 3-4 | 25 | 3 | 2 | 0 | 0 | 0 | 2 | 2 | 0 | 4 | 3 | 1 | 0 | 0 | 0 | 0 | 1 |
| 3-5 | 25 | 4 | 4 | 3 | 4 | 3 | 4 | 4 | 5 | 5 | 4 | 3 | 2 | 2 | 3 | 2 | 2 |
| 3-6 | 25 | 0 | 0 | 0 | 2 | 4 | 3 | 4 | 2 | 5 | 5 | 0 | 0 | 0 | 0 | 0 | 0 |
| 3-7 | 25 | 0 | 0 | 0 | 3 | 3 | 4 | 4 | 3 | 5 | 5 | 0 | 0 | 0 | 0 | 0 | 1 |
| 3-8 | 25 | 0 | 0 | 0 | 2 | 2 | 4 | 3 | 4 | 5 | 5 | 0 | 0 | 0 | 0 | 1 | 1 |
| 3-9 | 25 | 0 | 0 | 0 | 2 | 0 | 4 | 3 | 1 | 4 | 5 | 0 | 0 | 0 | 0 | 2 | 1 |
| 3-10 | 25 | 0 | 0 | 0 | 0 | 3 | 5 | 3 | — | 5 | 5 | 0 | 0 | 0 | 0 | 1 | 0 |
| 3-11 | 25 | 0 | 0 | 0 | 0 | 3 | 3 | 3 | 3 | 5 | 5 | 0 | 0 | 0 | 1 | 1 | 2 |
| 3-12 | 25 | 4 | 3 | 2 | 3 | 4 | 3 | 3 | 2 | 5 | 5 | 0 | 1 | 2 | 0 | 0 | 0 |
| 3-13 | 25 | 1 | 0 | 0 | 2 | 1 | 1 | 3 | 0 | 4 | 4 | 0 | 0 | 0 | 1 | 0 | 0 |
| 3-14 | 25 | 0 | 0 | 0 | 0 | 0 | 1 | 2 | 1 | 3 | 4 | 0 | 0 | 0 | 0 | 0 | 0 |
| 3-15 | 25 | 0 | 0 | 0 | 2 | 2 | 4 | 3 | 1 | 5 | 4 | 0 | 0 | 0 | 0 | 0 | 1 |
| 3-16 | 50 | 2 | 2 | 3 | 3 | 4 | 2 | 3 | 2 | 2 | 2 | 1 | 0 | 0 | 1 | 0 | 0 |
| 3-17 | 50 | 3 | 2 | 3 | 2 | 3 | 2 | 2 | 2 | 3 | 2 | 0 | 0 | 1 | 1 | 1 | 1 |
| 3-18 | 25 | 0 | 3 | 0 | 0 | 1 | 0 | 0 | 0 | 0 | 2 | 0 | 0 | 0 | 3 | 0 | 0 |
| 3-19 | 25 | 0 | 0 | 0 | 0 | 0 | 0 | 1 | 0 | 0 | 2 | 1 | 0 | 0 | 0 | 0 | 0 |
| 3-20 | 25 | 3 | 3 | 0 | 0 | 2 | 0 | 2 | 0 | 2 | 2 | 1 | 0 | 0 | 0 | 0 | 0 |
| 3-21 | 25 | 5 | 0 | 0 | 4 | 1 | 4 | 0 | 0 | 5 | 5 | 1 | 0 | 2 | 1 | 0 | 2 |

TABLE 4-4

| No. | Dose (g/a) | A | B | C | D | E | F | a |
|---|---|---|---|---|---|---|---|---|
| 4-1 | 20 | 5 | 5 | 5 | 5 | 5 | 5 | 2 |
| 4-2 | 20 | 5 | 5 | 5 | 5 | 3 | 5 | 3 |
| 4-3 | 10 | 5 | 5 | 5 | 5 | 4 | 5 | 3 |
| 4-4 | 20 | 5 | 1 | 5 | 5 | 4 | 3 | 3 |
| 4-5 | 10 | 5 | 3 | 5 | 5 | 0 | 1 | 3 |
| 4-6 | 10 | 5 | 2 | 4 | 5 | 3 | 1 | 3 |
| 4-7 | 10 | 5 | 3 | 2 | 5 | 0 | 0 | 3 |
| 4-8 | 10 | 4 | 3 | 2 | 5 | 3 | 0 | 2 |
| 4-9 | 10 | 5 | 4 | 5 | 5 | 4 | 0 | 0 |
| 4-10 | 10 | 5 | 5 | 5 | 5 | 3 | 5 | 3 |
| 4-11 | 10 | 5 | 5 | 5 | 5 | 2 | 5 | 0 |
| 4-12 | 10 | 5 | 5 | 5 | 5 | 0 | 0 | 0 |
| 4-13 | 10 | 5 | 3 | 5 | 5 | 0 | 2 | 0 |
| 4-14 | 10 | 5 | 5 | 5 | 5 | 5 | 5 | 3 |
| 4-15 | 10 | 5 | 5 | 5 | 5 | 0 | 0 | 0 |
| 4-16 | 10 | 5 | 5 | 5 | 5 | 5 | 5 | 1 |

TABLE 4-5

| No. | Dose (g/a) | A | B | C | D |
|---|---|---|---|---|---|
| 4-1 | 20 | 5 | 5 | 5 | 5 |
| 4-2 | 20 | 4 | — | — | 5 |
| 4-3 | 10 | 4 | 3 | 4 | 4 |
| 4-4 | 20 | 4 | 5 | 1 | 4 |
| 4-5 | 10 | 4 | 0 | 5 | 3 |
| 4-6 | 10 | 4 | 0 | 2 | 5 |

TABLE 4-5-continued

| No. | Dose (g/a) | A | B | C | D |
|---|---|---|---|---|---|
| 4-7 | 10 | 4 | 0 | 2 | 5 |
| 4-8 | 10 | 4 | 0 | 4 | 5 |
| 4-9 | 10 | 4 | 2 | 5 | 5 |
| 4-10 | 10 | 5 | 5 | 5 | 5 |
| 4-11 | 10 | 5 | 4 | 5 | 5 |
| 4-12 | 10 | 5 | 5 | 5 | 5 |
| 4-13 | 10 | 5 | 2 | 5 | 5 |
| 4-14 | 10 | 5 | 4 | 5 | 5 |
| 4-15 | 10 | 5 | 5 | 5 | 5 |
| 4-16 | 10 | 5 | 5 | 5 | 5 |

TABLE 4-6

| No. | Dose (g/a) | G | H | I | J | K | L | M | N | O | P | a | b | c | d | e | f |
|---|---|---|---|---|---|---|---|---|---|---|---|---|---|---|---|---|---|
| 4-1 | 50 | 5 | 5 | 5 | 5 | 5 | 5 | 5 | 5 | 5 | 5 | 5 | 5 | 5 | 5 | 5 | 5 |
| 4-2 | 50 | 5 | 5 | 3 | 5 | 5 | 5 | 5 | 5 | 5 | 5 | 5 | 3 | 2 | 3 | 2 | 4 |
| 4-3 | 25 | 5 | 5 | — | 0 | 5 | 4 | 5 | 3 | 5 | 5 | 2 | 1 | 2 | 1 | 2 | 3 |
| 4-4 | 50 | 5 | 5 | — | 4 | 5 | 5 | 5 | 4 | 5 | 5 | 3 | 2 | 1 | 2 | 2 | 2 |
| 4-5 | 25 | 5 | 3 | 2 | 3 | 4 | 2 | 5 | 0 | 5 | 5 | 2 | 0 | 0 | 0 | 0 | 1 |
| 4-6 | 25 | 5 | 4 | 0 | 3 | 4 | 1 | 5 | 2 | 5 | 5 | 2 | 1 | 0 | 0 | 0 | 2 |
| 4-7 | 25 | 4 | 3 | 0 | 4 | 3 | 2 | 5 | 3 | 5 | 5 | 3 | 1 | 0 | 0 | 0 | 2 |
| 4-8 | 25 | 4 | 4 | 0 | 3 | 3 | 2 | 5 | 3 | 5 | 5 | 3 | 1 | 0 | 1 | 0 | 2 |
| 4-9 | 25 | 4 | 4 | 0 | 3 | 4 | 0 | 5 | 0 | 4 | 3 | 2 | 0 | 0 | 0 | 0 | 2 |
| 4-10 | 25 | 3 | 2 | 0 | 0 | 3 | 3 | 5 | 2 | 5 | 5 | 1 | 0 | 0 | 0 | 0 | 3 |
| 4-11 | 25 | 4 | 4 | 0 | 3 | 4 | 0 | 5 | 2 | 5 | 5 | 1 | 0 | 0 | 0 | 0 | 3 |
| 4-12 | 25 | 5 | 5 | 0 | 1 | 3 | 0 | 5 | 3 | 5 | 5 | 0 | 0 | 0 | 0 | 0 | 4 |
| 4-13 | 25 | 4 | 4 | 2 | 3 | 4 | 0 | 4 | 3 | 5 | 4 | 2 | 0 | 0 | 0 | 1 | 3 |
| 4-14 | 25 | 5 | 5 | 0 | 3 | 4 | 3 | 5 | 2 | 5 | 5 | 3 | 0 | 1 | 0 | 1 | 4 |
| 4-15 | 25 | 5 | 5 | 3 | 5 | 4 | 0 | 5 | 0 | 5 | 5 | 3 | 0 | 0 | 0 | 0 | 4 |
| 4-16 | 25 | 5 | 5 | 5 | — | 5 | 4 | 5 | 5 | 5 | 5 | — | 0 | 5 | 1 | 3 | 5 |

TABLE 4-7

| No. | Dose (g/a) | G | H | I | J | K | L | M | N | O | P | a | b | c | d | e | f |
|---|---|---|---|---|---|---|---|---|---|---|---|---|---|---|---|---|---|
| 4-1 | 50 | 5 | 5 | 5 | 5 | 5 | 5 | 5 | 3 | 5 | 5 | 2 | 3 | 2 | 4 | 2 | 3 |
| 4-2 | 50 | 4 | 3 | 3 | 4 | 2 | 5 | 3 | 4 | 4 | 5 | 1 | 2 | 1 | 2 | 1 | 2 |
| 4-3 | 25 | 0 | 3 | 2 | 2 | 3 | 2 | 2 | 2 | 0 | 0 | 1 | 0 | 1 | 0 | 0 | 1 |
| 4-4 | 50 | 3 | 4 | 3 | 4 | 4 | 1 | 3 | 5 | 3 | 5 | 1 | 0 | 1 | 1 | 1 | 1 |
| 4-5 | 25 | 2 | 2 | 2 | 4 | 0 | 0 | 4 | 4 | 3 | 2 | 0 | 0 | 0 | 0 | 0 | 0 |
| 4-6 | 25 | 2 | 2 | 1 | 4 | 2 | 0 | 3 | 4 | 3 | 3 | 0 | 0 | 0 | 0 | 3 | 1 |
| 4-7 | 25 | 3 | 3 | 0 | 3 | 1 | 3 | 4 | 5 | 3 | 2 | 0 | 0 | 0 | 0 | 0 | 1 |
| 4-8 | 25 | 3 | 3 | 3 | 3 | 3 | 3 | 3 | 5 | 3 | 4 | 2 | 1 | 0 | 0 | 0 | 1 |
| 4-9 | 25 | 2 | 3 | 3 | 3 | 2 | 2 | 3 | 0 | 3 | 3 | 0 | 0 | 0 | 0 | 0 | 2 |
| 4-10 | 25 | 1 | 1 | 0 | 0 | 2 | 0 | 3 | 4 | 0 | 0 | 0 | 0 | 0 | 0 | 0 | 0 |
| 4-11 | 25 | 4 | 2 | 0 | 2 | 2 | 0 | 2 | 0 | 3 | 3 | 2 | 0 | 1 | 0 | 0 | 1 |
| 4-12 | 25 | 0 | 0 | 0 | 0 | 2 | 2 | 2 | 2 | 2 | 3 | 0 | 0 | 0 | 0 | 0 | 1 |
| 4-13 | 25 | 2 | 0 | 0 | 0 | 2 | 0 | 0 | 0 | 0 | 0 | 0 | 0 | 0 | 0 | 0 | 1 |
| 4-14 | 25 | 4 | 3 | 0 | 3 | 3 | 4 | 2 | 3 | 5 | 3 | 2 | 0 | 2 | 0 | 0 | 1 |
| 4-15 | 25 | 0 | 0 | 0 | 0 | 0 | 1 | 0 | 0 | 0 | 2 | 0 | 0 | 0 | 0 | 0 | 0 |
| 4-16 | 25 | 4 | 4 | 3 | 5 | 4 | 4 | 2 | 2 | 5 | 5 | 2 | 2 | 1 | 1 | 0 | 3 |

TABLE 5-4

| No. | Dose (g/a) | A | B | C | D | E | F | a |
|---|---|---|---|---|---|---|---|---|
| 5-1 | 10 | 3 | 0 | 0 | 2 | 0 | 0 | 0 |
| 5-4 | 9.28 | 3 | 0 | 0 | 3 | 0 | 0 | 1 |
| 5-5 | 20 | 4 | 0 | 2 | 5 | 0 | 0 | 0 |
| 5-6 | 20 | 4 | 4 | 5 | 5 | 5 | 1 | 0 |
| 5-7 | 10 | 0 | 0 | 3 | 5 | 2 | 0 | 0 |

TABLE 5-5

| No. | Dose (g/a) | A | B | C | D |
|---|---|---|---|---|---|
| 5-4 | 9.28 | 1 | 1 | 1 | 2 |
| 5-5 | 20 | 2 | 2 | 5 | 3 |
| 5-6 | 20 | 2 | 4 | 5 | 5 |

TABLE 5-6

| No. | Dose (g/a) | G | H | I | J | K | L | M | N | O | P | a | b | c | d | e | f |
|---|---|---|---|---|---|---|---|---|---|---|---|---|---|---|---|---|---|
| 5-1 | 25 | 0 | 0 | 0 | 0 | 0 | 0 | 4 | 0 | 3 | 4 | 0 | 0 | 0 | 0 | 0 | 0 |
| 5-3 | 50 | 0 | 0 | 0 | 0 | 4 | 0 | 3 | 0 | 3 | 3 | — | 0 | 0 | 0 | 0 | 0 |
| 5-4 | 23.2 | 4 | 3 | 0 | 0 | 1 | 2 | 5 | 4 | 3 | 4 | 1 | 1 | 0 | 0 | 0 | 1 |
| 5-5 | 50 | 0 | 0 | 0 | 0 | 0 | 0 | 0 | 0 | 3 | 2 | 0 | 0 | 0 | 0 | 0 | 0 |
| 5-6 | 50 | 2 | 0 | 0 | 0 | 0 | 0 | 0 | 0 | 4 | 5 | 0 | 0 | 0 | 0 | 0 | 0 |

TABLE 5-7

| No. | Dose (g/a) | G | H | I | J | K | L | M | N | O | P | a | b | c | d | e | f |
|---|---|---|---|---|---|---|---|---|---|---|---|---|---|---|---|---|---|
| 5-3 | 50 | 0 | 0 | 0 | 0 | 1 | 0 | 0 | 0 | 0 | 1 | 0 | 0 | 0 | 2 | 0 | 0 |
| 5-4 | 23.2 | 2 | 0 | 0 | 2 | 3 | 3 | 3 | 5 | 0 | 0 | 0 | 0 | 0 | 2 | 1 | 0 |

We claim:

1. A 4,5-disubstituted pyrimidine compound of the formula (I):

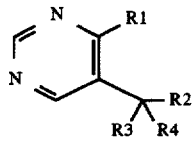

wherein R1 is a $C_1$ or a $C_2$ haloalkyl, R2 is a $C_1$–$C_8$ alkyl group, a $C_3$–$C_8$ cycloalkyl group, a $C_3$–$C_8$ cycloalkyl ($C_1$–$C_4$) alkyl group, a phenyl group which may be substituted {wherein the substituent is selected from the group consisting of a halogen atom, a $C_1$–$C_4$ alkyl group, a $C_1$–$C_4$ alkoxy group, a $C_1$–$C_4$ haloalkyl group, a $C_1$–$C_4$ haloalkoxy group, a $C_3$–$C_8$ alkenyl group, a $C_3$–$C_8$ alkynyl group, a $CO_2$ ($C_1$–$C_4$ alkyl) group, a N($C_1$–$C_3$ alkyl)$_2$ group, a cyano group, a nitro group, a sulfo group, an amino group, a hydroxy group, a mercapto group, a $SCH_3$ group, a $SO_2CH_3$ group, a phenoxy group and a phenyl group}, a thienyl group, a furyl group, a pyridyl group, a $C_1$–$C_6$ haloalkyl group, a $C_3$–$C_6$ halocycloalkyl group, a $C_3$–$C_8$ alkenyl group, a $C_3$–$C_8$ alkynyl group, a $C_1$–$C_2$ sulfonyl ($C_1$–$C_4$) alkyl group or $C_1$–$C_4$ alkylthio($C_3$–$C_6$)cycloalkyl group, R3 is a halogen atom, SH, $NH_2$, —O—R11 {wherein R11 is a $C_1$–$C_8$ alkyl group, a $C_3$–$C_8$ alkenyl group, a $C_3$–$C_8$ alkynyl group, a $C_3$–$C_6$ cycloalkyl group, $C_3$–$C_6$ cycloalkyl($C_1$ or $C_2$)alkyl group, a $C_1$–$C_6$ haloalkyl group, a $C_3$–$C_8$ haloalkenyl group, a $C_3$–$C_8$ haloalkynyl group, a $C_1$–$C_4$ alkoxy ($C_1$–$C_4$)alkyl group, a cyano ($C_1$–$C_4$)alkyl group, a $C_1$–$C_4$ alkylthio($C_1$–$C_4$)alkyl group, a $C_1$–$C_4$ alkoxycarbonyl($C_1$–$C_4$)alkyl group, a $C_1$–$C_4$ alkoxycarbonyl group, a carboxy($C_1$–$C_4$)alkyl group, a $C_1$–$C_4$ alkylcarbonyl group, a C(=O)NR21(R22) group (each of R21 and R22 is independently a hydrogen atom, a $C_1$–$C_4$ alkyl group, a $C_3$–$C_8$ alkenyl group or a $C_3$–$C_8$ alkynyl group), C(=S)NR21 (R22) group (R21 and R22 are as defined above), a hydroxy($C_1$–$C_4$)alkyl group, a $SO_2N(C_1$–$C_6$ alkyl)$_2$ group, $CO(C_1$–$C_6$ alkyl) group, a $CO_2(C_1$–$C_6$ alkyl) group, a SO ($C_1$–$C_6$ alkyl) group, a $SO_2(C_1$–$C_6$ alkyl) group, a phenethyl group, a phenacyl group, a 1- or 2-naphthyl group, a tetrahydropyranyl group, a tetrahydrothiopyranyl group, a 3-bromotetrahydropyranyl group, a 4-methoxytetrahydropyranyl group, a 4-methoxytetrahydrothiopyranyl group, a tetrahydrofuranyl group, a tetrahydrothiofuranyl group, a 1,4-dioxan-2-yl group, a 1-methoxycyclohexyl group, a benzyloxymethyl group, a 2,2,2-trichloroethoxymethyl group, a bis(2-chloroethoxy)methyl group, a 1-(2-chloroethoxy)ethyl group, a 2-methoxyethoxymethyl group, a 1-methyl-1-benzyloxyethyl group, a tertiary butyldimethylsilyl group, a trimethylsilyl group, a triethylsilyl group, a 2-thenyl group, a furfuryl group, a 2-thenoyl group, a phenyl group which may be substituted (wherein the substituent is selected from the group consisting of a halogen atom, a $C_1$–$C_4$ alkyl group, a $C_1$–$C_4$ alkoxy group, a $C_1$–$C_4$ haloalkyl group, a $C_1$–$C_4$ haloalkoxy group, a $C_3$–$C_8$ alkenyl group, a $C_3$–$C_8$ alkynyl group, a $CO_2(C_1$–$C_4$ alkyl) group, a $N(C_1$–$C_3$ alkyl)$_2$ group, a cyano group, a nitro group, a $SCH_3$ group, a $SO_2CH_3$ group, a phenoxy group and a phenyl group), a benzyl group which may be substituted (wherein the substituent is selected from the group consisting of a halogen atom, a $C_1$–$C_4$ alkyl group, a $C_1$–$C_4$ alkoxy group, a $C_1$–$C_4$ haloalkyl group, a $C_1$–$C_4$ haloalkoxy group, a $C_3$–$C_6$ alkenyl group, a $C_3$–$C_8$ alkynyl group, a $CO_2(C_1$–$C_4$ alkyl) group, a $N(C_1$–$C_3$ alkyl)$_2$ group, a cyano group, a nitro group, a $SCH_3$ group, a $SO_2CH_3$ group, a phenoxy group and a phenyl group), a —Q— phenyl group which may be substituted (wherein Q is a $C_2$–$C_6$ saturated or unsaturated carbon chain which may be branched, and the substituent of the phenyl group is selected from the group consisting of a halogen atom, a $C_1$–$C_4$ alkyl group, a $C_1$–$C_4$alkoxy group, a $C_1$–$C_4$ haloalkyl group, a $C_1$–$C_4$ haloalkoxy group, a $C_3$–$C_8$ alkenyl group, a $C_3$–$C_8$ alkynyl group, a $CO_2(C_1$–$C_4$ alkyl) group, a $N(C_1$–$C_3$ alkyl)$_2$ group, a cyano group, a nitro group, a $SCH_3$ group, a $SO_2CH_3$ group, a phenoxy group and a phenyl group), a —Q—$CO_2$R23 group (wherein Q is a $C_2$–$C_6$ saturated or unsaturated carbon chain which may be branched, and R23 is a $C_1$–$C_4$ alkyl group), a benzoyl group which may be substituted (wherein the substituent is selected from the group consisting of a halogen atom, a $C_1$–$C_4$ alkyl group, a $C_1$–$C_4$ alkoxy group, a $C_1$–$C_4$ haloalkyl group, a $C_1$–$C_4$ haloalkoxy group, a $C_3$–$C_8$ alkenyl group, a $C_3$–$C_8$ alkynyl group, a $CO_2$($C_1$–$C_4$ alkyl) group, a N ($C_1$–$C_3$ alkyl)$_2$ group, a cyano group, a nitro group, a $SCH_3$ group, a $SO_2CH_3$ group, a phenoxy group and a phenyl group), or a benzenesulfonyl group which may be substituted (wherein the substituent is selected from the group consisting of a halogen atom, a $C_1$–$C_4$ alkyl group, a $C_1$–$C_4$ alkoxy group, a $C_1$–$C_4$ haloalkyl group, a $C_1$–$C_4$ haloalkoxy group, a $C_3$–$C_8$ alkenyl group, a $C_3$–$C_8$ alkynyl group, a $CO_2$($C_1$–$C_4$ alkyl) group, a N($C_1$–$C_3$ alkyl)$_2$ group, a cyano group, a nitro group, a $SCH_3$ group, a $SO_2CH_3$ group, a phenoxy group and a phenyl group)}, —S—R11 (wherein R11 is as defined above), —N(R11)R12 (wherein R11 is as defined above, and R12 is a hydrogen atom, a $C_1$–$C_8$ alkyl group, $C_3$–$C_8$ alkenyl group, a $C_3$–$C_8$ alkynyl group, a $C_3$–$C_6$ cycloalkyl group, a $C_3$–$C_6$ cycloalkyl($C_1$ or $C_2$)alkyl group, a phenyl group, a benzyl group, a $C_1$–$C_6$ alkoxy group, a formyl group, a $C_1$–$C_6$ acyl group, a —NHR24 group (wherein R24 is a $C_1$–$C_6$ alkyl group), a $C_1$–$C_6$ alkylsulfonyl group or a benzoyl group), where in —N(R11)R12, R11 and R12 may form a 3- to 8-membered saturated, unsaturated or partially saturated heterocyclic ring together with the N atom to which R11 and R12 are bonded, where the constituting elements of the ring is selected from the group consisting of a nitrogen atom, an oxygen atom, a sulfur atom and a carbon atom, and the heterocyclic ring may be substituted (wherein the substituent is selected from the group consisting of a halogen atom, a $C_1$–$C_8$ alkyl group, a $C_1$–$C_8$ alkoxy group, a $C_1$–$C_6$ haloalkyl group, a $C_1$–$C_6$ haloalkoxy group, a $C_1$–$C_8$ acyl group, a $C_3$–$C_8$ alkenyl group, a $C_3$–$C_8$ alkynyl group, a benzoyl group and a phenyl group), or —NH(R12) {R12 is as defined above }, R4 is a hydrogen atom, a halogen atom, a $C_1$–$C_6$ alkyl group, a $C_1$–$C_6$ alkoxy group, a $C_3$–$C_6$ cycloalkyl group, a $C_3$–$C_8$ alkenyl group, a $C_3$–$C_8$ alkynyl group, a $C_1$–$C_6$ haloalkyl group, a $C_3$–$C_6$ halocycloalkyl group, a $C_3$–$C_6$ cycloalkoxy group, a $C_3$–$C_8$ alkenyloxy group, a $C_3$–$C_8$ alkynyloxy group, a $C_1$–$C_6$ haloalkoxy group, a $C_3$–$C_6$ halocycloalkoxy group, a $C_1$–$C_6$ alkylthio group, or a phenyl group which may be substituted {wherein the substituent is selected from the group consisting of a halogen atom, a $C_1$–$C_4$ alkyl group, a $C_1$–$C_4$ alkoxy group, a $C_1$–$C_3$ haloalkyl group, a $C_1$–$C_3$ haloalkoxy group, a $C_3$–$C_8$ alkenyl group, a $C_3$–$C_8$ alkynyl group, a $CO_2$($C_1$–$C_2$ alkyl) group, a N($C_1$–$C_3$ alkyl)$_2$ group, a phenoxy group and a phenyl group}, R3 and R4 may form a 5- to 6-membered ring which may be substituted, where the constituting elements thereof are groups selected from the group consisting of an oxygen atom, $CH_2$, $CH_2CH_2$, $CH_2C(=CH_2)$ and $CH_2CBr_2$, together with the C atom to which R3 and R4 are bonded {wherein the substituent is selected from the group consisting of a halogen atom, a $CH_2OH$ group, a $CH_2SH$ group, a $CH_2NH_2$ group, a $CH_2OSi$($CH_3$)$_3$ group, a $CH_2O$-tetrahydropyranyl group, a $C_1$–$C_4$ alkoxy $C_1$–$C_2$ alkoxymethyl group, a $CH_2OCH_2$-cyclopropyl group, a phenyl $C_1$–$C_4$ alkoxymethyl group which may be substituted (wherein the substituent is selected from the group consisting of a halogen atom, a $C_1$–$C_4$ alkyl group, a $C_1$–$C_4$ alkoxy group, a $C_1$–$C_4$ haloalkyl group and a nitro group), a phenyl $C_1$–$C_4$ alkylthiomethyl group which may be substituted (wherein the substituent is selected from the group consisting of a halogen atom, a $C_1$–$C_4$ alkyl group, a $C_1$–$C_4$ alkoxy group, a $C_1$–$C_4$ haloalkyl group and a nitro group), a phenylthiomethyl group which may be substituted (wherein the substituent is selected from the group consisting of a halogen atom, a $C_1$–$C_4$ alkyl group, a $C_1$–$C_4$ alkoxy group, a $C_1$–$C_4$ haloalkyl group and a nitro group), a piperidyl group, a pyridylmethyl group, a pyridyl group, a morpholinomethyl group, a piperazinomethyl group, a pyrrolidinylmethyl group, a piperdininomethyl group, a pyrrolylmethyl group, a phenylaminomethyl group which may be substituted (wherein the substituent is selected from the group consisting of a halogen atom, a $C_1$–$C_4$ alkyl group, a $C_1$–$C_4$ alkoxy group, a $C_1$–$C_4$ haloalkyl group and a nitro group), a phenyl $C_1$–$C_4$ alkytaminomethyl group which may be substituted (wherein the substituent is selected from the group consisting of a halogen atom, a $C_1$–$C_4$ alkyl group, a $C_1$–$C_4$ alkoxy group, a $C_1$–$C_4$ haloalkyl group and a nitro group), a 4-phenylpipersazinomethyl group, a N-benzyl-N-methylaminomethyl group, a 4-(4-acylpiperazinyl)phenoxymethyl group, a 4-(4-isopropylpiperazinyl)phenoxymethyl group, a 4-{4-{2,4-dihydro-2-1(1-methylpropyl)-3H-1,2,4-triazol-3-one-4-yl}phenyl}piperazino}phenxoymethyl group, a $C_1$–$C_{16}$ alkyl group, a $C_1$–$C_8$ alkoxy group, a $C_1$–$C_8$ haloalkyl group, a $C_1$–$C_{16}$ haloalkoxy group, a $C_2$–$C_8$ alkenyl group, a $C_2$–$C_8$ alkynyl group, a $C_1$–$C_{18}$ alkoxymethyl group, a $C_2$–$C_{18}$ alkenyloxymethyl group, a $C_2$–$C_{18}$ alkynyloxymethyl group, a $C_2$–$C_{18}$ alkenylthiomethyl group, a $C_2$–$C_8$ alkenylaminomethyl group, a 3-substituted-1-pyrrolylmethyl group, a $C_1$–$C_4$ alkylthiomethyl group, a $C_1$–$C_6$ alkylaminomethyl group, a $C_1$–$C_{19}$ alkylcarbonyloxymethyl group, a $C_2$–$C_{19}$ alkenylcarbonyloxymethyl group, a phenyl $C_{1-3}$ alkyl group, a ($C_1$–$C_6$ alkyl)$_2$ aminomethyl group (wherein the alkyl groups as substituents of the amino group may form a 5- or 6-membered cyclocyclic ring), a phenyoxymethyl group which may be substituted (the substituent of the phenyl group is selected from the group consisting of a halogen atom, a $C_1$–$C_4$ alkyl group, a $C_1$–$C_4$ alkoxy group, a $C_1$–$C_4$ haloalkyl group, a $C_1$–$C_4$ haloalkoxy group, a $C_3$–$C_8$ alkenyl group, a $C_3$–$C_8$ alkynyl group, a $CO_2$($C_1$–$C_4$ alkyl) group, a N($C_1$–$C_3$ alkyl)$_2$ group, a cyano group, a nitro group, a $SCH_3$ group, a $SO_2CH_3$ group, a phenoxy group and a phenyl group), and a phenyl group which may be substituted (wherein the substituent is selected from the group consisting of a halogen atom, a nitro group, a $C_1$–$C_4$ alkyl group, a $C_1$–$C_4$ haloalkoxy group, a N($C_1$–$C_3$ alkyl)$_2$ group, a phenoxy group and a phenyl group)}, provided that when the carbon atom substituted by R3 and R4 is an optically active carbon atom, the racemate and both of the two isolated optical isomers are included, and when two optically active sites are present in the molecule, the diastereomer mixture and all of the isolated two diastererromers and four optical isomers are included, and R3 and R4 may together form =NH, =NNH: , =NOH, =NOR11 (wherein R11 is as defined above, and the geometrical isomers include the E/Z mixture and both of the isolated E and Z), =NO—Q—R11 (wherein Q and R11 are as defined above, and the geometrical isomers include the E/Z mixture and both of the isolated E and Z), =NO—Q—CO$_2$-(C$_1$–C$_4$ alkyl group) (wherein Q is as defined above, and the geometrical isomers include the E/Z mixture and both of the isolated E and Z), or =NNR11(R16) (wherein R11 is as defined above, R16 is a hydrogen atom, a C$_1$–C$_6$ alkyl group, a C$_3$–C$_8$ alkenyl group, a C$_3$–C$_8$ alkynyl group, a benzyl group or a phenyl group, and the geometrical isomers include the E/Z mixture and both of the isolated E and Z), and wherein at least one of R1, R2, R3 and R4 contains an element other than carbon and fluorine.

2. The compound according to claim 1, wherein R1 is CF$_2$X (wherein X is a chlorine atom or a bromine atom).

3. The compound according to claim 2, wherein R2 is a phenyl group which may be substituted (wherein the substituent is selected from the group consisting of a halogen atom, a C$_1$–C$_4$ alkyl group, a C$_1$–C$_4$ alkoxy group, a trifluoromethoxy group and a trifluoromethyl group), a thienyl group, a furyl group or a pyridyl group; R3 is a halogen atom, a C$_1$–C$_8$ alkoxy group, a C$_3$–C$_6$ cycloalkyloxy group, a phenoxy group which may be substituted (wherein the substituent is selected from the group consisting of a halogen atom, a C$_1$–C$_4$ alkyl group, a C$_1$–C$_4$ alkoxy group and a trifluoromethyl group), a tetrahydropyranyloxy group, a phenyl C$_1$–C$_4$ alkoxy group which may be substituted (wherein the substituent is selected from the group consisting of a halogen atom, a C$_1$–C$_4$ alkyl group and a C$_1$–C$_4$ alkoxy group), a C$_3$–C$_6$ cycloalkyl C$_1$ or C$_2$alkoxy group, a C$_3$–C$_6$ alkenyloxy group, a C$_3$–C$_6$ alkynyloxy group, a C$_1$–C$_4$ alkoxycarbonyl(C$_1$–C$_4$)alkoxy group, a C$_1$–C$_4$ alkoxycarbonyloxy group, a C$_1$–C$_4$ alkoxy(C$_1$–C$_4$) alkoxy group, a C$_1$–C$_4$ alkylthio(C$_1$–C$_4$)alkoxy group, a cyano C$_1$–C$_4$ alkoxy group, a mono or di C$_1$–C$_4$ alkylaminocarbonyloxy group, a mono or di C$_1$–C$_4$ alkylaminothiocarbonyloxy group, a C$_1$–C$_4$ alkylcarbonyloxy group, a C$_1$–C$_4$ alkylsulfonyloxy group, a di C$_1$–C$_4$ alkylaminosulfonyloxy group, a mercapto group, a C$_1$–C$_4$ alkylthio group, a phenylthio group, a benzylthio group, a C$_3$–C$_6$ alkenylthio group, a C$_3$–C$_6$ alkynylthio group, a C$_1$–C$_4$ alkoxycarbonyl (C$_1$–C$_3$)alkylthio group, a C$_1$–C$_4$alkoxycarbonylthio group, a C$_1$–C$_4$ alkoxy C$_1$–C$_4$ alkylthio group, a cyano C$_1$–C$_4$ alkylthio group, a mono or di C$_1$–C$_4$ alkylaminocarbonylthio group, a mono or di C$_1$–C$_4$ alkylaminothiocarbonylthio group, a C$_1$–C$_4$ alkylthiocarbonylthio group, an amino group, a mono or di C$_1$–C$_4$ alkylamino group, a methyl(methoxy)amino group, a methoxyamino group, a hydroxy C$_1$–C$_4$ alkylamino group, a mono or di C$_3$–C$_5$ alkenylamino group, a mono or di C$_3$–C$_5$ alkynylamino group, a carboxy C$_1$–C$_4$ alkylamino group, a C$_1$–C$_4$ alkoxycarbonyl C$_1$–C$_4$ alkylamino group, a C$_1$–C$_4$ alkoxycarbonyl C$_1$–C$_4$ alkyl(methyl)amino group, a C$_3$–C$_6$ cycloalkylamino group, a phenylamino group, a phenyl C$_1$–C$_4$ alkylamino group which may be substituted (wherein the substituent is selected from the group consisting of a halogen, methyl and methoxy), a benzyl(methyl)amino group, a benzyl(formyl) amino group, a phenyl(formyl)amino group, a C$_1$–C$_4$ alkylsulfonylamino group, a mono or di C$_1$–C$_4$ alkylaminosulfonylamino group, a cyano C$_1$–C$_4$ alkylamino group, a C$_1$–C$_4$ alkylcarbonylamino group, a mono or di C$_1$–C$_4$ alkylaminocarbonylamino group, a mono or di C$_1$–C$_4$ alkylaminothiocarbonylamino group, a mono or di C$_1$–C$_4$ alkylhydrazino group, a di C$_1$–C$_4$ alkylamino group, an imidazolyl group, a triazol-1-yl group, a morpholino group, a dimethyl-substituted morpholino group, a piperazino group, a piperidino group, a pyrrolidinyl group or an aziridinyl group; and R4 is a hydrogen atom or a methyl group.

4. The compound according to claim 2, wherein R2 is a phenyl group which may be substituted (wherein the substituent is a halogen, a C$_1$–C$_4$ alkyl group, a C$_1$–C$_4$ alkoxy group or a trifluoromethyl group), a thienyl group, a furyl group or a pyridyl group; and R3 and R4 form together with the carbon atom to which R3 and R4 are bonded, a 1,3-dioxane ring which may be substituted (wherein the substituent is a methylene group or a halogen atom), or a 1,3-dioxolan ring which may be substituted (wherein the substituent is a C$_1$–C$_8$ alkyl group, a halo C$_1$–C$_4$ alkyl group, a methoxymethyl group or a C$_3$–C$_6$ alkenyl group).

5. The compound according to claim 2, wherein R2 is a C$_1$–C$_8$ alkyl group, a C$_3$–C$_6$ halocycloalkyl group, a C$_3$–C$_6$ cycloalkyl group or a C$_3$–C$_6$ cycloalkyl C$_1$ or C$_2$ alkyl group; and R3 and R4 together form a formula

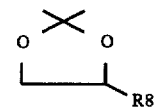

together with the carbon atom to which R3 and R4 are bonded, wherein R8 is a hydrogen atom, a C$_1$–C$_{20}$ alkyl group, a phenyl group which may be substituted by a nitro group, a phenyl C$_{1-3}$ alkyl group, a C$_3$–C$_6$ alkenyl group, a halo C$_1$–C$_8$ alkyl group, a C$_1$–C$_{18}$ alkoxymethyl group, a benzyloxymethyl group which may be substituted (the substituent is selected from the group consisting of a methoxy group, a methyl group and a halogen atom), a phenoxymethyl group which may be substituted (wherein the substituent is selected from the group consisting of a methoxy group, a C$_1$–C$_4$ alkyl group, a halogen atom and a nitro group), an allyloxymethyl group, a propinyloxymethyl group, a hydroxymethyl group, a trimethylsilyloxymethyl group, a tetrahydropyranyloxymethyl group, a methoxymethoxymethyl group, a cyclopropylmethoxymethyl group, a mono or di C$_1$–C$_{12}$ alkylaminomethyl group, an aminomethyl group, a phenylamino C$_1$–C$_4$ alkyl group which may be substituted by a nitro group, a phenylalkylaminomethyl group which may be substituted by a halogen atom, a C$_3$–C$_6$ cycloalkylaminomethyl group, a pyrrolidinylmethyl group, a piperazinomethyl group, a morpholinomethyl group, a piperidinomethyl group, a C$_1$–C$_4$ alkylthiomethyl group, a mercaptomethyl group, a phenylthiomethyl group which may be substituted by a halogen atom, a phenyl C$_1$–C$_4$ alkylthiomethyl group which may be substituted by a halogen atom, a C$_1$–C$_{17}$ alkylcarbonyloxymethyl group, a C$_3$–C$_6$ alkenylcarbonyloxymethyl group, a benzoyloxymethyl group, a piperidyl group, a 4-phenylpiperazinomethyl group, a 4-(4-acylpiperazinyl) phenoxymethyl group, a 3-substituted-1-pyrrolylmethyl group, a 4-[4-[4-[2,4-dihydro-2-(1-methylpropyl)-3H-1,2,4-triazol-3-one-4-yl]phenyl]piperazino]phenoxymethyl group, a pyridyl group or a pyridylmethyl group.

6. The compound according to claim 2, wherein R2 is a C$_1$–C$_8$ alkyl group or a C$_3$–C$_6$ cycloalkyl group; and R3 and R4 together form a 1,3-dioxane ring which may be substituted (wherein the substituent is a methylene group or a halogen atom) together with the carbon atom to which R3 and R4 are bonded.

7. The compound according to claim 2, wherein R2 is a C$_1$–C$_8$ alkyl group, a C$_3$–C$_6$ cycloalkyl group or a C$_3$–C$_6$ cycloalkyl C$_1$ or C$_2$ alkyl group; R3 is an amino group, a mono or di C$_1$–C$_4$ alkylamino group, a hydroxy C$_1$–C$_4$ alkylamino group, a cyano C$_1$–C$_4$ alkylamino group, a C$_1$–C$_4$ alkoxycarbonylmethyl(methyl)amino group, a C$_3$–C$_6$ alkenylamino group, a C$_3$–C$_6$ alkynylamino group, a phenylamino group which may be substituted by a halogen atom, a phenyl $C_1$–$C_4$ alkylamino group which may be substituted (wherein the substituent is selected from the group consisting of a halogen atom, a $C_1$–$C_4$ alkyl group, a trifluoromethyl group and a methoxy group), a phenyl $C_1$–$C_4$ alkyl(formyl)amino group which may be substituted by a halogen atom, a $C_1$–$C_4$ alkyl(formyl)amino group, a phenyl $C_{1-4}$ alkyl($C_1$–$C_4$ alkyl)amino group which may be substituted by a halogen atom, a diphenylmethylamino group, a thienylmethylamino group, a morpholino group, a dimethyl-substituted morpholino group, a thiomorpholino group, a piperidino group, a dimethyl-substituted piperidino group, an aziridyl group, a dimethylaziridyl group, a pyrrolyl group, a pyrrolidyl group, a $C_1$–$C_3$ alkyl-substituted piperidyl group, a methyl-substituted piperazyl group, a phenyl-substituted piperazyl group, a $C_6$ or $C_7$ alkyleneimino group, an imidazol-1-yl group, a pyrazol-1-yl group, a triazol-1-yl group, a phenyl-substituted piperidyl group, a benzyl-substituted piperidyl group, a dimethylamino-substituted piperidyl group, a trifluoromethylpiperidyl group, a perhydroquinolyl group, a tetrahydroquinolyl group, a tetrahydro-mono or dimethyl-substituted quinolyl group, a dihydro-dimethyl-substituted quinolyl group or a dihydro-dimethyl-chloroquinolyl group; and R4 is a hydrogen atom.

8. The compound according to claim 2, wherein R2 is a $C_1$–$C_6$ alkyl group, a $C_3$–$C_6$ cycloalkyl group or a $C_3$–$C_6$ cycloalkyl $C_1$ or $C_2$ alkyl group; R3 is an O—R11 group, wherein R11 is a $C_1$–$C_6$ alkyl group, a $C_3$–$C_6$ cycloalkyl group, a $C_3$–$C_5$ alkenyl group, a $C_3$–$C_5$ alkynyl group, a halo $C_1$–$C_4$ alkyl group, a halo $C_3$–$C_5$ alkenyl group, a phenyl group which may be substituted (wherein the substituent is selected from the group consisting of a halogen atom, a $C_1$–$C_4$ alkyl group and a methoxy group), a phenyl $C_1$–$C_4$ alkyl group which may be substituted (wherein the substituent is selected from the group consisting of a halogen atom, a $C_1$–$C_4$ alkyl group and a methoxy group), a $C_1$–$C_4$ alkylcarbonyl group, a phenylcarbonyl group which may be substituted (wherein the substituent is selected from the group consisting of a halogen atom, a $C_1$–$C_4$ alkyl group and a methoxy group), a benzylcarbonyl group, a $C_1$–$C_4$ alkylsulfonyl group, a phenylsulfonyl group which may be substituted (wherein the substituent is selected from the group consisting of a halogen atom, a $C_1$–$C_4$ alkyl group and a methoxy group), a $C_1$–$C_4$ alkoxy $C_1$–$C_4$ alkyl group which may be substituted by a halogen, a $C_1$–$C_4$ alkylthiomethyl group, a mono or di $C_1$–$C_4$ alkylaminocarbonyl group, a mono or di $C_1$–$C_4$ alkylaminothiocarbonyl group, a $C_1$–$C_4$ alkoxycarbonyl group, a $C_1$–$C_4$ alkoxycarbonyl $C_1$–$C_2$ alkyl group, a cyanomethyl group, a tetrahydropyranyl group, a 3-bromotetrahydropyranyl group, a methoxytetrahydropyranyl group, a tetrahydrothiopyranyl group which may be substituted by a methoxy group, a tetrahydrofuranyl group, a tetrahydrothiofuranyl group, a 1,4-dioxan-2-yl group, a methoxy-substituted cyclohexyl group, a $C_1$–$C_2$ alkoxy $C_1$–$C_2$ alkoxymethyl group, a benzyloxymethyl group or a $C_{1-4}$ trialkylsilyl group; and R4 is a hydrogen atom.

9. The compound according to claim 2, wherein R2 is a $C_{1-6}$ alkyl group, a phenyl group which may be substituted (wherein the substituent is selected from the group consisting of a halogen atom, a $C_1$–$C_4$ alkyl group, a $C_1$–$C_4$ alkoxy group and a trifluoromethyl group), a thienyl group, a furyl group or a pyridyl group; and R3 and R4 together form a formula =N—R5, wherein R5 is a $C_1$–$C_6$ alkoxy group, a $C_3$–$C_6$ cycloalkyloxy group, a $C_3$–$C_6$ alkenyloxy group, a $C_3$–$C_6$ alkynyloxy group, a $C_1$–$C_4$ alkoxycarbonyl $C_1$–$C_4$ alkoxy group, a carbonylmethoxy group, a benzyloxy group which may be substituted by a halogen atom, a hydroxy group, a mono or di $C_1$–$C_4$ alkylamino group, a phenylamino group which may be substituted (wherein the substituent is selected from the group consisting of a halogen atom, a $C_1$–$C_4$ alkyl group, a methoxy group and a trifluoromethyl group), a benzylamino group which may be substituted by a halogen atom or a benzyloxy group which may be substituted (wherein the substituent is selected from the group consisting of a $C_1$–$C_4$ alkyl group, a halogen atom and a methoxy group).

10. A herbicide comprising a carrier and an herbicidally effective amount of a 4,5-disubstituted pyrimidine compound of the formula (I):

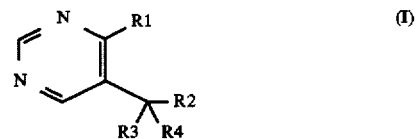

wherein R1 is a $C_1$ or a $C_2$ haloalkyl, R2 is a $C_1$–$C_8$ alkyl group, a $C_3$–$C_8$ cycloalkyl group, a $C_3$–$C_8$ cycloallcyl ($C_1$–$C_4$) alkyl group, a phenyl group which may be substituted {wherein the substituent is selected from the group consisting of a halogen atom, a $C_1$–$C_4$ alkyl group, a $C_1$–$C_4$ alkoxy group, a $C_1$–$C_4$ haloalkyl group, a haloalkoxy group, a $C_3$–$C_8$ alkenyl group, a $C_3$–$C_8$ alkynyl group, a $CO_2$ ($C_1$–$C_4$ alkyl) group, a $N(C_1$–$C_3$ alkyl$)_2$ group, a cyano group, a nitro group, a sulfo group, an amino group, a hydroxy group, a mercapto group, a $SCH_3$ group, a $SO_2CH_3$ group, a phenoxy group and a phenyl group}, a thienyl group, a furyl group, a pyridyl group, a $C_1$–$C_6$ haloalkyl group, a $C_3$–$C_6$ halocycloalkyl group, a $C_3$–$C_8$ alkenyl group, a $C_3$–$C_8$ alkynyl group, a $C_1$–$C_2$ sulfonyl ($C_1$–$C_4$)alkyl group or $C_1$–$C_4$ alkylthio($C_3$–$C_6$)cycloalkyl group, R3 is a halogen atom, SH, $NH_2$, —O—R11 {wherein R11 is a $C_1$–$C_8$ alkyl group, a $C_3$–$C_8$ alkenyl group, a $C_3$–$C_8$ alkynyl group, a $C_3$–$C_6$ cycloalkyl group, $C_3$–$C_6$ cycloalkyl($C_1$ or $C_2$)alkyl group, a $C_1$–$C_6$ haloalkyl group, a $C_3$–$C_8$ haloalkenyl group, a $C_3$–$C_8$ haloalkynyl group, a $C_1$–$C_4$ alkoxy ($C_1$–$C_4$)alkyl group, a cyano ($C_1$–$C_4$alkyl group, a $C_1$–$C_4$ alkylthio($C_1$–$C_4$)alkyl group, a $C_1$–$C_4$ alkoxycarbonyl($C_1$–$C_4$)alkyl group, a $C_1$–$C_4$ alkoxycarbonyl group, a carboxy($C_1$–$C_4$)alkyl group, a $C_1$–$C_4$ alkylcarbonyl group, a C(=O)NR21(R22) group (each of R21 and R22 is independently a hydrogen atom, a $C_1$–$C_4$ alkyl group, a $C_3$–$C_8$ alkenyl group or a $C_3$–$C_8$ alkynyl group), C(=S)NR21 (R22) group (R21 and R22 are as defined above), a hydroxy($C_1$–$C_4$)alkyl group, a $SO_2N(C_1$–$C_6$ alkyl$)_2$ group, $CO(C_1$–$C_6$ alkyl) group, a $CO_2(C_1$–$C_6$ alkyl) group, a SO ($C_1$–$C_6$ alkyl) group, a $SO_2(C_1$–$C_6$ alkyl) group, a phenethyl group, a phenacyl group, a 1- or 2-naphthyl group, a tetrahydropyranyl group, a tetrahydrothiopyranyl group, a 3-bromotetrahydropyranyl group, a 4-methoxytetrahydropyranyl group, a 4-methoxytetrahydrothiopyranyl group, a tetrahydrofuranyl group, a tetrahydrothiofuranyl group, a 1,4-dioxan-2-yl group, a 1-methoxycyclohexyl group, a benzyloxymethyl group, a 2,2,2-trichloroethoxymethyl group, a bis(2-chloroethoxy)methyl group, a 1-(2-chloroethoxy)ethyl group, a 2-methoxyethoxymethyl group, a 1-methyl-1-benzyloxyethyl group, a tertiary butyldimethylsilyl group, a trimethylsilyl group, a triethylsilyl group, a 2-thenyl group, a furfuryl group, a 2-thenoyl group, a phenyl group which may be substituted (wherein the substituent is selected from the group consisting of a halogen atom, a $C_1$–$C_4$ alkyl group, a $C_1$–$C_4$ alkoxy group, a $C_1$–$C_4$ haloalkyl group, a $C_1$–$C_4$ haloalkoxy group, a $C_3$–$C_8$ alkenyl group, a $C_3$–$C_8$ alkynyl group, a $CO_2(C_1$–$C_4$ alkyl) group, a $N(C_1$–$C_3$ alkyl)$_2$ group, a cyano group, a nitro group, a $SCH_3$ group, a $SO_2CH_3$ group, a phenoxy group and a phenyl group), a benzyl group which may be substituted (wherein the substituent is selected from the group consisting of a halogen atom, a $C_1$–$C_4$ alkyl group, a $C_1$–$C_4$ alkoxy group, a $C_1$–$C_4$ haloalkyl group, a $C_1$–$C_4$ haloalkoxy group, a $C_3$–$C_8$ alkenyl group, a $C_3$–$C_8$ alkynyl group, a $CO_2(C_1$–$C_4$ alkyl) group, a $N(C_1$–$C_3$ alkyl)$_2$ group, a cyano group, a nitro group, a $SCH_3$ group, a $SO_2CH_3$ group, a phenoxy group and a phenyl group), a —Q— phenyl group which may be substituted (wherein Q is a $C_2$–$C_6$ saturated or unsaturated carbon chain which may be branched, and the substituent of the phenyl group is selected from the group consisting of a halogen atom, a $C_1$–$C_4$ alkyl group, a $C_1$–$C_4$ alkoxy group, a $C_1$–$C_4$ haloalkyl group, a $C_1$–$C_4$ haloalkoxy group, a $C_3$–$C_8$ alkenyl group, a $C_3$–$C_8$ alkynyl group, a $CO_2(C_1$–$C_4$ alkyl) group, a $N(C_1$–$C_3$ alkyl)$_2$ group, a cyano group, a nitro group, a $SCH_3$ group, a $SO_2CH_3$ group, a phenoxy group and a phenyl group), a —Q—$CO_2R23$ group (wherein Q is a $C_2$–$C_6$ saturated or unsaturated carbon chain which may be branched, and R23 is a $C_1$–$C_4$ alkyl group), a benzoyl group which may be substituted (wherein the substituent is selected from the group consisting of a halogen atom, a $C_1$–$C_4$ alkyl group, a $C_1$–$C_4$ alkoxy group, a $C_1$–$C_4$ haloalkyl group, a $C_1$–$C_4$ haloalkoxy group, a $C_3$–$C_8$ alkenyl group, a $C_3$–$C_8$ alkynyl group, a $CO_2(C_1$–$C_4$ alkyl) group, a N ($C_1$–$C_3$ alkyl)$_2$ group, a cyano group, a nitro group, a $SCH_3$ group, a $SO_2CH_3$ group, a phenoxy group and a phenyl group), or a benzenesulfonyl group which may be substituted (wherein the substituent is selected from the group consisting of a halogen atom, a $C_1$–$C_4$ alkyl group, a $C_1$–$C_4$ alkoxy group, a $C_1$–$C_4$ haloakyl group, a $C_1$–$C_4$ haloalkoxy group, a $C_3$–$C_8$ alkenyl group, a $C_3$–$C_8$ alkynyl group, a $CO_2(C_1$–$C_4$ alkyl) group, a $N(C_1$–$C_3$ alkyl)$_2$ group, a cyano group, a nitro group, a $SCH_3$ group, a $SO_2CH_3$ group, a phenoxy group and a phenyl group)}, —S—R11 (wherein R11 is as defined above), —N(R11)R12 (wherein R11 is as defined above, and R12 is a hydrogen atom, a $C_1$–$C_8$ alkyl group, $C_3$–$C_8$ alkenyl group, a $C_3$–$C_8$ alkynyl group, a $C_3$–$C_6$ cycloalkyl group, a $C_3$–$C_6$ cycloalkyl($C_1$ or $C_2$)alkyl group, a phenyl group, a benzyl group, a $C_1$–$C_6$ alkoxy group, a formyl group, a $C_1$–$C_6$ acyl group, a —NHR24 group (wherein R24 is a $C_1$–$C_6$ alkyl group), a $C_1$–$C_6$ alkylsulfonyl group or a benzoyl group), where in —N(R11)R12, R11 and R12 may form a 3 to 8-membered saturated, unsaturated or partially saturated heterocyclic ring together with the N atom to which R11 and R12 are bonded, where the constituting elements of the ring is selected from the group consisting of a nitrogen atom, an oxygen atom, a sulfur atom and a carbon atom, and the heterocyclic ring may be substituted (wherein the substituent is selected from the group consisting of a halogen atom, a $C_1$–$C_8$ alkyl group, a $C_1$–$C_8$ alkoxy group, a $C_1$–$C_6$ haloalkyl group, a $C_1$–$C_6$ haloalkoxy group, a $C_1$–$C_8$ acyl group, a $C_3$–$C_8$ alkenyl group, a $C_3$–$C_8$ alkynyl group, a benzoyl group and a phenyl group), or —NH(R12) {R12 is as defined above}, R4 is a hydrogen atom, a halogen atom, a $C_1$–$C_6$ alkyl group, a $C_1$–$C_6$ alkoxy group, a $C_3$–$C_6$ cycloalkyl group, a $C_3$–$C_8$ alkenyl group, a $C_3$–$C_8$ alkynyl group, a $C_1$–$C_6$ haloalkyl group, a $C_3$–$C_6$ halocycloalkyl group, a $C_3$–$C_6$ cycloalkoxy group, a $C_3$–$C_8$ alkenyloxy group, a $C_3$–$C_8$ alkynyloxy group, a $C_1$–$C_6$ haloalkoxy group, a $C_3$–$C_6$ halocycloalkoxy group, a $C_1$–$C_6$ alkylthio group, or a phenyl group which may be substituted {wherein the substituent is selected from the group consisting of a halogen atom, a $C_1$–$C_4$ alkyl group, a $C_1$–$C_4$ alkoxy group, a $C_1$–$C_3$ haloalkyl group, a $C_1$–$C_3$ haloalkoxy group, a $C_3$–$C_8$ alkenyl group, a $C_1$–$C_8$ alkynyl group, a $CO_2(C_1$–$C_2$ alkyl) group, a $N(C_1$–$C_3$ alkyl)$_2$ group, a phenoxy group and a phenyl group}, R3 and R4 may form a 5- to 6-membered ring which may be substituted, where the constituting elements thereof are groups selected from the group consisting of an oxygen atom, $CH_2$, $CH_2CH_2$, $CH_2C(=CH_2)$ and $CH_2CBr2$, together with the C atom to which R3 and R4 are bonded {wherein the substituent is selected from the group consisting of a halogen atom, a $CH_2OH$ group, a $CH_2SH$ group, a $CH_2NH_2$ group, a $CH_2OSi$ $(CH_3)_3$ group, a $CH_2O$-tetrahydropyranyl group, a $C_1$–$C_4$ alkoxy $C_1$–$C_2$ alkoxymethyl group, a $CH_2OCH_2$-cyclopropyl group, a phenyl $C_1$–$C_4$ alkoxymethyl group which may be substituted (wherein the substituent is selected from the group consisting of a halogen atom, a $C_1$–$C_4$ alkyl group, a $C_1$–$C_4$ alkoxy group,haloalkyl group and a haloalkyl group and a nitro group), substituted (wherein the substituent is selected from the group consisting of a halogen atom, a $C_1$–$C_4$ alkyl group, a $C_1C_4$ alkoxy group, a $C_1$–$C_4$ haloalkyl group and a nitro group), a phenylthiomethyl group which may be substituted (wherein the substituent is selected from the group consisting of a halogen atom, a $C_1$–$C_4$ alkyl group, a $C_1$–$C_4$ alkoxy group, a $C_1$–$C_4$ haloalkyl group and a nitro group), a piperidyl group, a pyridylmethyl group, a pyridyl group, a morpholinomethyl group, a piperazinomethyl group, a pyrrolidinylmethyl group, a piperdininomethyl group, a pyrrolylmethyl group, a phenylaminomethyl group which may be substituted (wherein the substituent is selected from the group consisting of a halogen atom, a $C_1$–$C_4$ alkyl group, a $C_1$–$C_4$ alkoxy group, a $C_1$–$C_4$ haloalkyl group and a nitro group), a phenyl $C_1$–$C_4$ alkylaminomethyl group which may be substituted (wherein the substituent is selected from the group consisting of a halogen atom, a $C_1$–$C_4$ alkyl group, a $C_1$–$C_4$ alkoxy group, a $C_1$–$C_4$ haloalkyl group and a nitro group), a 4-phenylpipersazinomethyl group, a N-benzyl-N-methylarninomethyl group, a 4-(4-acylpiperazinyl) phenoxymethyl group, a 4-(4-isopropylpiperazinyl) phenoxymethyl group, a 4-{4-{4-{2,4-dihydro-2-1(1-methylpropyl)-3 H-1,2,4-triazol-3-one-4-yl }phenyl}piperazino}phenxoymethyl group, a $C_1$–$C_{16}$ alkyl group, a $C_1$–$C_{18}$ alkoxy group, a $C_1$–$C_8$ haloalkyl group, a $C_1$–$C_{16}$ haloalkoxy group, a $C_2$–$C_8$ alkenyl group, a $C_2$–$C_8$ alkynyl group, a $C_1$–$C_8$ alkoxymethyl group, a $C_2$–$C_{18}$ alkenyloxymethyl group, a $C_2$–$C_{18}$ alkynyloxymethyl group, a $C_2$–$C_{18}$ alkenylthiomethyl group, a $C_2$–$C_8$ alkenylaminomethyl group, a 3-substituted-1-pyrrolylmethyl group, a $C_1$–$C_4$ alkylthiomethyl group, a $C_1$–$C_6$ alkylaminomethyl group, a $C_1$–$C_{19}$ alkylcarbonyloxymethyl group, a $C_2$–$C_{19}$ alkenylcarbonyloxymethyl group, a phenyl $C_{1-3}$ alkyl group, a $(C_1-C_6$ alkyl$)_2$ aminomethyl group (wherein the alkyl groups as substituents of the amino group may form a 5- or 6-membered cyclocyclic ring), a phenyoxymethyl group which may be substituted (the substituent of the phenyl group is selected from the group consisting of a halogen atom, a $C_1-C_4$ alkyl group, a $C_1-C_4$ alkoxy group, a $C_1-C_4$ haloalkyl group, a $C_1-C_4$ haloalkoxy group, a $C_3-C_8$ alkenyl group, a $C_3-C_8$ alkynyl group, a $CO_2(C_1-C_4$ alkyl) group, a $N(C FC_3$ alkyl$)_2$ group, a cyano group, a nitro group, a $SCH_3$ group, a $SO_2CH_3$ group, a phenoxy group and a phenyl group), and a phenyl group which may be substituted (wherein the substituent is selected from the group consisting of a halogen atom, a nitro group, a $C_1-C_4$ alkyl group, a $C_1-C_4$ haloalkoxy group, a $N(C_1-C_3$ alkyl$)_2$ group, a phenoxy group and a phenyl group)}, provided that when the carbon atom substituted by R3 and R4 is an optically active carbon atom, the racemate and both of the two isolated optical isomers are included, and when two optically active sites are present in the molecule, the diastereomer mixture and all of the isolated two diastereromers and four optical isomers are included, and R3 and R4 may together form =NH, =NNH$_2$, =NOH, =NOR11 (wherein R11 is as defined above, and the geometrical isomers include the E/Z mixture and both of the isolated E and Z), =NO—Q—R11 (wherein Q and R11 are as defined above, and the geometrical isomers include the E/Z mixture and both of the isolated E and Z), =NO—Q—CO$_2$-(C$_1$-C$_4$ alkyl group) (wherein Q is as defined above, and the geometrical isomers include the E/Z mixture and both of the isolated E and Z), or =NNR1 1(R16) (wherein R11 is as defined above, R16 is a hydrogen atom, a $C_1-C_6$ alkyl group, a $C_3-C_8$ alkenyl group, a $C_3-C_8$ alkynyl group, a benzyl group or a phenyl group, and the geometrical isomers include the E/Z mixture and both of the isolated E and Z).

11. A method of treating broad-leafed weeds in an agricultural field, comprising applying to soil or weed foliage in said field, an herbicidally effective amount of a 4,5-disubstituted pyrimidine compound formula (I):

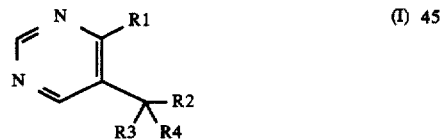

(I)

wherein R1 is a $C_1$ or a $C_2$ haloalkyl, R2 is a $C_1-C_8$ alkyl group, a $C_3-C_8$ cycloalkyl group, a $C_3-C_8$ cycloalkyl ($C_1-C_4$) alkyl group, a phenyl group which may be substituted {wherein the substituent is selected from the group consisting of a halogen atom, a $C_1-C_4$ alkyl group, a $C_1-C_4$ alkoxy group, a $C_1-C_4$ haloalkyl group, a $C_1-C_4$ haloalkoxy group, a $C_3-C_8$ alkenyl group, a $C_3-C_8$ alkynyl group, a $CO_2$ ($C_1-C_4$ alkyl) group, a $N(C_1-C_3$ alkyl$)_2$ group, a cyano group, a nitro group, a sulfo group, an amino group, a hydroxy group, a mercapto group, a $SCH_3$ group, a $SO_2CH_3$ group, a phenoxy group and a phenyl group}, a thienyl group, a furyl group, a pyridyl group, a $C_1-C_6$ haloalkyl group, a $C_3-C_6$ halocycloalkyl group, a $C_3-C_8$ alkenyl group, a $C_3-C_8$ alkynyl group, a $C_1-C_2$ sulfonyl ($C_1-C_4$)alkyl group or $C_1-C_4$ alkylthio($C_3-C_6$)cycloalkyl group, R3 is a halogen atom, SH, NH$_2$)

—O—R11 {wherein R11 is a $C_1-C_8$ alkyl group, a $C_3-C_8$ alkenyl group, a $C_3-C_8$ alkynyl group, a $C_3-C_6$ cycloalkyl group, $C_3-C_6$ cycloalkyl(Q or $C_2$)alkyl group, a $C_1-C_6$ haloalkyl group, a $C_3-C_6$ haloalkenyl group, a $C_3-C_8$ haloalkynyl group, a $C_1-C_4$ alkoxy ($C_1-C_4$)alkyl group, a cyano ($C_1-C_4$)alkyl group, a $C_1-C_4$ alkylthio($C_1-C_4$)alkyl group, a $C_1-C_4$ alkoxycarbonyl($C_1-C_4$)alkyl group, a $C_1-C_4$ alkoxycarbonyl group, a carboxy($C_1-C_4$)alkyl group, a $C_1-C_4$ alkylcarbonyl group, a C(=O)NR21(R22) group (each of R21 and R22 is independently a hydrogen atom, a $C_1-C_4$ alkyl group, a $C_3-C_8$ alkenyl group or a $C_3-C_8$ alkynyl group), C(=S)NR21 (R22) group (R21 and R22 are as defined above), a hydroxy($C_1-C_4$)alkyl group, a $SO_2N(C_1-C_6$ alkyl$)_2$ group, $CO(C_1-C_6$ alkyl) group, a $CO_2(C_1-C_6$ alkyl) group, a SO ($C_1-C_6$ alkyl) group, a $SO_2(C_1-C_6$ alkyl) group, a phenethyl group, a phenacyl group, a 1- or 2-naphthyl group, a tetrahydropyranyl group, a tetrahydrothiopyranyl group, a 3-bromotetrahydropyranyl group, a 4-methoxytetrahydropyranyl group, a 4-methoxytetrahydrothiopyranyl group, a tetrahydrofuranyl group, a tetrahydrothiofuranyl group, a 1,4-dioxan-2-yl group, a 1-methoxycyclohexyl group, a benzyloxymethyl group, a 2,2,2-trichloroethoxymethyl group, a bis(2-chloroethoxy)methyl group, a 1-(2-chloroethoxy)ethyl group, a 2-methoxyethoxymethyl group, a 1-methyl-1-benzyloxyethyl group, a tertiary butyldimethylsilyl group, a trimethylsilyl group, a triethylsilyl group, a 2-thenyl group, a furfuryl group, a 2-thenoyl group, a phenyl group which may be substituted (wherein the substituent is selected from the group consisting of a halogen atom, a $C_1-C_4$ alkyl group, a $C_1-C_4$ alkoxy group, a $C_1-C_4$ haloalkyl group, a $C_1-C_4$ haloalkoxy group, a $C_3-C_8$ alkenyl group, a $C_3-C_8$ alkynyl group, a $CO_2(C_1-C_4$ alkyl) group, a $N(C_1-C_3$ alkyl$)_2$ group, a cyano group, a nitro group, a $SCH_3$ group, a $SO_2CH_3$ group, a phenoxy group and a phenyl group), a benzyl group which may be substituted (wherein the substituent is selected from the group consisting of a halogen atom, a $C_1-C_4$ alkyl group, a $C_1-C_4$ alkoxy group, a $C_1-C_4$ haloallcyl group, a $C_1-C_4$ haloalkoxy group, a $C_3-C_8$ alkenyl group, a $C_3-C_8$ alkynyl group, a $CO_2(C_1-C_4$ alkyl) group, a $N(C_1-C_3$ alkyl$)_2$ group, a cyano group, a nitro group, a $SCH_3$ group, a $SO_2CH_3$ group, a phenoxy group and a phenyl group), a —Q— phenyl group which may be substituted (wherein Q is a $C_2-C_6$ saturated or unsaturated carbon chain which may be branched, and the substituent of the phenyl group is selected from the group consisting of a halogen atom, a $C_1-C_4$ alkyl group, a $C_1-C_4$ alkoxy group, a $C_1-C_4$ haloalkyl group, a $C_1-C_4$ haloalkoxy group, a $C_3-C_8$ alkenyl group, a $C_3-C_8$ alkynyl group, a $CO_2(CrC_4$ alkyl) group, a $N(C_1-C_3$ alkyl$)_2$ group, a cyano group, a nitro group, a $SCH_3$ group, a $SO_2CH_3$ group, a phenoxy group and a phenyl group), a —Q—CO$_2$R23 group (wherein Q is a $C_2-C_6$ saturated or unsaturated carbon chain which may be branched, and R23 is a $C_1-C_4$ alkyl group), a benzoyl group which may be substituted (wherein the substituent is selected from the group consisting of a halogen atom, a $C_1-C_4$ alkyl group, a $C_1-C_4$ alkoxy group, a $C_1-C_4$ haloalkyl group, a $C_1-C_4$ haloalkoxy group, a $C_3-C_8$ alkenyl group, a $C_3-C_8$ alkynyl group, a $CO_2(C_1-C_4$ alkyl) group, a N ($C_1-C_3$ alkyl$)_2$ group, a cyano group, a nitro group, a $SCH_3$ group, a $SO_2CH_3$ group, a phenoxy group and a phenyl group), or a benzenesulfonyl group which may be substituted (wherein the substituent is selected from the group consisting of a halogen atom, a $C_1$–$C_4$ alkyl group, a $C_1$–$C_4$ alkoxy group, a $C_1$–$C_4$ haloalkyl group, a $C_1$–$C_4$ haloalkoxy group, a $C_3$–$C_8$ alkenyl group, a $C_2(C_1$–$C_4$ alkyl) group, a $N(C_1$–$C_3$ alkyl)$_2$ group, a cyano group, a nitro group, a $SCH_3$ group, a $SO_2CH_3$ group, a phenoxy group and a phenyl group)}, —S—R11 (wherein R11 is as defined above), —N(R11)R12 (wherein R11 is as defined above, and R12 is a hydrogen atom, a $C_1$–$C_8$ alkyl group, $C_3$–$C_8$ alkenyl group, a $C_3$–$C_8$ alkynyl group, a $C_3$–$C_6$ cycloalkyl group, a $C_3$–$C_6$ cycloalkyl($C_1$ or $C_2$)alkyl group, a phenyl group, a benzyl group, a $C_1$–$C_6$ alkoxy group, a formyl group, a $C_1$–$C_6$ acyl group, a —NHR24 group (wherein R24 is a $C_1$–$C_6$ alkyl group), a $C_1$–$C_6$ alkylsulfonyl group or a benzoyl group), where in —N(R11)R12, R11 and R12 may form a 3- to 8-membered saturated, unsaturated or partially saturated heterocyclic ring together with the N atom to which R11 and R12 are bonded, where the constituting elements of the ring is selected from the group consisting of a nitrogen atom, an oxygen atom, a sulfur atom and a carbon atom, and the heterocyclic ring may be substituted (wherein the substituent is selected from the group consisting of a halogen atom, a $C_1$–$C_8$ alkyl group, a $C_1$–$C_8$ alkoxy group, a $C_1$–$C_6$ haloalkyl group, a $C_1$–$C_6$ haloalkoxy group, a $C_1$–$C_8$ acyl group, a $C_3$–$C_8$ alkenyl group, a $C_3$–$C_8$ alkynyl group, a benzoyl group and a phenyl group), or —NH(R12) {R12 is as defined above}, R4 is a hydrogen atom, a halogen atom, a $C_1$–$C_6$ alkyl group, a $C_1$–$C_6$ alkoxy group, a $C_3$–$C_6$ cycloalkyl group, a $C_3$–$C_8$ alkenyl group, a $C_3$–$C_8$ alkynyl group, a $C_1$–$C_6$ haloalkyl group, a $C_3$–$C_6$ halocycloalkyl group, a $C_3$–$C_6$ cycloalkoxy group, a $C_3$–$C_6$ alkenyloxy group, a $C_3$–$C_8$ alkynyloxy group, a $C_1$–$C_6$ haloalkoxy group, a $C_3$–$C_6$ halocycloalkoxy group, a $C_1$–$C_6$ alkylthio group, or a phenyl group which may be substituted {wherein the substituent is selected from the group consisting of a halogen atom, a $C_1$–$C_4$ alkyl group, a $C_1$–$C_4$ alkoxy group, a $C_1$–$C_3$ haloalkyl group, a $C_1$–$C_3$ haloalkoxy group, a $C_3$–$C_8$ alkenyl group, a $C_3$–$C_8$ alkynyl group, a $CO_2(C_1$–$C_2$ alkyl) group, a $N(C_1$–$C_3$ alkyl)$_2$ group, a phenoxy group and a phenyl group}, R3 and R4 may form a 5- to 6-membered ring which may be substituted, where the constituting elements thereof are groups selected from the group consisting of an oxygen atom, $CH_2$, $CH_2CH_2$, $CH_2C(\!\!=\!\!CH_2)$ and $CH_2CBr_2$, together with the C atom to which R3 and R4 are bonded {wherein the substituent is selected from the group consisting of a halogen atom, a $CH_2OH$ group, a $CH_2SH$ group, a $CH_2NH_2$ group, a $CH_2OSi$ $(CH_3)_3$ group, a $CH_2O$-tetrahydropyranyl group, a $C_1$–$C_4$ alkoxy $C_1$–$C_2$ alkoxymethyl group, a $CH_2OCH_2$-cyclopropyl group, a phenyl $C_1$–$C_4$ alkoxymethyl group which may be substituted (wherein the substituent is selected from the group consisting of a halogen atom, a $C_1$–$C_4$ alkyl group, a $C_1$–$C_4$ alkoxy group, a $C_1$–$C_4$ haloalkyl group and a nitro group), a phenyl $C_1$–$C_4$ alkylthiomethyl group which may be substituted (wherein the substituent is selected from the group consisting of a halogen atom, a $C_1$–$C_4$ alkyl group, a $C_1$–$C_4$ alkoxy group, a $C_1$–$C_4$ haloalkyl group and a nitro group), a phenylthiomethyl group which may be substituted (wherein the substituent is selected from the group consisting of a halogen atom, a $C_1$–$C_4$ alkyl group, a $C_1$–$C_4$ alkoxy group, a $C_1$–$C_4$ haloalkyl group and a nitro group), a piperidyl group, a pyridylmethyl group, a pyridyl group, a morpholinomethyl group, a piperazinomethyl group, a pyrrolidinylmethyl group, a piperdininomethyl group, a pyrrolylmethyl group, a phenylaminomethyl group which may be substituted (wherein the substituent is selected from the group consisting of a halogen atom, a $C_1$–$C_4$ alkyl group, a $C_1$–$C_4$ alkoxy group, a $C_1$–$C_4$ haloalkyl group and a nitro group), a phenyl $C_1$–$C_4$ alkylaminomethyl group which may be substituted (wherein the substituent is selected from the group consisting of a halogen atom, a $C_1$–$C_4$ alkyl group, a $C_1$–$C_4$ alkoxy group, a $C_1$–$C_4$ haloalkyl group and a nitro group), a 4-phenylpipersazinomethyl group, a N-benzyl-N-methylaminomethyl group, a 4-(4-acylpiperazinyl)phenoxymethyl group, a 4-(4-isopropylpiperazinyl)phenoxymethyl group, a 4-{4-{4-{2,4-dihydro-2-(1- methylpropyl)-3 H-1,2,4-triazol-3-one-4-yl }phenyl }piperazino }phenxoymethyl group, a $C_1$–$C_{16}$ alkyl group, a $C_1$–$C_{18}$ alkoxy group, a $C_1$–$C_8$ haloalkyl group, a $C_1$–$C_{16}$ haloalkoxy group, a $C_2$–$C_8$ alkenyl group, a $C_2$–$C_8$ alkynyl group, a $C_1$–$C_8$ alkoxymethyl group, a $C_2$–$C_{18}$ alkenyloxymethyl group, a $C_2$–$C_{18}$ alkynyloxymethyl group, a $C_2$–$C_{18}$ alkenylthiomethyl group, a $C_2$–$C_8$ alkenylaminomethyl group, a 3-substituted-1-pyrrolylmethyl group, a $C_1$–$C_4$ alkylthiomethyl group, a $C_1$–$C_6$ alkylaminomethyl group, a $C_1$–$C_{19}$ alkylcarbonyloxymethyl group, a $C_2$–$C_{19}$ alkenylcarbonyloxymethyl group, a phenyl $C_{1-3}$ alkyl group, a $(C_1$–$C_6$ alkyl)$_2$ aminomethyl group (wherein the alkyl groups as substituents of the amino group may form a 5- or 6-membered cyclocyclic ring), a phenyoxymethyl group which may be substituted (the substituent of the phenyl group is selected from the group consisting of a halogen atom, a $C_1$–$C_4$ alkyl group, a $C_1$–$C_4$ alkoxy group, a $C_1$–$C_4$ haloalkyl group, a $C_1$–$C_4$ haloalkoxy group, a $C_3$–$C_8$ alkenyl group, a $C_3$–$C_8$ alkynyl group, a $CO_2(C_1$–$C_4$ alkyl) group, a $N(C_1$–$C_3$ alkyl)$_2$ group, a cyano group, a nitro group, a $SCH_3$ group, a $SO_2CH_3$ group, a phenoxy group and a phenyl group), and a phenyl group which may be substituted (wherein the substituent is selected from the group consisting of a halogen atom, a nitro group, a $C_1$–$C_4$ alkyl group, a $C_1$–$C_4$ haloalkoxy group, a $N(C_1$–$C_3$ alkyl)$_2$ group, a phenoxy group and a phenyl group)}, provided that when the carbon atom substituted by R3 and R4 is an optically active carbon atom, the racemate and both of the two isolated optical isomers are included, and when two optically active sites are present in the molecule, the diastereomer mixture and all of the isolated two diastereromers and four optical isomers are included, and R3 and R4 may together form =NH, =NNH$_2$, =NOH, =NOR11 (wherein R11 is as defined above, and the geometrical isomers include the E/Z mixture and both of the isolated E and Z), =NO—Q—R11 (wherein Q and R11 are as defined above, and the geometrical isomers include the E/Z mixture and both of the isolated E and Z), =NO—Q—CO$_2$-(C$_1$–C$_4$ alkyl group) (wherein Q is as defined above, and the geometrical isomers include the E/Z mixture and both of the isolated E and Z), or =NNR1 l(R16) (wherein R11 is as defined above, R16 is a hydrogen atom, a $C_1$–$C_6$ alkyl group, a $C_3$–$C_8$ alkenyl group, a $C_3$–$C_8$ alkynyl group, a benzyl group or a phenyl group, and the geometrical isomers include the E/Z mixture and both of the isolated E and Z).

* * * * *

UNITED STATES PATENT AND TRADEMARK OFFICE
CERTIFICATE OF CORRECTION

PATENT NO. : 5,716,904
DATED : February 10, 1998
INVENTOR(S) : Jun SATOW et al.

It is certified that error appears in the above-identified patent and that said Letters Patent is hereby corrected as shown below:

On the title page, Item [30], the Foreign Application Priority Data, sixth line is missing. It should read:

--Oct. 13, 1994    [JP]    JAPAN............6-247466--

Signed and Sealed this

Twelfth Day of May, 1998

Attest:

Attesting Officer

BRUCE LEHMAN

Commissioner of Patents and Trademarks